United States Patent
Ward et al.

[11] Patent Number: 6,130,186
[45] Date of Patent: Oct. 10, 2000

[54] COMPOSITION AND METHOD FOR TREATING PLANTS WITH EXOGENOUS CHEMICALS

[75] Inventors: Anthony J. I. Ward, Clayton; Jisheng Ge, Affton; Joseph J. Sandbrink, Des Peres; Xiaodong C. Xu, St. Louis, all of Mo.

[73] Assignee: Monsanto Company, Saint Louis, Mo.

[21] Appl. No.: 08/957,631

[22] Filed: Oct. 24, 1997

Related U.S. Application Data

[60] Provisional application No. 60/029,317, Oct. 25, 1996, and provisional application No. 60/039,789, Mar. 4, 1997.

[51] Int. Cl.$^7$ ..................................................... A01N 25/30
[52] U.S. Cl. .......................... 504/116; 504/206; 504/235; 504/250; 514/561; 514/563; 514/772
[58] Field of Search ..................................... 504/116, 206, 504/235, 250; 514/561, 563, 772

[56] References Cited

U.S. PATENT DOCUMENTS

| | | | |
|---|---|---|---|
| 3,723,512 | 3/1973 | Niederprum | 260/501.15 |
| 4,115,313 | 9/1978 | Lyon | 252/309 |
| 4,235,871 | 11/1980 | Papahadjopoulos | 424/19 |
| 4,311,712 | 1/1982 | Evans | 424/365 |
| 4,394,149 | 7/1983 | Szoka | 71/28 |
| 4,481,026 | 11/1984 | Prisbylla | 71/86 |
| 4,506,831 | 3/1985 | Ghyczy | 239/10 |
| 4,567,161 | 1/1986 | Posanski | 514/23 |
| 4,576,626 | 3/1986 | Bauer | 71/28 |
| 4,681,617 | 7/1987 | Ghyczy | 71/86 |
| 4,822,407 | 4/1989 | Esposito | 71/94 |
| 4,840,659 | 6/1989 | Franz | 71/86 |
| 4,874,553 | 10/1989 | Hager | 260/403 |
| 4,902,333 | 2/1990 | Quimby | 71/79 |
| 5,037,847 | 8/1991 | Sutter | 514/427 |
| 5,123,950 | 6/1992 | Homma | 71/11 |
| 5,131,946 | 7/1992 | Franke | 71/90 |
| 5,264,213 | 11/1993 | Shibahara | 424/409 |
| 5,332,573 | 7/1994 | Yamaguchi | 504/117 |
| 5,332,714 | 7/1994 | Albrecht | 504/116 |
| 5,482,529 | 1/1996 | Ahlnas | 71/33 |
| 5,693,593 | 12/1997 | Arnold | 504/206 |
| 5,821,195 | 10/1998 | Sandbrink | 504/206 |

FOREIGN PATENT DOCUMENTS

| | | | |
|---|---|---|---|
| 91373/82 | of 1982 | Australia . | |
| 2099631 | of 1994 | Canada . | |
| 0019384 | of 1980 | European Pat. Off. . | |
| 0 068 293 | 1/1983 | European Pat. Off. . | |
| 0 068 294 | 1/1983 | European Pat. Off. . | |
| 0 068 295 | 1/1983 | European Pat. Off. . | |
| 0 124 351 | 11/1984 | European Pat. Off. . | |
| 0 095 071 | 7/1985 | European Pat. Off. . | |
| 0 237 880 | 9/1987 | European Pat. Off. | A01N 25/02 |
| 0 342 685 | 11/1989 | European Pat. Off. . | |
| 0 394 211 | 10/1990 | European Pat. Off. | A01N 25/14 |
| 0 503 989 | 9/1992 | European Pat. Off. . | |
| 0 579 052 | 1/1994 | European Pat. Off. | A01N 25/02 |
| 0 579 951 | 1/1994 | European Pat. Off. . | |
| 0 582 561 | 2/1994 | European Pat. Off. . | |
| 0 597 488 | 5/1994 | European Pat. Off. . | |
| 0 638 236 | 2/1995 | European Pat. Off. . | |
| 3226498 A1 | of 1984 | Germany . | |
| 32 26 498 | 1/1984 | Germany | A01N 25/32 |
| 51-035436 | 3/1976 | Japan . | |
| 51-035437 | 3/1976 | Japan . | |
| 61-229804 | 10/1986 | Japan . | |
| 5-148105 | 6/1993 | Japan . | |
| 8-225402 | 9/1996 | Japan . | |
| 83/4882 | 7/1983 | South Africa . | |
| 1 337 467 | 11/1973 | United Kingdom . | |
| 2 188 900 | 10/1987 | United Kingdom . | |
| 2 247 622 | 3/1992 | United Kingdom . | |
| 2 257 044 | 1/1993 | United Kingdom . | |
| WO 83/03608 | 10/1983 | WIPO . | |
| WO 87/04595 | 8/1987 | WIPO . | |
| WO 88/06881 | 9/1988 | WIPO . | |
| WO 90/07272 | 7/1990 | WIPO . | |
| WO 92/06596 | 10/1992 | WIPO . | |
| WO 92/18103 | 10/1992 | WIPO . | |
| WO 93/05652 | 4/1993 | WIPO . | |
| WO 93/21763 | 11/1993 | WIPO . | |
| WO 94/20072 | 9/1994 | WIPO . | |
| WO 95/13795 | 5/1995 | WIPO . | |
| WO 95/13796 | 5/1995 | WIPO . | |
| WO 95/20944 | 8/1995 | WIPO . | |
| 95/31970 | 11/1995 | WIPO | A61K 9/127 |
| WO 96/18302 | 6/1996 | WIPO . | |
| WO 96/28973 | 9/1996 | WIPO . | |
| WO 97/05779 | 2/1997 | WIPO . | |
| WO 97/36494 | 10/1997 | WIPO . | |
| WO98/06259 | 2/1998 | WIPO . | |

OTHER PUBLICATIONS

Anderson & Panetta (1995). Fireweed response to boom-spray applications of different herbicides and adjuvants. Plant Protection Quarterly 10(4), 152–153.

Anon. (no date). LI–700. Brochure of Agridyne, Pont–du–Casse, France.

(List continued on next page.)

*Primary Examiner*—S. Mark Clardy
*Attorney, Agent, or Firm*—James C. Forbes

[57] ABSTRACT

Methods and compositions are disclosed wherein exogenous chemicals are applied to plants to generate a desired biological response. One embodiment of the present invention is a plant treatment composition that comprises an exogenous chemical and a first excipient substance. The first excipient substance is an amphiphilic quaternary ammonium compound or mixture of such compounds, having the formula

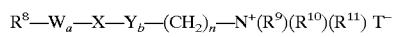

$$R^8-W_a-X-Y_b-(CH_2)_n-N^+(R^9)(R^{10})(R^{11})\ T^-$$

wherein $R^8$ represents the hydrophobic moiety and is a hydrocarbyl or haloalkyl group having from about 6 to about 22 carbon atoms, W and Y are independently O or NH, a and b are independently 0 or 1 but at least one of a and b is 1, X is CO, SO or $SO_2$, n is 2 to 4, $R^9$, $R^{10}$ and $R^{11}$ are independently $C_{1-4}$ alkyl, and T is a suitable anion.

50 Claims, No Drawings

OTHER PUBLICATIONS

Anon. (1995). McCutcheon's vol. 1: Emulsifiers & Detergents. North American Edition, pp. 4, 8, 9, 42, 48, 149, 163, 164, 316.

Anon. (1996). The right tool for the right job? Adveriesement by Loveland Industries, Inc. Farm Chemicals, Oct. 1996, p. 51.

Balneaves (1992). A comparison of surfactants to aid control of gorse and scotch broom with herbicides. Plant Protection Quarterly 7(4), 174–177.

Boothroyd et al. (1993). *Alopecurus myosuroides* control using fenoxaprop ethyl dose adjustments, adjuvants and mixes. Proceedings, Brighton Crop Protection Conference, vol. 2, 601–606.

Bridges (1989). Adjuvant and pH effects on sethoxydim and clethodim activity on rhizome johnsongrass (*Sorghum halepense*). Weed Technology 3, 615–620.

Bridges et al. (1991). Effect of adjuvant on foliar absorption and activity of clethodim and polar degradation products of clethodim. Weed Science 39, 543–547.

Bridges et al. (1992). Stability and activity of clethodim as influenced by pH, UV light and adjuvant. In Foy, ed.: Adjuvants for Agrochemicals, 215–223. Boca Raton: CRC Press.

Foy (1996). Adjuvants—current trends and technology. Pesticide Formulation Adjuvant Technology (Formulations Forum 1994), 323–352. Boca Raton: CRC Press.

Froment & Cooper (1994). Evalulation of fenoxaprop ethyl alone and in mixtures against blackgrass (*Alopecurus myosuroides*) in winter wheat. Tests of Agrochemicals and Cultivars 15, 60–61.

Gimesi (1986). Increasing the phytotoxicity of glyphosate by using subsidiary materials. Novenytermeles 35, 319–324. Abstract in English.

Glass (1988). Entrapment of herbicides $^{14}C$–picloram and $^{14}C$–dicamba in phospholipid vesicles. Pesticide Biochemistry and Physiology 32, 93–96. Abstract only.

Harker (1992). Effects of various adjuvants on sethoxydim activity. Weed Technology 6, 865–870.

Hart et al. (1992). Influence of adjuvants on the efficacy, absorption and spray retention of primisulfuron. Weed Technology 6, 592–598.

Harvey (1989). A guide to agricultural spray adjuvants used in the United States, 1990–91 ed., p. 94, Fresno: Thomson Publications.

Krawczyk (1996). Lecithin: consider the possibilities. Inform 7(11), 1158–1167.

Lasic (1997). Liposomes in Gene Delivery. Chap. 6, pp. 67–112. Boca Raton: CRC Press.

Leskovar & Boales (1996). Azadirachtin: potential use for controlling lepidopterous insects and increasing marketability of cabbage. Horticultural Science 31, 405–409.

Linert & Chasman (1993). The effects of fluorochemical surfactants on recoatability. Leaflet distributed by 3M Company, 2 pp., based on article in American Paint & Coatings Journal, Dec. 20, 1993.

Miller et al. (1996). The influence of adjuvants on droplet production. FRI Bulletin 193 (Proceedings, Fourth International Symposium on Adjuvants for Agrochemicals, 1995), 95–102.

Nalewaja (1986). Seed oils with herbicides. Mededelingen Faculteit Landbouwwetenschappen Rijksuniversiteit Gent 51(2a), 301–310.

Parnham (1996). The importance of phospholipid terminology. Inform 7(11), 1168–1175.

Percival & Baker (1990). Chlorophyll fluorescence—a possible application in plant growth regulator research. Monograph, British Society of Plant Growth Regulation 19, 1–14.

Quinn (1985). The chemico–physical properties of membrane lipids and their relevance to plant growth and protection. In St. John, ed.: Frontiers of Membrane Research in Agriculture (Beltsville Symposium 9), 55–75.

Quinn et al. (1986). An evaluation of soya lecithin in crop spray performance. Altomisation and Spray Technology 2, 235–246.

Rahman et al. (1994). Control of phenoxy herbicide resistant nodding thistle (*Carduus nutans*) in pasture. Proceedings, New Zealand Plant Protection Conference 47, 68–74.

Rimmer et al. (1992). Nutrient application to potatoes and wheat with various spray adjuvants. Abstracts, Third International Symposium on Adjuvants for Agrochemicals. No page number.

Salakhutdinov et al. (1992). Polymorphous transformations in model membranes caused by amphiphilic fungicides. Doklady Akademii Nauk Respubliki Uzbekistan 1, 45–46.

Schönherr (1993). Effects of monodisperse alcohol ethoxylates on mobility of 2,4–D in insolated plant cuticles. Pesticide Science 38, 155–164.

Schönherr & Baur (1994). Modelling penetration of plant cuticles by crop protection agents and effects of adjuvants on their rates of penetration. Pesticide Science 42, 185–208.

Swietlik (1989). Adjuvants affect the efficacy of glyphosate on selected perennial weeds. Horticultural Science 24, 470–472.

Wallach & Philippot (1993). New type of lipid vesicle: Novasome™. In Gregoriadis, ed.: Liposome Technology, 2nd ed., vol. 1, pp. 141–156. Boca Raton: CRC Press.

Wells (1989). Adjuvants, glyphosate efficacy and post–spraying rainfall. Plant Protection Quarterly 4(4), 158–164.

Whitson & Adam (1990). Leafy spurge (*Euphorbia esula* L.) control with various adjuvants combined with picloram and fluroxypyr. Proceedings, Western Society of Weed Science 43, 37.

Woznica & Messersmith (1994). Evaluation of adjuvants for glyphosate. Materialy Sesji Naukowej Instytutu Ochrony Roslin 34(2), 98–101. Abstract in English.

Woznika & Messersmith (1994). Glyphosate retention and absorption by cattail (*Typha X glauca* Godr.) as influenced by nonionic surfactants. Roczniki Nauk Roiniczych, Ser. E 24, 87–91.

Wyrill & Burnside (1977). Glyphosate toxicity to common milkweed and hemp dogbane as influenced by surfactants. Weed Science 25, 275–287.

Yaduraju & Ahuja (1995). Response of herbicide resistant *Phalaris minor* to pre– and post–emergence herbicides, herbicide mixtures and adjuvants. Proceedings, Brighton Crop Protection Conference, vol. 1, 225–230.

Wyrill, J.B. and Burnshide, O.C., Glyphosate Toxicity to Common Milkweed and Hemp Dogbane as Influenced by Surfactants, *Weed Science,* vol. 25., No. 3, May 1997, pp. 275–287 XP002034447.

COMPOSITION AND METHOD FOR TREATING PLANTS WITH EXOGENOUS CHEMICALS

This application claims the benefit of provisional application Ser. No. 60/029,317, filed Oct. 25, 1996; and provisional application Ser. No. 60/039,789, filed Mar. 4, 1997. Each of those applications is incorporated here by reference.

BACKGROUND OF THE INVENTION

This invention relates to formulations and methods for enhancing the efficacy of exogenous chemicals used in treating plants. An exogenous chemical, as defined herein, is any chemical substance, whether naturally or synthetically derived, which (a) has biological activity or is capable of releasing in a plant an ion, moiety or derivative which has biological activity, and (b) is applied to a plant with the intent or result that the chemical substance or its biologically active ion, moiety or derivative enter living cells or tissues of the plant and elicit a stimulatory, inhibitory, regulatory, therapeutic, toxic or lethal response in the plant itself or in a pathogen, parasite or feeding organism present in or on the plant. Examples of exogenous chemical substances include, but are not limited to, chemical pesticides (such as herbicides, algicides, fungicides, bactericides, viricides, insecticides, aphicides, miticides, nematicides, molluscicides, and the like), plant growth regulators, fertilizers and nutrients, gametocides, defoliants, desiccants, mixtures thereof, and the like.

Exogenous chemicals, including foliar-applied herbicides, have at times been formulated with surfactants, so that when water is added, the resulting sprayable composition is more easily and effectively retained on the foliage (e.g., the leaves or other photosynthesizing organs) of plants. Surfactants can also bring other benefits, including improved contact of spray droplets with a waxy leaf surface and, in some cases, improved penetration of the accompanying exogenous chemical into the interior of leaves. Through these and perhaps other effects, surfactants have long been known to increase the biological effectiveness of herbicide compositions, or other compositions of exogenous chemicals, when added to or included in such compositions. Thus, for example, the herbicide glyphosate (N-phosphonomethylglycine) has been formulated with surfactants such as polyoxyalkylene-type surfactants including, among other surfactants, polyoxyalkylene alkylamines. Commercial formulations of glyphosate herbicide marketed under the trademark ROUNDUP® have been formulated with a surfactant composition based on such a polyoxyalkylene alkylamine, in particular a polyethoxylated tallowamine, this surfactant composition being identified as MON 0818. Surfactants have generally been combined with glyphosate or other exogenous chemicals either in a commercial concentrate (herein referred to as a "coformulation"), or in a diluted mixture that is prepared from separate compositions, one comprising an exogenous chemical (e.g. glyphosate) and another comprising surfactant, prior to use in the field (i.e., a tank mix).

Various combinations of exogenous chemicals and surfactants or other adjuvants have been tested in the past. In some instances, the addition of a particular surfactant has not produced uniformly positive or negative changes in the effect of the exogenous chemical on the plant (e.g., a surfactant that may enhance the activity of a particular herbicide on certain weeds may interfere with, or antagonize, the herbicidal efficacy on another weed species).

Some surfactants tend to degrade fairly rapidly in aqueous solutions. As a result, surfactants that exhibit this property can only be used effectively in tank mixes (i.e., mixed with the other ingredients in solution or dispersion in the tank soon before spraying is to occur), rather than being coformulated in an aqueous composition with the other ingredients in the first instance. This lack of stability, or inadequate shelf-life, has hindered the use of certain surfactants in some exogenous chemical formulations.

Other surfactants, though chemically stable, are physically incompatible with certain exogenous chemicals, particularly in concentrate coformulations. For example, most classes of nonionic surfactant, including polyoxyethylene alkylether surfactants, do not tolerate solutions of high ionic strength, as for example in a concentrated aqueous solution of a salt of glyphosate. Physical incompatibility can also lead to inadequate shelf-life. Other problems that can arise from such incompatibility include the formation of aggregates large enough to interfere with commercial handling and application, for example by blocking spray nozzles.

Another problem that has been observed in the past is the effect of environmental conditions on uptake of an exogenous chemical composition into foliage of a plant. For example, conditions such as temperature, relative humidity, presence or absence of sunlight, and health of the plant to be treated, can affect the uptake of a herbicide into the plant. As a result, spraying exactly the same herbicidal composition in two different situations can result in different herbicidal control of the sprayed plants.

One consequence of the above-described variability is that often a higher rate of herbicide per unit area is applied than might actually be required in that situation, in order to be certain that adequate control of undesired plants will be achieved. For similar reasons, other foliar-applied exogenous chemicals are also typically applied at significantly higher rates than needed to give the desired biological effect in the particular situation where they are used, to allow for the natural variability that exists in efficiency of foliar uptake. A need therefore exists for compositions of exogenous chemicals that, through more efficient uptake into plant foliage, allow reduced use rates.

Many exogenous chemicals are commercially packaged as a liquid concentrate that contains a significant amount of water. The packaged concentrate is shipped to distributors or retailers. Ultimately the packaged concentrate ends up in the hands of an end user, who further dilutes the concentrate by adding water in accordance with label instructions on the package. The dilute composition thus prepared is then sprayed on plants.

A significant portion of the cost of such packaged concentrates is the cost of transporting the concentrate from the manufacturing site to the location where the end user purchases it. Any liquid concentrate formulation that contained relatively less water and thus more exogenous chemical would reduce the cost per unit amount of exogenous chemical. However, one important limit on the ability of the manufacturer to increase the loading of the exogenous chemical in the concentrate is the stability of that formulation. With some combinations of ingredients, a limit will be reached at which any further reduction of water content in the concentrate will cause it to become unstable (e.g., to separate into discrete layers), which may make it commercially unacceptable.

Accordingly, a need exists for improved formulations of exogenous chemicals, particularly herbicides, that are stable, effective, less sensitive to environmental conditions, and permit the use of reduced amounts of exogenous chemical to achieve the desired biological effect in or on plants. A need also exists for stable liquid concentrate formulations of exogenous chemicals that contain less water and more exogenous chemical than prior art concentrates.

SUMMARY OF THE INVENTION

The present invention relates to novel methods and compositions wherein exogenous chemicals are applied to plants to generate a desired biological response.

One embodiment of the present invention is a plant treatment composition that comprises (a) an exogenous chemical, and (b) a first excipient substance. The first excipient substance is an amphiphilic quaternary ammonium compound or mixture of such compounds, having the formula

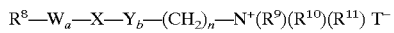

$$R^8-W_a-X-Y_b-(CH_2)_n-N^+(R^9)(R^{10})(R^{11})\ T^- \qquad V$$

wherein $R^8$ represents the hydrophobic moiety and is a hydrocarbyl or haloalkyl group having from about 6 to about 22 carbon atoms, W and Y are independently O or NH, a and b are independently 0 or 1 but at least one of a and b is 1, X is CO, SO or $SO_2$, n is 2 to 4, $R^9$, $R^{10}$ and $R^{11}$ are independently $C_{1-4}$ alkyl, and T is a suitable anion. $R^8$ in one particular embodiment is hydrocarbyl having about 12 to about 18 carbon atoms. $R^8$ can also be fluorinated. In one specific embodiment, $R^8$ is perfluorinated, and preferably has about 6 to about 12 carbon atoms. Suitable agriculturally acceptable anions T include hydroxide, chloride, bromide, iodide, sulfate, phosphate and acetate. In one particularly preferred embodiment, $R^8$ is saturated perfluoroalkyl having about 6 to about 12 carbon atoms, X is CO or $SO_2$, Y is NH, a is 0, b is 1, n is 3, $R^9$, $R^{10}$ and $R^{11}$ are methyl, and T is selected from the group consisting of chloride, bromide and iodide.

An "excipient substance" as that term is used in this patent is any substance other than an exogenous chemical and water that is added to the composition. "Excipient substances" include inert ingredients, although an excipient substance useful in the present invention does not have to be devoid of biological activity. "Amphiphilic" means having at least one polar, water-soluble head group which is hydrophilic and at least one water-insoluble organic tail which is hydrophobic, contained within the same molecule.

The first excipient substance is present in the composition in an adjuvant amount, i.e. an amount sufficient to provide visibly improved biological effectiveness of the exogenous chemical by comparison with a composition lacking the first excipient substance, and the exogenous chemical is present in the composition in an amount sufficient to provide biological effect in the presence of said adjuvant amount of the first excipient substance. "Visibly improved" in the present context means that, in a side-by-side comparison, a difference in biological effectiveness in favor of the composition of the invention would be evident to an experienced technician in the art relating to the particular class of exogenous chemical being applied; for example a weed scientist in the case where the exogenous chemical is a herbicide.

A wide variety of exogenous chemicals can be used in the compositions and methods of the present invention. A preferred class is foliar-applied exogenous chemicals, i.e. exogenous chemicals that are normally applied post-emergence to foliage of plants. A preferred subclass of foliar-applied exogenous chemicals is those that are water-soluble. By "water-soluble" in this context is meant having a solubility in distilled water at 25° C. greater than about 1% by weight.

Especially preferred water-soluble exogenous chemicals are salts that have an anion portion and a cation portion. In one embodiment of the invention, at least one of the anion and cation portions is biologically active and has a molecular weight of less than about 300. Particular examples of such exogenous chemicals where the cation portion is biologically active are paraquat, diquat and chlormequat. More commonly it is the anion portion that is biologically active.

Another preferred subclass of exogenous chemicals is those that exhibit systemic biological activity in the plant. Within this subclass, an especially preferred group of exogenous chemicals is N-phosphonomethylglycine and its herbicidal derivatives. N-phosphonomethylglycine, often referred to by its common name glyphosate, can be used in its acid form, but is more preferably used in the form of a salt. Any water-soluble salt of glyphosate can be used in the practice of this invention. Some preferred salts include the sodium, potassium, ammonium, mono-, di-, tri- and tetra-$C_{1-4}$-alkylammonium, mono-, di- and tri-$C_{1-4}$-alkanolammonium, mono-, di- and tri-$C_{1-4}$-alkylsulfonium and sulfoxonium salts. The ammonium, monoisopropylammonium and trimethylsulfonium salts of glyphosate are especially preferred. Mixtures of salts can also be useful in certain situations.

In one preferred embodiment, the weight/weight ratio of the first excipient substance to the exogenous chemical is between about 1:3 and about 1:100.

Compositions of the present invention can be used in methods of treating plants. Foliage of a plant is contacted with a biologically effective amount of the composition. "Contacting" in this context means placing the composition on the foliage.

A composition of the present invention comprising an exogenous chemical and a first excipient substance as described above can have a number of different physical forms. For example, the composition can further comprise water in an amount effective to make the composition a dilute aqueous composition ready for application to foliage of a plant. Such a composition typically contains about 0.02 to about 2 percent by weight of the exogenous chemical, but for some purposes can contain up to about 10 percent by weight or even more of the exogenous chemical.

Alternatively, the composition can be a shelf-stable concentrate composition comprising the exogenous chemical substance in an amount of about 10 to about 90 percent by weight. Such shelf-stable concentrates can be, for example, (1) a solid composition comprising the exogenous chemical substance in an amount of about 30 to about 90 percent by weight, such as a water-soluble or water-dispersible granular formulation, or (2) a composition that further comprises a liquid diluent, wherein the composition comprises the exogenous chemical substance in an amount of about 10 to about 60 percent by weight. In this latter embodiment, it is especially preferred for the exogenous chemical substance to be water-soluble and present in an aqueous phase of the composition in an amount of about 15 to about 45 percent by weight of the composition. In particular, such a composition can be, for example, an aqueous solution concentrate or an emulsion having an oil phase. If it is an emulsion, it can more specifically be, for example, an oil-in-water emulsion, a water-in-oil emulsion, or a water-in-oil-in-water multiple emulsion.

As described above, one embodiment of the invention is a sprayable composition that comprises an exogenous chemical, an aqueous diluent, and a first excipient substance. The term "spray composition" is sometimes used herein to mean a sprayable composition.

In a related embodiment of the invention, a concentrate composition is provided which, upon dilution, dispersion or dissolution in water forms the sprayable composition just described. The concentrate composition contains a reduced amount of the aqueous diluent, or, in a particular embodiment, is a dry composition having less than about 5% water by weight. Typically a concentrate composition of the invention contains at least about 10% by weight of the exogenous chemical, preferably at least about 15%.

In one embodiment of the invention, the composition further comprises a second excipient substance which is a liposome-forming material. One class of liposome-forming material is an amphiphilic compound or mixture of such compounds, preferably having two hydrophobic moieties, each of which is a saturated alkyl or acyl chain having from about 8 to about 22 carbon atoms. The amphiphilic compound or mixture of such compounds having said two hydrophobic moieties with about 8 to about 22 carbon atoms preferably constitutes from about 40 to 100 percent by weight of all amphiphilic compounds having two hydrophobic moieties present in the liposome-forming material. Preferably the liposome-forming material has a hydrophilic head group comprising a cationic group. More preferably, the cationic group is an amine or ammonium group.

In a preferred embodiment of the invention, the second excipient substance comprises a liposome-forming compound having a hydrophobic moiety comprising two independently saturated or unsaturated hydrocarbyl groups $R^1$ and $R^2$ each independently having about 7 to about 21 carbon atoms. A number of subclasses of such liposome-forming compounds are known.

One subclass has the formula $$N^+(CH_2R^1)((CH_2R^2)(R^3)(R^4)\ Z^- \qquad I$$

wherein $R^3$ and $R^4$ are independently hydrogen, $C_{1-4}$ alkyl or $C_{1-4}$ hydroxyalkyl and Z is a suitable anion.

A second subclass has the formula $$N^+(R^5)(R^6)(R^7)CH_2CH(OCH_2R^1)CH_2(OCH_2R^2)\ Z^- \qquad II$$

wherein $R^5$, $R^6$ and $R^7$ are independently hydrogen, $C_{1-4}$ alkyl or $C_{1-4}$ hydroxyalkyl and Z is a suitable anion.

A third subclass has the formula $$N^+(R^5)(R^6)(R^7)CH_2CH(OCOR^1)CH_2(OCOR^2)\ Z^- \qquad III$$

wherein $R^5$, $R^6$, $R^7$ and Z are as defined above.

A fourth subclass has the formula $$N^+(R^5)(R^6)(R^7)CH_2CH_2OPO(O^-)OCH_2CH(OCOR^1)CH_2(OCOR^2) \qquad IV$$

wherein $R^5$, $R^6$, and $R^7$ are as defined above.

Compounds of formulas I–IV will have the indicated formulas in an acid medium, for example at a pH of 4 and may have the same formulas at other pH's as well. It should be understood, however, that compositions of the present invention are not limited to use at a pH of 4.

It is preferred that about 40–100 percent of the $R^1$ and $R^2$ groups present in the second excipient substance are saturated straight chain alkyl groups having about 7 to about 21 carbon atoms. Examples of suitable agriculturally acceptable anions Z include hydroxide, chloride, bromide, iodide, sulfate, phosphate and acetate.

In all of the above subclasses of liposome-forming substances, the hydrophilic moiety comprises a cationic group, specifically an amine or ammonium group. The compound as a whole is in some cases cationic (as in I, II and III) and in some cases neutral (as in IV). Where the amine group is quaternary, it behaves as a cationic group independently of pH. Where the amine group is secondary or tertiary, it behaves as a cationic group when protonated, i.e. in an acid medium, for example at a pH of 4.

Other subclasses of liposome-forming substances having two hydrophobic chains each comprising a $C_{7-21}$ hydrocarbyl group can also be used as the second excipient substance in compositions of the invention. While substances having a cationic group in the hydrophilic moiety are preferred, nonionic or anionic substances can be used if desired.

In another embodiment, the second excipient substance is a phospholipid selected from the group consisting of di-$C_{8-22}$-alkanoylphosphatidylcholines and di-$C_{8-22}$-alkanoylphosphatidylethanolamines. In a particular preferred embodiment the second excipient substance is a dipalmitoyl or distearoyl ester of phosphatidylcholine or a mixture thereof.

Aqueous compositions of the present invention can comprise supramolecular aggregates formed from the first and/or second excipient substances. In one preferred embodiment, the second excipient substance is a vesicle-forming amphiphilic substance, such as a vesicle-forming lipid, and when the substance is dispersed in water the majority (greater than 50% by weight, preferably greater than 75% by weight) of the second excipient substance is present as vesicles or liposomes. In another preferred embodiment the second excipient substance is present as bilayers or multilamellar structures which are not organized as vesicles or liposomes. Compositions of the present invention can also include, without limitation, colloidal systems such as emulsions (water/oil, oil/water, or multiple, e.g., water/oil/water), foams, microemulsions, and suspensions or dispersions of microparticulates, nanoparticulates, or microcapsules. Compositions of the invention can include more than one type of aggregate or colloidal system; examples include liposomes or vesicles dispersed in a microemulsion, and compositions having characteristics of both emulsions and suspensions, e.g. suspo-emulsions. The present invention also encompasses any formulation, which may or may not contain a significant amount of water, that on dilution in an aqueous medium forms such colloidal systems, and/or systems comprising vesicles, liposomes, bilayers or multilamellar structures, so long as the other requirements stipulated herein are met.

The weight ratio of each of the first and second excipient substances to the exogenous chemical preferably is between about 1:3 and about 1:100. We have been surprised by the high level of biological effectiveness, specifically herbicidal effectiveness of a glyphosate composition, exhibited at such low ratios of such excipient substances to exogenous chemical. Higher ratios can also be effective but are likely to be uneconomic in most situations and increase the risk of producing an antagonistic effect on effectiveness of the exogenous chemical. The low amounts of excipient substances present in preferred compositions of the present invention permit high cost-effectiveness by comparison with prior art compositions showing similar effectiveness. It is surprising that the enhancement of biological activity that has been observed when using the present invention can be achieved with the addition of relatively small amounts of such excipient substances.

In any of the above particular embodiments, the exogenous chemical and/or first excipient substance can be encapsulated within or associated with aggregates (e.g., liposomes) formed by the second excipient substance, but do not necessarily have to be so encapsulated or associated. "Associated" in this context means bound to or at least partly intercalated in some fashion in a vesicle wall, as opposed to being encapsulated. In yet another embodiment of the invention where the second excipient substance forms liposomes, the exogenous chemical and/or first excipient substance is not encapsulated in or associated with the liposomes at all. Although the present invention does not exclude the possibility of so encapsulating or associating the exogenous chemical, a presently preferred dilute sprayable liposomal composition encapsulates less than 5% by weight of the exogenous chemical that is present in the overall composition. Another dilute sprayable liposomal embodiment of the present invention has no substantial amount (i.e., less than 1% by weight) of the exogenous chemical encapsulated in the liposomes. As a droplet of such a liposomal composition dries on foliage of a plant, the proportion of the exogenous chemical that is encapsulated in the liposomes may change.

An alternative embodiment is a composition that does not itself comprise an exogenous chemical, but is intended for application to a plant in conjunction with or as a carrier for the application of an exogenous chemical. This composition comprises a first excipient substance and may further comprise a second excipient substance as described above. Such a composition may be sprayable, in which case it also comprises an aqueous diluent, or it may be a concentrate, requiring dilution, dispersion or dissolution in water to provide a sprayable composition. Thus, this embodiment of the invention can be provided as a stand-alone product and applied to a plant, diluted as appropriate with water, simultaneously with the application of an exogenous chemical (for example in tank mix with the exogenous chemical), or before or after the application of the exogenous chemical, preferably within about 96 hours before or after application of the exogenous chemical.

The compositions and methods of the present invention have a number of advantages. They provide enhanced biological activity of exogenous chemicals in or on plants in comparison with prior formulations, either in terms of greater ultimate biological effect, or obtaining an equivalent biological effect while using a reduced application rate of exogenous chemical. Certain herbicide formulations of the present invention can avoid antagonism that has been observed in some prior art herbicide formulations, and can minimize quick production of necrotic lesions on leaves that in some situations hinder overall translocation of herbicide in the plant. Certain herbicide compositions of the invention modify the spectrum of activity of the herbicide across a range of plant species. For example, certain formulations of the present invention containing glyphosate can provide good herbicidal activity against broadleaf weeds while not losing any herbicidal effectiveness on narrowleaf weeds. Others can enhance herbicidal effectiveness on narrowleaf weeds to a greater extent than on broadleaf weeds. Still others can have enhanced effectiveness which is specific to a narrow range of species or even a single species.

Another advantage of the present invention is that it employs relatively small amounts of the first and second excipient substances in relation to the amount of exogenous chemical employed. This makes the compositions and methods of the present invention relatively inexpensive, and also tends to reduce instability problems in specific compositions where one or both excipient substances are physically incompatible with the exogenous chemical.

Further, compositions of the present invention are less sensitive in some instances to environmental conditions such as relative humidity at the time of application to the plant. Also, the present invention allows the use of smaller amounts of herbicides or other pesticides, while still obtaining the required degree of control of weeds or other undesired organisms.

DESCRIPTION OF ILLUSTRATIVE EMBODIMENTS

Examples of exogenous chemical substances that can be included in compositions of the present invention include, but are not limited to, chemical pesticides (such as herbicides, algicides, fungicides, bactericides, viricides, insecticides, aphicides, miticides, nematicides, molluscicides and the like), plant growth regulators, fertilizers and nutrients, gametocides, defoliants, desiccants, mixtures thereof and the like. In one embodiment of the invention, the exogenous chemical is polar.

A preferred group of exogenous chemicals are those that are normally applied post-emergence to the foliage of plants, i.e. foliar-applied exogenous chemicals.

Some exogenous chemicals useful in the present invention are water-soluble, for example salts that comprise biologically active ions, and also comprise counterions, which may be biologically inert or relatively inactive. A particularly preferred group of these water-soluble exogenous chemicals or their biologically active ions or moieties are systemic in plants, that is, they are to some extent translocated from the point of entry in the foliage to other parts of the plant where they can exert their desired biological effect. Especially preferred among these are herbicides, plant growth regulators and nematicides, particularly those that have a molecular weight, excluding counterions, of less than about 300. More especially preferred among these are exogenous chemical compounds having one or more functional groups selected from amine, carboxylate, phosphonate and phosphinate groups.

Among such compounds, an even more preferred group are herbicidal or plant growth regulating exogenous chemical compounds having at least one of each of amine, carboxylate, and either phosphonate or phosphinate functional groups. Salts of N-phosphonomethylglycine are examples of this group of exogenous chemicals. Further examples include salts of glufosinate, for instance the ammonium salt (ammonium DL-homoalanin-4-yl (methyl) phosphinate).

Another preferred group of exogenous chemicals which can be applied by the method of the invention are nematicides such as those disclosed in U.S. Pat. No. 5,389,680, the disclosure of which is incorporated herein by reference. Preferred nematicides of this group are salts of 3,4,4-trifluoro-3-butenoic acid or of N-(3,4,4-trifluoro-1-oxo-3-butenyl)glycine.

Exogenous chemicals which can usefully be applied by the method of the present invention are normally, but not exclusively, those which are expected to have a beneficial effect on the overall growth or yield of desired plants such as crops, or a deleterious or lethal effect on the growth of undesirable plants such as weeds. The method of the present invention is particularly useful for herbicides, especially those that are normally applied post-emergence to the foliage of unwanted vegetation.

Herbicides which can be applied by the method of the present invention include but are not limited to any listed in standard reference works such as the "Herbicide Handbook," *Weed Science Society of America,* 1994, 7th Edition, or the "Farm Chemicals Handbook," Meister Publishing Company, 1997 Edition. Illustratively these herbicides include acetanilides such as acetochlor, alachlor and metolachlor, aminotriazole, asulam, bentazon, bialaphos, bipyridyls such as paraquat, bromacil, cyclohexenones such as clethodim and sethoxydim, dicamba, diflufenican, dinitroanilines such as pendimethalin, diphenylethers such as acifluorfen, fomesafen and oxyfluorfen, fatty acids such as $C_{9-10}$ fatty acids, fosamine, flupoxam, glufosinate, glyphosate, hydroxybenzonitriles such as bromoxynil, imidazolinones such as imazaquin and imazethapyr, isoxaben, norflurazon, phenoxies such as 2,4-D, phenoxypropionates such as diclofop, fluazifop and quizalofop, picloram, propanil, substituted ureas such as fluometuron and isoproturon, sulfonylureas such as chlorimuron, chlorsulfuron, halosulfuron, metsulfuron, primisulfuron, sulfometuron and sulfosulfuron, thiocarbamates such as triallate, triazines such as atrazine and metribuzin, and triclopyr. Herbicidally active derivatives of any known herbicide are also within the scope of the present invention. A herbicidally active derivative is any compound which is a minor structural modification, most commonly but not restrictively a salt or ester, of a known herbicide. These compounds retain the essential activity of the parent herbicide, but may not necessarily have a potency equal to that of the parent herbicide. These compounds may convert to the parent herbicide before or after they enter the treated plant. Mixtures or coformulations of a herbicide with other ingredients, or of more than one herbicide, may likewise be employed.

An especially preferred herbicide is N-phosphonomethylglycine (glyphosate), a salt, adduct or ester thereof, or a compound which is converted to glyphosate in plant tissues or which otherwise provides glyphosate ion. Glyphosate salts that can be used according to this invention include but are not restricted to alkali metal, for example sodium and potassium, salts; ammonium salt; alkylamine, for example dimethylamine and isopropylamine, salts; alkanolamine, for example ethanolamine, salts, alkylsulfonium, for example trimethylsulfonium, salts; sulfoxonium salts; and mixtures thereof. The herbicidal compositions sold by Monsanto Company as ROUNDUP® and ACCORD® contain the monoisopropylamnine (IPA) salt of N-phosphonomethylglycine. The herbicidal compositions sold by Monsanto Company as ROUNDUP® Dry and RIVAL® contain the monoammonium salt of N-phosphonomethylglycine. The herbicidal composition sold by Monsanto Company as ROUNDUP® Geoforce contains the monosodium salt of N-phosphonomethylglycine. The herbicidal composition sold by Zeneca as TOUCHDOWN® contains the trimethylsulfonium salt of N-phosphonomethylglycine. The herbicidal properties of N-phosphonomethylglycine and its derivatives were first discovered by Franz, then disclosed and patented in U.S. Pat. No. 3,799,758, issued Mar. 26, 1974. A number of herbicidal salts of N-phosphonomethylglycine were patented by Franz in U.S. Pat. No. 4,405,531, issued Sep. 20, 1983. The disclosures of both of these patents are hereby incorporated by reference.

Because the commercially most important herbicidal derivatives of N-phosphonomethylglycine are certain salts thereof, the glyphosate compositions useful in the present invention will be described in more detail with respect to such salts. These salts are well known and include ammonium, IPA, alkali metal (such as the mono-, di-, and trisodium salts, and the mono-, di-, and tripotassium salts), and trimethylsulfonium salts. Salts of N-phosphonomethylglycine are commercially significant in part because they are water soluble. The salts listed immediately above are highly water soluble, thereby allowing for highly concentrated solutions that can be diluted at the site of use. In accordance with the method of this invention as it pertains to glyphosate herbicide, an aqueous solution containing a herbicidally effective amount of glyphosate and other components in accordance with the invention is applied to foliage of plants. Such an aqueous solution can be obtained by dilution of a concentrated glyphosate salt solution with water, or dissolution or dispersion in water of a dry (e.g. granular, powder, tablet or briquette) glyphosate formulation.

Exogenous chemicals should be applied to plants at a rate sufficient to give the desired biological effect. These application rates are usually expressed as amount of exogenous chemical per unit area treated, e.g. grams per hectare (g/ha). What constitutes a "desired effect" varies according to the standards and practice of those who investigate, develop, market and use a specific class of exogenous chemicals. For example, in the case of a herbicide, the amount applied per unit area to give 85% control of a plant species as measured by growth reduction or mortality is often used to define a commercially effective rate.

Herbicidal effectiveness is one of the biological effects that can be enhanced through this invention. "Herbicidal effectiveness," as used herein, refers to any observable measure of control of plant growth, which can include one or more of the actions of (1) killing, (2) inhibiting growth, reproduction or proliferation, and (3) removing, destroying, or otherwise diminishing the occurrence and activity of plants.

The herbicidal effectiveness data set forth herein report "inhibition" as a percentage following a standard procedure in the art which reflects a visual assessment of plant mortality and growth reduction by comparison with untreated plants, made by technicians specially trained to make and record such observations. In all cases, a single technician makes all assessments of percent inhibition within any one experiment or trial. Such measurements are relied upon and regularly reported by Monsanto Company in the course of its herbicide business.

The selection of application rates that are biologically effective for a specific exogenous chemical is within the skill of the ordinary agricultural scientist. Those of skill in the art will likewise recognize that individual plant conditions, weather and growing conditions, as well as the specific exogenous chemical and formulation thereof selected, will affect the efficacy achieved in practicing this invention. Useful application rates for exogenous chemicals employed can depend upon all of the above conditions. With respect to the use of the method of this invention for glyphosate herbicide, much information is known about appropriate application rates. Over two decades of glyphosate use and published studies relating to such use have provided abundant information from which a weed control practitioner can select glyphosate application rates that are herbicidally effective on particular species at particular growth stages in particular environmental conditions.

Herbicidal compositions of glyphosate or derivatives thereof are used to control a very wide variety of plants worldwide. Such compositions can be applied to a plant in a herbicidally effective amount, and can effectively control one or more plant species of one or more of the following genera without restriction: Abutilon, Amaranthus, Artemisia, Asclepias, Avena, Axonopus, Borreria, Brachiaria, Brassica, Bromus, Chenopodium, Cirsium, Commelina, Convolvulus, Cynodon, Cyperus, Digitaria, Echinochloa, Eleusine, Elymus, Equisetum, Erodium, Helianthus, Imperata, Ipomoea, Kochia, Lolium, Malva, Oryza, Ottochloa, Panicum, Paspalum, Phalaris, Phragmites, Polygonum, Portulaca, Pteridium, Pueraria, Rubus, Salsola, Setaria, Sida, Sinapis, Sorghum, Triticum, Typha, Ulex, Xanthium, and Zea.

Particularly important species for which glyphosate compositions are used are exemplified without limitation by the following:

Annual broadleaves:
  velvetleaf (*Abutilon theophrasti*)
  pigweed (*Amaranthus spp.*)
  buttonweed (*Borreria spp.*)
  oilseed rape, canola, indian mustard, etc. (*Brassica spp.*)
  commelina (*Commelina spp.*)
  filaree (*Erodium spp.*)
  sunflower (*Helianthus spp.*)
  morningglory (*Ipomoea spp.*)
  kochia (*Kochia scoparia*)
  mallow (*Malva spp.*)
  wild buckwheat, smartweed, etc. (*Polygonum spp.*)
  purslane (*Portulaca spp.*)
  russian thistle (*Salsola spp.*)
  sida (*Sida spp.*)
  wild mustard (*Sinapis arvensis*)
  cocklebur (*Xanthium spp.*)
Annual narrowleaves:
  wild oat (*Avena fatua*)
  carpetgrass (*Axonopus spp.*)
  downy brome (*Bromus tectorum*)
  crabgrass (*Digitaria spp.*)
  barnyardgrass (*Echinochloa crus-galli*)
  goosegrass (*Eleusine indica*)
  annual ryegrass (*Lolium multiflorum*)
  rice (*Oryza sativa*)
  ottochloa (*Ottochloa nodosa*)
  bahiagrass (*Paspalum notatum*)
  canarygrass (*Phalaris spp.*)
  foxtail (*Setaria spp.*)
  wheat (*Triticum aestivum*)
  corn (*Zea mays*)
Perennial broadleaves:
  mugwort (*Artemisia spp.*)
  milkweed (*Asclepias spp.*)
  canada thistle (*Cirsium arvense*)
  field bindweed (*Convolvulus arvensis*)
  kudzu (*Pueraria spp.*)
Perennial narrowleaves:
  brachiaria (*Brachiaria spp.*)
  bermudagrass (*Cynodon dactylon*)
  yellow nutsedge (*Cyperus esculentus*)
  purple nutsedge (*C. rotundus*)
  quackgrass (*Elymus repens*)
  lalang (*Imperata cylindrica*)
  perennial ryegrass (*Lolium perenne*)
  guineagrass (*Panicum maximum*)
  dallisgrass (*Paspalum dilatatum*)
  reed (*Phragmites spp.*)
  johnsongrass (*Sorghum halepense*)
  cattail (*Typha spp.*)
Other perennials:
  horsetail (*Equisetum spp.*)
  bracken (*Pteridium aquilinum*)
  blackberry (*Rubus spp.*)
  gorse (*Ulex europaeus*)

Thus, the method of the present invention, as it pertains to glyphosate herbicide, can be useful on any of the above species.

Effectiveness in greenhouse tests, usually at exogenous chemical rates lower than those normally effective in the field, is a proven indicator of consistency of field performance at normal use rates. However, even the most promising composition sometimes fails to exhibit enhanced performance in individual greenhouse tests. As illustrated in the Examples herein, a pattern of enhancement emerges over a series of greenhouse tests; when such a pattern is identified this is strong evidence of biological enhancement that will be useful in the field.

Compositions of the present invention comprise as a first excipient substance one or more cationic surfactant compounds having formula V above. In compounds of formula V, $R^8$ unless perfluorinated preferably has from about 12 to about 18 carbon atoms. $R^8$ is preferably perfluorinated, in which case it preferably has from about 6 to about 12 carbon atoms. Preferably n is 3. $R^9$ groups are preferably methyl.

Sulfonylamino compounds of formula V are especially preferred. Suitable examples include 3-(((heptadecafluorooctyl)sulfonyl)amino)-N,N,N-trimethyl-1-propaminium iodide, available for example as Fluorad FC-135 from 3M Company, and the corresponding chloride. It is believed that Fluorad FC-754 of 3M Company is the corresponding chloride.

Fluoro-organic surfactants such as the cationic types falling within formula V belong to a functional category of surfactants known in the art as "superspreaders" or "superwetters". As a class "superspreaders" or "superwetters" are very effective in reducing surface tension of aqueous compositions containing relatively low concentrations of these surfactants. In many applications fluoro-organic surfactants can substitute for organosilicone surfactants which are likewise "superspreaders" or "superwetters". An example is found in European patent application 0 394 211 which discloses that either organosilicone or fluoro-organic surfactants can be used interchangeably in solid granular formulations of pesticides to improve dissolution rate.

Two major problems have limited interest in "superspreaders" and "superwetters" by formulators of exogenous chemicals such as pesticides. The first is high unit cost. The second is that although surfactants of this functional category can enhance performance of an exogenous chemical on some species, for example by assisting penetration of the exogenous chemical into the interior of leaves via stomata, they can be antagonistic, sometimes severely so, to performance of the same exogenous chemical on other species.

Surprisingly, a subclass of fluoro-organic surfactants has now been found to be essentially non-antagonistic at concentrations which nevertheless provide useful adjuvant effects. This subclass comprises cationic fluoro-organic surfactants of formula V and others having a property profile in common with those of formula V. The lack of antagonism makes this subclass very different from other fluoro-organic "superspreaders" or "superwetters". Further, it has been found that these non-antagonistic fluoro-organic surfactants can be useful at concentrations low enough to be cost-effective. Data in the Examples herein for compositions comprising Fluorad FC-135 or Fluorad FC-754 illustrate the unexpected properties of this subclass.

Derivatives of Fluorad FC-754, herein described as "FC-acetate" and "FC-salicylate," have been prepared by the following procedure. (1) The solvent in a sample of Fluorad FC-754 is gently evaporated off by heating in a glass beaker at 70–80° C., to leave a solid residue. (2) The solid residue is allowed to cool to room temperature. (3) A 1 g aliquot of the residue is placed in a centrifuge tube and dissolved in 5 ml isopropanol. (4) A saturated solution of potassium hydroxide (KOH) is prepared in isopropanol. (5) This solution is added drop by drop to the solution of FC-754 residue; this results in formation of a precipitate and addition of KOH solution continues until no further precipitate forms. (6) The tube is centrifuged at 4000 rpm for 5 minutes. (7) More KOH solution is added to check if precipitation is complete; if not, the tube is centrifuged again. (8) The supernatant is decanted into another glass tube. (9) A saturated solution of acetic acid (or salicylic acid) is prepared in isopropanol. (10) This solution is added to the supernatant in an amount sufficient to lower pH to 7. (11) Isopropanol is evaporated from this neutralized solution by heating at 60° C. until completely dry. (12) The residue (either the acetate or salicylate salt) is dissolved in a suitable amount of water and is then ready for use.

Compositions of the present invention can optionally comprise a second excipient substance which is one or more amphiphilic liposome-forming substances. These include various lipids of synthetic, animal, or plant origin, including phospholipids, ceramides, sphingolipids, dialkyl surfactants, and polymeric surfactants. A variety of these materials are known to those skilled in the art, and are commercially available. Lecithins are particularly rich in phospholipids and can be derived from a number of plant and animal sources. Soybean lecithin is one particular example of a relatively inexpensive commercially available material that includes such substances.

Many other substances have been described which can be used to form liposomes; the present invention includes compositions comprising any such liposome-forming substances, so long as other requirements set out above are met, and use of such compositions for enhancing biological effectiveness of exogenous chemicals applied to foliage of plants. For example, U.S. Pat. No. 5,580,859, incorporated here by reference, discloses liposome-forming substances having a cationic group, including N-(2,3-di-(9-(Z)-octadecenyloxy))-prop-1-yl-N,N,N-trimethylammonium chloride (DOTMA) and 1,2-bis(oleoyloxy)-3-(trimethylammonio)propane (DOTAP). Liposome-forming substances which are not themselves cationic, but do contain a cationic group as part of the hydrophilic moiety, include for example dioleoylphosphatidylcholine (DOPC) and dioleoylphosphatidylethanolamine (DOPE). Liposome-forming substances that do not contain a cationic group include dioleoylphosphatidylglycerol (DOPG). Any of these liposome-forming substances can be used with or without the addition of cholesterol.

Cationic liposome-forming substances having a hydrophobic moiety comprising two hydrocarbyl chains are accompanied by a counterion (anion), identified as Z in formulas I, II and III above. Any suitable anion can be used, including agriculturally acceptable anions such as hydroxide, chloride, bromide, iodide, sulfate, phosphate and acetate. In a specific embodiment where the exogenous chemical has a biologically active anion, that anion can serve as the counterion for the liposome-forming substance. For example, glyphosate can be used in its acid form together with the hydroxide of a cationic liposome-forming substance such as a compound of formula I.

Compounds of formula I known in the art to be liposome-forming include distearyldimethylammonium chloride and bromide (also known in the art as DODAC and DODAB respectively). Compounds of formula II known in the art to be liposome-forming include DOTMA referenced above and dimyristooxypropyldimethylhydroxyethylammonium bromide (DMRIE). Compounds of formula III known in the art to be liposome-forming include dioleoyloxy-3-(dimethylammonio)propane (DODAP) and DOTAP referenced above. Compounds of formula IV known in the art to be liposome-forming include DOPC and DOPE, both referenced above.

In many liposome-forming substances known in the art, the hydrophobic hydrocarbyl chains are unsaturated, having one or more double bonds. Particularly commonly used in the pharmaceutical art are dioleyl or dioleoyl compounds. A potential problem with these is that in an oxidizing environment they become oxidized at the site of the double bond. This can be inhibited by including in the formulation an antioxidant such as ascorbic acid. Alternatively the problem can be avoided by use of liposome-forming substances wherein a high proportion of the hydrophobic hydrocarbyl chains are fully saturated. Thus in a preferred embodiment of the invention, $R^1$ and $R^2$ in formulas I–IV are independently saturated straight-chain alkyl groups. Particularly preferred compositions use liposome-forming substances in which $R^1$ and $R^2$ are both palmityl (cetyl) or palmitoyl or, alternatively, are both stearyl or stearoyl groups.

Phospholipids, because of their low cost and favorable environmental properties, are particularly favored among liposome-forming substances in the method and compositions of the invention. Vegetable lecithins, such as soybean lecithin, have successfully been used in accordance with the invention. The phospholipid content of the lecithin product can range from about 10% to close to 100%. While acceptable results have been obtained with crude lecithin (10–20% phospholipid), it is generally preferred to use lecithin that is at least partially de-oiled, so that the phospholipid content is in the region of about 45% or more. Higher grades, such as 95%, provide excellent results but the much higher cost is unlikely to be justified for most applications.

The phospholipid component of lecithin, or any phospholipid composition used in the present invention, may comprise one or more phosphatides of natural or synthetic origin. Each of these phosphatides is generally a phosphoric ester that on hydrolysis yields phosphoric acid, fatty acid(s), polyhydric alcohol and, typically, a nitrogenous base. A phosphatide component may be present in a partially hydrolyzed form, e.g. as phosphatidic acid. Suitable phosphatides include, without limitation, phosphatidylcholine, hydrogenated phosphatidylcholine, phosphatidylinositol, phosphatidylserine, phosphatidic acid, phosphatidylglycerol, phosphatidylethanolamine, N-acyl phosphatidylethanolamine, and mixtures of any of these.

In vegetable lecithins a high proportion of the hydrophobic hydrocarbyl chains of the phospholipid compounds are typically unsaturated. One preferred embodiment of compositions in accordance with the present invention comprises both saturated phospholipid and unsaturated phospholipid, with the weight ratio of saturated phospholipid to unsaturated phospholipid being greater than about 1:2. In various particularly preferred embodiments, (1) at least 50% by weight of the phospholipids are di-$C_{12-22}$-saturated alkanoyl phospholipid, (2) at least 50% by weight of the phospholipids are di-$C_{16-18}$-saturated alkanoyl phospholipid, (3) at least 50% by weight of the phospholipids are distearoyl phospholipid, (4) at least 50% by weight of the phospholipids are dipalmitoyl phospholipid, or (5) at least 50% by weight of the phospholipids are distearoyl phosphatidylcholine, dipalmitoyl phosphatidylcholine, or a mixture thereof. Higher proportions of saturated alkanoyl phospholipids are generally found in lecithins of animal origin, such as for example egg yolk lecithin, than in vegetable lecithins.

Phospholipids are known to be chemically unstable, at least in acid media, where they tend to degrade to their lyso-counterparts. Thus where phospholipids rather than more stable liposome-forming substances are used, it is usually preferable to adjust the pH of the composition upward. In the case of glyphosate compositions, the pH of a composition based on a mono-salt such as the monoisopropylammonium (IPA) salt is typically around 5 or lower. When phospholipids are used as the first excipient substance in a glyphosate composition of the invention, it will therefore be preferable to raise the pH of the composition, for example to around 7. Any convenient base can be used for this purpose; it will often be most convenient to use the same base as used in the glyphosate salt, for example isopropylamine in the case of glyphosate IPA salt.

Compositions in accordance with the present invention are typically prepared by combining water, the exogenous chemical and the first excipient substance, as well as the second excipient substance if one is used. The first excipient substance typically disperses readily in water. This is the case for example with Fluorad FC-135 or Fluorad FC-754, and simple mixing with mild agitation is usually sufficient to provide an aqueous composition. However, where the second excipient substance requires high shear to disperse in water, as is the case for example with most forms of lecithin, it is presently preferred to sonicate or microfluidize the second excipient substance in water. This can be done before or after the first excipient substance and/or the exogenous chemical is added. The sonication or microfluidization will generally produce liposomes or other aggregate structures other than simple micelles. The precise nature, including average size, of liposomes or other aggregates depends among other things on the energy input during sonication or microfluidization. Higher energy input generally results in smaller liposomes. Although it is possible to entrap or otherwise bind loosely or tightly the exogenous chemical in or on liposomes or with other supramolecular aggregates, the exogenous chemical does not need to be so entrapped or bound, and in fact the present invention is effective when the exogenous chemical is not entrapped or bound in the aggregates at all.

In a particular embodiment of the invention, the liposomes or other aggregates have an average diameter of at least 20 nm, more preferably at least 30 nm. We have determined by light scattering that certain liposomal compositions of the invention have average liposome diameters ranging from 54 to 468 nm as calculated using linear fit and from 38 to 390 nm as calculated using quadratic fit.

The concentrations of the various components will vary, in part depending on whether a concentrate is being prepared that will be further diluted before spraying onto a plant, or whether a solution or dispersion is being prepared that can be sprayed without further dilution.

In an aqueous glyphosate formulation that includes a cationic fluoro-organic surfactant and lecithin, suitable concentrations can be: glyphosate 0.1–400 g a.e./l, fluoro-organic surfactant 0.001–10% by weight, and soybean lecithin 0.001–10% by weight. In the absence of lecithin, the same ranges of concentration given above for glyphosate and fluoro-organic surfactant are useful.

In solid glyphosate formulations, higher concentrations of ingredients are possible because of the elimination of most of the water.

Weight/weight ratios of ingredients may be more important than absolute concentrations. For example, in a glyphosate formulation containing lecithin and a cationic fluoro-organic surfactant, the ratio of lecithin to glyphosate a.e. preferably is in the range from about 1:3 to about 1:100. It is generally preferred to use a ratio of lecithin to glyphosate a.e. close to as high as can be incorporated in the formulation while maintaining stability, in the presence of an amount of the fluoro-organic surfactant s sufficient to give the desired enhancement of herbicidal effectiveness. For example, a lecithin/glyphosate a.e. ratio in the range from about 1:3 to about 1:10 will generally be found useful, although lower ratios, from about 1:10 to about 1:100, can have benefits on particular weed species in particular situations. The ratio of fluoro-organic surfactant to glyphosate a.e. is likewise preferably in the range from about 1:3 to about 1:100. Because fluoro-organic surfactants tend to have relatively high cost, it will generally be desirable to keep this ratio as low as possible consistent with achieving the desired herbicidal effectiveness.

The ratio of fluoro-organic surfactant to lecithin, where present, is preferably in the range from about 1:10 to about 10:1, more preferably in the range from about 1:3 to about 3:1 and most preferably around 1:1. The ranges disclosed herein can be used by one of skill in the art to prepare compositions of the invention having suitable concentrations and ratios of ingredients. Preferred or optimum concentrations and ratios of ingredients for any particular use or situation can be determined by routine experimentation.

Although the combination of the components might be done in a tank mix, it is preferred in the present invention that the combination be made further in advance of the application to the plant, in order to simplify the tasks required of the person who applies the material to plants. We have found, however, that in some cases the biological effectiveness of a liposome-containing composition prepared from scratch as a dilute spray composition is superior to that of a composition having the same ingredients at the same concentrations but diluted from a previously prepared concentrate formulation.

Although various compositions of the present invention are described herein as comprising certain listed materials, in some preferred embodiments of the invention the compositions consist essentially of the indicated materials.

Optionally, other agriculturally acceptable materials can be included in the compositions. For example, more than one exogenous chemical can be included. Also, various agriculturally acceptable adjuvants can be included, whether or not their purpose is to directly contribute to the effect of the exogenous chemical on a plant. For example, when the exogenous chemical is a herbicide, liquid nitrogen fertilizer or ammonium sulfate might be included in the composition. As another example, stabilizers can be added to the composition. In some instances it might be desirable to include microencapsulated acid in the composition, to lower the pH of a spray solution on contact with a leaf. One or more surfactants can also be included. Surfactants mentioned here by trade name, and other surfactants that can be useful in the method of the invention, are indexed in standard reference works such as McCutcheon's Emulsifiers and Detergents, 1997 edition, Handbook of Industrial Surfactants, 2nd Edition, 1997, published by Gower, and International Cosmetic Ingredient Dictionary, 6th Edition, 1995.

The compositions of the present invention can be applied to plants by spraying, using any conventional means for spraying liquids, such as spray nozzles, atomizers, or the like. Compositions of the present invention can be used in precision farming techniques, in which apparatus is employed to vary the amount of exogenous chemical applied to different parts of a field, depending on variables such as the particular plant species present, soil composition, and the like. In one embodiment of such techniques, a global positioning system operated with the spraying apparatus can be used to apply the desired amount of the composition to different parts of a field.

The composition at the time of application to plants is preferably dilute enough to be readily sprayed using standard agricultural spray equipment. Preferred application rates for the present invention vary depending upon a number of factors, including the type and concentration of active ingredient and the plant species involved. Useful rates for applying an aqueous composition to a field of foliage can range from about 25 to about 1,000 liters per hectare (l/ha) by spray application. The preferred application rates for aqueous solutions are in the range from about 50 to about 300 l/ha.

Many exogenous chemicals (including glyphosate herbicide) must be taken up by living tissues of the plant and translocated within the plant in order to produce the desired biological (e.g., herbicidal) effect. Thus, it is important that a herbicidal composition not be applied in such a manner as to excessively injure and interrupt the normal functioning of the local tissue of the plant so quickly that translocation is reduced. However, some limited degree of local injury can be insignificant, or even beneficial, in its impact on the biological effectiveness of certain exogenous chemicals.

A large number of compositions of the invention are illustrated in the Examples that follow. Many concentrate compositions of glyphosate have provided sufficient herbicidal effectiveness in greenhouse tests to warrant field testing on a wide variety of weed species under a variety of application conditions.

Aqueous compositions tested in the field having a cationic fluoro-organic surfactant as the first excipient substance and soybean lecithin (45% phospholipid, Avanti) as the second excipient substance have included:

|  |  | % w/w |  |  |  |
| --- | --- | --- | --- | --- | --- |
| Field composition | Glyphosate g a.e./l | Lecithin | Fluorad FC-135 | Fluorad FC-754 | MON 0818 |
| F-122 | 167 | 6.0 | 8.3 |  | 4.0 |
| F-123 | 168 | 6.0 |  | 8.3 | 4.0 |
| F-124 | 228 | 2.0 |  | 2.0 | 0.5 |
| F-125 | 347 | 3.0 |  | 3.0 | 0.5 |
| F-126 | 344 | 1.0 |  | 1.0 | 0.5 |
| F-127 | 111 | 8.0 | 8.0 |  | 0.5 |
| F-128 | 228 | 6.0 |  | 3.0 | 6.0 |
| F-129 | 228 | 6.0 |  | 6.0 | 6.0 |
| F-130 | 228 | 3.3 |  | 5.0 | 0.5 |
| F-131 | 228 | 5.0 |  | 5.0 | 0.8 |
| F-132 | 372 | 3.0 |  | 3.0 | 0.8 |
| F-133 | 372 | 3.0 |  | 5.0 | 0.8 |
| F-134 | 372 | 3.0 |  | 12.0 | 0.8 |

The above compositions were prepared by process (v) as described in the Examples.

Dry compositions tested in the field have included:

| Field composition | % w/w | | | | Type of surfactant | Type of colloidal particulate |
| --- | --- | --- | --- | --- | --- | --- |
| | Glyphosate a.e. | Lecithin | Surfactant | Colloidal particulate | | |
| F-162 | 67 | 10.0 | 10.0 + 1.5 | 1.0 | Fluorad FC-754 + Ethomeen T/25 | Aerosil 380 |
| F-163 | 73 | 7.0 | 7.0 + 1.5 | 1.0 | Fluorad FC-754 + Ethomeen T/25 | Aerosil 380 |

The above compositions were prepared by the following procedure. Ammonium glyphosate powder was added to a blender. Excipient ingredients were slowly added, together with sufficient water to wet the powder and form a stiff dough. The blender was operated for sufficient time to thoroughly mix all ingredients. The dough was then transferred to extrusion apparatus and was extruded to form granules, which were finally dried in a fluid bed dryer.

EXAMPLES

In the following Examples illustrative of the invention, greenhouse tests were conducted to evaluate relative herbicidal effectiveness of glyphosate compositions. Compositions included for comparative purposes included the following:

Formulation B: which consists of 41% by weight of glyphosate IPA salt in aqueous solution. This formulation is sold in the USA by Monsanto Company under the ACCORD® trademark.

Formulation C: which consists of 41% by weight of glyphosate IPA salt in aqueous solution with a coformulant (15% by weight) of a surfactant (MON 0818 of Monsanto Company) based on polyoxyethylene (15) tallowamine. This formulation is sold in Canada by Monsanto Company under the ROUNDUP® trademark.

Formulation J: which consists of 41% by weight of glyphosate IPA salt in aqueous solution, together with surfactant. This formulation is sold in the USA by Monsanto Company under the ROUNDUP® ULTRA trademark.

Formulation K: which consists of 75% by weight of glyphosate ammonium salt together with surfactant, as a water-soluble dry granular formulation. This formulation is sold in Australia by Monsanto Company under the ROUNDUP® DRY trademark.

Formulations B, C and J contain 356 grams of glyphosate acid equivalent per liter (g a.e./l). Formulation K contains 680 grams of glyphosate acid equivalent per kilogram (g a.e./kg).

Various proprietary excipients were used in compositions of the Examples. They may be identified as follows:

| Trade name | Manufacturer | Chemical description |
| --- | --- | --- |
| Aerosil 90 | Degussa | amorphous silica, 90 m$^2$/g |
| Aerosol OT | Cytec | dioctyl sulfosuccinate, Na salt |
| Agrimul PG-2069 | Henkel | $C_{9-11}$ alkylpolyglycoside |
| Aluminum oxide C | Degussa | aluminum oxide, 100 m$^2$/g |
| Arcosolve DPM | Arco | dipropyleneglycol monomethyl ether |
| Diacid 1550 | Westvaco | cyclocarboxypropyl oleic acid |
| Emphos PS-21A | Witco | alcohol ethoxylate phosphate ester |
| Ethomeen C/12 | Akzo | cocoamine 2EO |

-continued

| Trade name | Manufacturer | Chemical description |
|---|---|---|
| Ethomeen T/25 | Akzo | tallowamine 15EO |
| Fluorad FC-120 | 3M | $C_{9-10}$ perfluoroalkyl sulfonate, $NH_4$ salt |
| Fluorad FC-129 | 3M | fluorinated alkyl carboxylate, K salt |
| Fluorad FC-135 | 3M | fluorinated alkyl quaternary ammonium iodide |
| Fluorad FC-170C | 3M | fluorainated alcohol EO |
| Fluorad FC-171 | 3M | fluorinated alkanol EO |
| Fluorad FC-431 | 3M | fluorinated alkyl ester |
| Fluorad FC-750 | 3M | fluorinated alkyl quaternary ammonium iodide |
| Fluorad FC-751 | 3M | fluorinated amphoteric surfactant |
| Fluorad FC-754 | 3M | fluorinated alkyl quaternary ammonium chloride |
| Fluorad FC-760 | 3M | fluorinated alkanol EO |
| Genapol UD-030 | Hoechst | $C_{11}$ oxo alcohol 3EO |
| Kelzan | Monsanto | xanthan gum |
| MON 0818 | Monsanto | tallowamine 15EO-based surfactant |
| Neodol 25-3 | Shell | $C_{12-15}$ linear alcohol 3EO |
| Silwet 800 | Witco | heptamethyltrisiloxane EO |
| Silwet L-77 | Witco | heptamethyltrisiloxane 7EO methyl ether |
| Titanium dioxide P25 | Degussa | titanium dioxide, average particle size 21 nm |
| Triton RW-20 | Union Carbide | alkylamine 2EO |
| Triton RW-50 | Union Carbide | alkylamine 5EO |
| Triton RW-75 | Union Carbide | alkylamine 7.5EO |
| Triton RW-100 | Union Carbide | alkylamine 10EO |
| Triton RW-150 | Union Carbide | alkylamine 15EO |
| Westvaco H-240 | Westvaco | dicarboxylate surfactant, K salt |

Fluorad FC-135, though defined only generically as above in 3M product literature and in standard directories, has been specifically identified as $$C_8F_{17}SO_2NH(CH_2)_3N^+(CH_3)_3 \ I^-$$

in a paper by J. Linert & J. N. Chasman of 3M, titled "The effects of fluorochemical surfactants on recoatability" in the Dec. 20, 1993 issue of American Paint & Coatings Journal, and reprinted as a trade brochure by 3M. Fluorad FC-750 is believed to be based on the same surfactant. Fluorad FC-754 is believed to have the structure $$C_8F_{17}SO_2NH(CH_2)_3N^+(CH_3)_3 \ Cl^-$$

that is, identical to Fluorad FC-135 but with a chloride anion replacing iodide.

The following surfactants, identified in the examples as "Surf H1" to "Surf H5", have hydrocarbyl groups as the hydrophobic moiety but otherwise bear some structural similarity to the above Fluorad surfactants. They were synthesized and characterized under contract to Monsanto Company.

Surf H1: $C_{12}H_{25}SO_2NH(CH_2)_3N^+(CH_3)_3 \ I^-$
Surf H2: $C_{17}H_{35}CONH(CH_2)_3N^+(CH_3)_3 \ I^-$
Surf H3: $C_{11}H_{23}CONH(CH_2)_3N^+(CH_3)_3 \ I^-$
Surf H4: cis-$C_8H_{17}CH=CH(CH_2)_7CONH(CH_2)_3N^+(CH_3)_3 \ I^-$
Surf H5: $C_7H_{15}CONH(CH_2)_3N^+(CH_3)_3 \ I^-$ Fatty alcohol ethoxylate surfactants are referred to in the Examples by their generic names as given in the International Cosmetic Ingredient Dictionary, 6th Edition, 1995 (Cosmetic, Toiletry and Fragrance Association, Washington, D.C.). They were interchangeably sourced from various manufacturers, for example:

Laureth-23: Brij 35 (ICI), Trycol 5964 (Henkel).
Ceteth-10: Brij 56 (ICI).
Ceteth-20: Brij 58 (ICI).
Steareth-10: Brij 76 (ICI).
Steareth-20: Brij 78 (ICI), Emthox 5888-A (Henkel), STA-20 (Heterene).
Steareth-30: STA-30 (Heterene).
Steareth-100: Brij 700 (ICI).
Ceteareth-15: CS-15 (Heterene).
Ceteareth-20: CS-20 (Heterene).
Ceteareth-27: Plurafac A-38 (BASF).
Ceteareth-55: Plurafac A-39 (BASF).
Oleth-2: Brij 92 (ICI).
Oleth-10: Brij 97 (ICI).
Oleth-20: Brij 98 (ICI), Trycol 5971 (Henkel).

Where a proprietary excipient is a surfactant supplied as a solution in water or other solvent, the amount to be used was calculated on a true surfactant basis, not an "as is" basis. For example, Fluorad FC-135 is supplied as 50% true surfactant, together with 33% isopropanol and 17% water; thus to provide a composition containing 0.1% w/w Fluorad FC-135 as reported herein, 0.2 g of the product as supplied was included in 100 g of the composition. The amount of lecithin, however, is always reported herein on an "as is" basis, regardless of the content of phospholipid in the lecithin sample used.

Spray compositions of the Examples contained an exogenous chemical, such as glyphosate IPA salt, in addition to the excipient ingredients listed. The amount of exogenous chemical was selected to provide the desired rate in grams per hectare (g/ha) when applied in a spray volume of 93 l/ha. Several exogenous chemical rates were applied for each composition. Thus, except where otherwise indicated, when spray compositions were tested, the concentration of exogenous chemical varied in direct proportion to exogenous chemical rate, but the concentration of excipient ingredients was held constant across different exogenous chemical rates.

Concentrate compositions were tested by dilution, dissolution or dispersion in water to form spray compositions. In these spray compositions prepared from concentrates, the concentration of excipient ingredients varied with that of exogenous chemical.

Except where otherwise indicated, aqueous spray compositions were prepared by one of the following processes (i), (ii) or (iii).

(i) For compositions not containing lecithin or phospholipids, aqueous compositions were prepared by simple mixing of ingredients under mild agitation.

(ii) A weighed quantity of lecithin in powder form was dissolved in 0.4 ml chloroform in a 100 ml bottle. The resulting solution was air-dried to leave a thin film of lecithin, to which was added 30 ml deionized water. The bottle and its contents were then sonicated in a Fisher Sonic Dismembrator, Model 550, fitted with a 2.4 cm probe tip, set at output level 8, and operated continuously for 3 minutes. The resulting aqueous dispersion of lecithin was then allowed to cool to room temperature, and formed a lecithin stock which was later mixed in the required amounts with other ingredients under mild agitation. In some cases, as indicated in the Examples, certain ingredients were added to the lecithin in water before sonication, so that the lecithin and these ingredients were sonicated together. Without being bound by theory, it is believed that by sonicating a formulation ingredient together with lecithin, at least some of that ingredient becomes encapsulated within, or otherwise bound to or trapped by, vesicles or other aggregates formed by phospholipids present in the lecithin.

(iii) The procedure of process (ii) was followed except that, before sonication, the step of forming a lecithin solution in chloroform was omitted. Instead, lecithin in powder form was placed in a beaker, water was added and the beaker and its contents were then sonicated.

Except where otherwise indicated, aqueous concentrate compositions were prepared by one of the following processes (iv), (v), (viii) or (ix).

(iv) A weighed amount of lecithin powder of the type indicated was placed in a beaker and deionized water was added in no more than the amount required for the desired final composition. The beaker and its contents were then placed in a Fisher Sonic Dismembrator, Model 550, fitted with a 2.4 cm probe tip, set at output level 8, and operated for 5 minutes. The resulting lecithin dispersion formed the basis to which other ingredients were added with mild agitation to make the aqueous concentrate formulation. The order of addition of these ingredients was varied and was sometimes found to affect the physical stability of the concentrate formulation. Where a fluoro-organic surfactant such as Fluorad FC-135 or FC-754 was to be included, it was generally added first, followed by other surfactants if required and then by the exogenous chemical. Where the exogenous chemical used was glyphosate IPA salt, this was added in the form of a 62% (45% a.e.) solution by weight, at a pH of 4.4 to 4.6. A final adjustment with water took place if necessary as the last step. In some cases certain ingredients of the concentrate formulation were added before rather than after sonication, so that they were sonicated with the lecithin.

(v) A weighed amount of lecithin powder of the type indicated was placed in a beaker and deionized water was added in sufficient quantity to provide, after sonication as detailed below, a lecithin stock at a convenient concentration, normally in the range from 10% to 20% w/w and typically 15% w/w. The beaker and its contents were then placed in a Fisher Sonic Dismembrator, Model 550, fitted with a 2.4 cm probe tip with the pulse period set at 15 seconds with 1 minute intervals between pulses to allow cooling. Power output was set at level 8. After a total of 3 minutes of sonication (12 pulse periods) the resulting lecithin stock was finally adjusted to the desired concentration if necessary with deionized water. To prepare an aqueous concentrate formulation, the following ingredients were mixed in the appropriate proportions with mild agitation, normally in the order given although this was sometimes varied and was found in some cases to affect the physical stability of the concentrate formulation: (a) exogenous chemical, for example glyphosate IPA salt as a 62% w/w solution at pH 4.4–4.6; (b) lecithin stock; (c) other ingredients if required; and (d) water.

(viii) Surfactant-containing aqueous solution concentrates having no oil component or lecithin were prepared as follows. A concentrated (62% w/w) aqueous solution of glyphosate IPA salt was added in the desired amount to a weighed quantity of the selected surfactant(s). If the surfactant selected is not free-flowing at ambient temperature, heat was applied to bring the surfactant into a flowable condition before adding the glyphosate solution. The required amount of water was added to bring the concentration of glyphosate and other ingredients to the desired level. The composition was finally subjected to high-shear mixing, typically using a Silverson L4RT-A mixer fitted with a medium emulsor screen, operated for 3 minutes at 7,000 rpm.

(ix) For compositions containing a colloidal particulate, the required amount by weight of the selected colloidal particulate was suspended in a concentrated (62% w/w) aqueous solution of glyphosate IPA salt and agitated with cooling to ensure homogeneity. To the resulting suspension was added the required amount by weight of the selected surfactant(s). For a surfactant which is not free-flowing at ambient temperature, heat was applied to bring the surfactant into a flowable condition before adding it to the suspension. In those instances where an oil, such as butyl stearate, was also to be included in the composition, the oil was first thoroughly mixed with the surfactant and the surfactant-oil mixture added to the suspension. To complete the aqueous concentrate, the required amount of water was added to bring the concentration of glyphosate and other ingredients to the desired level. The concentrate was finally subjected to high-shear mixing, typically using a Silverson L4RT-A mixer fitted with a medium emulsor screen, operated for 3 minutes at 7,000 rpm.

(x) The procedure for preparing aqueous concentrate formulations containing lecithin and butyl stearate was different from that followed for other lecithin-containing concentrates. Exogenous chemical, for example glyphosate IPA salt, was first added, with mild agitation, to deionized water in a formulation jar. The selected surfactant (other than lecithin) was then added, while continuing the agitation, to form a preliminary exogenous chemical/ surfactant mixture. Where the surfactant is not free-flowing at ambient temperature, the order of addition was not as above. Instead, the non-free-flowing surfactant was first added to water together with any other surfactant (other than lecithin) required in the composition, and was then heated to 55° C. in a shaker bath for 2 hours. The resulting mixture was allowed to cool, then exogenous chemical was added with mild agitation to form the preliminary exogenous chemical/ surfactant mixture. A weighed amount of the selected lecithin was added to the preliminary exogenous chemical/ surfactant mixture, with stirring to break up lumps. The mixture was left for about 1 hour to allow the lecithin to hydrate, then butyl stearate was added, with further stirring until no phase separation occurred. The mixture was then transferred to a microfluidizer (Microfluidics International Corporation, Model M-110F) and microfluidized for 3 to 5 cycles at 10,000 psi (69 MPa). In each cycle, the formulation jar was rinsed with microfluidized mixture. In the last cycle, the finished composition was collected in a clean dry beaker.

The following procedure was used for testing compositions of the Examples to determine herbicidal effectiveness, except where otherwise indicated.

Seeds of the plant species indicated were planted in 85 mm square pots in a soil mix which was previously steam sterilized and prefertilized with a 14—14—14 NPK slow release fertilizer at a rate of 3.6 kg/m3. The pots were placed in a greenhouse with sub-irrigation. About one week after emergence, seedlings were thinned as needed, including removal of any unhealthy or abnormal plants, to create a uniform series of test pots.

The plants were maintained for the duration of the test in the greenhouse where they received a minimum of 14 hours of light per day. If natural light was insufficient to achieve the daily requirement, artificial light with an intensity of approximately 475 microeinsteins was used to make up the difference. Exposure temperatures were not precisely controlled but averaged about 27° C. during the day and about 18° C. during the night. Plants were sub-irrigated throughout the test to ensure adequate soil moisture levels.

Pots were assigned to different treatments in a fully randomized experimental design with 3 replications. A set of pots was left untreated as a reference against which effects of the treatments could later be evaluated.

EXAMPLE 1

Glyphosate-containing spray compositions were prepared by tank-mixing Formulations B and C with excipients as shown in Table 1.

Velvetleaf (*Abutilon theophrasti*, ABUTH) and Japanese millet (*Echinochloa crus-galli*, ECHCF) plants were grown and treated by the standard procedures given above. Applications of spray compositions were made 16 days after planting ABUTH and 16 days after planting ECHCF, and evaluation of herbicidal inhibition was done 18 days after application. Results, averaged for all replicates of each treatment, are shown in Table 1.

TABLE 1

| Glyphosate composition | Glyphosate rate g a.e./ha | Additive | Additive rate % v/v | % Inhibition ABUTH | ECHCF |
|---|---|---|---|---|---|
| Formulation C | 175 | none | | 40 | 75 |
| | 350 | | | 69 | 89 |
| | 500 | | | 97 | 100 |
| Formulation B | 175 | none | | 45 | 37 |
| | 350 | | | 73 | 66 |
| | 500 | | | 83 | 97 |
| Formulation B | 175 | L-77 | 0.25 | 64 | 30 |
| | 175 | | 0.50 | 77 | 27 |
| Formulation B | 175 | FC-135 | 0.25 | 55 | 72 |
| | 175 | | 0.50 | 73 | 61 |
| Formulation B | 175 | FC-135 + L-77 8:1 | 0.50 | 71 | 58 |
| | 175 | FC-135 + L-77 4:1 | 0.50 | 76 | 61 |
| | 175 | FC-135 + L-77 2:1 | 0.50 | 63 | 56 |
| | 175 | FC-135 + L-77 1:1 | 0.50 | 77 | 40 |
| | 175 | FC-135 + L-77 1:2 | 0.50 | 54 | 23 |
| | 175 | FC-135 + L-77 1:4 | 0.50 | 76 | 31 |
| | 175 | FC-135 + L-77 1:8 | 0.50 | 53 | 29 |
| Formulation B | 175 | FC-135 + L-77 8:1 | 0.25 | 51 | 48 |
| | 175 | FC-135 + L-77 4:1 | 0.25 | 37 | 47 |
| | 175 | FC-135 + L-77 2:1 | 0.25 | 45 | 37 |
| | 175 | FC-135 + L-77 1:1 | 0.25 | 65 | 27 |
| | 175 | FC-135 + L-77 1:2 | 0.25 | 45 | 29 |
| | 175 | FC-135 + L-77 1:4 | 0.25 | 60 | 17 |
| | 175 | FC-135 + L-77 1:8 | 0.25 | 52 | 15 |

Application of glyphosate compositions was made by spraying with a track sprayer fitted with a 9501E nozzle calibrated to deliver a spray volume of 93 liters per hectare (l/ha) at a pressure of 166 kilopascals (kPa). After treatment, pots were returned to the greenhouse until ready for evaluation.

Treatments were made using dilute aqueous compositions. These could be prepared as spray compositions directly from their ingredients, or by dilution with water of preformulated concentrate compositions.

For evaluation of herbicidal effectiveness, all plants in the test were examined by a single practiced technician, who recorded percent inhibition, a visual measurement of the effectiveness of each treatment by comparison with untreated plants. Inhibition of 0% indicates no effect, and inhibition of 100% indicates that all of the plants are completely dead. Inhibition of 85% or more is in most cases considered acceptable for normal herbicidal use; however in greenhouse tests such as those of the Examples it is normal to apply compositions at rates which give less than 85% inhibition, as this makes it easier to discriminate among compositions having different levels of effectiveness.

Tank mixtures of Fluorad FC-135 with Formulation B gave markedly superior herbicidal effectiveness on ABUTH by comparison with Formulation C, but did not match the herbicidal effectiveness of Formulation C on ECHCF. The antagonism of glyphosate activity on ECHCF seen with the nonionic organosilicone surfactant Silwet L-77 did not occur with the cationic fluoro-organic surfactant Fluorad FC-135.

EXAMPLE 2

Aqueous spray compositions were prepared containing glyphosate sodium or IPA salts and excipient ingredients as shown in Table 2a. Process (ii) was followed for all compositions, using soybean lecithin (10–20% phospholipid, Sigma Type II-S). Without adjustment, the pH of the compositions was approximately 5. For those compositions having a pH of approximately 7 as shown in Table 2a, the pH was adjusted using the same base (sodium hydroxide or IPA) that formed the glyphosate salt.

TABLE 2a

| Spray composition | Lecithin g/l | % w/w Fluorad FC-135 | L-77 | Components sonicated with lecithin | Glyphosate salt | pH |
|---|---|---|---|---|---|---|
| 2-01 | 5.0 | | | none | IPA | 5 |
| 2-02 | 5.0 | | 0.50 | none | IPA | 5 |
| 2-03 | 5.0 | | | none | Na | 7 |
| 2-04 | 5.0 | | 0.50 | none | Na | 7 |
| 2-05 | 5.0 | | | none | IPA | 7 |
| 2-06 | 5.0 | | 0.50 | none | IPA | 7 |
| 2-07 | 5.0 | | | none | Na | 5 |
| 2-08 | 5.0 | | 0.50 | none | Na | 5 |
| 2-09 | 2.5 | | | none | IPA | 5 |
| 2-10 | 2.5 | 0.50 | | none | IPA | 5 |
| 2-11 | 5.0 | 0.50 | | none | IPA | 5 |
| 2-12 | 5.0 | 0.33 | 0.17 | none | IPA | 5 |
| 2-13 | 5.0 | | 0.50 | L-77 | IPA | 5 |
| 2-14 | 5.0 | | 0.50 | L-77 | Na | 7 |
| 2-15 | 5.0 | | 0.50 | L-77 | IPA | 7 |
| 2-16 | 5.0 | | 0.50 | L-77 | Na | 5 |

Velvetleaf (*Abutilon theophrasti*, ABUTH) and Japanese millet (*Echinochloa crus-galli*, ECHCF) plants were grown and treated by the standard procedures given above. Applications of spray compositions were made 16 days after planting ABUTH and ECHCF, and evaluation of herbicidal inhibition was done 17 days after application.

Formulation C, alone and tank mixed with 0.5% Silwet L-77, were applied as comparative treatments. Results, averaged for all replicates of each treatment, are shown in Table 2b.

TABLE 2b

| Spray composition | Glyphosate rate g a.e./ha | % Inhibition ABUTH | ECHCF |
|---|---|---|---|
| Formulation C | 100 | 8 | 54 |
| | 200 | 54 | 75 |
| | 300 | 77 | 90 |
| Formulation C + Silwet L-77 0.5% v/v | 100 | 62 | 10 |
| | 200 | 91 | 25 |
| | 300 | 95 | 27 |
| 2-01 | 100 | 59 | 64 |
| | 200 | 74 | 83 |
| | 300 | 82 | 99 |
| 2-02 | 100 | 66 | 44 |
| | 200 | 73 | 45 |
| | 300 | 92 | 76 |
| 2-03 | 100 | 17 | 29 |
| | 200 | 37 | 72 |
| | 300 | 70 | 89 |
| 2-04 | 100 | 48 | 24 |
| | 200 | 67 | 50 |
| | 300 | 81 | 61 |
| 2-05 | 100 | 40 | 44 |
| | 200 | 77 | 89 |
| | 300 | 79 | 95 |
| 2-06 | 100 | 76 | 43 |
| | 200 | 87 | 74 |
| | 300 | 90 | 85 |
| 2-07 | 100 | 40 | 50 |
| | 200 | 66 | 54 |
| | 300 | 84 | 83 |
| 2-08 | 100 | 69 | 34 |
| | 200 | 57 | 70 |
| | 300 | 78 | 66 |
| 2-09 | 100 | 44 | 62 |
| | 200 | 83 | 82 |
| | 300 | 90 | 91 |
| 2-10 | 100 | 84 | 83 |
| | 200 | 97 | 85 |
| | 300 | 95 | 93 |
| 2-11 | 100 | 79 | 65 |
| | 200 | 89 | 84 |
| | 300 | 98 | 98 |
| 2-12 | 100 | 74 | 63 |
| | 200 | 93 | 84 |
| | 300 | 94 | 92 |
| 2-13 | 100 | 86 | 85 |
| | 200 | 91 | 92 |
| | 300 | 97 | 97 |
| 2-14 | 100 | 56 | 17 |
| | 200 | 69 | 48 |
| | 300 | 87 | 81 |
| 2-15 | 100 | 61 | 39 |
| | 200 | 87 | 73 |
| | 300 | 83 | 78 |
| 2-16 | 100 | 42 | 32 |
| | 200 | 35 | 78 |
| | 300 | 59 | 85 |

Surprisingly strong herbicidal effectiveness was observed with compositions 2-10 and 2-11 containing lecithin and Fluorad FC-1 35 on both ABUTH and ECHCF, by comparison with otherwise similar compositions (2-09 and 2-01) lacking the Fluorad FC-135. Herbicidal effectiveness of composition 2-11 at the 100 g a.e./ha glyphosate rate was superior to that of Formulation C at a threefold higher rate on ABUTH and superior to that of Formulation C at a twofold higher rate on ECHCF.

EXAMPLE 3

Aqueous spray compositions were prepared containing glyphosate IPA salt and excipient ingredients as shown in Table 3a. Process (ii), indicated in Table 3a as involving "high" sonication power, was followed for all compositions, except that for composition 3-06 a different sonication procedure, referred to as "low" sonication power, was used. In this procedure the lecithin in water was sonicated in a Fisher Model FS 14H ultrasonic bath for 30 minutes. Soybean lecithin (10–20% phospholipid, Sigma Type II-S) was used for all compositions. Without adjustment, the pH of the compositions was approximately 5. For those compositions having a pH of approximately 7 as shown in Table 3a, the pH was adjusted using the same base (sodium hydroxide or IPA) that formed the glyphosate salt.

TABLE 3a

| Spray composition | Lecithin g/l | % w/w Fluorad FC-135 | L-77 | Components sonicated with lecithin | pH | Sonication power |
|---|---|---|---|---|---|---|
| 3-01 | 5.0 | | | none | 5 | high |
| 3-02 | 5.0 | | 0.50 | none | 5 | high |
| 3-03 | 5.0 | | 0.50 | L-77 | 5 | high |
| 3-04 | 5.0 | | 0.50 | glyphosate | 5 | high |
| 3-05 | 5.0 | | 0.50 | L-77, glyphosate | 5 | high |
| 3-06 | 5.0 | | | none | 7 | low |
| 3-07 | 5.0 | | | none | 7 | high |
| 3-08 | 5.0 | | 0.50 | none | 7 | high |
| 3-09 | 5.0 | | 0.50 | L-77 | 7 | high |
| 3-10 | 5.0 | | 0.50 | glyphosate | 7 | high |
| 3-11 | 5.0 | | 0.50 | L-77, glyphosate | 7 | high |
| 3-12 | 5.0 | 0.50 | | none | 5 | high |
| 3-13 | 5.0 | 0.50 | | FC-135 | 5 | high |

TABLE 3a-continued

| Spray composition | Lecithin g/l | % w/w Fluorad FC-135 | L-77 | Components sonicated with lecithin | pH | Sonication power |
|---|---|---|---|---|---|---|
| 3-14 | 5.0 | 0.50 | | glyphosate | 5 | high |
| 3-15 | 5.0 | 0.17 | 0.33 | FC-135, glyphosate | 5 | high |
| 3-16 | 5.0 | 0.17 | 0.33 | none | 5 | high |
| 3-17 | 5.0 | 0.17 | 0.33 | FC-135, L-77 | 5 | high |
| 3-18 | 10.0 | | | none | 5 | high |
| 3-19 | 20.0 | | | none | 5 | high |
| 3-20 | 10.0 | | 0.50 | none | 5 | high |
| 3-21 | 10.0 | | 0.50 | L-77 | 5 | high |
| 3-22 | 20.0 | | 0.50 | L-77 | 5 | high |
| 3-23 | 20.0 | | 0.50 | L-77, glyphosate | 5 | high |

Velvetleaf (*Abutilon theophrasti*, ABUTH) and Japanese millet (*Echinochloa crus-galli*, ECHCF) plants were grown and treated by the standard procedures given above. Applications of spray compositions were made 18 days after planting ABUTH and ECHCF, and evaluation of herbicidal inhibition was done 16 days after application.

Formulations B and C, alone and tank mixed with 0.5% Silwet L-77, were applied as comparative treatments. Results, averaged for all replicates of each treatment, are shown in Table 3b.

TABLE 3b

| Spray composition | Glyphosate rate g a.e./ha | % Inhibition ABUTH | ECHCF |
|---|---|---|---|
| Formulation B | 100 | 11 | 12 |
| | 200 | 55 | 43 |
| | 300 | 65 | 38 |
| Formulation B + Silwet L-77 0.5% v/v | 100 | 77 | 5 |
| | 200 | 95 | 10 |
| | 300 | 95 | 17 |
| Formulation C | 100 | 33 | 42 |
| | 200 | 63 | 98 |
| | 300 | 85 | 99 |
| Formulation C + Silwet L-77 0.5% v/v | 100 | 78 | 7 |
| | 200 | 95 | 19 |
| | 300 | 98 | 54 |
| 3-01 | 100 | 63 | 22 |
| | 200 | 77 | 69 |
| | 300 | 92 | 82 |
| 3-02 | 100 | 79 | 30 |
| | 200 | 96 | 67 |
| | 300 | 98 | 70 |
| 3-03 | 100 | 81 | 29 |
| | 200 | 96 | 70 |
| | 300 | 97 | 86 |
| 3-04 | 100 | 85 | 32 |
| | 200 | 94 | 60 |
| | 300 | 98 | 61 |
| 3-05 | 100 | 82 | 34 |
| | 200 | 98 | 60 |
| | 300 | 96 | 69 |
| 3-06 | 100 | 55 | 40 |
| | 200 | 91 | 69 |
| | 300 | 97 | 90 |
| 3-07 | 100 | 77 | 29 |
| | 200 | 93 | 82 |
| | 300 | 97 | 100 |
| 3-08 | 100 | 83 | 48 |
| | 200 | 95 | 67 |
| | 300 | 94 | 74 |
| 3-09 | 100 | 83 | 37 |
| | 200 | 95 | 75 |
| | 300 | 99 | 83 |
| 3-10 | 100 | 77 | 36 |
| | 200 | 99 | 75 |

TABLE 3b-continued

| Spray composition | Glyphosate rate g a.e./ha | % Inhibition ABUTH | ECHCF |
|---|---|---|---|
| | 300 | 98 | 69 |
| 3-11 | 100 | 81 | 38 |
| | 200 | 94 | 81 |
| | 300 | 97 | 76 |
| 3-12 | 100 | 56 | 47 |
| | 200 | 91 | 90 |
| | 300 | 97 | 95 |
| 3-13 | 100 | 81 | 41 |
| | 200 | 94 | 58 |
| | 300 | 97 | 84 |
| 3-14 | 100 | 77 | 37 |
| | 200 | 94 | 70 |
| | 300 | 96 | 94 |
| 3-15 | 100 | 76 | 61 |
| | 200 | 95 | 79 |
| | 300 | 96 | 85 |
| 3-16 | 100 | 95 | 84 |
| | 200 | 94 | 56 |
| | 300 | 75 | 32 |
| 3-17 | 100 | 78 | 44 |
| | 200 | 93 | 86 |
| | 300 | 94 | 87 |
| 3-18 | 100 | 59 | 27 |
| | 200 | 94 | 84 |
| | 300 | 96 | 100 |
| 3-19 | 100 | 74 | 44 |
| | 200 | 94 | 74 |
| | 300 | 95 | 95 |
| 3-20 | 100 | 79 | 62 |
| | 200 | 89 | 78 |
| | 300 | 92 | 93 |
| 3-21 | 100 | 66 | 69 |
| | 200 | 80 | 79 |
| | 300 | 86 | 88 |
| 3-22 | 100 | 44 | 69 |
| | 200 | 83 | 97 |
| | 300 | 74 | 94 |
| 3-23 | 100 | 50 | 71 |
| | 200 | 68 | 91 |
| | 300 | 85 | 76 |

Composition 3-12 containing lecithin and Fluorad FC-135 again showed surprisingly high herbicidal effectiveness by comparison with composition 3-01, lacking the Fluorad FC-135, and also by comparison with Formulation C. When efforts were made to encapsulate Fluorad FC-135 or glyphosate (compositions 3-13 or 3-14 respectively) in lecithin liposomes by sonication in the presence of the ingredients sought to be encapsulated, some further enhancement of herbicidal effectiveness was evident on ABUTH, but effectiveness was reduced on ECHCF. Overall, the best activity in this test was obtained without encapsulation.

EXAMPLE 4

Compositions 3-01 to 3-12 of Example 3 were tested in this Example. Black nightshade (*Solanum nigrum*, SOLNI) plants were grown and treated by the standard procedures given above. Applications of spray compositions were made 26 days after planting SOLNI and evaluation of herbicidal inhibition was done 16 days after application.

Formulations B and C, alone and tank mixed with 0.5% Silwet L-77, were applied as comparative treatments. Results, averaged for all replicates of each treatment, are shown in Table 4.

TABLE 4

| Spray composition | Glyphosate rate g a.e./ha | % Inhibition SOLNI |
|---|---|---|
| Formulation B | 100 | 28 |
|  | 200 | 35 |
|  | 300 | 70 |
| Formulation B + | 100 | 85 |
| Silwet L-77 0.5% v/v | 200 | 98 |
|  | 300 | 97 |
| Formulation C | 100 | 30 |
|  | 200 | 58 |
|  | 300 | 70 |
| Formulation C + | 100 | 78 |
| Silwet L-77 0.5% v/v | 200 | 82 |
|  | 300 | 94 |
| 3-01 | 100 | 47 |
|  | 200 | 77 |
|  | 300 | 93 |
| 3-02 | 100 | 33 |
|  | 200 | 50 |
|  | 300 | 78 |
| 3-03 | 100 | 36 |
|  | 200 | 79 |
|  | 300 | 90 |
| 3-04 | 100 | 33 |
|  | 200 | 72 |
|  | 300 | 84 |
| 3-05 | 100 | 38 |
|  | 200 | 68 |
|  | 300 | 82 |
| 3-06 | 100 | 84 |
|  | 200 | 92 |
|  | 300 | 96 |
| 3-07 | 100 | 58 |
|  | 200 | 75 |
|  | 300 | 85 |
| 3-08 | 100 | 50 |
|  | 200 | 83 |
|  | 300 | 91 |
| 3-09 | 100 | 50 |
|  | 200 | 72 |
|  | 300 | 83 |
| 3-10 | 100 | 53 |
|  | 200 | 75 |
|  | 300 | 78 |
| 3-11 | 100 | 75 |
|  | 200 | 96 |
|  | 300 | 100 |
| 3-12 | 100 | 62 |
|  | 200 | 93 |
|  | 300 | 99 |

Composition 3-12 containing lecithin and Fluorad FC-135, as in the test of Example 3, showed remarkably strong herbicidal effectiveness, this time on SOLNI.

EXAMPLE 5

Aqueous spray compositions were prepared containing glyphosate IPA salt and excipient ingredients as shown in Table 5a. Process (ii) was followed for all compositions, using soybean lecithin (20% phospholipid, Avanti). The pH of all compositions was approximately 5.

TABLE 5a

| Spray composition | Lecithin g/l | Fluorad FC-135 % w/w | Silwet L-77 % w/w | KCl % w/w | Components sonicated with lecithin |
|---|---|---|---|---|---|
| 5-01 | 5.0 |  |  |  | glyphosate |
| 5-02 | 5.0 |  | 0.50 |  | L-77 |
| 5-03 | 5.0 |  | 0.50 |  | L-77 |
| 5-04 | 5.0 |  | 1.00 |  | L-77 |
| 5-05 | 5.0 |  | 0.20 |  | none |
| 5-06 | 5.0 |  | 1.00 |  | none |
| 5-07 | 5.0 |  | 0.20 |  | L-77, glyphosate |
| 5-08 | 5.0 |  | 0.50 |  | L-77, glyphosate |
| 5-09 | 5.0 |  | 1.00 |  | L-77, glyphosate |
| 5-10 | 2.5 |  | 0.10 |  | L-77 |
| 5-11 | 2.5 |  | 0.25 |  | L-77 |
| 5-12 | 2.5 |  | 0.50 |  | L-77 |
| 5-13 | 2.5 |  | 0.10 |  | none |
| 5-14 | 2.5 |  | 0.25 |  | none |
| 5-15 | 2.5 |  | 0.10 |  | L-77, glyphosate |
| 5-16 | 2.5 |  | 0.25 |  | L-77, glyphosate |
| 5-17 | 2.5 |  | 0.50 |  | L-77, glyphosate |
| 5-18 | 5.0 |  | 0.50 | 0.02 | L-77 |
| 5-19 | 5.0 |  | 0.50 | 0.02 | L-77, glyphosate |
| 5-20 | 5.0 | 0.50 |  |  | none |
| 5-21 | 5.0 | 0.50 |  |  | glyphosate |
| 5-22 | 5.0 | 0.33 | 0.17 |  | none |
| 5-23 | 5.0 | 0.33 | 0.17 |  | glyphosate |

Velvetleaf *Abutilon theophrasti*, ABUTH) and Japanese millet *Echinochloa crus-galli*, ECHCF) plants were grown and treated by the standard procedures given above. Applications of spray compositions were made 18 days after planting ABUTH and 16 days after planting ECHCF, and evaluation of herbicidal inhibition was done 17 days after application.

Formulations B and C, alone and tank mixed with 0.5% Silwet L-77, were applied as comparative treatments. Results, averaged for all replicates of each treatment, are shown in Table 5b.

TABLE 5b

| Spray composition | Glyphosate rate g a.e./ha | % Inhibition ABUTH | % Inhibition ECHCF |
|---|---|---|---|
| Formulation B | 200 | 47 | 83 |
|  | 300 | 64 | 84 |
|  | 400 | 71 | 90 |
| Formulation B + | 200 | 83 | 58 |
| Silwet L-77 0.5% v/v | 300 | 94 | 76 |
|  | 400 | 100 | 85 |
| Formulation C | 200 | 46 | 96 |
|  | 300 | 68 | 90 |
|  | 400 | 75 | 93 |
| Formulation C + | 200 | 81 | 66 |
| Silwet L-77 0.5% v/v | 300 | 93 | 68 |
|  | 400 | 96 | 86 |
| 5-01 | 200 | 70 | 91 |
|  | 300 | 74 | 100 |
|  | 400 | 93 | 94 |
| 5-02 | 200 | 81 | 95 |
|  | 300 | 68 | 100 |
|  | 400 | 81 | 100 |
| 5-03 | 200 | 78 | 100 |
|  | 300 | 99 | 83 |
|  | 400 | 98 | 99 |
| 5-04 | 200 | 89 | 95 |
|  | 300 | 93 | 95 |
|  | 400 | 86 | 100 |
| 5-05 | 200 | 60 | 89 |
|  | 300 | 79 | 100 |
|  | 400 | 86 | 100 |
| 5-06 | 200 | 76 | 100 |
|  | 300 | 84 | 100 |
|  | 400 | 100 | 96 |
| 5-07 | 200 | 65 | 97 |

TABLE 5b-continued

| Spray composition | Glyphosate rate g a.e./ha | % Inhibition ABUTH | % Inhibition ECHCF |
|---|---|---|---|
|  | 300 | 78 | 97 |
|  | 400 | 77 | 100 |
| 5-08 | 200 | 82 | 100 |
|  | 300 | 95 | 100 |
|  | 400 | 96 | 100 |
| 5-09 | 200 | 78 | 99 |
|  | 300 | 89 | 99 |
|  | 400 | 90 | 100 |
| 5-10 | 200 | 66 | 100 |
|  | 300 | 79 | 98 |
|  | 400 | 89 | 100 |
| 5-11 | 200 | 67 | 95 |
|  | 300 | 81 | 100 |
|  | 400 | 97 | 100 |
| 5-12 | 200 | 76 | 88 |
|  | 300 | 79 | 100 |
|  | 400 | 95 | 96 |
| 5-13 | 200 | 59 | 85 |
|  | 300 | 66 | 93 |
|  | 400 | 67 | 100 |
| 5-14 | 200 | 56 | 89 |
|  | 300 | 67 | 100 |
|  | 400 | 83 | 100 |
| 5-15 | 200 | 54 | 100 |
|  | 300 | 63 | 100 |
|  | 400 | 78 | 100 |
| 5-16 | 200 | 46 | 88 |
|  | 300 | 73 | 100 |
|  | 400 | 86 | 100 |
| 5-17 | 200 | 81 | 98 |
|  | 300 | 83 | 97 |
|  | 400 | 92 | 96 |
| 5-18 | 200 | 56 | 92 |
|  | 300 | 64 | 100 |
|  | 400 | 74 | 100 |
| 5-19 | 200 | 64 | 94 |
|  | 300 | 80 | 97 |
|  | 400 | 80 | 96 |
| 5-20 | 200 | 88 | 91 |
|  | 300 | 96 | 100 |
|  | 400 | 98 | 98 |
| 5-21 | 200 | 92 | 94 |
|  | 300 | 100 | 100 |
|  | 400 | 100 | 100 |
| 5-22 | 200 | 88 | 97 |
|  | 300 | 93 | 95 |
|  | 400 | 95 | 100 |
| 5-23 | 200 | 79 | 100 |
|  | 300 | 96 | 100 |
|  | 400 | 97 | 96 |

Glyphosate activity on ECHCF in this test was too high to make meaningful comparisons. However, on ABUTH, composition 5-20 containing lecithin and Fluorad FC-135 exhibited remarkably strong herbicidal effectiveness by comparison with composition 5-01 (no Fluorad FC-135) and Formulation C. As in previous testing, a slight further advantage on ABUTH was obtained by efforts to encapsulate the glyphosate in lecithin liposomes, as in composition 5-21. Compositions 5-22 and 5-23, containing both Fluorad FC-135 and Silwet L-77 in addition to lecithin, also showed remarkably good herbicidal effectiveness.

EXAMPLE 6

Compositions 5-01 to 5-23 of Example 5 were tested in this Example. Morningglory (*Ipomoea spp.,* IPOSS) plants were grown and treated by the standard procedures given above. Applications of spray compositions were made 14 days after planting IPOSS and evaluation of herbicidal inhibition was done 19 days after application.

Formulations B and C, alone and tank mixed with 0.5% Silwet L-77, were applied as comparative treatments. Results, averaged for all replicates of each treatment, are shown in Table 6.

TABLE 6

| Spray composition | Glyphosate rate g a.e./ha | % Inhibition IPOSS |
|---|---|---|
| Formulation B | 200 | 40 |
| | 400 | 66 |
| Formulation B + Silwet L-77 0.5% v/v | 200 | 68 |
| | 400 | 79 |
| Formulation C | 200 | 62 |
| | 400 | 71 |
| Formulation C + Silwet L-77 0.5% v/v | 200 | 70 |
| | 400 | 72 |
| 5-01 | 200 | 64 |
| | 400 | 77 |
| 5-02 | 200 | 68 |
| | 400 | 75 |
| 5-03 | 200 | 68 |
| | 400 | 72 |
| 5-04 | 200 | 69 |
| | 400 | 72 |
| 5-05 | 200 | 64 |
| | 400 | 78 |
| 5-06 | 200 | 80 |
| | 400 | 89 |
| 5-07 | 200 | 69 |
| | 400 | 74 |
| 5-08 | 200 | 60 |
| | 400 | 72 |
| 5-09 | 200 | 79 |
| | 400 | 84 |
| 5-10 | 200 | 69 |
| | 400 | 78 |
| 5-11 | 200 | 52 |
| | 400 | 72 |
| 5-12 | 200 | 69 |
| | 400 | 88 |
| 5-13 | 200 | 72 |
| | 400 | 74 |
| 5-14 | 200 | 68 |
| | 400 | 69 |
| 5-15 | 200 | 68 |
| | 400 | 70 |
| 5-16 | 200 | 55 |
| | 400 | 69 |
| 5-17 | 200 | 52 |
| | 400 | 67 |
| 5-18 | 200 | 65 |
| | 400 | 67 |
| 5-19 | 200 | 54 |
| | 400 | 70 |
| 5-20 | 200 | 74 |
| | 400 | 100 |
| 5-21 | 200 | 72 |
| | 400 | 91 |
| 5-22 | 200 | 81 |
| | 400 | 84 |
| 5-23 | 200 | 79 |
| | 400 | 90 |

Once again, surprisingly strong herbicidal effectiveness, this time on IPOSS, was exhibited by compositions 5-20 to 5-23, all of which contain lecithin and Fluorad FC-135.

EXAMPLE 7

Aqueous spray compositions were prepared containing glyphosate IPA salt and excipient ingredients as shown in Table 7a. Process (ii) was followed for all compositions, using soybean lecithin (20% phospholipid, Avanti). The pH of all compositions was adjusted to approximately 7.

TABLE 7a

| Spray composition | Lecithin g/l | Fluorad FC-135 | Silwet L-77 | Components sonicated with lecithin |
|---|---|---|---|---|
| | | % w/w | | |
| 7-01 | 5.0 | | 0.50 | L-77 |
| 7-02 | 5.0 | | 0.25 | L-77 |
| 7-03 | 5.0 | | 0.10 | L-77 |
| 7-04 | 5.0 | | | none |
| 7-05 | 2.5 | | 0.50 | L-77 |
| 7-06 | 2.5 | | 0.25 | L-77 |
| 7-07 | 2.5 | | 0.10 | L-77 |
| 7-08 | 1.0 | | 0.50 | L-77 |
| 7-09 | 1.0 | | 0.25 | L-77 |
| 7-10 | 2.5 | | 0.10 | L-77 |
| 7-11 | 2.5 | 0.25 | 0.25 | L-77 |
| 7-12 | 2.5 | 0.17 | 0.33 | L-77 |
| 7-13 | 2.5 | 0.33 | 0.17 | L-77 |
| 7-14 | 2.5 | 0.50 | | none |
| 7-15 | 2.5 | 0.25 | | none |
| 7-16 | 2.5 | 0.10 | | none |
| 7-17 | 2.5 | | 0.25 | glyphosate |
| 7-18 | 2.5 | | 0.10 | glyphosate |
| 7-19 | 2.5 | | 0.50 | glyphosate |
| 7-20 | 5.0 | | 0.50 | L-77, glyphosate |
| 7-21 | 2.5 | | 0.25 | L-77, glyphosate |
| 7-22 | 1.0 | | 0.25 | L-77, glyphosate |
| 7-23 | 1.0 | | 0.10 | L-77, glyphosate |

Velvetleaf (*Abutilon theophrasti*, ABUTH), Japanese millet (*Echinochloa crus-galli*, ECHCF), and prickly sida (*Sida spinosa*, SIDSP) plants were grown and treated by the standard procedures given above. Applications of spray compositions were made 20 days after planting ABUTH and ECHCF. Planting date for SIDSP was not recorded. Evaluation of herbicidal inhibition was done 19 days after application.

Formulations B and C, alone and tank mixed with 0.5% Silwet L-77, were applied as comparative treatments. Results, averaged for all replicates of each treatment, are shown in Table 7b.

TABLE 7b

| Spray composition | Glyphosate rate g a.e./ha | % Inhibition ABUTH | ECHCF | SIDSP |
|---|---|---|---|---|
| Formulation B | 150 | 33 | 39 | 29 |
| | 250 | 44 | 43 | 66 |
| | 350 | 83 | 45 | 60 |
| Formulation B + | 150 | 81 | 7 | 46 |
| Silwet L-77 0.5% v/v | 250 | 88 | 21 | 64 |
| | 350 | 96 | 32 | 66 |
| Formulation C | 150 | 61 | 59 | 58 |
| | 250 | 77 | 92 | 85 |
| | 350 | 91 | 92 | 83 |
| Formulation C + | 150 | 76 | 10 | 65 |
| Silwet L-77 0.5% v/v | 250 | 87 | 17 | 60 |
| | 350 | 92 | 39 | 64 |
| 7-01 | 150 | 87 | 43 | 47 |
| | 250 | 88 | 41 | 60 |
| | 350 | 96 | 53 | 66 |
| 7-02 | 150 | 66 | 51 | 61 |
| | 250 | 85 | 81 | 63 |
| | 350 | 84 | 89 | 75 |
| 7-03 | 150 | 66 | 54 | 65 |
| | 250 | 70 | 63 | 60 |
| | 350 | 94 | 96 | 87 |
| 7-04 | 150 | 73 | 58 | 61 |
| | 250 | 85 | 83 | 90 |
| | 350 | 91 | 100 | 83 |
| 7-05 | 150 | 76 | 44 | 49 |
| | 250 | 85 | 55 | 56 |
| | 350 | 93 | 79 | 64 |
| 7-06 | 150 | 64 | 73 | 56 |
| | 250 | 71 | 78 | 61 |
| | 350 | 81 | 79 | 77 |
| 7-07 | 150 | 53 | 41 | 59 |
| | 250 | 74 | 78 | 68 |
| | 350 | 78 | 90 | 75 |
| 7-08 | 150 | 83 | 33 | 59 |
| | 250 | 82 | 39 | 75 |
| | 350 | 95 | 59 | 69 |
| 7-09 | 150 | 78 | 32 | 46 |
| | 250 | 85 | 42 | 75 |
| | 350 | 91 | 62 | 67 |
| 7-10 | 150 | 26 | 36 | 43 |
| | 250 | 69 | 73 | 75 |
| | 350 | 76 | 81 | 73 |
| 7-11 | 150 | 83 | 79 | 72 |
| | 250 | 96 | 93 | 78 |
| | 350 | 99 | 97 | 84 |
| 7-12 | 150 | 78 | 57 | 58 |
| | 250 | 89 | 78 | 66 |
| | 350 | 94 | 93 | 75 |
| 7-13 | 150 | 83 | 84 | 54 |
| | 250 | 94 | 93 | 67 |
| | 350 | 99 | 97 | 93 |
| 7-14 | 150 | 80 | 68 | 69 |
| | 250 | 85 | 88 | 79 |
| | 350 | 97 | 94 | 99 |
| 7-15 | 150 | 75 | 80 | 62 |
| | 250 | 93 | 93 | 76 |
| | 350 | 95 | 91 | 94 |
| 7-16 | 150 | 75 | 69 | 60 |
| | 250 | 88 | 91 | 77 |
| | 350 | 89 | 92 | 75 |
| 7-17 | 150 | 77 | 69 | 67 |
| | 250 | 88 | 91 | 86 |
| | 350 | 93 | 97 | 96 |
| 7-18 | 150 | 71 | 63 | 66 |
| | 250 | 74 | 85 | 82 |
| | 350 | 89 | 85 | 83 |
| 7-19 | 150 | 74 | 62 | 77 |
| | 250 | 86 | 80 | 93 |
| | 350 | 92 | 96 | 96 |
| 7-20 | 150 | 39 | 46 | 38 |
| | 250 | 80 | 49 | 69 |
| | 350 | 91 | 64 | 69 |
| 7-21 | 150 | 65 | 50 | 34 |
| | 250 | 64 | 52 | 52 |
| | 350 | 78 | 67 | 62 |
| 7-22 | 150 | 68 | 18 | 35 |
| | 250 | 79 | 42 | 43 |
| | 350 | 87 | 49 | 58 |
| 7-23 | 150 | 24 | 46 | 38 |
| | 250 | 62 | 49 | 42 |
| | 350 | 91 | 53 | 67 |

Compositions 7-14 to 7-16, containing 0.25% lecithin together with Fluorad FC-135, provided excellent herbicidal effectiveness on all three species tested. Even at the lowest concentration of Fluorad FC-135 (0.1% in composition 7-16), effectiveness was substantially maintained on ABUTH and ECHCF, although some loss of effectiveness was evident on SIDSP. Compositions 7-11 to 7-13, containing lecithin, Fluorad FC-135 and Silwet L-77, also performed well in this test, not showing the antagonism on ECHCF characteristic of compositions containing Silwet L-77 but no Fluorad FC-135.

EXAMPLE 8

Aqueous spray compositions were prepared containing glyphosate IPA salt and excipient ingredients as shown in Table 8a. Process (ii) was followed for all compositions, using soybean lecithin (20% phospholipid, Avanti).

Aqueous spray compositions were prepared containing glyphosate IPA salt and excipient ingredients as shown in Table 8a. The pH of all compositions was adjusted to approximately 7.

TABLE 8a

| Spray composition | Lecithin g/l | Fluorad FC-135 | Silwet L-77 | Components sonicated with lecithin |
|---|---|---|---|---|
| | | % w/w | | |
| 8-01 | 5.0 | | 0.50 | L-77 |
| 8-02 | 5.0 | | 0.25 | L-77 |
| 8-03 | 5.0 | | 0.10 | L-77 |
| 8-04 | 5.0 | | | none |
| 8-05 | 2.5 | | 0.50 | L-77 |
| 8-06 | 2.5 | | 0.25 | L-77 |
| 8-07 | 2.5 | | 0.10 | L-77 |
| 8-08 | 1.0 | | 0.50 | L-77 |
| 8-09 | 1.0 | | 0.25 | L-77 |
| 8-10 | 2.5 | | 0.10 | L-77 |
| 8-11 | 2.5 | 0.25 | 0.25 | L-77 |
| 8-12 | 2.5 | 0.17 | 0.33 | L-77 |
| 8-13 | 2.5 | 0.33 | 0.17 | L-77 |
| 8-14 | 2.5 | 0.50 | | none |
| 8-15 | 2.5 | 0.25 | | none |
| 8-16 | 2.5 | 0.10 | | none |
| 8-17 | 2.5 | | 0.25 | glyphosate |
| 8-18 | 2.5 | | 0.10 | glyphosate |
| 8-19 | 2.5 | | 0.50 | glyphosate |

Yellow nutsedge (*Cyperus esculentus*, CYPES) plants were grown and treated by the standard procedures given above. Applications of spray compositions were made 21 days after planting CYPES, and evaluation of herbicidal inhibition was done 27 days after application.

Formulations B and C, alone and tank mixed with 0.5% Silwet L-77, were applied as comparative treatments. Results, averaged for all replicates of each treatment, are shown in Table 8b.

TABLE 8b

| Spray composition | Glyphosate rate g a.e./ha | % Inhibition CYPES |
|---|---|---|
| Formulation B | 500 | 92 |
| | 1000 | 95 |
| | 5000 | 100 |
| Formulation B + Silwet L-77 0.5% v/v | 500 | 100 |
| | 1000 | 87 |
| | 5000 | 100 |
| Formulation C | 500 | 87 |
| | 1000 | 96 |
| | 5000 | 100 |
| Formulation C + Silwet L-77 0.5% v/v | 500 | 98 |
| | 1000 | 94 |
| | 5000 | 100 |
| 8-01 | 500 | 91 |
| | 1000 | 100 |
| | 1500 | 97 |
| 8-02 | 500 | 83 |
| | 1000 | 100 |
| | 1500 | 100 |
| 8-03 | 500 | 90 |
| | 1000 | 88 |
| | 1500 | 71 |
| 8-04 | 500 | 88 |
| | 1000 | 100 |
| | 1500 | 100 |
| 8-05 | 500 | 84 |
| | 1000 | 99 |
| | 1500 | 95 |
| 8-06 | 500 | 90 |
| | 1000 | 88 |
| | 1500 | 99 |
| 8-07 | 500 | 78 |
| | 1000 | 94 |
| | 1500 | 97 |
| 8-08 | 500 | 93 |
| | 1000 | 96 |
| | 1500 | 100 |
| 8-09 | 500 | 87 |
| | 1000 | 88 |
| | 1500 | 100 |
| 8-10 | 500 | 86 |
| | 1000 | 100 |
| | 1500 | 100 |
| 8-11 | 500 | 95 |
| | 1000 | 94 |
| | 1500 | 100 |
| 8-12 | 500 | 92 |
| | 1000 | 92 |
| | 1500 | 100 |
| 8-13 | 500 | 87 |
| | 1000 | 97 |
| | 1500 | 100 |
| 8-14 | 500 | 82 |
| | 1000 | 100 |
| | 1500 | 100 |
| 8-15 | 500 | 85 |
| | 1000 | 90 |
| | 1500 | 95 |
| 8-16 | 500 | 87 |
| | 1000 | 91 |
| | 1500 | 100 |
| 8-17 | 500 | 83 |
| | 1000 | 90 |
| | 1500 | 95 |
| 8-18 | 500 | 93 |
| | 1000 | 100 |
| | 1500 | 95 |
| 8-19 | 500 | 86 |
| | 1000 | 95 |
| | 1500 | 100 |

The commercial standard Formulation C exhibited very high herbicidal effectiveness in this test and for this reason it is not possible to discern enhancements. There is a suggestion at the lowest glyphosate rate (500 g a.e./ha), effectiveness of compositions containing lecithin and Fluorad FC-135 (8-14 to 8-16) on CYPES surprisingly improved with decreasing Fluorad FC-135 concentration.

EXAMPLE 9

Aqueous spray compositions were prepared containing glyphosate IPA salt and excipient ingredients as shown in Table 9a. Process (ii) was followed for all compositions, using soybean lecithin (20% phospholipid, Avanti). The pH of all compositions was adjusted to approximately 7.

TABLE 9a

| Spray composition | Lecithin g/l | Fluorad FC-135 | Silwet L-77 | Components sonicated with lecithin |
|---|---|---|---|---|
| | | % w/w | | |
| 9-01 | 5.0 | | | none |
| 9-02 | 5.0 | | 0.50 | none |
| 9-03 | 5.0 | | 0.50 | L-77 |
| 9-04 | 2.5 | | | none |
| 9-05 | 2.5 | | 0.50 | none |

TABLE 9a-continued

| Spray composition | Lecithin g/l | Fluorad FC-135 | Silwet L-77 | Components sonicated with lecithin |
|---|---|---|---|---|
| | | % w/w | | |
| 9-06 | 2.5 | | 0.50 | L-77 |
| 9-07 | 1.0 | | | none |
| 9-08 | 1.0 | | 0.50 | none |
| 9-09 | 1.0 | | 0.50 | L-77 |
| 9-10 | 0.5 | | | none |
| 9-11 | 0.5 | | 0.50 | none |
| 9-12 | 0.5 | | 0.50 | L-77 |
| 9-13 | 1.0 | | 0.25 | none |
| 9-14 | 1.0 | | 0.25 | L-77 |
| 9-15 | 1.0 | | 0.10 | none |
| 9-16 | 1.0 | | 0.10 | L-77 |
| 9-17 | 1.0 | 0.50 | | none |
| 9-18 | 1.0 | 0.20 | | none |
| 9-19 | 1.0 | 0.10 | | none |
| 9-20 | 0.5 | 0.50 | | none |
| 9-21 | 0.5 | 0.20 | | none |

Velvetleaf (*Abutilon theophrasti*, ABUTH) and Japanese millet (*Echinochloa crus-galli*, ECHCF) plants were grown and treated by the standard procedures given above. There was no record of the dates of planting. Evaluation of herbicidal inhibition was done 16 days after application.

In addition to compositions 9-01 to 9-21, spray compositions were prepared by tank mixing Formulations B and C with 0.5% Fluorad FC-135. Formulations B and C, alone and tank mixed with 0.5% Silwet L-77, were applied as comparative treatments. Results, averaged for all replicates of each treatment, are shown in Table 9b.

TABLE 9b

| Spray composition | Glyphosate rate g a.e./ha | % Inhibition ABUTH | ECHCF |
|---|---|---|---|
| Formulation B | 150 | 64 | 77 |
| | 250 | 81 | 80 |
| | 350 | 88 | 97 |
| Formulation B + Silwet L-77 0.5% v/v | 150 | 42 | 38 |
| | 250 | 56 | 49 |
| | 350 | 67 | 64 |
| Formulation C | 150 | 61 | 89 |
| | 250 | 75 | 91 |
| | 350 | 92 | 99 |
| Formulation C + Silwet L-77 0.5% v/v | 150 | 92 | 40 |
| | 250 | 95 | 40 |
| | 350 | 94 | 74 |
| Formulation B + Fluorad FC-135 0.5% w/v | 150 | 87 | 34 |
| | 250 | 90 | 44 |
| | 350 | 97 | 47 |
| Formulation C + Fluorad FC-135 0.5% w/v | 150 | 79 | 85 |
| | 250 | 77 | 86 |
| | 350 | 92 | 91 |
| 9-01 | 150 | 75 | 69 |
| | 250 | 84 | 89 |
| | 350 | 98 | 98 |
| 9-02 | 150 | 86 | 54 |
| | 250 | 96 | 74 |
| | 350 | 99 | 86 |
| 9-03 | 150 | 86 | 66 |
| | 250 | 91 | 77 |
| | 350 | 96 | 86 |
| 9-04 | 150 | 68 | 73 |
| | 250 | 97 | 85 |
| | 350 | 94 | 92 |
| 9-05 | 150 | 90 | 55 |
| | 250 | 96 | 69 |
| | 350 | 91 | 82 |
| 9-06 | 150 | 87 | 43 |

TABLE 9b-continued

| Spray composition | Glyphosate rate g a.e./ha | % Inhibition ABUTH | ECHCF |
|---|---|---|---|
| | 250 | 91 | 68 |
| | 350 | 97 | 83 |
| 9-07 | 150 | 56 | 76 |
| | 250 | 81 | 88 |
| | 350 | 89 | 96 |
| 9-08 | 150 | 85 | 35 |
| | 250 | 93 | 51 |
| | 350 | 98 | 66 |
| 9-09 | 150 | 94 | 45 |
| | 250 | 97 | 47 |
| | 350 | 98 | 52 |
| 9-10 | 150 | 62 | 60 |
| | 250 | 85 | 78 |
| | 350 | 93 | 88 |
| 9-11 | 150 | 90 | 32 |
| | 250 | 92 | 42 |
| | 350 | 98 | 59 |
| 9-12 | 150 | 93 | 38 |
| | 250 | 93 | 56 |
| | 350 | 95 | 72 |
| 9-13 | 150 | 85 | 39 |
| | 250 | 89 | 66 |
| | 350 | 94 | 79 |
| 9-14 | 150 | 83 | 70 |
| | 250 | 93 | 45 |
| | 350 | 93 | 70 |
| 9-15 | 150 | 65 | 54 |
| | 250 | 85 | 79 |
| | 350 | 91 | 89 |
| 9-16 | 150 | 75 | 65 |
| | 250 | 83 | 79 |
| | 350 | 90 | 84 |
| 9-17 | 150 | 81 | 94 |
| | 250 | 88 | 97 |
| | 350 | 100 | 99 |
| 9-18 | 150 | 79 | 89 |
| | 250 | 95 | 91 |
| | 350 | 98 | 98 |
| 9-19 | 150 | 77 | 85 |
| | 250 | 91 | 96 |
| | 350 | 95 | 97 |
| 9-20 | 150 | 77 | 71 |
| | 250 | 86 | 92 |
| | 350 | 100 | 93 |
| 9-21 | 150 | 75 | 91 |
| | 250 | 84 | 97 |
| | 350 | 96 | 95 |

Compositions of this Example (9-17 to 9-21) containing very low concentrations of lecithin and Fluorad FC-135 exhibited remarkably high herbicidal effectiveness. Even a composition (9-19) with just 0.1% lecithin and 0.1% Fluorad FC-135 was much more effective on ABUTH than commercial standard Formulation C, and equally as effective on ECHCF as Formulation C. The apparently strong antagonism on ECHCF seen when Formulation B was tank mixed with 0.5% Fluorad FC-135 in this test is uncharacteristic and has not been seen in other tests (see, for example, Example 12 herein); indeed the data for this set of treatments is so out of line that it is believed they may be due to an error in application.

EXAMPLE 10

Aqueous spray compositions were prepared containing glyphosate IPA salt and excipient ingredients as shown in Table 10a. Process (iii) was followed for all compositions, using soybean lecithin (20% phospholipid, Avanti). The pH of all compositions was adjusted to approximately 7.

TABLE 10a

| Spray composition | Lecithin g/l | % w/w Fluorad FC-135 | Silwet L-77 | Methyl caprate | Sodium cholate | Components sonicated with lecithin |
|---|---|---|---|---|---|---|
| 10-01 | 5.0 | | | | | none |
| 10-02 | 5.0 | | 0.50 | | | none |
| 10-03 | 5.0 | | 0.50 | | | L-77 |
| 10-04 | 2.5 | | | | | none |
| 10-05 | 0.5 | | | | | none |
| 10-06 | 2.5 | | 0.50 | | | none |
| 10-07 | 2.5 | | 0.50 | | | L-77 |
| 10-08 | 0.5 | | 0.50 | | | none |
| 10-09 | 0.5 | | 0.50 | | | L-77 |
| 10-10 | 2.5 | 0.25 | | | | none |
| 10-11 | 2.5 | 0.10 | | | | none |
| 10-12 | 2.5 | 0.05 | | | | none |
| 10-13 | 0.5 | 0.25 | | | | none |
| 10-14 | 0.5 | 0.10 | | | | none |
| 10-15 | 0.5 | 0.05 | | | | none |
| 10-16 | 2.5 | | | 0.10 | | Me caprate |
| 10-17 | 2.5 | | | | 0.10 | Na cholate |

Velvetleaf (*Abutilon theophrasti,* ABUTH) and Japanese millet (*Echinochloa crus-galli,* ECHCF) plants were grown and treated by the standard procedures given above. Applications of spray compositions were made 18 days after planting ABUTH and 21 days after planting ECHCF, and evaluation of herbicidal inhibition was done 18 days after application.

In addition to compositions 10-01 to 10-17, spray compositions were prepared by tank mixing Formulations B and C with Fluorad FC-135 at various concentrations. Formulations B and C, alone and tank mixed with 0.5% Silwet L-77, were applied as comparative treatments. Results, averaged for all replicates of each treatment, are shown in Table 10b.

TABLE 10b

| Spray composition | Glyphosate rate g a.e./ha | % Inhibition ABUTH | ECHCF |
|---|---|---|---|
| Formulation B | 200 | 53 | 69 |
| | 300 | 76 | 85 |
| | 400 | 77 | 81 |
| Formulation B + Silwet L-77 0.5% v/v | 200 | 100 | 28 |
| | 300 | 100 | 35 |
| | 400 | 100 | 47 |
| Formulation C | 200 | 57 | 81 |
| | 300 | 73 | 90 |
| | 400 | 98 | 94 |
| Formulation C + Silwet L-77 0.5% v/v | 200 | 99 | 28 |
| | 300 | 98 | 53 |
| | 400 | 99 | 56 |
| Formulation B + Fluorad FC-135 0.25% w/v | 200 | 76 | 85 |
| | 300 | 95 | 81 |
| | 400 | 100 | 100 |
| Formulation B + Fluorad FC-135 0.1% w/v | 200 | 77 | 70 |
| | 300 | 94 | 81 |
| | 400 | 98 | 87 |
| Formulation B + Fluorad FC-135 0.05% w/v | 200 | 65 | 73 |
| | 300 | 84 | 94 |
| | 400 | 88 | 96 |
| Formulation C + Fluorad FC-135 0.25% w/v | 200 | 83 | 78 |
| | 300 | 98 | 94 |
| | 400 | 97 | 95 |
| Formulation C + Fluorad FC-135 0.1% w/v | 200 | 65 | 66 |
| | 300 | 89 | 86 |
| | 400 | 97 | 89 |
| Formulation C + Fluorad FC-135 0.05% w/v | 200 | 70 | 78 |
| | 300 | 79 | 84 |

TABLE 10b-continued

| Spray composition | Glyphosate rate g a.e./ha | % Inhibition ABUTH | ECHCF |
|---|---|---|---|
| | 400 | 96 | 98 |
| 10-01 | 200 | 93 | 71 |
| | 300 | 91 | 89 |
| | 400 | 97 | 97 |
| 10-02 | 200 | 95 | 59 |
| | 300 | 97 | 68 |
| | 400 | 99 | 79 |
| 10-03 | 200 | 97 | 55 |
| | 300 | 98 | 62 |
| | 400 | 100 | 76 |
| 10-04 | 200 | 83 | 72 |
| | 300 | 87 | 84 |
| | 400 | 95 | 100 |
| 10-05 | 200 | 69 | 78 |
| | 300 | 92 | 93 |
| | 400 | 98 | 97 |
| 10-06 | 200 | 94 | 61 |
| | 300 | 99 | 67 |
| | 400 | 100 | 76 |
| 10-07 | 200 | 99 | 52 |
| | 300 | 99 | 63 |
| | 400 | 100 | 80 |
| 10-08 | 200 | 96 | 47 |
| | 300 | 99 | 57 |
| | 400 | 99 | 55 |
| 10-09 | 200 | 99 | 23 |
| | 300 | 98 | 58 |
| | 400 | 100 | 53 |
| 10-10 | 200 | 89 | 91 |
| | 300 | 91 | 99 |
| | 400 | 98 | 100 |
| 10-11 | 200 | 81 | 91 |
| | 300 | 91 | 99 |
| | 400 | 92 | 100 |
| 10-12 | 200 | 66 | 96 |
| | 300 | 86 | 100 |
| | 400 | 94 | 99 |
| 10-13 | 200 | 80 | 97 |
| | 300 | 98 | 98 |
| | 400 | 99 | 100 |
| 10-14 | 200 | 68 | 92 |
| | 300 | 89 | 100 |
| | 400 | 99 | 98 |
| 10-15 | 200 | 84 | 95 |
| | 300 | 94 | 100 |
| | 400 | 97 | 100 |
| 10-16 | 200 | 73 | 94 |
| | 300 | 89 | 100 |
| | 400 | 99 | 100 |
| 10-17 | 200 | 58 | 94 |
| | 300 | 77 | 96 |
| | 400 | 90 | 90 |

Tank mixture of Fluorad FC-135 at concentrations as low as 0.05% with Formulation B resulted in remarkably strong herbicidal efficacy in this test. The antagonism on ECHCF seen with the nonionic organosilicone surfactant Silwet L-77 did not occur with the cationic fluoro-organic surfactant Fluorad FC-135. Noteworthy was the outstanding herbicidal effectiveness provided by a composition (10-15) containing just 0.05% lecithin and 0.05% Fluorad FC-135. In this test addition of 0.1% methyl caprate to 0.25% lecithin, the methyl caprate being sonicated together with the lecithin, enhanced performance on ECHCF but not on ABUTH (compare compositions 10-16 and 10-04).

EXAMPLE 11

Compositions 10-01 to 10-17 of Example 10, and tank mixtures of Formulations B and C with Fluorad FC-135, were tested in this Example. Prickly sida (*Sida spinosa,* SIDSP) plants were grown and treated by the standard procedures given above. Applications of spray compositions were made 22 days after planting SIDSP, and evaluation of herbicidal inhibition was done 19 days after application.

Formulations B and C, alone and tank mixed with 0.5% Silwet L-77, were applied as comparative treatments. Results, averaged for all replicates of each treatment, are shown in Table 11.

TABLE 11

| Spray composition | Glyphosate rate g a.e./ha | % Inhibition SIDSP |
|---|---|---|
| Formulation B | 200 | 46 |
|  | 300 | 75 |
|  | 400 | 80 |
| Formulation B + Silwet L-77 0.5% v/v | 200 | 96 |
|  | 300 | 89 |
|  | 400 | 87 |
| Formulation C | 200 | 80 |
|  | 300 | 98 |
|  | 400 | 98 |
| Formulation C + Silwet L-77 0.5% v/v | 200 | 75 |
|  | 300 | 91 |
|  | 400 | 94 |
| Formulation B + Fluorad FC-135 0.25% w/v | 200 | 82 |
|  | 300 | 94 |
|  | 400 | 98 |
| Formulation B + Fluorad FC-135 0.1% w/v | 200 | 70 |
|  | 300 | 93 |
|  | 400 | 88 |
| Formulation B + Fluorad FC-135 0.05% w/v | 200 | 79 |
|  | 300 | 92 |
|  | 400 | 99 |
| Formulation C + Fluorad FC-135 0.25% w/v | 200 | 79 |
|  | 300 | 97 |
|  | 400 | 97 |
| Formulation C + Fluorad FC-135 0.1% w/v | 200 | 90 |
|  | 300 | 96 |
|  | 400 | 97 |
| Formulation C + Fluorad FC-135 0.05% w/v | 200 | 80 |
|  | 300 | 96 |
|  | 400 | 99 |
| 10-01 | 200 | 93 |
|  | 300 | 97 |
|  | 400 | 98 |
| 10-02 | 200 | 71 |
|  | 300 | 89 |
|  | 400 | 89 |
| 10-03 | 200 | 71 |
|  | 300 | 87 |
|  | 400 | 98 |
| 10-04 | 200 | 76 |
|  | 300 | 100 |
|  | 400 | 100 |
| 10-05 | 200 | 91 |
|  | 300 | 99 |
|  | 400 | 97 |
| 10-06 | 200 | 57 |

TABLE 11-continued

| Spray composition | Glyphosate rate g a.e./ha | % Inhibition SIDSP |
|---|---|---|
|  | 300 | 95 |
|  | 400 | 88 |
| 10-07 | 200 | 64 |
|  | 300 | 68 |
|  | 400 | 94 |
| 10-08 | 200 | 89 |
|  | 300 | 96 |
|  | 400 | 99 |
| 10-09 | 200 | 80 |
|  | 300 | 77 |
|  | 400 | 94 |
| 10-10 | 200 | 90 |
|  | 300 | 94 |
|  | 400 | 98 |
| 10-11 | 200 | 81 |
|  | 300 | 100 |
|  | 400 | 96 |
| 10-12 | 200 | 86 |
|  | 300 | 92 |
|  | 400 | 95 |
| 10-13 | 200 | 86 |
|  | 300 | 99 |
|  | 400 | 100 |
| 10-14 | 200 | 97 |
|  | 300 | 100 |
|  | 400 | 100 |
| 10-15 | 200 | 99 |
|  | 300 | 100 |
|  | 400 | 100 |
| 10-16 | 200 | 92 |
|  | 300 | 100 |
|  | 400 | 100 |
| 10-17 | 200 | 92 |
|  | 300 | 99 |
|  | 400 | 100 |

Herbicidal effectiveness of Formulation C was very high on SIDSP in this test and accordingly enhancements are difficult to discern. However, remarkably strong performance was again seen with composition 10-15, containing just 0.05% lecithin and 0.05% Fluorad FC-135.

EXAMPLE 12

Aqueous spray compositions were prepared containing glyphosate IPA salt and excipient ingredients as shown in Table 12a. Process (iii) was followed for all compositions, using soybean lecithin (20% phospholipid, Avanti). The pH of all compositions was adjusted to approximately 7.

TABLE 12a

| | | % w/w | | | | Components |
|---|---|---|---|---|---|---|
| Spray comp. | Lecithin g/l | Fluorad FC-135 | Silwet L-77 | Other (*) | (*) Other ingredient | sonicated with lecithin |
| 12-01 | 5.0 | | | | | none |
| 12-02 | 5.0 | | 0.50 | | | L-77 |
| 12-03 | 2.5 | | | | | none |
| 12-04 | 2.5 | 0.50 | | | | none |
| 12-05 | 2.5 | 0.20 | | | | none |
| 12-06 | 2.5 | 0.10 | | | | none |
| 12-07 | 5.0 | | | 0.50 | Diacid 1550 | Diacid |
| 12-08 | 5.0 | | | 0.10 | Diacid 1550 | Diacid |
| 12-09 | 2.5 | | | 0.25 | Diacid 1550 | Diacid |
| 12-10 | 2.5 | 0.25 | | 0.05 | Diacid 1550 | Diacid |

TABLE 12a-continued

| Spray comp. | Lecithin g/l | Fluorad FC-135 | Silwet L-77 | Other (*) | (*) Other ingredient | Components sonicated with lecithin |
|---|---|---|---|---|---|---|
| | | % w/w | | | | |
| 12-11 | 5.0 | 0.10 | | 0.50 | Genapol UD-030 | Genapol |
| 12-12 | 5.0 | 0.05 | | 0.20 | Genapol UD-030 | Genapol |
| 12-13 | 5.0 | 0.25 | | 0.50 | Neodol 25-3 | Neodol |
| 12-14 | 5.0 | 0.10 | | 0.20 | Neodol 25-3 | Neodol |

Velvetleaf (*Abutilon theophrasti*, ABUTH), Japanese millet (*Echinochloa crus-galli*, ECHCF) and morningglory (*Ipomoea spp.*, IPOSS) plants were grown and treated by the standard procedures given above. Applications of spray compositions were made 16 days after planting ABUTH, 18 days after planting ECHCF and 9 days after planting IPOSS. Evaluation of herbicidal inhibition was done 15 days after application.

In addition to compositions 12-01 to 12-14, spray compositions were prepared by tank mixing Formulations B and C with Fluorad FC-135 at various concentrations. Formulations B and C, alone and tank mixed with 0.5% Silwet L-77, were applied as comparative treatments. Results, averaged for all replicates of each treatment, are shown II in Table 12b.

TABLE 12b

| Spray composition | Glyphosate rate g a.e./ha | % Inhibition | | |
|---|---|---|---|---|
| | | ABUTH | ECHCF | IPOSS |
| Formulation B | 200 | 24 | 53 | 33 |
| | 300 | 47 | 37 | 37 |
| | 400 | 64 | 46 | 64 |
| Formulation B + Silwet L-77 0.5% v/v | 200 | 85 | 3 | 66 |
| | 300 | 97 | 19 | 77 |
| | 400 | 98 | 18 | 82 |
| Formulation C | 200 | 39 | 69 | 38 |
| | 300 | 71 | 90 | 67 |
| | 400 | 87 | 100 | 76 |
| Formulation C + Silwet L-77 0.5% v/v | 200 | 90 | 8 | 72 |
| | 300 | 95 | 50 | 79 |
| | 400 | 100 | 90 | 73 |
| Formulation B + Fluorad FC-135 0.5% w/v | 200 | 75 | 71 | 65 |
| | 300 | 94 | 92 | 79 |
| | 400 | 98 | 100 | 77 |
| Formulation B + Fluorad FC-135 0.25% w/v | 200 | 75 | 67 | 67 |
| | 300 | 85 | 73 | 71 |
| | 400 | 96 | 97 | 75 |
| Formulation B + Fluorad FC-135 0.1% w/v | 200 | 61 | 53 | 48 |
| | 300 | 82 | 98 | 72 |
| | 400 | 95 | 86 | 70 |
| Formulation C + Fluorad FC-135 0.5% w/v | 200 | 81 | 61 | 69 |
| | 300 | 75 | 75 | 71 |
| | 400 | 84 | 84 | 77 |
| Formulation C + Fluorad FC-135 0.25% w/v | 200 | 35 | 58 | 67 |
| | 300 | 68 | 97 | 64 |
| | 400 | 92 | 96 | 73 |
| Formulation C + Fluorad FC-135 0.1% w/v | 200 | 40 | 84 | 51 |
| | 300 | 79 | 94 | 58 |
| | 400 | 99 | 86 | 74 |
| 12-01 | 200 | 69 | 69 | 62 |
| | 300 | 82 | 82 | 73 |
| | 400 | 88 | 84 | 77 |
| 12-02 | 200 | 81 | 75 | 67 |
| | 300 | 83 | 74 | 72 |
| | 400 | 95 | 93 | 75 |
| 12-03 | 200 | 48 | 69 | 70 |
| | 300 | 82 | 93 | 71 |
| | 400 | 94 | 100 | 72 |
| 12-04 | 200 | 68 | 78 | 64 |
| | 300 | 90 | 94 | 76 |
| | 400 | 96 | 99 | 79 |
| 12-05 | 200 | 75 | 86 | 68 |
| | 300 | 86 | 95 | 72 |
| | 400 | 96 | 89 | 80 |
| 12-06 | 200 | 80 | 95 | 57 |
| | 300 | 85 | 82 | 60 |
| | 400 | 96 | 91 | 73 |
| 12-07 | 200 | 41 | 72 | 64 |
| | 300 | 76 | 82 | 68 |
| | 400 | 80 | 98 | 77 |
| 12-08 | 200 | 40 | 71 | 70 |
| | 300 | 51 | 91 | 76 |
| | 400 | 77 | 98 | 72 |
| 12-09 | 200 | 43 | 74 | 64 |
| | 300 | 58 | 95 | 76 |
| | 400 | 73 | 100 | 77 |
| 12-10 | 200 | 43 | 85 | 65 |
| | 300 | 74 | 75 | 65 |
| | 400 | 83 | 99 | 76 |
| 12-11 | 200 | 39 | 71 | 66 |
| | 300 | 61 | 88 | 71 |
| | 400 | 89 | 99 | 73 |
| 12-12 | 200 | 54 | 57 | 59 |
| | 300 | 79 | 77 | 75 |
| | 400 | 89 | 84 | 71 |
| 12-13 | 200 | 69 | 72 | 69 |
| | 300 | 59 | 66 | 69 |
| | 400 | 86 | 81 | 76 |
| 12-14 | 200 | 54 | 62 | 65 |
| | 300 | 65 | 77 | 69 |
| | 400 | 84 | 81 | 74 |

Tank mixtures of Formulation B with Fluorad FC-135 gave greater herbicidal effectiveness than Formulation C alone, without the attendant antagonism on ECHCF so characteristic of Silwet L-77. Addition of Fluorad FC-135 to glyphosate compositions containing 0.25% lecithin enhanced herbicidal effectiveness on ABUTH and ECHCF, but not, in this test, on IPOSS (compare compositions 12-04 to 12-06 with composition 12-03).

EXAMPLE 13

Compositions 12-01 to 12-14 of Example 12, and tank mixtures of Formulations B and C with Fluorad FC-135, were tested in this Example. Prickly sida (*Sida spinosa*, SIDSP) plants were grown and treated by the standard procedures given above. Applications of spray compositions were made 23 days after planting SIDSP, and evaluation of herbicidal inhibition was done 19 days after application.

Formulations B and c, alone and tank mixed with 0.5% Silwet L-77, were applied as comparative treatments. Results, averaged for all replicates of each treatment, are shown in Table 13.

TABLE 13

| Spray composition | Glyphosate rate g a.e./ha | % Inhibition SIDSP |
|---|---|---|
| Formulation B | 200 | 37 |
|  | 300 | 47 |
|  | 400 | 50 |
| Formulation B + Silwet L-77 0.5% v/v | 200 | 93 |
|  | 300 | 100 |
|  | 400 | 99 |
| Formulation C | 200 | 47 |
|  | 300 | 63 |
|  | 400 | 86 |
| Formulation C + Silwet L-77 0.5% v/v | 200 | 88 |
|  | 300 | 92 |
|  | 400 | 99 |
| Formulation B + Fluorad FC-135 0.5% w/v | 200 | 51 |
|  | 300 | 79 |
|  | 400 | 84 |
| Formulation B + Fluorad FC-135 0.25% w/v | 200 | 49 |
|  | 300 | 53 |
|  | 400 | 85 |
| Formulation B + Fluorad FC-135 0.1% w/v | 200 | 44 |
|  | 300 | 58 |
|  | 400 | 70 |
| Formulation C + Fluorad FC-135 0.5% w/v | 200 | 74 |
|  | 300 | 89 |
|  | 400 | 97 |
| Formulation C + Fluorad FC-135 0.25% w/v | 200 | 52 |
|  | 300 | 70 |
|  | 400 | 75 |
| Formulation C + Fluorad FC-135 0.1% w/v | 200 | 45 |
|  | 300 | 74 |
|  | 400 | 87 |
| 12-01 | 200 | 62 |
|  | 300 | 76 |
|  | 400 | 89 |
| 12-02 | 200 | 59 |
|  | 300 | 54 |
|  | 400 | 73 |
| 12-03 | 200 | 56 |
|  | 300 | 89 |
|  | 400 | 80 |
| 12-04 | 200 | 72 |
|  | 300 | 89 |
|  | 400 | 96 |
| 12-05 | 200 | 66 |
|  | 300 | 87 |
|  | 400 | 84 |
| 12-06 | 200 | 60 |
|  | 300 | 74 |
|  | 400 | 86 |
| 12-07 | 200 | 57 |
|  | 300 | 78 |
|  | 400 | 89 |
| 12-08 | 200 | 59 |
|  | 300 | 67 |
|  | 400 | 70 |
| 12-09 | 200 | 57 |
|  | 300 | 65 |
|  | 400 | 74 |
| 12-10 | 200 | 53 |
|  | 300 | 77 |
|  | 400 | 77 |
| 12-11 | 200 | 58 |
|  | 300 | 71 |
|  | 400 | 87 |
| 12-12 | 200 | 54 |
|  | 300 | 70 |
|  | 400 | 82 |
| 12-13 | 200 | 65 |
|  | 300 | 75 |
|  | 400 | 82 |
| 12-14 | 200 | 61 |
|  | 300 | 77 |
|  | 400 | 81 |

On SIDSP in this test, tank mix addition of Fluorad FC-135 to Formulation B enhanced herbicidal effectiveness over that obtained with Formulation C alone, only at the 0.5% concentration of Fluorad FC-135. Likewise, when added to a glyphosate composition containing 0.25% lecithin, Fluorad FC-135 enhanced herbicidal effectiveness most significantly at the 0.5% concentration (composition 12-04).

EXAMPLE 14

Aqueous spray compositions were prepared containing glyphosate IPA salt and excipient ingredients as shown in Table 14a. Process (iii) was followed for all compositions, using soybean lecithin (20% phospholipid, Avanti). The following compositions had a pH of approximately 5: 14-01, 14-03, 14-07, 14-08, 14-10 and 14-12 to 14-17. All others were adjusted to a pH of approximately 7.

TABLE 14a

| Spray composition | Lecithin g/l | Fluorad FC-135 | Silwet L-77 | Diacid 1550 | Components sonicated with lecithin |
|---|---|---|---|---|---|
| | | % w/w | | | |
| 14-01 | 5.0 | | | | none |
| 14-02 | 5.0 | | | | none |
| 14-03 | 2.5 | | | | none |
| 14-04 | 2.5 | | | | none |
| 14-05 | 5.0 | | | | glyphosate |
| 14-06 | 5.0 | | 0.50 | | L-77 |
| 14-07 | 5.0 | | 0.50 | | L-77 |
| 14-08 | 2.5 | | 0.50 | | L-77 |
| 14-09 | 2.5 | | 0.50 | | L-77 |
| 14-10 | 2.5 | | 0.25 | | glyphosate |
| 14-11 | 2.5 | | 0.25 | | glyphosate |
| 14-12 | 2.5 | 0.25 | | | none |
| 14-13 | 2.5 | 0.25 | | | glyphosate |
| 14-14 | 2.5 | 0.10 | | | none |
| 14-15 | 2.5 | 0.10 | | | glyphosate |
| 14-16 | 2.5 | | 0.25 | 0.25 | L-77, Diacid |
| 14-17 | 2.5 | | 0.10 | 0.05 | L-77, Diacid |

Velvetleaf (*Abutilon theophrasti*, ABUTH) and Japanese millet (*Echinochloa crus-galli*, ECHCF) plants were grown and treated by the standard procedures given above. Applications of spray compositions were made 17 days after planting ABUTH and 20 days after planting ECHCF, and evaluation of herbicidal inhibition was done 20 days after application.

In addition to compositions 14-01 to 14-17, spray compositions were prepared by tank mixing Formulations B and C with Fluorad FC-135 at two concentrations. Formulations B and C, alone and tank mixed with 0.5% and 0.25% Silwet L-77, were applied as comparative treatments. Results, averaged for all replicates of each treatment, are shown in Table 14b.

TABLE 14b

| Spray composition | Glyphosate rate g a.e./ha | % Inhibition ABUTH | % Inhibition ECHCF |
|---|---|---|---|
| Formulation B | 200 | 53 | 43 |
|  | 300 | 73 | 50 |
|  | 400 | 91 | 74 |
| Formulation B + Silwet L-77 0.5% v/v | 200 | 86 | 24 |
|  | 300 | 88 | 15 |
|  | 400 | 94 | 58 |
| Formulation B + Silwet L-77 0.25% w/v | 200 | 80 | 22 |
|  | 300 | 93 | 38 |
|  | 400 | 87 | 38 |
| Formulation C | 200 | 56 | 88 |
|  | 300 | 86 | 98 |

TABLE 14b-continued

| Spray composition | Glyphosate rate g a.e./ha | % Inhibition ABUTH | % Inhibition ECHCF |
|---|---|---|---|
| Formulation C + Silwet L-77 0.5% v/v | 200 | 94 | 98 |
|  | 200 | 87 | 23 |
|  | 300 | 93 | 52 |
|  | 400 | 91 | 60 |
| Formulation C + Silwet L-77 0.25% v/v | 200 | 79 | 42 |
|  | 300 | 83 | 73 |
|  | 400 | 87 | 95 |
| Formulation B + Fluorad FC-135 0.25% w/v | 200 | 79 | 49 |
|  | 300 | 89 | 77 |
|  | 400 | 94 | 85 |
| Formulation B + Fluorad FC-135 0.1% w/v | 200 | 73 | 64 |
|  | 300 | 89 | 68 |
|  | 400 | 92 | 75 |
| Formulation C + Fluorad FC-135 0.25% w/v | 200 | 73 | 86 |
|  | 300 | 75 | 90 |
|  | 400 | 90 | 95 |
| Formulation C + Fluorad FC-135 0.1% w/v | 200 | 53 | 97 |
|  | 300 | 89 | 96 |
|  | 400 | 91 | 99 |
| 14-01 | 200 | 71 | 66 |
|  | 300 | 89 | 62 |
|  | 400 | 97 | 85 |
| 14-02 | 200 | 83 | 52 |
|  | 300 | 89 | 72 |
|  | 400 | 82 | 93 |
| 14-03 | 200 | 54 | 53 |
|  | 300 | 89 | 84 |
|  | 400 | 93 | 77 |
| 14-04 | 200 | 81 | 38 |
|  | 300 | 94 | 76 |
|  | 400 | 98 | 88 |
| 14-05 | 200 | 85 | 53 |
|  | 300 | 95 | 80 |
|  | 400 | 94 | 91 |
| 14-06 | 200 | 80 | 0 |
|  | 300 | 95 | 100 |
|  | 400 | 98 | 94 |
| 14-07 | 200 | 72 | 50 |
|  | 300 | 95 | 84 |
|  | 400 | 98 | 92 |
| 14-08 | 200 | 81 | 69 |
|  | 300 | 99 | 83 |
|  | 400 | 100 | 80 |
| 14-09 | 200 | 86 | 38 |
|  | 300 | 94 | 80 |
|  | 400 | 96 | 90 |
| 14-10 | 200 | 58 | 67 |
|  | 300 | 82 | 85 |
|  | 400 | 92 | 90 |
| 14-11 | 200 | 83 | 64 |
|  | 300 | 88 | 74 |
|  | 400 | 90 | 88 |
| 14-12 | 200 | 89 | 90 |
|  | 300 | 100 | 88 |
|  | 400 | 100 | 98 |
| 14-13 | 200 | 95 | 91 |
|  | 300 | 93 | 97 |
|  | 400 | 100 | 98 |
| 14-14 | 200 | 88 | 93 |
|  | 300 | 93 | 85 |
|  | 400 | 98 | 90 |
| 14-15 | 200 | 85 | 87 |
|  | 300 | 98 | 98 |
|  | 400 | 96 | 100 |
| 14-16 | 200 | 76 | 72 |
|  | 300 | 83 | 87 |
|  | 400 | 89 | 97 |
| 14-17 | 200 | 53 | 67 |
|  | 300 | 48 | 62 |
|  | 400 | 82 | 85 |

Compositions 14-12 to 14-15, containing 0.25% lecithin together with Fluorad FC-135, exhibited much greater herbicidal effectiveness on both ABUTH and ECHCF than composition 14-03, containing 0.25% lecithin but no Fluorad FC-135, or even composition 14-01, containing 0.5% lecithin but no Fluorad FC-135. No great or consistent difference was seen between compositions where glyphosate had been sonicated together with the lecithin (14-13 and 14-15) than where the lecithin had been sonicated alone (14-12 and 14-14).

EXAMPLE 15

Compositions 14-01 to 14-17 of Example 14, and tank mixtures of Formulations B and C with Fluorad FC-135, were tested in this Example. Prickly sida (*Sida spinosa*, SIDSP) plants were grown and treated by the standard procedures given above. Applications of spray compositions were made 22 days after planting SIDSP, and evaluation of herbicidal inhibition was done 19 days after application.

Formulations B and C, alone and tank mixed with 0.5% and 0.25% Silwet L-77, were applied as comparative treatments. Results, averaged for all replicates of each treatment, are shown in Table 15.

TABLE 15

| Spray composition | Glyphosate rate g a.e./ha | % Inhibition SIDSP |
|---|---|---|
| Formulation B | 200 | 23 |
|  | 300 | 37 |
|  | 400 | 32 |
| Formulation B + Silwet L-77 0.5% v/v | 200 | 30 |
|  | 300 | 39 |
|  | 400 | 45 |
| Formulation B + Silwet L-77 0.25% w/v | 200 | 28 |
|  | 300 | 49 |
|  | 400 | 28 |
| Formulation C | 200 | 41 |
|  | 300 | 54 |
|  | 400 | 84 |
| Formulation C + Silwet L-77 0.5% v/v | 200 | 43 |
|  | 300 | 66 |
|  | 400 | 86 |
| Formulation C + Silwet L-77 0.25% v/v | 200 | 17 |
|  | 300 | 35 |
|  | 400 | 58 |
| Formulation B + Fluorad FC-135 0.25% w/v | 200 | 48 |
|  | 300 | 60 |
|  | 400 | 62 |
| Formulation B + Fluorad FC-135 0.1% w/v | 200 | 31 |
|  | 300 | 47 |
|  | 400 | 75 |
| Formulation C + Fluorad FC-135 0.25% w/v | 200 | 43 |
|  | 300 | 57 |
|  | 400 | 71 |
| Formulation C + Fluorad FC-135 0.1% w/v | 200 | 32 |
|  | 300 | 71 |
|  | 400 | 63 |
| 14-01 | 200 | 51 |
|  | 300 | 55 |
|  | 400 | 76 |
| 14-02 | 200 | 51 |
|  | 300 | 68 |
|  | 400 | 84 |
| 14-03 | 200 | 55 |
|  | 300 | 51 |
|  | 400 | 72 |
| 14-04 | 200 | 50 |
|  | 300 | 64 |
|  | 400 | 75 |
| 14-05 | 200 | 46 |
|  | 300 | 53 |
|  | 400 | 61 |
| 14-06 | 200 | 40 |
|  | 300 | 44 |
|  | 400 | 73 |
| 14-07 | 200 | 23 |
|  | 300 | 32 |

TABLE 15-continued

| Spray composition | Glyphosate rate g a.e./ha | % Inhibition SIDSP |
|---|---|---|
|  | 400 | 39 |
| 14-08 | 200 | 18 |
|  | 300 | 44 |
|  | 400 | 57 |
| 14-09 | 200 | 25 |
|  | 300 | 30 |
|  | 400 | 43 |
| 14-10 | 200 | 19 |
|  | 300 | 36 |
|  | 400 | 38 |
| 14-11 | 200 | 35 |
|  | 300 | 48 |

TABLE 15-continued

| Spray composition | Glyphosate rate g a.e./ha | % Inhibition SIDSP |
|---|---|---|
|  | 400 | 57 |
| 14-12 | 200 | 65 |
|  | 300 | 80 |
|  | 400 | 88 |
| 14-13 | 200 | 68 |
|  | 300 | 75 |
|  | 400 | 87 |
| 14-14 | 200 | 76 |
|  | 300 | 76 |
|  | 400 | 72 |
| 14-15 | 200 | 54 |
|  | 300 | 73 |
|  | 400 | 84 |
| 14-16 | 200 | 44 |
|  | 300 | 51 |
|  | 400 | 63 |
| 14-17 | 200 | 23 |
|  | 300 | 45 |
|  | 400 | 57 |

Compositions 14-12 to 14-15, containing 0.25% lecithin together with Fluorad FC-135, exhibited greater herbicidal effectiveness on SIDSP than composition 14-03, containing 0.25% lecithin but no Fluorad FC-135, or even composition 14-01, containing 0.5% lecithin but no Fluorad FC-135. No great or consistent difference was seen between compositions where glyphosate had been sonicated together with the lecithin (14-13 and 14-15) than where the lecithin had been sonicated alone (14-12 and 14-14).

EXAMPLE 16

Aqueous spray compositions were prepared containing glyphosate IPA salt and excipient ingredients as shown in Table 16a. Process (iii) was followed for all compositions, using soybean lecithin (20% phospholipid, Avanti). The pH of all compositions was adjusted to approximately 7.

TABLE 16a

| Spray comp. | Lecithin g/l | Fluorad FC-135 | Other (*) | (*) Other ingredient | Components sonicated with lecithin |
|---|---|---|---|---|---|
| 16-01 | 2.5 |  |  |  | none |
| 16-02 | 2.5 |  |  |  | glyphosate |
| 16-03 | 2.5 | 0.25 |  |  | none |
| 16-04 | 2.5 | 0.25 |  |  | glyphosate |
| 16-05 | 2.5 |  | 0.25 | Silwet 800 | none |
| 16-06 | 2.5 |  | 0.25 | Silwet 800 | Silwet 800 |
| 16-07 | 2.5 |  | 0.25 | Silwet 800 | Silwet, glyphosate |
| 16-08 | 0.5 |  |  |  | none |
| 16-09 | 0.5 |  |  |  | glyphosate |
| 16-10 | 0.5 | 0.05 |  |  | none |
| 16-11 | 0.5 | 0.05 |  |  | glyphosate |
| 16-12 | 0.5 | 0.03 | 0.02 | Silwet L-77 | Silwet L-77 |
| 16-13 | 0.5 |  | 0.05 | methyl caprate | Me caprate |
| 16-14 | 0.5 | 0.05 | 0.05 | methyl caprate | Me caprate |
| 16-15 | 0.5 | 0.05 | 0.05 | methyl caprate | Me caprate, glyphosate |
| 16-16 | 0.5 |  | 0.01 | PVA | none |
| 16-17 | 0.5 |  | 0.01 | PVA | glyphosate |
| 16-18 | 0.5 | 0.05 | 0.01 | PVA | glyphosate |
| 16-19 | 0.5 |  | 0.05 + 0.01 | L-77 + PVA | Silwet L-77 |

Velvetleaf (*Abutilon theophrasti*, ABUTH) and Japanese millet (*Echinochloa crus-galli*, ECHCF) plants were grown and treated by the standard procedures given above. Applications of spray compositions were made 19 days after planting ABUTH and 21 days after planting ECHCF, and evaluation of herbicidal inhibition was done 17 days after application.

In addition to compositions 16-01 to 16-19, spray compositions were prepared by tank mixing Formulations B and C with Fluorad FC-135 at two concentrations. Formulations B and C, alone and tank mixed with 0.5% Silwet 800, were applied as comparative treatments. Results, averaged for all replicates of each treatment, are shown in Table 16b.

TABLE 16b

| Spray composition | Glyphosate rate g a.e./ha | % Inhibition ABUTH | % Inhibition ECHCF |
|---|---|---|---|
| Formulation B | 150 | 13 | 28 |
|  | 250 | 37 | 51 |
|  | 350 | 56 | 38 |
| Formulation B + Silwet 800 0.25% v/v | 150 | 81 | 15 |
|  | 250 | 89 | 17 |
|  | 350 | 91 | 20 |
| Formulation C | 150 | 32 | 65 |

TABLE 16b-continued

| Spray composition | Glyphosate rate g a.e./ha | % Inhibition ABUTH | % Inhibition ECHCF |
|---|---|---|---|
|  | 250 | 59 | 91 |
|  | 350 | 85 | 89 |
| Formulation C + | 150 | 91 | 17 |
| Silwet 800 0.25% v/v | 250 | 91 | 23 |
|  | 350 | 95 | 48 |
| Formulation B + | 150 | 31 | 58 |
| Fluorad FC-135 0.25% w/v | 250 | 53 | 68 |
|  | 350 | 71 | 84 |
| Formulation B + | 150 | 31 | 29 |
| Fluorad FC-135 0.05% w/v | 250 | 44 | 69 |
|  | 350 | 95 | 79 |
| Formulation C + | 150 | 46 | 45 |
| Fluorad FC-135 0.25% w/v | 250 | 69 | 79 |
|  | 350 | 86 | 77 |
| Formulation C + | 150 | 44 | 57 |
| Fluorad FC-135 0.05% w/v | 250 | 60 | 87 |
|  | 350 | 86 | 88 |
| 16-01 | 150 | 55 | 50 |
|  | 250 | 87 | 81 |
|  | 350 | 89 | 88 |
| 16-02 | 150 | 56 | 54 |
|  | 250 | 89 | 69 |
|  | 350 | 87 | 98 |
| 16-03 | 150 | 89 | 68 |
|  | 250 | 89 | 84 |
|  | 350 | 91 | 90 |
| 16-04 | 150 | 63 | 68 |
|  | 250 | 89 | 86 |
|  | 350 | 99 | 89 |
| 16-05 | 150 | 81 | 51 |
|  | 250 | 87 | 84 |
|  | 350 | 94 | 26 |
| 16-06 | 150 | 67 | 0 |
|  | 250 | 93 | 62 |
|  | 350 | 94 | 81 |
| 16-07 | 150 | 81 | 35 |
|  | 250 | 84 | 51 |
|  | 350 | 95 | 62 |
| 16-08 | 150 | 59 | 51 |
|  | 250 | 84 | 69 |
|  | 350 | 98 | 90 |
| 16-09 | 150 | 64 | 59 |
|  | 250 | 85 | 61 |
|  | 350 | 94 | 96 |
| 16-10 | 150 | 73 | 74 |
|  | 250 | 87 | 83 |
|  | 350 | 98 | 96 |
| 16-11 | 150 | 76 | 64 |
|  | 250 | 88 | 79 |
|  | 350 | 94 | 81 |
| 16-12 | 150 | 59 | 46 |
|  | 250 | 82 | 88 |
|  | 350 | 92 | 82 |
| 16-13 | 150 | 61 | 45 |
|  | 250 | 90 | 69 |
|  | 350 | 93 | 90 |
| 16-14 | 150 | 76 | 50 |
|  | 250 | 95 | 73 |
|  | 350 | 99 | 91 |
| 16-15 | 150 | 78 | 67 |
|  | 250 | 95 | 80 |
|  | 350 | 99 | 85 |
| 16-16 | 150 | 48 | 42 |
|  | 250 | 77 | 87 |
|  | 350 | 87 | 75 |
| 16-17 | 150 | 47 | 63 |
|  | 250 | 85 | 67 |
|  | 350 | 90 | 78 |
| 16-18 | 150 | 55 | 46 |
|  | 250 | 82 | 77 |
|  | 350 | 90 | 87 |
| 16-19 | 150 | 32 | 23 |
|  | 250 | 43 | 31 |
|  | 350 | 76 | 65 |

As in Example 10, glyphosate compositions (16-10 and 16-11) containing just 0.05% lecithin and 0.05% Fluorad FC-135 exhibited surprisingly great herbicidal efficacy in this test. Sonicating the lecithin in the presence of glyphosate in an effort to encapsulate some of the glyphosate (composition 16-11) did not give an advantage in performance over sonicating the lecithin alone (composition 16-10); indeed on ECHCF herbicidal efficacy was slightly better without such efforts to encapsulate the glyphosate. Addition of methyl caprate to compositions containing lecithin with or without Fluorad FC-135 (16-13 to 16-15) improved herbicidal effectiveness on ABUTH but had little effect on ECHCF.

EXAMPLE 17

Aqueous spray compositions were prepared containing glyphosate IPA salt and excipient ingredients as shown in Table 17a. Process (iii) was followed for all compositions, using soybean lecithin (20% phospholipid, Avanti). The pH of all compositions was adjusted to approximately 7.

TABLE 17a

| Spray composition | Lecithin g/l | % w/w Fluorad FC-135 | Other (*) | (*) Other ingredient | Components sonicated with lecithin |
|---|---|---|---|---|---|
| 17-01 | 2.5 | | | | none |
| 17-02 | 2.5 | 0.25 | | | none |
| 17-03 | 2.5 | 0.25 | | | glyphosate |
| 17-04 | 2.5 | 0.25 | 0.025 | PVA | none |
| 17-05 | 1.0 | | | | none |
| 17-06 | 1.0 | | | | glyphosate |
| 17-07 | 1.0 | 0.10 | | | none |
| 17-08 | 1.0 | 0.10 | | | glyphosate |
| 17-09 | 1.0 | 0.05 | | | none |
| 17-10 | 1.0 | 0.05 | | | glyphosate |
| 17-11 | 1.0 | | 0.100 | PVA | none |
| 17-12 | 1.0 | | 0.025 | PVA | none |
| 17-13 | 1.0 | 0.05 | 0.025 | PVA | none |
| 17-14 | 1.0 | | 0.100 | sodium cholate | Na cholate |
| 17-15 | 1.0 | | 0.020 | sodium cholate | Na cholate |
| 17-16 | 1.0 | 0.05 | 0.020 | sodium cholate | Na cholate |
| 17-17 | 0.5 | | | | none |
| 17-18 | 0.5 | 0.05 | | | glyphosate |
| 17-19 | 0.5 | 0.05 | 0.020 | sodium cholate | Na cholate |

Velvetleaf (*Abutilon theophrasti,* ABUTH) and Japanese millet (*Echinochloa crus-galli,* ECHCF) plants were grown and treated by the standard procedures given above. Applications of spray compositions were made 19 days after planting ABUTH and 21 days after planting ECHCF, and evaluation of herbicidal inhibition was done 16 days after application.

In addition to compositions 17-01 to 17-19, spray compositions were prepared by tank mixing Formulations B and C with Fluorad FC-135 at various concentrations. Formulations B and C alone were applied as comparative treatments. Results, averaged for all replicates of each treatment, are shown in Table 17b.

TABLE 17b

| Spray composition | Glyphosate rate g a.e./ha | % Inhibition ABUTH | ECHCF |
|---|---|---|---|
| Formulation B | 200 | 32 | 25 |
| | 300 | 50 | 34 |
| | 400 | 54 | 35 |

TABLE 17b-continued

| Spray composition | Glyphosate rate g a.e./ha | % Inhibition ABUTH | ECHCF |
|---|---|---|---|
| Formulation C | 200 | 59 | 92 |
|  | 300 | 76 | 100 |
|  | 400 | 93 | 97 |
| Formulation B + Fluorad FC-135 0.25% w/v | 200 | 43 | 48 |
|  | 300 | 64 | 52 |
|  | 400 | 84 | 71 |
| Formulation B + Fluorad FC-135 0.1% w/v | 200 | 61 | 78 |
|  | 300 | 65 | 59 |
|  | 400 | 100 | 86 |
| Formulation B + Fluorad FC-135 0.05% w/v | 200 | 58 | 30 |
|  | 300 | 82 | 55 |
|  | 400 | 88 | 77 |
| Formulation C + Fluorad FC-135 0.25% w/v | 200 | 53 | 55 |
|  | 300 | 76 | 68 |
|  | 400 | 88 | 93 |
| Formulation C + Fluorad FC-135 0.1% w/v | 200 | 59 | 70 |
|  | 300 | 89 | 85 |
|  | 400 | 93 | 83 |
| Formulation C + Fluorad FC-135 0.05% w/v | 200 | 60 | 72 |
|  | 300 | 82 | 100 |
|  | 400 | 94 | 94 |
| 17-01 | 200 | 73 | 52 |
|  | 300 | 88 | 80 |
|  | 400 | 94 | 90 |
| 17-02 | 200 | 83 | 80 |
|  | 300 | 96 | 83 |
|  | 400 | 97 | 95 |
| 17-03 | 200 | 86 | 73 |
|  | 300 | 95 | 79 |
|  | 400 | 98 | 94 |
| 17-04 | 200 | 73 | 72 |
|  | 300 | 94 | 86 |
|  | 400 | 96 | 93 |
| 17-05 | 200 | 67 | 68 |
|  | 300 | 94 | 74 |
|  | 400 | 96 | 91 |
| 17-06 | 200 | 65 | 61 |
|  | 300 | 79 | 82 |
|  | 400 | 91 | 81 |
| 17-07 | 200 | 75 | 65 |
|  | 300 | 92 | 84 |
|  | 400 | 98 | 91 |
| 17-08 | 200 | 66 | 70 |
|  | 300 | 87 | 96 |
|  | 400 | 97 | 97 |
| 17-09 | 200 | 83 | 73 |
|  | 300 | 91 | 83 |
|  | 400 | 97 | 89 |
| 17-10 | 200 | 89 | 70 |
|  | 300 | 92 | 79 |
|  | 400 | 91 | 74 |
| 17-11 | 200 | 65 | 58 |
|  | 300 | 86 | 86 |
|  | 400 | 97 | 100 |
| 17-12 | 200 | 75 | 64 |
|  | 300 | 79 | 85 |
|  | 400 | 91 | 87 |
| 17-13 | 200 | 79 | 53 |
|  | 300 | 81 | 83 |
|  | 400 | 96 | 88 |
| 17-14 | 200 | 56 | 69 |
|  | 300 | 80 | 95 |
|  | 400 | 92 | 93 |
| 17-15 | 200 | 57 | 77 |
|  | 300 | 67 | 91 |
|  | 400 | 88 | 90 |
| 17-16 | 200 | 88 | 82 |
|  | 300 | 85 | 87 |
|  | 400 | 76 | 72 |
| 17-17 | 200 | 53 | 66 |
|  | 300 | 71 | 72 |
|  | 400 | 87 | 83 |
| 17-18 | 200 | 89 | 85 |
|  | 300 | 79 | 72 |
|  | 400 | 65 | 60 |

TABLE 17b-continued

| Spray composition | Glyphosate rate g a.e./ha | % Inhibition ABUTH | ECHCF |
|---|---|---|---|
| 17-19 | 200 | 77 | 65 |
|  | 300 | 87 | 85 |
|  | 400 | 92 | 94 |

In glyphosate compositions containing lecithin and Fluorad FC-135, no consistent difference in herbicidal effectiveness was observed between those where lecithin was sonicated alone (17-02, 17-07, 17-09) and those where glyphosate and lecithin were sonicated together (17-03, 17-08, 17-10). The anomalous inversion of the apparent rate response to glyphosate seen with composition 17-18 is believed to be the result of an error in application or recording and the data for this composition should be ignored in this Example.

EXAMPLE 18

Aqueous spray compositions were prepared containing glyphosate IPA salt and excipient ingredients as shown in Table 18a. Process (iii) was followed for all compositions, using soybean lecithin (20% phospholipid, Avanti). The pH of all compositions was adjusted to approximately 7.

TABLE 18a

| Spray composition | Lecithin g/l | % w/w Fluorad FC-135 | PVA | Components sonicated with lecithin |
|---|---|---|---|---|
| 18-01 | 2.5 |  |  | none |
| 18-02 | 1.0 |  |  | none |
| 18-03 | 0.5 |  |  | none |
| 18-04 | 0.2 |  |  | none |
| 18-05 | 1.0 | 0.25 |  | none |
| 18-06 | 1.0 | 0.25 |  | glyphosate |
| 18-07 | 1.0 | 0.10 |  | none |
| 18-08 | 1.0 | 0.10 |  | glyphosate |
| 18-09 | 0.5 | 0.05 |  | none |
| 18-10 | 0.5 | 0.05 |  | glyphosate |
| 18-11 | 2.5 |  | 0.10 | none |

*Hemp sesbania* (*Sesbania exaltata*, SEBEX) plants were grown and treated by the standard procedures given above. Applications of spray compositions were made 22 days after planting SEBEX, and evaluation of herbicidal inhibition was done 21 days after application.

In addition to compositions 18-01 to 18-11, spray compositions were prepared by tank mixing Formulations B and C with Fluorad FC-135 at various concentrations. Formulations B and C alone, and Formulation B tank mixed with 0.1% PVA (polyvinyl alcohol), were applied as comparative treatments. Results, averaged for all replicates of each treatment, are shown in Table 18b.

TABLE 18b

| Spray composition | Glyphosate rate g a.e./ha | % Inhibition SEBEX |
|---|---|---|
| Formulation B | 500 | 43 |
|  | 1000 | 54 |
|  | 1500 | 44 |
| Formulation B + PVA 0.1% w/v | 500 | 53 |
|  | 1000 | 45 |

TABLE 18b-continued

| Spray composition | Glyphosate rate g a.e./ha | % Inhibition SEBEX |
|---|---|---|
|  | 1500 | 44 |
| Formulation C | 500 | 56 |
|  | 1000 | 62 |
|  | 1500 | 63 |
| Formulation B + | 500 | 40 |
| Fluorad FC-135 0.25% w/v | 1000 | 45 |
|  | 1500 | 60 |
| Formulation B + | 500 | 33 |
| Fluorad FC-135 0.1% w/v | 1000 | 51 |
|  | 1500 | 53 |
| Formulation B + | 500 | 21 |
| Fluorad FC-135 0.05% w/v | 1000 | 18 |
|  | 1500 | 29 |
| Formulation C + | 500 | 34 |
| Fluorad FC-135 0.25% w/v | 1000 | 41 |
|  | 1500 | 58 |
| Formulation C + | 500 | 50 |
| Fluorad FC-135 0.1% w/v | 1000 | 43 |
|  | 1500 | 52 |
| Formulation C + | 500 | 48 |
| Fluorad FC-135 0.05% w/v | 1000 | 49 |
|  | 1500 | 46 |
| 18-01 | 500 | 22 |
|  | 1000 | 33 |
|  | 1500 | 37 |
| 18-02 | 500 | 16 |
|  | 1000 | 24 |
|  | 1500 | 28 |
| 18-03 | 500 | 15 |
|  | 1000 | 24 |
|  | 1500 | 27 |
| 18-04 | 500 | 17 |
|  | 1000 | 13 |
|  | 1500 | 31 |
| 18-05 | 500 | 28 |
|  | 1000 | 64 |
|  | 1500 | 68 |
| 18-06 | 500 | 64 |
|  | 1000 | 51 |
|  | 1500 | 61 |
| 18-07 | 500 | 65 |
|  | 1000 | 51 |
|  | 1500 | 63 |
| 18-08 | 500 | 50 |
|  | 1000 | 56 |
|  | 1500 | 30 |
| 18-09 | 500 | 40 |
|  | 1000 | 59 |
|  | 1500 | 66 |
| 18-10 | 500 | 31 |
|  | 1000 | 23 |
|  | 1500 | 49 |
| 18-11 | 500 | 43 |
|  | 1000 | 39 |
|  | 1500 | 74 |

Glyphosate activity on SEBEX was extremely weak in this test and no firm conclusions can be drawn.

EXAMPLE 19

Aqueous spray compositions were prepared containing glyphosate IPA salt and excipient ingredients as shown in Table 19a. Process (iii) was followed for all compositions, using soybean lecithin (20% phospholipid, Avanti). The pH of all compositions was adjusted to approximately 7.

TABLE 19a

| Spray composition | Lecithin g/l | % w/w Fluorad FC-135 | Components sonicated with lecithin |
|---|---|---|---|
| 19-01 | 2.5 |  | none |
| 19-02 | 1.0 |  | none |
| 19-03 | 0.5 |  | none |
| 19-04 | 0.2 |  | none |
| 19-05 | 1.0 | 0.25 | none |
| 19-06 | 1.0 | 0.25 | glyphosate |

Sicklepod (*Cassia obtusifolia*, CASOB) plants were grown and treated by the standard procedures given above. Applications of spray compositions were made 22 days after planting CASOB, and evaluation of herbicidal inhibition was done 21 days after application.

In addition to compositions 19-01 to 19-06, spray compositions were prepared by tank mixing Formulations B and C with Fluorad FC-135 at two concentrations. Formulations B and C alone were applied as comparative treatments. Results, averaged for all replicates of each treatment, are shown in Table 19b.

TABLE 19b

| Spray composition | Glyphosate rate g a.e./ha | % Inhibition CASOB |
|---|---|---|
| Formulation B | 500 | 35 |
|  | 800 | 37 |
|  | 1200 | 34 |
| Formulation C | 500 | 49 |
|  | 800 | 49 |
|  | 1200 | 66 |
| Formulation B + | 500 | 45 |
| Fluorad FC-135 0.25% w/v | 800 | 50 |
|  | 1200 | 71 |
| Formulation B + | 500 | 49 |
| Fluorad FC-135 0.1% w/v | 800 | 49 |
|  | 1200 | 78 |
| Formulation C + | 500 | 60 |
| Fluorad FC-135 0.25% w/v | 800 | 75 |
|  | 1200 | 68 |
| Formulation C + | 500 | 47 |
| Fluorad FC-135 0.1% w/v | 800 | 85 |
|  | 1200 | 74 |
| 19-01 | 500 | 54 |
|  | 800 | 51 |
|  | 1200 | 43 |
| 19-02 | 500 | 37 |
|  | 800 | 69 |
|  | 1200 | 52 |
| 19-03 | 500 | 35 |
|  | 800 | 51 |
|  | 1200 | 43 |
| 19-04 | 500 | 71 |
|  | 800 | 69 |
|  | 1200 | 57 |
| 19-05 | 500 | 47 |
|  | 800 | 73 |
|  | 1200 | 89 |
| 19-06 | 500 | 49 |
|  | 800 | 51 |
|  | 1200 | 73 |

On CASOB, the addition of Fluorad FC-135 to a glyphosate composition containing lecithin significantly enhanced herbicidal effectiveness (compare compositions 19-05 and 19-02). However, where glyphosate was sonicated together with the lecithin (composition 19-06), herbicidal effectiveness was reduced.

EXAMPLE 20

Aqueous spray compositions were prepared containing glyphosate IPA salt and excipient ingredients as shown in Table 20a. Process (iii) was followed for all compositions, using soybean lecithin (20% phospholipid, Avanti). The pH of all compositions was adjusted to approximately 7.

TABLE 20a

| Spray composition | Lecithin g/l | Fluorad FC-135 | Diacid 1550 | Components sonicated with lecithin |
|---|---|---|---|---|
| | | % w/w | | |
| 20-01 | 2.5 | | | none |
| 20-02 | 0.5 | | | none |
| 20-03 | 0.2 | | | none |
| 20-04 | 2.5 | 0.05 | | none |
| 20-05 | 0.5 | 0.05 | | none |
| 20-06 | 0.2 | 0.05 | | none |
| 20-07 | 0.5 | | 0.05 | Diacid |

Common lambsquarter (*Chenopodium album*, CHEAL) plants were grown and treated by the standard procedures given above. Applications of spray compositions were made 31 days after planting CHEAL, and evaluation of herbicidal inhibition was done 18 days after application.

In addition to compositions 20-01 to 20-07, spray compositions were prepared by tank mixing Formulations B and C with 0.5% Fluorad FC-135. Formulations B and C alone were applied as comparative treatments. Results, averaged for all replicates of each treatment, are shown in Table 20b.

TABLE 20b

| Spray composition | Glyphosate rate g a.e./ha | % Inhibition CHEAL |
|---|---|---|
| Formulation B | 150 | 0 |
| | 250 | 0 |
| | 350 | 3 |
| Formulation C | 150 | 18 |
| | 250 | 68 |
| | 350 | 98 |
| Formulation B + | 150 | 0 |
| Fluorad FC-135 0.05% w/v | 250 | 10 |
| | 350 | 5 |
| Formulation C + | 150 | 3 |
| Fluorad FC-135 0.05% w/v | 250 | 50 |
| | 350 | 60 |
| 20-01 | 150 | 0 |
| | 250 | 27 |
| | 350 | 60 |
| 20-02 | 150 | 0 |
| | 250 | 5 |
| | 350 | 8 |
| 20-03 | 150 | 5 |
| | 250 | 0 |
| | 350 | 8 |
| 20-04 | 150 | 18 |
| | 250 | 29 |
| | 350 | 63 |
| 20-05 | 150 | 17 |
| | 250 | 14 |
| | 350 | 87 |
| 20-06 | 150 | 44 |
| | 250 | 40 |
| | 350 | 38 |
| 20-07 | 150 | 10 |
| | 250 | 35 |
| | 350 | 73 |

Glyphosate activity on CHEAL was very weak in this test and no definitive conclusions can be drawn. However, none of the compositions of the invention performed as well as the commercial standard Formulation C in this test. Fluorad FC-135 at the extremely low concentration of 0.05% was ineffective as a tank-mix additive, but addition of 0.05% Fluorad FC-135 did enhance the performance of compositions containing lecithin (compare compositions 20-04 to 20-06 with 20-01 to 20-03).

EXAMPLE 21

Aqueous spray compositions were prepared containing glyphosate IPA salt and excipient ingredients as shown in Table 21a. Process (iii) was followed for all compositions, using soybean lecithin (20% phospholipid, Avanti). The pH of all compositions was adjusted to approximately 7.

TABLE 21a

| Spray composition | Lecithin g/l | Fluorad FC-135 | Aerosol OT | Methyl caprate | Components sonicated with lecithin |
|---|---|---|---|---|---|
| | | % w/w | | | |
| 21-01 | 2.5 | | | | none |
| 21-02 | 2.5 | | | | glyphosate |
| 21-03 | 1.0 | | | | none |
| 21-04 | 1.0 | | | | glyphosate |
| 21-05 | 0.5 | | | | none |
| 21-06 | 0.5 | | | | glyphosate |
| 21-07 | 0.2 | | | | none |
| 21-08 | 0.2 | | | | glyphosate |
| 21-09 | 0.5 | | 0.05 | | none |
| 21-10 | 0.5 | | 0.05 | | AOT, glyphosate |
| 21-11 | 0.5 | | 0.05 | | AOT |
| 21-12 | 2.5 | 0.25 | | | none |
| 21-13 | 0.5 | 0.05 | | | none |
| 21-14 | 0.5 | 0.05 | | | glyphosate |
| 21-15 | 0.5 | | | 0.05 | Me caprate |
| 21-16 | 0.5 | 0.05 | | 0.05 | Me caprate |
| 21-17 | 0.2 | 0.02 | | | none |
| 21-18 | 0.2 | 0.02 | | | glyphosate |
| 21-19 | 0.2 | | | 0.02 | Me caprate |

Velvetleaf (*Abutilon theophrasti*, ABUTH), Japanese millet (*Echinochloa crus-galli*, ECHCF), and prickly sida (*Sida spinosa*, SIDSP) plants were grown and treated by the standard procedures given above. Applications of spray compositions were made 19 days after planting ABUTH and 22 days after planting ECHCF. No record was found for the planting date for SIDSP. Evaluation of herbicidal inhibition was done 20 days after application.

In addition to compositions 21-01 to 21-19, spray compositions were prepared by tank mixing Formulations B and C with Fluorad FC-135 at various concentrations. Formulations B and C alone were applied as comparative treatments. Results, averaged for all replicates of each treatment, are shown in Table 21b.

TABLE 21b

| Spray composition | Glyphosate rate g a.e./ha | % Inhibition | | |
|---|---|---|---|---|
| | | ABUTH | ECHCF | SIDSP |
| Formulation B | 150 | 16 | 23 | 30 |
| | 250 | 17 | 33 | 57 |
| | 350 | 24 | 43 | 65 |
| Formulation C | 150 | 18 | 58 | 53 |
| | 250 | 30 | 71 | 79 |
| | 350 | 49 | 83 | 94 |
| Formulation B + | 150 | 27 | 59 | 56 |
| Fluorad FC-135 0.25% w/v | 250 | 45 | 84 | 81 |
| | 350 | 55 | 82 | 91 |
| Formulation B + | 150 | 17 | 43 | 56 |
| Fluorad FC-135 0.1% w/v | 250 | 21 | 56 | 75 |
| | 350 | 64 | 80 | 90 |
| Formulation B + | 150 | 22 | 27 | 38 |
| Fluorad FC-135 0.02% w/v | 250 | 37 | 49 | 69 |
| | 350 | 48 | 68 | 94 |

TABLE 21b-continued

| Spray composition | Glyphosate rate g a.e./ha | % Inhibition ABUTH | ECHCF | SIDSP |
|---|---|---|---|---|
| Formulation C + | 150 | 41 | 41 | 59 |
| Fluorad FC-135 0.25% w/v | 250 | 57 | 53 | 85 |
|  | 350 | 67 | 67 | 94 |
| Formulation C + | 150 | 26 | 39 | 67 |
| Fluorad FC-135 0.05% w/v | 250 | 46 | 66 | 88 |
|  | 350 | 75 | 73 | 93 |
| Formulation C + | 150 | 30 | 52 | 66 |
| Fluorad FC-135 0.02% w/v | 250 | 67 | 50 | 89 |
|  | 350 | 61 | 88 | 92 |
| 21-01 | 150 | 35 | 62 | 64 |
|  | 250 | 63 | 77 | 90 |
|  | 350 | 71 | 83 | 85 |
| 21-02 | 150 | 35 | 44 | 67 |
|  | 250 | 53 | 79 | 86 |
|  | 350 | 58 | 92 | 90 |
| 21-03 | 150 | 37 | 50 | 71 |
|  | 250 | 53 | 76 | 90 |
|  | 350 | 73 | 63 | 97 |
| 21-04 | 150 | 29 | 46 | 61 |
|  | 250 | 43 | 77 | 85 |
|  | 350 | 70 | 85 | 96 |
| 21-05 | 150 | 12 | 36 | 59 |
|  | 250 | 43 | 55 | 83 |
|  | 350 | 53 | 77 | 87 |
| 21-06 | 150 | 19 | 69 | 67 |
|  | 250 | 62 | 47 | 84 |
|  | 350 | 58 | 60 | 95 |
| 21-07 | 150 | 14 | 59 | 59 |
|  | 250 | 39 | 63 | 75 |
|  | 350 | 46 | 77 | 91 |
| 21-08 | 150 | 36 | 37 | 64 |
|  | 250 | 38 | 68 | 82 |
|  | 350 | 47 | 80 | 79 |
| 21-09 | 150 | 8 | 35 | 27 |
|  | 250 | 9 | 51 | 56 |
|  | 350 | 36 | 58 | 67 |
| 21-10 | 150 | 5 | 33 | 24 |
|  | 250 | 15 | 73 | 47 |
|  | 350 | 30 | 66 | 67 |
| 21-11 | 150 | 38 | 49 | 73 |
|  | 250 | 62 | 75 | 89 |
|  | 350 | 71 | 75 | 98 |
| 21-12 | 150 | 7 | 41 | 21 |
|  | 250 | 18 | 67 | 38 |
|  | 350 | 30 | 64 | 61 |
| 21-13 | 150 | 39 | 72 | 65 |
|  | 250 | 65 | 55 | 76 |
|  | 350 | 70 | 68 | 90 |
| 21-14 | 150 | 51 | 53 | 66 |
|  | 250 | 60 | 82 | 85 |
|  | 350 | 65 | 83 | 95 |
| 21-15 | 150 | 15 | 59 | 61 |
|  | 250 | 31 | 54 | 83 |
|  | 350 | 57 | 67 | 84 |
| 21-16 | 150 | 36 | 79 | 66 |
|  | 250 | 50 | 60 | 95 |
|  | 350 | 71 | 95 | 95 |
| 21-17 | 150 | 30 | 52 | 75 |
|  | 250 | 54 | 60 | 84 |
|  | 350 | 48 | 84 | 93 |
| 21-18 | 150 | 43 | 75 | 69 |
|  | 250 | 47 | 78 | 88 |
|  | 350 | missing | missing | 90 |
| 21-19 | 150 | 13 | 42 | 61 |
|  | 250 | 29 | 51 | 79 |
|  | 350 | 42 | 69 | 90 |

In this test the concentration of Fluorad FC-135 which had to be added in tank-mix to Formulation B to bring its herbicidal performance up to that of Formulation C was approximately 0.25% for ECHCF, 0.1% for SIDSP and 0.02% for ABUTH. The herbicidal effectiveness of composition 21-12 (0.25% lecithin, 0.25% Fluorad FC-135) was uncharacteristically weak in this test. However, composition 21-13 (0.05% lecithin, 0.05% Fluorad FC-135) performed well as in previous tests, exceeding the herbicidal effectiveness of Formulation C on ABUTH, at least equalling it on SIDSP and not quite equalling it on ECHCF. Contrary to results obtained in other tests, improved effectiveness on ECHCF and SIDSP was obtained by sonicating the glyphosate with the lecithin (composition 21-14 versus 21-13). The inclusion of methyl caprate (compositions 21-15 and 21-16) also improved efficacy on these species. Surprisingly high herbicidal effectiveness was seen in this test with compositions containing ultra-low concentrations of lecithin and Fluorad FC-135 (0.02% of each, 21-17 and 21-18).

EXAMPLE 22

Aqueous concentrate compositions were prepared containing glyphosate IPA salt and excipient ingredients as shown in Table 22a. Process (iv) was followed for all compositions, using soybean lecithin (20% phospholipid, Avanti). The pH of these compositions was not recorded.

TABLE 22a

| Concentrate composition | % w/w | | | |
|---|---|---|---|---|
| | Glyphosate a.e. | Lecithin | MON 0818 | Fluorad FC-135 |
| 22-01 | 10 | | | 5.0 |
| 22-02 | 10 | | | 10.0 |
| 22-03 | 10 | | | 12.5 |
| 22-04 | 10 | | | 15.0 |
| 22-05 | 10 | | | 20.0 |
| 22-06 | 10 | | | 30.0 |
| 22-07 | 15 | 4.0 | 1.0 | |
| 22-08 | 20 | 5.0 | 0.5 | |
| 22-09 | 20 | 5.0 | 1.0 | |
| 22-10 | 20 | 5.0 | 2.0 | |
| 22-11 | 20 | 4.0 | 1.0 | |
| 22-12 | 25 | 5.0 | 0.5 | |
| 22-13 | 25 | 5.0 | 1.0 | |
| 22-14 | 25 | 5.0 | 2.0 | |
| 22-15 | 25 | 4.0 | 1.0 | |
| 22-16 | 25 | 5.0 | 5.0 | |

Velvetleaf (*Abutilon theophrasti*, ABUTH) and Japanese millet (*Echinochloa crus-galli*, ECHCF) plants were grown and treated by the standard procedures given above. Applications of spray compositions were made 14 days after planting ABUTH and 16 days after planting ECHCF, and evaluation of herbicidal inhibition was done 14 days after application.

Formulation C was applied as a comparative treatment. Results, averaged for all replicates of each treatment, are shown in Table 22b.

TABLE 22b

| Concentrate composition | Glyphosate rate g a.e./ha | % Inhibition ABUTH | ECHCF |
|---|---|---|---|
| Formulation C | 56 | 13 | 45 |
|  | 112 | 43 | 75 |
|  | 224 | 64 | 94 |
|  | 448 | 88 | 97 |
| 22-01 | 112 | 38 | 61 |
|  | 224 | 56 | 80 |
|  | 448 | 76 | 97 |
| 22-02 | 112 | 50 | 51 |
|  | 224 | 69 | 91 |
|  | 448 | 81 | 97 |
| 22-03 | 112 | 51 | 63 |

TABLE 22b-continued

| Concentrate composition | Glyphosate rate g a.e./ha | % Inhibition ABUTH | ECHCF |
|---|---|---|---|
| | 224 | 64 | 83 |
| | 448 | 81 | 96 |
| 22-04 | 112 | 53 | 61 |
| | 224 | 71 | 91 |
| | 448 | 78 | 95 |

TABLE 22b-continued

| Concentrate composition | Glyphosate rate g a.e./ha | % Inhibition ABUTH | ECHCF |
|---|---|---|---|
| 22-05 | 112 | 41 | 56 |
| | 224 | 70 | 85 |
| | 448 | 75 | 97 |
| 22-06 | 112 | 38 | 53 |
| | 224 | 63 | 89 |
| | 448 | 75 | 94 |
| 22-07 | 112 | 48 | 53 |
| | 224 | 49 | 84 |
| | 448 | 75 | 90 |
| 22-08 | 112 | 31 | 60 |
| | 224 | 53 | 84 |
| | 448 | 66 | 90 |
| 22-09 | 112 | 26 | 56 |
| | 224 | 53 | 85 |
| | 448 | 78 | 96 |
| 22-10 | 112 | 36 | 60 |
| | 224 | 53 | 85 |
| | 448 | 79 | 98 |
| 22-11 | 112 | 41 | 59 |
| | 224 | 49 | 73 |
| | 448 | 76 | 95 |
| 22-12 | 112 | 30 | 56 |
| | 224 | 50 | 74 |
| | 448 | 65 | 89 |
| 22-13 | 112 | 34 | 55 |
| | 224 | 44 | 80 |
| | 448 | 73 | 95 |
| 22-14 | 112 | 39 | 61 |
| | 224 | 56 | 85 |
| | 448 | 69 | 91 |
| 22-15 | 112 | 31 | 55 |
| | 224 | 56 | 69 |
| | 448 | 79 | 95 |
| 22-16 | 112 | 29 | 64 |
| | 224 | 58 | 86 |
| | 448 | 78 | 91 |

None of the concentrate compositions of this Example containing 10% glyphosate a.e. and varying amounts of Fluorad FC-135 (22-01 to 22-06) exhibited greater herbicidal effectiveness than the commercial standard Formulation C. It should be noted that the amounts of Fluorad FC-135 used in this Example were extremely high, the weight/weight ratio of Fluorad FC-135 to glyphosate a.e. ranging from 1:2 to 3:1.

EXAMPLE 23

Aqueous concentrate compositions were prepared containing glyphosate IPA salt and excipient ingredients as shown in Table 23a. Process (iv) was followed for all compositions, using soybean lecithin (20% phospholipid, Avanti). The pH of all compositions was approximately 5.

TABLE 23a

| Concentrate composition | Glyphosate a.e. | % w/w Lecithin | MON 0818 | Fluorad FC-135 | Components sonicated with lecithin |
|---|---|---|---|---|---|
| 23-01 | 20 | 5.0 | 2.0 | | none |
| 23-02 | 20 | 4.0 | 1.0 | | none |
| 23-03 | 20 | 5.0 | 2.0 | | glyphosate |
| 23-04 | 20 | 4.0 | 1.0 | | glyphosate |
| 23-05 | 20 | 5.0 | 2.0 | 5.0 | none |

Velvetleaf (*Abutilon theophrasti*, ABUTH) and Japanese millet (*Echinochloa crus-galli*, ECHCF) plants were grown and treated by the standard procedures given above. Applications of spray compositions were made 16 days after planting ABUTH and 18 days after planting ECHCF, and evaluation of herbicidal inhibition was done 14 days after application.

Formulations B and C were applied as comparative treatments. Results, averaged for all replicates of each treatment, are shown in Table 23b.

TABLE 23b

| Concentrate composition | Glyphosate rate g a.e./ha | % Inhibition ABUTH | ECHCF |
|---|---|---|---|
| Formulation B | 112 | 33 | 53 |
| | 224 | 58 | 78 |
| | 336 | 80 | 89 |
| | 448 | 79 | 88 |
| Formulation C | 112 | 49 | 79 |
| | 224 | 59 | 94 |
| | 336 | 84 | 100 |
| | 448 | 95 | 100 |
| 23-01 | 112 | 39 | 66 |
| | 224 | 63 | 93 |
| | 336 | 81 | 98 |
| | 448 | 86 | 100 |
| 23-02 | 112 | 29 | 46 |
| | 224 | 55 | 83 |
| | 336 | 79 | 91 |
| | 448 | 85 | 95 |
| 23-03 | 112 | 30 | 59 |
| | 224 | 60 | 98 |
| | 336 | 80 | 100 |
| | 448 | 81 | 100 |
| 23-04 | 112 | 26 | 51 |
| | 224 | 53 | 83 |
| | 336 | 76 | 86 |
| | 448 | 86 | 99 |
| 23-05 | 112 | 46 | 51 |
| | 224 | 59 | 89 |
| | 336 | 79 | 96 |
| | 448 | 89 | 98 |

Concentrate composition, 23-05 (5% lecithin, 2% MON 0818, 5% Fluorad FC-135) did not exhibit greater herbicidal effectiveness in this test than composition 23-01 lacking the Fluorad FC-135.

EXAMPLE 24

Aqueous spray compositions were prepared containing glyphosate IPA salt and excipient ingredients as shown in Table 24a. Process (iii) was followed for all compositions, using soybean lecithin (20% phospholipid, Avanti). The pH of these compositions was not recorded.

TABLE 24a

| Spray composition | Lecithin g/l | % w/w Fluorad FC-135 | Components sonicated with lecithin |
|---|---|---|---|
| 24-01 | 2.5 | | none |
| 24-02 | 1.0 | | none |
| 24-03 | 0.5 | | none |
| 24-04 | 0.2 | | none |
| 24-05 | 0.1 | | none |
| 24-06 | 2.5 | 0.25 | none |
| 24-07 | 0.5 | 0.05 | none |
| 24-08 | 0.2 | 0.02 | none |
| 24-09 | 0.2 | 0.02 | glyphosate |
| 24-10 | 0.2 | 0.02 | FC-135 |
| 24-11 | 0.1 | 0.01 | none |
| 24-12 | 0.1 | 0.01 | glyphosate |
| 24-13 | 0.1 | 0.02 | FC-135 |
| 24-14 | 0.5 | 0.02 | none |
| 24-15 | 0.5 | 0.02 | glyphosate |
| 24-16 | 0.5 | 0.02 | FC-135 |

Yellow nutsedge (*Cyperus esculentus*, CYPES) plants were grown and treated by the standard procedures given above. Applications of spray compositions were made 29 days after planting, and evaluation of herbicidal inhibition was done 33 days after application.

In addition to compositions 24-01 to 24-16, spray compositions were prepared by tank mixing Formulations B and C with Fluorad FC-135 at various concentrations. Formulations B and C alone were applied as comparative treatments. Results, averaged for all replicates of each treatment, are shown in Table 24b.

TABLE 24b

| Spray composition | Glyphosate rate g a.e./ha | % Inhibition CYPES |
|---|---|---|
| Formulation B | 400 | 32 |
| | 750 | 68 |
| | 1000 | 70 |
| Formulation C | 400 | 25 |
| | 750 | 66 |
| | 1000 | 89 |
| Formulation B + Fluorad FC-135 0.25% w/v | 400 | 49 |
| | 750 | 75 |
| | 1000 | 82 |
| Formulation B + Fluorad FC-135 0.05% w/v | 400 | 53 |
| | 750 | 74 |
| | 1000 | 64 |
| Formulation B + Fluorad FC-135 0.02% w/v | 400 | 56 |
| | 750 | 83 |
| | 1000 | 83 |
| Formulation B + Fluorad FC-135 0.01% w/v | 400 | 61 |
| | 750 | 67 |
| | 1000 | 88 |
| Formulation C + Fluorad FC-135 0.25% w/v | 400 | 73 |
| | 750 | 47 |
| | 1000 | 79 |
| Formulation C + Fluorad FC-135 0.05% w/v | 400 | 50 |
| | 750 | 73 |
| | 1000 | 81 |
| Formulation C + Fluorad FC-135 0.02% w/v | 400 | 41 |
| | 750 | 79 |
| | 1000 | 81 |
| Formulation C + Fluorad FC-135 0.01% w/v | 400 | 67 |
| | 750 | 77 |
| | 1000 | 72 |
| 24-01 | 400 | 62 |
| | 750 | 73 |
| | 1000 | 100 |
| 24-02 | 400 | 61 |
| | 750 | 85 |
| | 1000 | 92 |
| 24-03 | 400 | 81 |
| | 750 | 83 |
| | 1000 | 87 |
| 24-04 | 400 | 59 |
| | 750 | 79 |
| | 1000 | 79 |
| 24-05 | 400 | 69 |
| | 750 | 69 |
| | 1000 | 91 |
| 24-06 | 400 | 75 |
| | 750 | 80 |
| | 1000 | 96 |
| 24-07 | 400 | 65 |
| | 750 | 69 |
| | 1000 | 89 |
| 24-08 | 400 | 67 |
| | 750 | 69 |
| | 1000 | 87 |
| 24-09 | 400 | 76 |
| | 750 | 77 |
| | 1000 | 80 |
| 24-10 | 400 | 71 |
| | 750 | 75 |
| | 1000 | 86 |
| 24-11 | 400 | 69 |
| | 750 | 77 |
| | 1000 | 85 |
| 24-12 | 400 | 59 |
| | 750 | 85 |
| | 1000 | 95 |
| 24-13 | 400 | 61 |
| | 750 | 75 |
| | 1000 | 81 |
| 24-14 | 400 | 64 |
| | 750 | 83 |
| | 1000 | 90 |
| 24-15 | 400 | 53 |
| | 750 | 81 |
| | 1000 | 86 |
| 24-16 | 400 | 85 |
| | 750 | 86 |
| | 1000 | 81 |

The tank-mix treatments of this Example show surprisingly little effect on herbicidal effectiveness on CYPES of reducing Fluorad FC-135 concentration from 0.25% all the way down to 0.01%. At this extraordinarily low concentration, the tank mix of Formulation B with Fluorad FC-135 still performed equal or better than Formulation C alone. Lecithin alone was an unexpectedly effective excipient for glyphosate in this test (see compositions 24-01 to 24-05) and the addition of Fluorad FC-135 to lecithin did not in every case give further enhancement of herbicidal efficacy.

EXAMPLE 25

Glyphosate-containing spray compositions were prepared by tank-mixing Formulation B with excipients as shown in Table 25. Soybean lecithin (20% phospholipid, Avanti) was used in the form of a 10% dispersion prepared by sonication as in process (iii).

Velvetleaf (*Abutilon theophrasti,* ABUTH) and Japanese millet (*Echinochloa crus-galli,* ECHCF) plants were grown and treated by the standard procedures given above. Applications of spray compositions were made 21 days after planting ABUTH and 21 days after planting ECHCF, and evaluation of herbicidal inhibition was done 21 days after application. Results, averaged for all replicates of each treatment, are shown in Table 25.

TABLE 25

| Glyphosate composition | Glyphosate rate g a.e./ha | Additive | Add. rate % w/v | % Inhibition ABUTH | % Inhibition ECHCF |
|---|---|---|---|---|---|
| Formulation B | 56 | | | 3 | 17 |
| | 112 | | | 7 | 38 |
| | 224 | | | 30 | 58 |
| | 336 | | | 60 | 67 |
| None | 0 | MON 0818 | 5.0 | 7 | 30 |
| | | Fluorad FC-135 | 5.0 | 5 | 3 |
| | | lecithin | 5.0 | 0 | 0 |
| Formulation B | 56 | MON 0818 | 0.005 | 0 | 48 |
| | 112 | | | 3 | 60 |
| | 224 | | | 53 | 85 |
| | 336 | | | 58 | 87 |
| Formulation B | 56 | MON 0818 | 0.01 | 3 | 50 |
| | 112 | | | 10 | 67 |
| | 224 | | | 52 | 87 |
| | 336 | | | 67 | 92 |
| Formulation B | 56 | MON 0818 | 0.05 | 7 | 52 |
| | 112 | | | 10 | 67 |
| | 224 | | | 60 | 93 |
| | 336 | | | 68 | 96 |
| Formulation B | 56 | MON 0818 | 0.1 | 10 | 55 |
| | 112 | | | 12 | 70 |
| | 224 | | | 57 | 97 |
| | 336 | | | 80 | 97 |
| Formulation B | 56 | MON 0818 | 0.2 | 10 | 65 |
| | 112 | | | 22 | 70 |
| | 224 | | | 58 | 97 |
| | 336 | | | 85 | 97 |
| Formulation B | 56 | MON 0818 | 0.5 | 13 | 65 |
| | 112 | | | 33 | 77 |
| | 224 | | | 72 | 99 |
| | 336 | | | 88 | 100 |
| Formulation B | 56 | MON 0818 | 1.0 | 15 | 68 |
| | 112 | | | 55 | 80 |
| | 224 | | | 78 | 98 |
| | 336 | | | 95 | 100 |
| Formulation B | 56 | MON 0818 | 2.0 | 27 | 75 |
| | 112 | | | 62 | 78 |
| | 224 | | | 83 | 100 |
| | 336 | | | 100 | 99 |
| Formulation B | 56 | MON 0818 | 5.0 | 23 | 55 |
| | 112 | | | 53 | 77 |
| | 224 | | | 72 | 90 |
| | 336 | | | 97 | 88 |
| Formulation B | 56 | Fluorad FC-135 | 0.005 | 2 | 47 |
| | 112 | | | 10 | 50 |
| | 224 | | | 25 | 70 |
| | 336 | | | 55 | 78 |
| Formulation B | 56 | Fluorad FC-135 | 0.01 | 7 | 40 |
| | 112 | | | 15 | 57 |
| | 224 | | | 70 | 67 |
| | 336 | | | 80 | 80 |
| Formulation B | 56 | Fluorad FC-135 | 0.05 | 2 | 48 |
| | 112 | | | 15 | 57 |
| | 224 | | | 70 | 78 |
| | 336 | | | 78 | 88 |
| Formulation B | 56 | Fluorad FC-135 | 0.1 | 5 | 45 |
| | 112 | | | 18 | 58 |
| | 224 | | | 75 | 87 |
| | 336 | | | 80 | 90 |
| Formulation B | 56 | Fluorad FC-135 | 0.2 | 12 | 48 |
| | 112 | | | 27 | 60 |
| | 224 | | | 75 | 90 |
| | 336 | | | 97 | 93 |
| Formulation B | 56 | Fluorad FC-135 | 0.5 | 3 | 47 |
| | 112 | | | 12 | 57 |
| | 224 | | | 75 | 80 |
| | 336 | | | 78 | 83 |
| Formulation B | 56 | Fluorad FC-135 | 1.0 | 5 | 43 |
| | 112 | | | 10 | 52 |

TABLE 25-continued

| Glyphosate composition | Glyphosate rate g a.e./ha | Additive | Add. rate % w/v | % Inhibition ABUTH | ECHCF |
|---|---|---|---|---|---|
| | 224 | | | 77 | 75 |
| | 336 | | | 78 | 77 |
| Formulation B | 56 | Fluorad FC-135 | 2.0 | 7 | 42 |
| | 112 | | | 10 | 47 |
| | 224 | | | 65 | 65 |
| | 336 | | | 72 | 77 |
| Formulation B | 56 | Fluorad FC-135 | 5.0 | 2 | 38 |
| | 112 | | | 5 | 47 |
| | 224 | | | 63 | 60 |
| | 336 | | | 67 | 63 |
| Formulation B | 56 | lecithin | 0.005 | 0 | 10 |
| | 112 | | | 10 | 45 |
| | 224 | | | 67 | 70 |
| | 336 | | | 67 | 77 |
| Formulation B | 56 | lecithin | 0.01 | 2 | 20 |
| | 112 | | | 12 | 47 |
| | 224 | | | 63 | 70 |
| | 336 | | | 68 | 85 |
| Formulation B | 56 | lecithin | 0.05 | 3 | 32 |
| | 112 | | | 12 | 52 |
| | 224 | | | 63 | 73 |
| | 336 | | | 72 | 82 |
| Formulation B | 56 | lecithin | 0.1 | 8 | 37 |
| | 112 | | | 10 | 50 |
| | 224 | | | 65 | 73 |
| | 336 | | | 78 | 83 |
| Formulation B | 56 | lecithin | 0.2 | 5 | 45 |
| | 112 | | | 43 | 63 |
| | 224 | | | 68 | 82 |
| | 336 | | | 80 | 92 |
| Formulation B | 56 | lecithin | 0.5 | 13 | 50 |
| | 112 | | | 42 | 65 |
| | 224 | | | 67 | 88 |
| | 336 | | | 68 | 87 |
| Formulation B | 56 | lecithin | 1.0 | 13 | 52 |
| | 112 | | | 50 | 72 |
| | 224 | | | 67 | 80 |
| | 336 | | | 68 | 88 |
| Formulation B | 56 | lecithin | 2.0 | 10 | 53 |
| | 112 | | | 37 | 72 |
| | 224 | | | 72 | 88 |
| | 336 | | | 87 | 97 |
| Formulation B | 56 | lecithin | 5.0 | 10 | 50 |
| | 112 | | | 55 | 73 |
| | 224 | | | 72 | 80 |
| | 336 | | | 78 | 95 |

This test was an expanded rate titration study of MON 0818, Fluorad FC-135 and lecithin as tank-mix adjuvants for glyphosate as Formulation B. On ABUTH, the optimum adjuvant concentration was 2.0% for MON 0818, 0.2% for Fluorad FC-135 and 0.2% or higher for lecithin. On ECHCF, the optimum adjuvant concentration was 0.5% to 2.0% for MON 0818, 0.2% for Fluorad FC-135 and 2.0% for lecithin.

EXAMPLE 26

Aqueous spray compositions were prepared containing glyphosate IPA salt and excipient ingredients as shown in Table 26a. Process (iii) was followed for all compositions, using soybean lecithin (20% phospholipid, Avanti). The pH of all compositions was adjusted to approximately 7.

TABLE 26a

| Spray composition | Lecithin g/l | % w/w Fluorad FC-135 | Aerosol OT |
|---|---|---|---|
| 26-01 | | | 0.1 |
| 26-02 | | | 0.05 |
| 26-03 | | | 0.02 |
| 26-04 | | 0.1 | 0.1 |
| 26-05 | | 0.05 | 0.05 |
| 26-06 | | 0.02 | 0.02 |
| 26-07 | 1.0 | | 0.10 |
| 26-08 | 1.0 | 0.10 | 0.10 |
| 26-09 | 1.0 | | |
| 26-10 | 1.0 | 0.10 | |
| 26-11 | 0.5 | | |
| 26-12 | 0.5 | | 0.05 |
| 26-13 | 0.5 | 0.05 | |
| 26-14 | 0.5 | 0.05 | 0.05 |
| 26-15 | 0.2 | | |
| 26-16 | 0.2 | | 0.02 |

TABLE 26a-continued

| Spray composition | Lecithin g/l | % w/w Fluorad FC-135 | Aerosol OT |
|---|---|---|---|
| 26-17 | 0.2 | 0.02 | |
| 26-18 | 0.2 | 0.02 | 0.02 |

Velvetleaf (*Abutilon theophrasti*, ABUTH), Japanese millet (*Echinochloa crus-galli*, ECHCF) and prickly sida (*Sida spinosa*, SIDSP) plants were grown and treated by the standard procedures given above. Applications of spray compositions were made 16 days after planting ABUTH, 19 days after planting ECHCF, and 26 days after planting SIDSP. Evaluation of herbicidal inhibition was done for ABUTH and ECHCF 15 days after application and for SIDSP 21 days after application.

In addition to compositions 26-01 to 26-18, spray compositions were prepared by tank mixing Formulations B and C with Fluorad FC-135 at various concentrations. Formulations B and C alone were applied as comparative treatments. Results, averaged for all replicates of each treatment, are shown in Table 26b.

TABLE 26b

| Spray composition | Glyphosate rate g a.e./ha | % Inhibition ABUTH | ECHCF | SIDSP |
|---|---|---|---|---|
| Formulation B | 150 | 37 | 71 | 57 |
| | 250 | 57 | 79 | 69 |
| | 400 | 74 | 86 | 80 |
| | 500 | 79 | 89 | 74 |
| Formulation C | 150 | 48 | 42 | 58 |
| | 250 | 71 | 80 | 81 |
| | 400 | 88 | 100 | 88 |
| | 500 | 92 | 100 | 86 |
| Formulation B + Fluorad FC-135 0.1% w/v | 150 | 87 | 62 | 66 |
| | 250 | 87 | 96 | 70 |
| | 400 | 91 | 94 | 75 |
| Formulation B + Fluorad FC-135 0.05% w/v | 150 | 61 | 48 | 65 |
| | 250 | 81 | 69 | 71 |
| | 400 | 90 | 91 | 67 |
| Formulation B + Fluorad FC-135 0.02% w/v | 150 | 58 | 32 | 62 |
| | 250 | 75 | 49 | 51 |
| | 400 | 81 | 83 | 73 |
| Formulation C + Fluorad FC-135 0.1% w/v | 150 | 78 | 61 | 76 |
| | 250 | 79 | 77 | 81 |
| | 400 | 93 | 100 | 78 |
| Formulation C + Fluorad FC-135 0.05% w/v | 150 | 43 | 86 | 69 |
| | 250 | 79 | 100 | 80 |
| | 400 | 95 | 98 | 84 |
| Formulation C + Fluorad FC-135 0.02% w/v | 150 | 39 | 56 | 77 |
| | 250 | 77 | 100 | 86 |
| | 400 | 88 | 100 | 80 |
| 26-01 | 150 | 63 | 48 | 49 |
| | 250 | 70 | 69 | 66 |
| | 400 | 85 | 84 | 63 |
| 26-02 | 150 | 32 | 36 | 55 |
| | 250 | 64 | 74 | 65 |
| | 400 | 77 | 92 | 69 |
| 26-03 | 150 | 30 | 78 | 51 |
| | 250 | 59 | 79 | 66 |
| | 400 | 83 | 93 | 74 |
| 26-04 | 150 | 86 | 50 | 65 |
| | 250 | 74 | 98 | 71 |
| | 400 | 81 | 89 | 75 |
| 26-05 | 150 | 85 | 55 | 60 |
| | 250 | 81 | 75 | 73 |
| | 400 | 82 | 81 | 64 |
| 26-06 | 150 | 61 | 67 | 45 |
| | 250 | 66 | 78 | 61 |
| | 400 | 83 | 77 | 67 |

TABLE 26b-continued

| Spray composition | Glyphosate rate g a.e./ha | % Inhibition ABUTH | ECHCF | SIDSP |
|---|---|---|---|---|
| 26-07 | 150 | 46 | 38 | 44 |
| | 250 | 56 | 85 | 64 |
| | 400 | 75 | 96 | 78 |
| 26-08 | 150 | 88 | 63 | 70 |
| | 250 | 87 | 73 | 79 |
| | 400 | 91 | 82 | 75 |
| 26-09 | 150 | 63 | 72 | 61 |
| | 250 | 87 | 73 | 71 |
| | 400 | 89 | 87 | 80 |
| 26-10 | 150 | 81 | 72 | 61 |
| | 250 | 85 | 62 | 82 |
| | 400 | 87 | 89 | 76 |
| 26-11 | 150 | 54 | 57 | 68 |
| | 250 | 80 | 90 | 74 |
| | 400 | 84 | 95 | 66 |
| 26-12 | 150 | 27 | 53 | 47 |
| | 250 | 57 | 71 | 67 |
| | 400 | 72 | 91 | 70 |
| 26-13 | 150 | 78 | 59 | 64 |
| | 250 | 80 | 84 | 80 |
| | 400 | 89 | 76 | 77 |
| 26-14 | 150 | 84 | 52 | 68 |
| | 250 | 88 | 69 | 75 |
| | 400 | 90 | 84 | 66 |
| 26-15 | 150 | 51 | 57 | 55 |
| | 250 | 81 | 55 | 71 |
| | 400 | 88 | 83 | 69 |
| 26-16 | 150 | 40 | 68 | 46 |
| | 250 | 74 | 89 | 60 |
| | 400 | 77 | 98 | 63 |
| 26-17 | 150 | 64 | 44 | 58 |
| | 250 | 80 | 93 | 81 |
| | 400 | 87 | 99 | 69 |
| 26-18 | 150 | 64 | 87 | 50 |
| | 250 | 77 | 75 | 70 |
| | 400 | 90 | 89 | 50 |

This test was designed in part to explore the relative contribution of Fluorad FC-135 and lecithin to the herbicidal effectiveness of glyphosate compositions comprising both of these excipient substances. Fluorad FC-135 was applied as sole excipient at concentrations of 1.0%, 0.5% and 0.2% (see tank-mix treatments with Formulation B). Lecithin was applied as sole excipient at the same three concentrations in compositions 26-09, 26-11 and 26-15. Combinations of the two excipients at equal concentrations were applied in corresponding compositions 26-10, 26-13 and 26-17. The data are highly variable but an overall trend can be discerned. When only one of the two excipients was present, herbicidal effectiveness tended to drop off as the concentration of that excipient was reduced. When both excipients were present, there was scarcely any decline in herbicidal effectiveness as excipient concentration was reduced. Although averages of data from three glyphosate rates across three species can be misleading, it is helpful in this case to reduce the mass of individual data to the following such averages of percent inhibition:

| | |
|---|---|
| Glyphosate (Formulation B) | 68% |
| Glyphosate + 0.1% Fluorad FC-135 | 81% |
| Glyphosate + 0.05% Fluorad FC-135 | 71% |
| Glyphosate + 0.02% Fluorad FC-135 | 63% |
| Glyphosate + 0.1% lecithin | 76% |
| Glyphosate + 0.05% lecithin | 74% |
| Glyphosate + 0.02% lecithin | 68% |
| Glyphosate + 0.1% Fluorad FC-135 + 0.1% lecithin | 77% |

-continued

| | |
|---|---|
| Glyphosate + 0.05% Fluorad FC-135 + 0.05% lecithin | 76% |
| Glyphosate + 0.02% Fluorad FC-135 + 0.02% lecithin | 75% |
| Glyphosate commercial standard (Formulation C) | 73% |

Thus, when both excipients are used together, a fivefold decrease in excipient concentration results in a decline in overall herbicidal effectiveness of only 2 percentage points, still retaining overall effectiveness at least equal to that of the commercial standard.

EXAMPLE 27

Glyphosate-containing spray compositions were prepared by tank-mixing Formulations B with excipients as shown in Table 27. Soybean lecithin (20% phospholipid, Avanti) was used in the form of a 10% dispersion prepared by sonication as in process (iii).

Velvetleaf (*Abutilon theophrasti*, ABUTH) and Japanese millet (*Echinochloa crus-galli*, ECHCF) plants were grown and treated by the standard procedures given above. Applications of spray compositions were made 19 days after planting ABUTH and 15 days after planting ECHCF, and evaluation of herbicidal inhibition was done 19 days after application. Results, averaged for all replicates of each treatment, are shown in Table 27.

TABLE 27

| Glyphosate composition | Glyphosate rate g a.e./ha | Additive | Additive rate % v/v | % Inhibition ABUTH | ECHCF |
|---|---|---|---|---|---|
| Formulation B | 56 | none | | 0 | 3 |
| | 112 | | | 5 | 13 |
| | 224 | | | 40 | 40 |
| | 336 | | | 83 | 77 |
| Formulation B | 56 | Fluorad FC-135 | 0.005 | 0 | 7 |
| | 112 | | | 3 | 10 |
| | 224 | | | 45 | 53 |
| | 336 | | | 58 | 78 |
| Formulation B | 56 | Fluorad FC-135 | 0.01 | 0 | 8 |
| | 112 | | | 2 | 12 |
| | 224 | | | 45 | 60 |
| | 336 | | | 67 | 87 |
| Formulation B | 56 | Fluorad FC-135 | 0.05 | 2 | 8 |
| | 112 | | | 20 | 23 |
| | 224 | | | 72 | 88 |
| | 336 | | | 90 | 93 |
| Formulation B | 56 | Fluorad FC-135 | 0.1 | 3 | 10 |
| | 112 | | | 33 | 38 |
| | 224 | | | 73 | 88 |
| | 336 | | | 93 | 92 |
| Formulation B | 56 | Fluorad FC-135 | 0.2 | 10 | 17 |
| | 112 | | | 33 | 47 |
| | 224 | | | 77 | 85 |
| | 336 | | | 93 | 92 |
| Formulation B | 56 | Fluorad FC-135 | 0.5 | 7 | 13 |
| | 112 | | | 37 | 37 |
| | 224 | | | 80 | 85 |
| | 336 | | | 96 | 95 |
| Formulation B | 56 | Fluorad FC-135 | 1.0 | 3 | 7 |
| | 112 | | | 27 | 35 |
| | 224 | | | 72 | 87 |
| | 336 | | | 88 | 92 |
| Formulation B | 56 | Fluorad FC-135 | 2.0 | 0 | 0 |
| | 112 | | | 27 | 18 |
| | 224 | | | 72 | 75 |
| | 336 | | | 87 | 87 |
| Formulation B | 56 | Fluorad FC-135 | 5.0 | 0 | 0 |
| | 112 | | | 12 | 13 |
| | 224 | | | 43 | 50 |
| | 336 | | | 58 | 53 |
| Formulation B | 56 | lecithin/FC-135 (1:1) | 0.005 | 0 | 2 |
| | 112 | | | 7 | 13 |
| | 224 | | | 65 | 63 |
| | 336 | | | 83 | 82 |
| Formulation B | 56 | lecithin/FC-135 (1:1) | 0.01 | 0 | 0 |
| | 112 | | | 3 | 10 |
| | 224 | | | 42 | 63 |
| | 336 | | | 73 | 82 |
| Formulation B | 56 | lecithin/FC-135 (1:1) | 0.05 | 0 | 0 |
| | 112 | | | 42 | 13 |
| | 224 | | | 68 | 73 |
| | 336 | | | 98 | 73 |
| Formulation B | 56 | lecithin/FC-135 (1:1) | 0.1 | 0 | 0 |
| | 112 | | | 37 | 20 |
| | 224 | | | 62 | 68 |
| | 336 | | | 94 | 77 |
| Formulation B | 56 | lecithin/FC-135 (1:1) | 0.2 | 0 | 2 |

TABLE 27-continued

| Glyphosate composition | Glyphosate rate g a.e./ha | Additive | Additive rate % v/v | % Inhibition ABUTH | % Inhibition ECHCF |
|---|---|---|---|---|---|
| | 112 | | | 33 | 28 |
| | 224 | | | 67 | 68 |
| | 336 | | | 100 | 78 |
| Formulation B | 56 | lecithin/FC-135 (1:1) | 0.5 | 7 | 0 |
| | 112 | | | 40 | 18 |
| | 224 | | | 68 | 68 |
| | 336 | | | 90 | 73 |
| Formulation B | 56 | lecithin/FC-135 (1:1) | 1.0 | 17 | 3 |
| | 112 | | | 43 | 45 |
| | 224 | | | 83 | 88 |
| | 336 | | | 95 | 94 |
| Formulation B | 56 | lecithin/FC-135 (1:1) | 2.0 | 10 | 23 |
| | 112 | | | 32 | 42 |
| | 224 | | | 63 | 73 |
| | 336 | | | 88 | 87 |
| Formulation B | 56 | lecithin/FC-135 (1:1) | 5.0 | 2 | 3 |
| | 112 | | | 8 | 28 |
| | 224 | | | 50 | 72 |
| | 336 | | | 85 | 87 |
| Formulation B | 56 | lecithin | 0.005 | 2 | 2 |
| | 112 | | | 3 | 10 |
| | 224 | | | 45 | 50 |
| | 336 | | | 58 | 72 |
| Formulation B | 56 | lecithin | 0.01 | 0 | 2 |
| | 112 | | | 2 | 12 |
| | 224 | | | 40 | 52 |
| | 336 | | | 65 | 75 |
| Formulation B | 56 | lecithin | 0.05 | 2 | 2 |
| | 112 | | | 0 | 10 |
| | 224 | | | 40 | 45 |
| | 336 | | | 57 | 70 |
| Formulation B | 56 | lecithin | | 2 | 7 |
| | 112 | | | 2 | 13 |
| | 224 | | | 33 | 37 |
| | 336 | | | 48 | 67 |
| Formulation B | 56 | lecithin | 0.2 | 3 | 3 |
| | 112 | | | 3 | 13 |
| | 224 | | | 32 | 35 |
| | 336 | | | 47 | 68 |
| Formulation B | 56 | lecithin | 0.5 | 2 | 3 |
| | 112 | | | 8 | 15 |
| | 224 | | | 47 | 53 |
| | 336 | | | 67 | 65 |
| Formulation B | 56 | lecithin | 1.0 | 2 | 5 |
| | 112 | | | 10 | 15 |
| | 224 | | | 33 | 55 |
| | 336 | | | 70 | 77 |
| Formulation B | 56 | lecithin | 2.0 | 5 | 8 |
| | 112 | | | 12 | 17 |
| | 224 | | | 48 | 52 |
| | 336 | | | 68 | 77 |
| Formulation B | 56 | lecithin | 5.0 | 5 | 17 |
| | 112 | | | 23 | 17 |
| | 224 | | | 52 | 55 |
| | 336 | | | 73 | 78 |

This tank-mix study more clearly demonstrates the surprising interaction seen in Example 26 between lecithin and Fluorad FC-135 as excipients for glyphosate. For example, glyphosate alone over four rates gave average inhibition of ABUTH of 32%. Adding Fluorad FC-135 at a concentration of 0.5% boosted the average inhibition to 55%, but adding lecithin at the same concentration did not raise average inhibition above 32%. A 1:1 combination of both excipients at the same total concentration gave an average inhibition of 51 %. At a concentration of 0.1 %, Fluorad FC-135 gave average inhibition of 50%, lecithin 21% (i.e. a reduction in effectiveness of glyphosate) and the 1:1 combination 48%. Thus, as in Example 26, the decline in herbicidal effectiveness with reducing excipient rate was much less pronounced with the combination than with either excipient on its own.

EXAMPLE 28

Aqueous concentrate compositions were prepared containing glyphosate IPA salt and excipient ingredients as shown in Table 28a. Process (i) was followed for compositions 28-01 to 28-06. Process (iv) was followed for compositions 28-07 to 28-11, using soybean lecithin (20% phospholipid, Avanti). For compositions 28-12 and 28-13, process (iv) was also used, but Aerosol OT was the aggregate-forming material employed in place of lecithin. The pH of all compositions was approximately 5.

TABLE 28a

| Concentrate composition | Glyphosate a.e. | Lecithin | Fluorad FC-135 | MON 0818 | Other (*) | (*) Other components |
|---|---|---|---|---|---|---|
| 28-01 | 20 | | | | 1.0 | PVA |
| 28-02 | 20 | | 5.0 | | 1.0 | PVA |
| 28-03 | 20 | | 2.0 | | 1.0 | PVA |
| 28-04 | 20 | | 1.0 | | 1.0 | PVA |
| 28-05 | 20 | | | | 0.5 | Kelzan |
| 28-06 | 20 | | 2.0 | | 0.5 | Kelzan |
| 28-07 | 20 | 2.0 | | 0.04 | | |
| 28-08 | 20 | 2.0 | 2.0 | 0.04 | | |
| 28-09 | 20 | 2.0 | 2.0 | 0.02 | | |
| 28-10 | 20 | 2.0 | | 0.04 | 25.0 | Silwet 800 |
| 28-11 | 20 | 2.0 | 2.0 | 0.04 | 25.0 | Silwet 800 |
| 28-12 | 20 | | | | 5.0 | Aerosol OT |
| 28-13 | 20 | | | | 5.0 + 25.0 | Aerosol OT + Silwet 800 |

Velvetleaf (*Abutilon theophrasti,* ABUTH) and Japanese millet (*Echinochloa crus-galli,* ECHCF) plants were grown and treated by the standard procedures given above. Applications of spray compositions were made 14 days after planting ABUTH and 17 days after planting ECHCF, and evaluation of herbicidal inhibition was done 38 days after application.

Formulations B and C were applied as comparative treatments. Results, averaged for all replicates of each treatment, are shown in Table 28b.

TABLE 28b

| Concentrate composition | Glyphosate rate g a.e./ha | % Inhibition ABUTH | % Inhibition ECHCF |
|---|---|---|---|
| Formulation B | 56 | 0 | 8 |
| | 112 | 4 | 33 |
| | 224 | 45 | 40 |
| | 336 | 69 | 65 |
| Formulation C | 56 | 0 | 10 |
| | 112 | 5 | 43 |
| | 224 | 68 | 73 |
| | 336 | 87 | 94 |
| 28-01 | 112 | 0 | 40 |
| | 224 | 50 | 76 |
| | 336 | 76 | 85 |
| 28-02 | 112 | 1 | 35 |
| | 224 | 30 | 70 |
| | 336 | 69 | 96 |
| 28-03 | 112 | 6 | 35 |
| | 224 | 35 | 58 |
| | 336 | 65 | 84 |
| 28-04 | 112 | 1 | 35 |
| | 224 | 70 | 60 |
| | 336 | 69 | 85 |
| 28-05 | 112 | 1 | 35 |
| | 224 | 63 | 68 |
| | 336 | 80 | 88 |
| 28-06 | 112 | 0 | 25 |
| | 224 | 40 | 55 |
| | 336 | 66 | 73 |
| 28-07 | 112 | 11 | 35 |
| | 224 | 45 | 68 |
| | 336 | 65 | 86 |
| 28-08 | 112 | 9 | 38 |
| | 224 | 65 | 60 |
| | 336 | 66 | 75 |
| 28-09 | 112 | 10 | 33 |
| | 224 | 56 | 60 |
| | 336 | 78 | 75 |
| 28-10 | 112 | 30 | 5 |

TABLE 28b-continued

| Concentrate composition | Glyphosate rate g a.e./ha | % Inhibition ABUTH | % Inhibition ECHCF |
|---|---|---|---|
| | 224 | 79 | 30 |
| | 336 | 90 | 35 |
| 28-11 | 112 | 60 | 5 |
| | 224 | 79 | 33 |
| | 336 | 96 | 30 |
| 28-12 | 112 | 8 | 11 |
| | 224 | 53 | 40 |
| | 336 | 66 | 64 |
| 28-13 | 112 | 40 | 6 |
| | 224 | 91 | 33 |
| | 336 | 98 | 38 |

Concentrate compositions 28-08 and 28-09 did not in this test exhibit herbicidal effectiveness equal to Formulation C.

EXAMPLE 29

Aqueous spray compositions were prepared containing glyphosate IPA salt and excipient ingredients as shown in Table 29a. Process (iii) was followed for all compositions, using soybean lecithin (20% or 45% phospholipid as indicated below, both sourced from Avanti). The pH of all compositions was adjusted to approximately 7.

TABLE 29a

| Spray composition | Lecithin g/l | Lecithin phospholipid % | % w/w Fluorad FC-135 |
|---|---|---|---|
| 29-01 | 0.25 | 20 | |
| 29-02 | 0.05 | 20 | |
| 29-03 | 0.02 | 20 | |
| 29-04 | 0.01 | 20 | |
| 29-05 | 0.25 | 20 | 0.25 |
| 29-06 | 0.05 | 20 | 0.05 |
| 29-07 | 0.02 | 20 | 0.02 |
| 29-08 | 0.01 | 20 | 0.01 |
| 29-09 | 0.25 | 45 | |
| 29-10 | 0.05 | 45 | |
| 29-11 | 0.02 | 45 | |
| 29-12 | 0.01 | 45 | |
| 29-13 | 0.25 | 45 | 0.25 |
| 29-14 | 0.05 | 45 | 0.05 |

TABLE 29a-continued

| Spray composition | Lecithin g/l | phospholipid % | % w/w Fluorad FC-135 |
|---|---|---|---|
| 29-15 | 0.02 | 45 | 0.02 |
| 29-16 | 0.01 | 45 | 0.01 |

Yellow nutsedge (*Cyperus esculentus,* CYPES) plants were grown and treated by the standard procedures given above. Applications of spray compositions were made 27 days after planting CYPES. Evaluation was done 27 days after application.

In addition to compositions 29-01 to 29-15, spray compositions were prepared by tank mixing Formulations B and c with Fluorad FC-135 at various concentrations. Formulations B and C were applied as comparative treatments. Results, averaged for all replicates of each treatment, are shown in Table 29b.

TABLE 29b

| Spray composition | Glyphosate rate g a.e./ha | % Inhibition CYPES |
|---|---|---|
| Formulation B | 500 | 25 |
| | 800 | 41 |
| | 1200 | 59 |
| Formulation C | 500 | 29 |
| | 800 | 43 |
| | 1200 | 62 |
| Formulation B + Fluorad FC-135 0.25% w/v | 500 | 60 |
| | 800 | 57 |
| | 1200 | 79 |
| Formulation B + Fluorad FC-135 0.05% w/v | 500 | 63 |
| | 800 | 54 |
| | 1200 | 65 |
| Formulation B + Fluorad FC-135 0.02% w/v | 500 | 50 |
| | 800 | 71 |
| | 1200 | 60 |
| Formulation B + Fluorad FC-135 0.01% w/v | 500 | 27 |
| | 800 | 35 |
| | 1200 | 81 |
| Formulation C + Fluorad FC-135 0.25% w/v | 500 | 41 |
| | 800 | 72 |
| | 1200 | 75 |
| Formulation C + Fluorad FC-135 0.05% w/v | 500 | 52 |
| | 800 | 43 |
| | 1200 | 63 |
| Formulation C + Fluorad FC-135 0.02% w/v | 500 | 76 |
| | 800 | 72 |
| | 1200 | 82 |
| Formulation C + Fluorad FC-135 0.01% w/v | 500 | 38 |
| | 800 | 59 |
| | 1200 | 72 |
| 29-01 | 500 | 51 |
| | 800 | 70 |
| | 1200 | 64 |
| 29-02 | 500 | 58 |
| | 800 | 69 |
| | 1200 | 77 |
| 29-03 | 500 | 49 |
| | 800 | 67 |
| | 1200 | 85 |
| 29-04 | 500 | 51 |
| | 800 | 76 |
| | 1200 | 77 |
| 29-05 | 500 | 37 |
| | 800 | 73 |
| | 1200 | 100 |
| 29-06 | 400 | 72 |
| | 750 | 62 |
| | 1000 | 67 |
| 29-07 | 400 | 68 |
| | 750 | 75 |

TABLE 29b-continued

| Spray composition | Glyphosate rate g a.e./ha | % Inhibition CYPES |
|---|---|---|
| | 1000 | 86 |
| 29-08 | 400 | 59 |
| | 750 | 78 |
| | 1000 | 88 |
| 29-09 | 400 | 72 |
| | 750 | 80 |
| | 1000 | 88 |
| 29-10 | 400 | 67 |
| | 750 | 77 |
| | 1000 | 89 |
| 29-11 | 400 | 67 |
| | 750 | 75 |
| | 1000 | 66 |
| 29-12 | 400 | 55 |
| | 750 | 75 |
| | 1000 | 83 |
| 29-13 | 400 | 33 |
| | 750 | 59 |
| | 1000 | 73 |
| 29-14 | 400 | 63 |
| | 750 | 77 |
| | 1000 | 76 |
| 29-15 | 400 | 35 |
| | 750 | 75 |
| | 1000 | 88 |
| 29-16 | 400 | 77 |
| | 750 | 66 |
| | 1000 | 86 |

This test was conducted to investigate the effect of phospholipid content of lecithin on herbicidal efficacy of lecithin-containing glyphosate compositions. No clear pattern emerged from this study, but overall it appeared that the crude lecithin (20% phospholipid) provided greater herbicidal effectiveness on CYPES than the de-oiled lecithin (45% phospholipid), suggesting that the oil present in crude lecithin might be having an adjuvant effect on this species.

EXAMPLE 30

Aqueous spray compositions were prepared containing glyphosate IPA salt and excipient ingredients as shown in Table 30a. Process (iii) was followed for all compositions, using soybean lecithin (20%, 45% or 95% phospholipid as indicated below, all sourced from Avanti). The pH of all compositions was adjusted to approximately 7.

TABLE 30a

| Spray composition | Lecithin g/l | phospholipid % | % w/w Fluorad FC-135 |
|---|---|---|---|
| 30-01 | 0.5 | 20 | |
| 30-02 | 0.2 | 20 | |
| 30-03 | 0.1 | 20 | |
| 30-04 | 0.5 | 45 | |
| 30-05 | 0.2 | 45 | |
| 30-06 | 0.1 | 45 | |
| 30-07 | 0.5 | 95 | |
| 30-08 | 0.2 | 95 | |
| 30-09 | 0.1 | 95 | |
| 30-10 | 0.5 | 20 | 0.05 |
| 30-11 | 0.5 | 45 | 0.05 |
| 30-12 | 0.5 | 95 | 0.05 |
| 30-13 | 0.2 | 20 | 0.02 |
| 30-14 | 0.2 | 45 | 0.02 |
| 30-15 | 0.2 | 95 | 0.02 |
| 30-16 | 0.1 | 20 | 0.01 |

TABLE 30a-continued

| Spray composition | Lecithin | | % w/w Fluorad FC-135 |
|---|---|---|---|
| | g/l | phospholipid % | |
| 30-17 | 0.1 | 45 | 0.01 |
| 30-18 | 0.1 | 95 | 0.01 |

Velvetleaf (*Abutilon theophrasti*, ABUTH), Japanese millet (*Echinochloa crus-galli*, ECHCF) and prickly sida (*Sida spinosa*, SIDSP) plants were grown and treated by the standard procedures given above. Applications of spray compositions were made 17 days after planting ABUTH, 19 days after planting ECHCF, and 23 days after planting SIDSP. Evaluation of herbicidal inhibition was done 15 days after application.

In addition to compositions 30-01 to 30-18, spray compositions were prepared by tank mixing Formulations B and C with Fluorad FC-135 at various concentrations. Formulations B and C alone were applied as comparative treatments. Results, averaged for all replicates of each treatment, are shown in Table 30b.

TABLE 30b

| Spray composition | Glyphosate rate g a.e./ha | % Inhibition | | |
|---|---|---|---|---|
| | | ABUTH | ECHCF | SIDSP |
| Formulation B | 100 | 10 | 25 | 33 |
| | 200 | 22 | 29 | 49 |
| | 300 | 50 | 62 | 61 |
| | 400 | 62 | 62 | 64 |
| Formulation C | 100 | 14 | 40 | 34 |
| | 200 | 53 | 98 | 66 |
| | 300 | 74 | 100 | 84 |
| | 400 | 86 | 100 | 93 |
| Formulation B + Fluorad FC-135 0.05% w/v | 100 | 18 | 25 | 34 |
| | 200 | 50 | 58 | 52 |
| | 300 | 68 | 83 | 70 |
| Formulation B + Fluorad FC-135 0.02% w/v | 100 | 10 | 21 | 29 |
| | 200 | 64 | 40 | 46 |
| | 300 | 79 | 62 | 64 |
| Formulation B + Fluorad FC-135 0.01% w/v | 100 | 10 | 21 | 34 |
| | 200 | 34 | 27 | 44 |
| | 300 | 73 | 74 | 69 |
| Formulation C + Fluorad FC-135 0.05% w/v | 100 | 65 | 53 | 58 |
| | 200 | 73 | 77 | 65 |
| | 300 | 94 | 99 | 73 |
| Formulation C + Fluorad FC-135 0.02% w/v | 100 | 68 | 94 | 61 |
| | 200 | 63 | 93 | 66 |
| | 300 | 85 | 90 | 79 |
| Formulation C + Fluorad FC-135 0.01% w/v | 100 | 72 | 67 | 53 |
| | 200 | 69 | 99 | 61 |
| | 300 | 81 | 99 | 83 |
| 30-01 | 100 | 32 | 26 | 39 |
| | 200 | 72 | 60 | 56 |
| | 300 | 84 | 72 | 69 |
| 30-02 | 100 | 14 | 23 | 43 |
| | 200 | 70 | 42 | 63 |
| | 300 | 83 | 74 | 68 |
| 30-03 | 100 | 6 | 25 | 42 |
| | 200 | 55 | 47 | 57 |
| | 300 | 65 | 64 | 72 |
| 30-04 | 100 | 29 | 31 | 42 |
| | 200 | 55 | 65 | 60 |
| | 300 | 82 | 54 | 73 |
| 30-05 | 100 | 14 | 22 | 41 |
| | 200 | 32 | 35 | 66 |
| | 300 | 81 | 98 | 70 |
| 30-06 | 100 | 9 | 26 | 29 |
| | 200 | 47 | 48 | 57 |
| | 300 | 69 | 71 | 71 |
| 30-07 | 100 | 30 | 22 | 50 |
| | 200 | 73 | 50 | 69 |
| | 300 | 82 | 86 | 67 |
| 30-08 | 100 | 41 | 23 | 53 |
| | 200 | 57 | 38 | 69 |
| | 300 | 76 | 46 | 84 |
| 30-09 | 100 | 32 | 17 | 45 |
| | 200 | 60 | 37 | 67 |
| | 300 | 78 | 77 | 73 |
| 30-10 | 100 | 58 | 27 | 62 |
| | 200 | 91 | 42 | 79 |
| | 300 | 93 | 95 | 77 |
| 30-11 | 100 | 66 | 58 | 63 |
| | 200 | 91 | 79 | 69 |
| | 300 | 91 | 84 | 84 |
| 30-12 | 100 | 61 | 27 | 67 |
| | 200 | 90 | 72 | 77 |
| | 300 | 93 | 83 | 84 |
| 30-13 | 100 | 61 | 24 | 51 |
| | 200 | 88 | 48 | 69 |
| | 300 | 94 | 54 | 75 |
| 30-14 | 100 | 66 | 25 | 56 |
| | 200 | 90 | 49 | 72 |
| | 300 | 93 | 73 | 85 |
| 30-15 | 100 | 63 | 23 | 61 |
| | 200 | 88 | 33 | 72 |
| | 300 | 95 | 75 | 81 |
| 30-16 | 100 | 75 | 25 | 56 |
| | 200 | 87 | 37 | 74 |
| | 300 | 93 | 71 | 77 |
| 30-17 | 100 | 63 | 17 | 59 |
| | 200 | 92 | 27 | 73 |
| | 300 | 92 | 83 | 78 |
| 30-18 | 100 | 67 | 22 | 53 |
| | 200 | 91 | 38 | 68 |
| | 300 | 91 | 46 | 77 |

In general, across the three species included in this test, compositions containing the 45% phospholipid grade of soybean lecithin provided slightly greater herbicidal effectiveness than those containing the 20% grade. Any further improvement obtained by using the 95% grade was minimal and would likely not justify the considerably increased cost of this grade. The data of this test clearly show a non-additive interaction between lecithin and Fluorad FC-135. To take just one example for illustration, glyphosate alone (Formulation B) at 200 g a.e./ha gave 22% inhibition of ABUTH, 29% inhibition of ECHCF and 49% inhibition of SIDSP. Adding 0.02% Fluorad FC-135 brought these percentage inhibitions to 64%, 40% and 46% respectively. Alternatively, adding the 45% grade of lecithin at 0.02% (composition 30-05) resulted in percentage inhibitions of 32%, 35% and 36% respectively. Adding both these excipients, each at 0.02% (composition 30-14) gave percentage inhibitions of 90%, 49% and 72% respectively. Even adding both excipients so that the total excipient concentration was 0.02% (composition 30-17) resulted in percentage inhibitions of 92%, 27% and 73% respectively. Thus at least on the broadleaf species (ABUTH and SIDSP) there is strong evidence of a synergistic interaction between these two excipient substances.

EXAMPLE 31

Aqueous spray compositions were prepared containing glyphosate IPA salt and excipient ingredients as shown in Table 31a. Process (iii) was followed for all compositions, using lecithin (20% or 95% phospholipid from soybean, or 95% phospholipid from egg yolk, all sourced from Avanti). The pH of all compositions was adjusted to approximately 7.

TABLE 31a

| Spray composition | g/l | Lecithin phospholipid % | source | % w/w Fluorad FC-135 | Fluorad FC-754 |
|---|---|---|---|---|---|
| 31-01 | 0.05 | 95 | egg yolk | | |
| 31-02 | 0.02 | 95 | egg yolk | | |
| 31-03 | 0.01 | 95 | egg yolk | | |
| 31-04 | 0.05 | 95 | soybean | | |
| 31-05 | 0.02 | 95 | soybean | | |
| 31-06 | 0.01 | 95 | soybean | | |
| 31-07 | 0.05 | 95 | egg yolk | 0.05 | |
| 31-08 | 0.02 | 95 | egg yolk | 0.02 | |
| 31-09 | 0.01 | 95 | egg yolk | 0.01 | |
| 31-10 | 0.05 | 95 | soybean | 0.05 | |
| 31-11 | 0.02 | 95 | soybean | 0.02 | |
| 31-12 | 0.01 | 95 | soybean | 0.01 | |
| 31-13 | 0.05 | 20 | soybean | | 0.05 |
| 31-14 | 0.02 | 20 | soybean | | 0.02 |

Velvetleaf (*Abutilon theophrasti*, ABUTH) and Japanese millet (*Echinochloa crus-galli*, ECHCF) plants were grown and treated by the standard procedures given above. Applications of spray compositions were made 18 days after planting ABUTH and 19 days after planting ECHCF, and evaluation of herbicidal inhibition was done 15 days after application.

In addition to compositions 31-01 to 31-14, spray compositions were prepared by tank mixing Formulations B and C with Fluorad FC-135 or Fluorad FC-754 at various concentrations. Formulations B and C alone were applied as comparative treatments. Results, averaged for all replicates of each treatment, are shown in Table 31b.

TABLE 31b

| Spray composition | Glyphosate rate g a.e./ha | % Inhibition ABUTH | ECHCF |
|---|---|---|---|
| Formulation B | 100 | 1 | 27 |
| | 200 | 6 | 28 |
| | 300 | 21 | 35 |
| | 400 | 31 | 46 |
| Formulation C | 100 | 10 | 31 |
| | 200 | 28 | 36 |
| | 300 | 62 | 66 |
| | 400 | 77 | 74 |
| Formulation B + Fluorad FC-135 0.05% w/v | 100 | 19 | 24 |
| | 200 | 37 | 40 |
| | 300 | 62 | 52 |
| Formulation B + Fluorad FC-135 0.02% w/v | 100 | 7 | 13 |
| | 200 | 42 | 27 |
| | 300 | 56 | 57 |
| Formulation B + Fluorad FC-135 0.01% w/v | 100 | 23 | 19 |
| | 200 | 43 | 24 |
| | 300 | 60 | 40 |
| Formulation B + Fluorad FC-754 0.05% w/v | 100 | 19 | 23 |
| | 200 | 41 | 33 |
| | 300 | 67 | 62 |
| Formulation B + Fluorad FC-754 0.02% w/v | 100 | 12 | 19 |
| | 200 | 31 | 44 |
| | 300 | 61 | 45 |
| Formulation C + Fluorad FC-135 0.05% w/v | 100 | 37 | 39 |
| | 200 | 49 | 43 |
| | 300 | 66 | 62 |
| Formulation C + Fluorad FC-135 0.02% w/v | 100 | 18 | 31 |
| | 200 | 47 | 44 |
| | 300 | 68 | 49 |
| Formulation C + Fluorad FC-135 0.01% w/v | 100 | 26 | 27 |
| | 200 | 36 | 44 |
| | 300 | 54 | 82 |
| Formulation C + Fluorad FC-754 0.05% w/v | 100 | 34 | 32 |
| | 200 | 47 | 37 |
| | 300 | 62 | 62 |
| Formulation C + Fluorad FC-754 0.02% w/v | 100 | 28 | 32 |
| | 200 | 45 | 60 |
| | 300 | 43 | 75 |
| 31-01 | 100 | 16 | 36 |
| | 200 | 54 | 56 |
| | 300 | 66 | 61 |
| 31-02 | 100 | 23 | 43 |
| | 200 | 45 | 45 |
| | 300 | 65 | 51 |
| 31-03 | 100 | 31 | 35 |
| | 200 | 37 | 45 |
| | 300 | 53 | 60 |
| 31-04 | 100 | 24 | 35 |
| | 200 | 43 | 43 |
| | 300 | 78 | 50 |
| 31-05 | 100 | 24 | 36 |
| | 200 | 45 | 44 |
| | 300 | 58 | 66 |
| 31-06 | 100 | 31 | 24 |
| | 200 | 46 | 34 |
| | 300 | 52 | 51 |
| 31-07 | 100 | 49 | 33 |
| | 200 | 65 | 39 |
| | 300 | 73 | 63 |
| 31-08 | 100 | 48 | 25 |
| | 200 | 70 | 49 |
| | 300 | 73 | 69 |
| 31-09 | 100 | 45 | 27 |
| | 200 | 59 | 53 |
| | 300 | 71 | 84 |
| 31-10 | 100 | 60 | 30 |
| | 200 | 64 | 89 |
| | 300 | 75 | 99 |
| 31-11 | 100 | 47 | 51 |
| | 200 | 66 | 65 |
| | 300 | 80 | 78 |
| 31-12 | 100 | 49 | 39 |
| | 200 | 60 | 59 |
| | 300 | 67 | 84 |
| 31-13 | 100 | 50 | 30 |
| | 200 | 70 | 51 |
| | 300 | 68 | 66 |
| 31-14 | 100 | 54 | 33 |
| | 200 | 61 | 44 |
| | 300 | 79 | 66 |

In this test, glyphosate compositions containing egg yolk lecithin (31-01 to 31-03) performed similarly to those containing soybean lecithin (31-04 to 31-06) on ABUTH but were generally more effective than those containing soybean lecithin on ECHCF, at least in the absence of Fluorad FC-135. Addition of Fluorad FC-135, as in compositions 31-07 to 31-12, enhanced effectiveness of all compositions.

EXAMPLE 32

Aqueous spray compositions were prepared containing glyphosate IPA salt and excipient ingredients as shown in Table 32a. Process (iii) was followed for all compositions, using soybean lecithin (20% phospholipid, Avanti). The pH of all compositions was adjusted to approximately 7.

TABLE 32a

| Spray composition | Lecithin g/l | % w/w fluoro-organic | Type of fluoro-organic |
|---|---|---|---|
| 32-01 | 0.20 | | none |
| 32-02 | 0.20 | 0.02 | Fluorad FC-135 |
| 32-03 | 0.20 | 0.02 | Fluorad FC-431 |
| 32-04 | 0.20 | 0.02 | Fluorad FC-751 |
| 32-05 | 0.20 | 0.02 | Fluorad FC-170C |
| 32-06 | 0.20 | 0.02 | Fluorad FC-171 |
| 32-07 | 0.20 | 0.02 | Fluorad FC-754 |
| 32-08 | 0.50 | | none |
| 32-09 | 0.10 | | none |
| 32-10 | 0.04 | | none |
| 32-11 | 0.02 | | none |

Velvetleaf (*Abutilon theophrasti*, ABUTH), Japanese millet (*Echinochloa crus-galli*, ECHCF) and prickly sida (*Spida spinosa*, SIDSP) plants were grown and treated by the standard procedures given above. Applications of spray compositions were made 18 days after planting ABUTH and ECHCF, and 27 days after planting SIDSP. Evaluation of herbicidal inhibition was done 15 days after application.

In addition to compositions 32-01 to 32-11, spray compositions were prepared by tank mixing Formulations B and C with various fluoro-organic surfactants of the Fluorad range, all at 0.02%. Formulations B and C alone were applied as comparative treatments. Results, averaged for all replicates of each treatment, are shown in Table 32b.

TABLE 32b

| Spray composition | Glyphosate rate g a.e./ha | % Inhibition ABUTH | ECHCF | SIDSP |
|---|---|---|---|---|
| Formulation B | 150 | 8 | 35 | 35 |
| | 250 | 21 | 47 | 37 |
| | 350 | 31 | 36 | 56 |
| | 450 | 57 | 52 | 64 |
| Formulation C | 150 | 29 | 69 | 49 |
| | 250 | 55 | 90 | 67 |
| | 350 | 75 | 91 | 75 |
| | 450 | 82 | 91 | 85 |
| Formulation B + Fluorad FC-135 0.02% w/v | 150 | 17 | 43 | 36 |
| | 250 | 39 | 58 | 53 |
| | 350 | 52 | 53 | 68 |
| Formulation B + Fluorad FC-170C 0.02% w/v | 150 | 13 | 25 | 32 |
| | 250 | 31 | 47 | 36 |
| | 350 | 31 | 85 | 61 |
| Formulation B + Fluorad FC-171 0.02% w/v | 150 | 8 | 52 | 15 |
| | 250 | 10 | 47 | 44 |
| | 350 | 15 | 58 | 55 |
| Formulation B + Fluorad FC-431 0.02% w/v | 150 | 14 | 36 | 34 |
| | 250 | 23 | 53 | 53 |
| | 350 | 37 | 61 | 62 |
| Formulation B + Fluorad FC-751 0.02% w/v | 150 | 12 | 29 | 29 |
| | 250 | 30 | 38 | 41 |
| | 350 | 43 | 36 | 58 |
| Formulation B + Fluorad FC-754 0.02% w/v | 150 | 21 | 27 | 33 |
| | 250 | 31 | 36 | 49 |
| | 350 | 38 | 51 | 59 |
| Formulation C + Fluorad FC-135 0.02% w/v | 150 | 35 | 31 | 46 |
| | 250 | 66 | 87 | 58 |
| | 350 | 78 | 99 | 80 |
| Formulation C + Fluorad FC-170C 0.02% w/v | 150 | 29 | 68 | 41 |
| | 250 | 54 | 78 | 61 |
| | 350 | 59 | 86 | 78 |
| Formulation C + Fluorad FC-171 0.02% w/v | 150 | 20 | 96 | 35 |
| | 250 | 37 | 99 | 62 |
| | 350 | 55 | 100 | 65 |
| Formulation C + Fluorad FC-431 0.02% w/v | 150 | 20 | 94 | 41 |
| | 250 | 51 | 85 | 68 |
| | 350 | 66 | 97 | 74 |
| Formulation C + Fluorad FC-751 0.02% w/v | 150 | 15 | 67 | 38 |
| | 250 | 36 | 85 | 56 |
| | 350 | 60 | 100 | 72 |
| Formulation C + Fluorad FC-754 0.02% w/v | 150 | 33 | 78 | 37 |
| | 250 | 75 | 85 | 66 |
| | 350 | 82 | 94 | 80 |
| 32-01 | 150 | 25 | 35 | 45 |
| | 250 | 43 | 52 | 63 |
| | 350 | 60 | 90 | 77 |
| 32-02 | 150 | 65 | 37 | 58 |
| | 250 | 69 | 69 | 67 |
| | 350 | 66 | 69 | 78 |
| 32-03 | 150 | 14 | 40 | 41 |
| | 250 | 45 | 78 | 63 |
| | 350 | 55 | 92 | 75 |
| 32-04 | 150 | 19 | 48 | 48 |
| | 250 | 36 | 51 | 63 |
| | 350 | 65 | 69 | 70 |
| 32-05 | 150 | 47 | 34 | 45 |
| | 250 | 55 | 43 | 55 |
| | 350 | 63 | 58 | 75 |
| 32-06 | 150 | 23 | 36 | 46 |
| | 250 | 57 | 52 | 59 |
| | 350 | 61 | 73 | 67 |
| 32-07 | 150 | 67 | 59 | 58 |
| | 250 | 81 | 73 | 72 |
| | 350 | 80 | 76 | 76 |
| 32-08 | 150 | 37 | 49 | 60 |
| | 250 | 60 | 83 | 69 |
| | 350 | 67 | 93 | 49 |
| 32-09 | 150 | 19 | 63 | 51 |
| | 250 | 53 | 71 | 62 |
| | 350 | 55 | 74 | 82 |
| 32-10 | 150 | 19 | 70 | 51 |
| | 250 | 39 | 94 | 61 |
| | 350 | 63 | 87 | 73 |
| 32-11 | 150 | 16 | 51 | 50 |
| | 250 | 58 | 67 | 66 |
| | 350 | 69 | 92 | 73 |

Composition 32-07, containing 0.02% lecithin and 0.02% Fluorad FC-754, was equal or superior to composition 32-02, containing 0.02% lecithin and 0.02% Fluorad FC-135, in herbicidal effectiveness. This indicates that Fluorad FC-754 is an acceptable substitute for Fluorad FC-135 in such compositions. The other fluoro-organic surfactants tested in this Example, none of which is cationic, were less effective than the cationic fluoro-organics Fluorad FC-135 and Fluorad FC-754 as excipients in combination with lecithin. A possible exception was Fluorad FC-170C which gave good enhancement of glyphosate effectiveness on ECHCF only.

EXAMPLE 33

Aqueous concentrate compositions were prepared containing glyphosate IPA salt and excipient ingredients as shown in Table 33a. Process (v) was followed for all compositions, using soybean lecithin (20% phospholipid, Avanti). The pH of all compositions was approximately 5.

TABLE 33a

| Concentrate composition | Glyphosate a.e. | Lecithin | MON 0818 | Agrimul PG-2069 | Fluorad FC-135 |
|---|---|---|---|---|---|
| | | | % w/w | | |
| 33-01 | 30 | 3.0 | | 0.25 | 3.0 |
| 33-02 | 30 | 3.0 | | 0.25 | 1.0 |
| 33-03 | 30 | 3.0 | 0.25 | | 3.0 |
| 33-04 | 30 | 1.0 | 0.50 | | 3.0 |
| 33-05 | 30 | 1.0 | | 0.50 | 3.0 |
| 33-06 | 30 | 1.0 | | | 1.0 |
| 33-07 | 30 | 1.0 | | 0.25 | 1.0 |
| 33-08 | 30 | 3.0 | | 0.50 | 2.0 |
| 33-09 | 30 | 2.0 | | | 3.0 |
| 33-10 | 30 | 3.0 | 0.50 | | |

Velvetleaf (*Abutilon theophrasti*, ABUTH) and Japanese millet (*Echinochloa crus-galli*, ECHCF) plants were grown and treated by the standard procedures given above. Applications of spray compositions were made 14 days after planting ABUTH and 17 days after planting ECHCF, and evaluation of herbicidal inhibition was done 19 days after application.

Formulations C and J were applied as comparative treatments. Results, averaged for all replicates of each treatment, are shown in Table 33b.

TABLE 33b

| Concentrate composition | Glyphosate rate g a.e./ha | % Inhibition ABUTH | ECHCF |
|---|---|---|---|
| Formulation C | 56 | 3 | 5 |
| | 112 | 49 | 48 |
| | 224 | 79 | 83 |
| | 448 | 99 | 99 |
| Formulation J | 56 | 16 | 20 |
| | 112 | 40 | 43 |
| | 224 | 80 | 81 |
| | 448 | 97 | 99 |
| 33-01 | 56 | 4 | 5 |
| | 112 | 35 | 20 |
| | 224 | 81 | 51 |
| | 448 | 99 | 80 |
| 33-02 | 56 | 0 | 5 |
| | 112 | 4 | 20 |
| | 224 | 66 | 55 |
| | 448 | 94 | 80 |
| 33-03 | 56 | 1 | 5 |
| | 112 | 6 | 20 |
| | 224 | 78 | 74 |
| | 448 | 93 | 80 |
| 33-04 | 56 | 1 | 5 |
| | 112 | 1 | 15 |
| | 224 | 75 | 65 |
| | 448 | 95 | 80 |
| 33-05 | 56 | 0 | 5 |
| | 112 | 1 | 15 |
| | 224 | 75 | 65 |
| | 448 | 91 | 80 |
| 33-06 | 56 | 0 | 5 |
| | 112 | 3 | 15 |
| | 224 | 55 | 63 |
| | 448 | 91 | 79 |
| 33-07 | 56 | 1 | 5 |
| | 112 | 3 | 15 |
| | 224 | 48 | 55 |
| | 448 | 88 | 81 |
| 33-08 | 56 | 3 | 9 |
| | 112 | 3 | 20 |
| | 224 | 66 | 60 |
| | 448 | 89 | 80 |
| 33-09 | 56 | 0 | 5 |

TABLE 33b-continued

| Concentrate composition | Glyphosate rate g a.e./ha | % Inhibition ABUTH | ECHCF |
|---|---|---|---|
| | 112 | 5 | 10 |
| | 224 | 78 | 55 |
| | 448 | 97 | 80 |
| 33-10 | 56 | 0 | 5 |
| | 112 | 4 | 15 |
| | 224 | 21 | 55 |
| | 448 | 88 | 79 |

Concentrate compositions containing lecithin and Fluorad FC-135 did not exhibit herbicidal effectiveness superior to commercial standard Formulations C and J in this test.

EXAMPLE 34

Aqueous spray compositions were prepared containing glyphosate IPA salt and excipient ingredients as shown in Table 34a. Process (iii) was followed for all compositions, using soybean lecithin (20% phospholipid, Avanti). The pH of all compositions was adjusted to approximately 7.

TABLE 34a

| Spray composition | Lecithin g/l | % w/w Fluorad FC-135 |
|---|---|---|
| 34-01 | 0.25 | |
| 34-02 | 0.05 | |
| 34-03 | 0.02 | |
| 34-04 | 0.01 | |
| 34-05 | 0.25 | 0.25 |
| 34-06 | 0.05 | 0.05 |
| 34-07 | 0.02 | 0.02 |
| 34-08 | 0.01 | 0.01 |

Guineagrass (*Panicum maximum*, PANMA) plants were grown and treated by the standard procedures given above. Applications of spray compositions were made 78 days after planting PANMA, and evaluation of herbicidal inhibition was done 20 days after application.

In addition to compositions 34-01 to 34-08, spray compositions were prepared by tank mixing Formulations B and C with Fluorad FC-135 at various concentrations. Formulations B and C alone were applied as comparative treatments. Results, averaged for all replicates of each treatment, are shown in Table 34b.

TABLE 34b

| Spray composition | Glyphosate rate g a.e./ha | % Inhibition PANMA |
|---|---|---|
| Formulation B | 400 | 61 |
| | 800 | 89 |
| | 1500 | 93 |
| | 2000 | 97 |
| Formulation C | 400 | 85 |
| | 800 | 94 |
| | 1500 | 100 |
| | 2000 | 100 |
| Formulation B + | 400 | 76 |
| Fluorad FC-135 0.25% w/v | 800 | 78 |
| | 1500 | 97 |
| Formulation B + | 400 | 45 |
| Fluorad FC-135 0.05% w/v | 800 | 69 |
| | 1500 | 89 |
| Formulation B + | 400 | 39 |

TABLE 34b-continued

| Spray composition | Glyphosate rate g a.e./ha | % Inhibition PANMA |
|---|---|---|
| Fluorad FC-135 0.02% w/v | 800 | 71 |
|  | 1500 | 95 |
| Formulation B + | 400 | 52 |
| Fluorad FC-135 0.01% w/v | 800 | 78 |
|  | 1500 | 99 |
| Formulation C + | 400 | 82 |
| Fluorad FC-135 0.25% w/v | 800 | 97 |
|  | 1500 | 100 |
| Formulation C + | 400 | 63 |
| Fluorad FC-135 0.05% w/v | 800 | 93 |
|  | 1500 | 100 |
| Formulation C + | 400 | 73 |
| Fluorad FC-135 0.02% w/v | 800 | 98 |
|  | 1500 | 100 |
| Formulation C + | 400 | 66 |
| Fluorad FC-135 0.01% w/v | 800 | 97 |
|  | 1500 | 100 |
| 34-01 | 400 | 38 |
|  | 800 | 73 |
|  | 1500 | 92 |
| 34-02 | 400 | 64 |
|  | 800 | 83 |
|  | 1500 | 90 |
| 34-03 | 400 | 50 |
|  | 800 | 75 |
|  | 1500 | 99 |
| 34-04 | 400 | 48 |
|  | 800 | 88 |
|  | 1500 | 98 |
| 34-05 | 400 | 60 |
|  | 800 | 79 |
|  | 1500 | 99 |
| 34-06 | 400 | 58 |
|  | 800 | 86 |
|  | 1500 | 99 |
| 34-07 | 400 | 55 |
|  | 800 | 86 |
|  | 1500 | 93 |
| 34-08 | 400 | 60 |
|  | 800 | 91 |
|  | 1500 | 98 |

Exceptionally high glyphosate activity was seen in this test even with Formulation B and no firm conclusions can be drawn. However, none of the compositions containing lecithin and Fluorad FC-135 exceeded the effectiveness of commercial standard Formulation C on PANMA under the conditions of this test.

EXAMPLE 35

Aqueous concentrate compositions were prepared containing glyphosate IPA salt and excipient ingredients as shown in Table 35a. Process (v) was followed for all compositions, using soybean lecithin (20% phospholipid, Avanti). The pH of all compositions was approximately 5.

TABLE 35a

| | % w/w | | | | | |
|---|---|---|---|---|---|---|
| Concentrate composition | Glyphosate a.e. | Lecithin | Fluorad FC-135 | Fluorad FC-754 | MON 0818 | Agrimul PG-2069 |
| 35-01 | 30 | 3.0 | 3.0 | | | 0.25 |
| 35-02 | 30 | 3.0 | 1.0 | | | 0.25 |
| 35-03 | 30 | 3.0 | 3.0 | | 0.25 | |
| 35-04 | 30 | 1.0 | 3.0 | | 0.50 | |
| 35-05 | 30 | 1.0 | 3.0 | | | 0.50 |
| 35-06 | 30 | 1.0 | 1.0 | | | |

TABLE 35a-continued

| | % w/w | | | | | |
|---|---|---|---|---|---|---|
| Concentrate composition | Glyphosate a.e. | Lecithin | Fluorad FC-135 | Fluorad FC-754 | MON 0818 | Agrimul PG-2069 |
| 35-07 | 30 | 1.0 | 1.0 | | | 0.25 |
| 35-08 | 30 | 3.0 | 2.0 | | | 0.50 |
| 35-09 | 30 | 2.0 | 3.0 | | | |
| 35-10 | 30 | 3.0 | | | 0.50 | |
| 35-11 | 30 | 3.0 | | 3.0 | | 0.50 |
| 35-12 | 30 | 2.0 | | 1.0 | | 0.375 |
| 35-13 | 30 | 1.0 | | 2.0 | | 0.25 |
| 35-14 | 30 | 3.0 | | 3.0 | 0.50 | |
| 35-15 | 30 | 3.0 | | 3.0 | | 0.50 |
| 35-16 | 30 | 2.0 | | 1.0 | | 0.375 |
| 35-17 | 30 | 1.0 | | 2.0 | | 0.25 |
| 35-18 | 30 | 3.0 | | 3.0 | 0.50 | |

Quackgrass (*Elymus repens*, AGRRE) plants were grown and treated by the standard procedures given above. Applications of spray compositions were made 56 days after planting AGRRE, and evaluation of herbicidal inhibition was done 16 days after application.

Formulations B, C and J were applied as comparative treatments. Results, averaged for all replicates of each treatment, are shown in Table 35b.

TABLE 35b

| Concentration composition | Glyphosate rate g a.e./ha | % Inhibition AGRRE |
|---|---|---|
| Formulation B | 400 | 41 |
|  | 800 | 46 |
|  | 1000 | 55 |
|  | 1200 | 70 |
| Formulation C | 400 | 38 |
|  | 800 | 47 |
|  | 1000 | 77 |
|  | 1200 | 77 |
| Formulation J | 400 | 60 |
|  | 800 | 84 |
|  | 1000 | 77 |
|  | 1200 | 85 |
| 35-01 | 400 | 27 |
|  | 800 | 76 |
|  | 1000 | 79 |
| 35-02 | 400 | 49 |
|  | 800 | 66 |
|  | 1000 | 78 |
| 35-03 | 400 | 42 |
|  | 800 | 80 |
|  | 1000 | 83 |
| 35-04 | 400 | 31 |
|  | 800 | 71 |
|  | 1000 | 64 |
| 35-05 | 400 | 32 |
|  | 800 | 53 |
|  | 1000 | 59 |
| 35-06 | 400 | 27 |
|  | 800 | 39 |
|  | 1000 | 65 |
| 35-07 | 400 | 29 |
|  | 800 | 54 |
|  | 1000 | 61 |
| 35-08 | 400 | 38 |
|  | 800 | 65 |
|  | 1000 | 81 |
| 35-09 | 400 | 31 |
|  | 800 | 55 |
|  | 1000 | 67 |
| 35-10 | 400 | 43 |
|  | 800 | 38 |
|  | 1000 | 58 |

TABLE 35b-continued

| Concentration composition | Glyphosate rate g a.e./ha | % Inhibition AGRRE |
|---|---|---|
| 35-11 | 400 | 34 |
|  | 800 | 56 |
|  | 1000 | 75 |
| 35-12 | 400 | 29 |
|  | 800 | 51 |
|  | 1000 | 65 |
| 35-13 | 400 | 51 |
|  | 800 | 69 |
|  | 1000 | 83 |
| 35-14 | 400 | 39 |
|  | 800 | 63 |
|  | 1000 | 65 |
| 35-15 | 400 | 53 |
|  | 800 | 65 |
|  | 1000 | 77 |
| 35-16 | 400 | 43 |
|  | 800 | 65 |
|  | 1000 | 82 |
| 35-17 | 400 | 69 |
|  | 800 | 84 |
|  | 1000 | 94 |
| 35-18 | 400 | 69 |
|  | 800 | 92 |
|  | 1000 | 92 |

Compositions of the invention exhibiting superior herbicidal effectiveness to commercial standard Formulation C in this test on AGRRE included 35-01, 35-02, 35-03, 35-13 and 35-15 to 35-18. Compositions 35-17 and 35-18 were the most effective in this test, outperforming commercial standard Formulation J as well as Formulation C.

EXAMPLE 36

Aqueous concentrate compositions were prepared containing glyphosate IPA salt and excipient ingredients as shown in Table 36a. Process (v) was followed for all compositions, using soybean lecithin (20% phospholipid, Avanti). The order of addition of ingredients was varied in compositions 36-15 to 36-20 as shown below. The pH of all compositions was approximately 5.

TABLE 36a

| Conc. comp. | Glyphosate a.e. | Lecithin | Fluorad FC-135 | Agrimul PG-2069 | MON 0818 | Lecithin phospholipid % | order of addition (*) |
|---|---|---|---|---|---|---|---|
| 36-01 | 30 | 3.0 | 2.0 | 0.50 |  | 45 | A |
| 36-02 | 30 | 3.0 | 3.0 | 0.50 |  | 45 | A |
| 36-03 | 30 | 3.0 | 3.0 | 0.75 |  | 45 | A |
| 36-04 | 30 | 3.0 | 3.0 | 0.75 | 0.5 | 45 | A(**) |
| 36-05 | 30 | 3.0 | 3.0 | 1.00 |  | 45 | A |
| 36-06 | 30 | 3.0 | 3.0 | 2.00 |  | 45 | A |
| 36-07 | 30 | 3.0 | 3.0 | 3.00 |  | 45 | A |
| 36-08 | 30 | 3.0 | 3.0 | 4.00 |  | 45 | A |
| 36-09 | 30 | 3.0 | 2.0 | 0.50 |  | 20 | A |
| 36-10 | 30 | 3.0 | 2.0 | 0.50 |  | 20 | B |
| 36-11 | 30 | 3.0 | 2.0 | 0.50 |  | 20 | C |
| 36-12 | 30 | 3.0 | 2.0 | 0.50 |  | 20 | D |
| 36-13 | 30 | 3.0 | 2.0 | 0.50 |  | 20 | E |
| 36-14 | 30 | 3.0 | 2.0 | 0.50 |  | 20 | F |
| 36-15 | 30 | 3.0 | 3.0 | 0.50 |  | 20 | A |
| 36-16 | 30 | 3.0 | 3.0 | 0.50 |  | 20 | B |
| 36-17 | 30 | 3.0 | 3.0 | 0.50 |  | 20 | C |
| 36-18 | 30 | 3.0 | 3.0 | 0.50 |  | 20 | D |
| 36-19 | 30 | 3.0 | 3.0 | 0.50 |  | 20 | E |
| 36-20 | 30 | 3.0 | 3.0 | 0.50 |  | 20 | F |

(*)Order of addition:

| | 1st | 2nd | 3rd | 4th | 5th |
|---|---|---|---|---|---|
| A | lecithin | PG-2069 | FC-135 | water | glyphosate |
| B | lecithin | FC-135 | PG-2069 | water | glyphosate |
| C | glyphosate | water | FC-135 | PG-2069 | lecithin |
| D | glyphosate | water | PG-2069 | FC-135 | lecithin |
| E | glyphosate | lecithin | PG-2069 | FC-135 | water |
| F | glyphosate | lecithin | FC-135 | PG-2069 | water |

(**)where MON 0818 included, added with Agrimul PG-2069

Velvetleaf (*Abutilon theophrasti*, ABUTH) and Japanese millet (*Echinochloa crus-galli*, ECHCF) plants were grown and treated by the standard procedures given above. Applications of spray compositions were made 19 days after planting ABUTH and 22 days after planting ECHCF, and evaluation of herbicidal inhibition was done 17 days after application.

Formulations B, C and J were applied as comparative treatments. Results, averaged for all replicates of each treatment, are shown in Table 36b.

TABLE 36b

| Concentration composition | Glyphosate rate g a.e./ha | % Inhibition ABUTH | % Inhibition ECHCF |
|---|---|---|---|
| Formulation B | 200 | 38 | 73 |
|  | 400 | 51 | 64 |
|  | 600 | 67 | 89 |
|  | 800 | 72 | 86 |
| Formulation C | 200 | 57 | 75 |
|  | 400 | 77 | 98 |
|  | 600 | 92 | 97 |
|  | 800 | 100 | 100 |
| Formulation J | 200 | 50 | 52 |
|  | 400 | 73 | 99 |
|  | 600 | 88 | 99 |
|  | 800 | 98 | 98 |
| 36-01 | 200 | 49 | 64 |
|  | 400 | 72 | 59 |
|  | 600 | 78 | 87 |
| 36-02 | 200 | 54 | 72 |
|  | 400 | 78 | 71 |
|  | 600 | 97 | 90 |
| 36-03 | 200 | 57 | 62 |
|  | 400 | 80 | 78 |
|  | 600 | 89 | 87 |
| 36-04 | 200 | 46 | 39 |
|  | 400 | 74 | 64 |
|  | 600 | 86 | 78 |
| 36-05 | 200 | 49 | 29 |
|  | 400 | 74 | 79 |
|  | 600 | 83 | 90 |
| 36-06 | 200 | 49 | 65 |
|  | 400 | 70 | 88 |
|  | 600 | 87 | 88 |
| 36-07 | 200 | 49 | 51 |
|  | 400 | 67 | 77 |
|  | 600 | 81 | 83 |
| 36-08 | 200 | 42 | 59 |
|  | 400 | 70 | 67 |
|  | 600 | 78 | 80 |
| 36-09 | 200 | 45 | 28 |
|  | 400 | 73 | 85 |
|  | 600 | 87 | 98 |
| 36-10 | 200 | 57 | 82 |
|  | 400 | 76 | 89 |
|  | 600 | 87 | 98 |
| 36-11 | 200 | 56 | 80 |

TABLE 36b-continued

| Concentration composition | Glyphosate rate g a.e./ha | % Inhibition ABUTH | % Inhibition ECHCF |
|---|---|---|---|
|  | 400 | 84 | 84 |
|  | 600 | 85 | 100 |
| 36-12 | 200 | 57 | 81 |
|  | 400 | 78 | 98 |
|  | 600 | 87 | 94 |
| 36-13 | 200 | 54 | 86 |
|  | 400 | 73 | 72 |
|  | 600 | 96 | 97 |
| 36-14 | 200 | 56 | 73 |
|  | 400 | 69 | 98 |
|  | 600 | 85 | 94 |
| 36-15 | 200 | 40 | 41 |
|  | 400 | 85 | 88 |
|  | 600 | 83 | 96 |
| 36-16 | 200 | 53 | 59 |
|  | 400 | 73 | 76 |
|  | 600 | 84 | 73 |
| 36-17 | 200 | 39 | 53 |
|  | 400 | 65 | 86 |
|  | 600 | 86 | 81 |
| 36-18 | 200 | 49 | 31 |
|  | 400 | 69 | 52 |
|  | 600 | 73 | 75 |
| 36-19 | 200 | 47 | 50 |
|  | 400 | 74 | 86 |
|  | 600 | 88 | 98 |
| 36-20 | 200 | 51 | 42 |
|  | 400 | 68 | 94 |
|  | 600 | 90 | 98 |

Order of addition of ingredients apparently had some influence on herbicidal effectiveness of compositions 36-09 to 36-20. However, as most of these compositions showed poor short-term stability, it is likely that in at least some cases the uniformity of spray application was affected and the results are therefore difficult to interpret.

EXAMPLE 37

Aqueous concentrate compositions were prepared containing glyphosate IPA salt and excipient ingredients as shown in Table 37a. Process (iv) was followed for all compositions, using soybean lecithin (20% phospholipid, Avanti). The pH of all compositions was approximately 5.

TABLE 37a

| Concentrate composition | Glyphosate g a.e./l | Lecithin | Aerosol OT | MON 0818 | Fluorad FC-754 | Methyl caprate | PVA |
|---|---|---|---|---|---|---|---|
| 37-01 | 200 | 2.0 |  | 0.25 |  |  |  |
| 37-02 | 300 | 3.0 |  | 0.50 |  |  |  |
| 37-03 | 300 | 3.0 |  | 0.50 |  |  | 2.0 |
| 37-04 | 200 | 2.0 |  | 0.25 |  |  | 1.5 |
| 37-05 | 200 | 2.0 |  | 0.25 | 1.0 |  | 1.0 |
| 37-06 | 200 | 2.0 |  | 0.25 |  | 1.0 | 1.0 |
| 37-07 | 200 | 2.0 |  | 0.25 | 2.0 |  |  |
| 37-08 | 200 |  | 2.0 | 0.25 |  |  |  |
| 37-09 | 300 |  | 3.0 | 0.50 |  |  |  |
| 37-10 | 300 |  | 3.0 | 0.50 |  |  | 2.0 |
| 37-11 | 200 |  | 2.0 | 0.25 |  |  | 1.5 |
| 37-12 | 200 |  | 2.0 | 0.25 | 1.0 |  |  |
| 37-13 | 200 |  | 2.0 | 0.25 |  | 1.0 |  |
| 37-14 | 200 |  | 2.0 | 0.25 |  | 1.0 | 1.5 |
| 37-15 | 200 |  | 2.0 | 0.25 | 2.0 |  |  |

Velvetleaf (*Abutilon theophrasti*, ABUTH) and Japanese millet (*Echinochloa crus-galli*, ECHCF) plants were grown and treated by the standard procedures given above. Applications of spray compositions were made 16 days after planting ABUTH and 13 days after planting ECHCF, and evaluation of herbicidal inhibition was done 20 days after application.

Compositions containing PVA were too viscous to spray and were not tested for herbicidal effectiveness. Formulations B, C and J were applied as comparative treatments. Results, averaged for all replicates of each treatment, are shown in Table 37b.

TABLE 37b

| Concentrate composition | Glyphosate rate g a.e./ha | % Inhibition ABUTH | % Inhibition ECHCF |
|---|---|---|---|
| Formulation B | 112 | 5 | 4 |
|  | 224 | 48 | 8 |
|  | 336 | 73 | 20 |
|  | 448 | 94 | 50 |
| Formulation C | 112 | 30 | 45 |
|  | 224 | 91 | 81 |
|  | 336 | 98 | 81 |
|  | 448 | 100 | 99 |
| Formulation J | 112 | 50 | 35 |
|  | 224 | 80 | 65 |
|  | 336 | 97 | 88 |
|  | 448 | 100 | 90 |
| 37-01 | 112 | 11 | 8 |
|  | 224 | 50 | 40 |
|  | 336 | 71 | 61 |
|  | 448 | 93 | 78 |
| 37-02 | 112 | 5 | 6 |
|  | 224 | 64 | 58 |
|  | 336 | 78 | 60 |
|  | 448 | 84 | 65 |
| 37-07 | 112 | 5 | 3 |
|  | 224 | 46 | 38 |
|  | 336 | 73 | 83 |
|  | 448 | 93 | 66 |
| 37-08 | 112 | 8 | 13 |
|  | 224 | 43 | 46 |
|  | 336 | 73 | 65 |
|  | 448 | 83 | 70 |
| 37-09 | 112 | 1 | 5 |
|  | 224 | 23 | 25 |
|  | 336 | 65 | 33 |
|  | 448 | 91 | 58 |
| 37-12 | 112 | 0 | 5 |
|  | 224 | 58 | 48 |
|  | 336 | 73 | 63 |
|  | 448 | 91 | 63 |
| 37-13 | 112 | 0 | 10 |
|  | 224 | 53 | 38 |
|  | 336 | 73 | 45 |
|  | 448 | 88 | 50 |
| 37-15 | 112 | 28 | 10 |
|  | 224 | 50 | 53 |
|  | 336 | 80 | 63 |
|  | 448 | 88 | 91 |

Concentrate compositions containing lecithin and Fluorad FC-754 or methyl caprate did not exhibit herbicidal effectiveness equal to that of the commercial standards in this test.

EXAMPLE 38

Aqueous concentrate compositions were prepared containing glyphosate IPA salt and excipient ingredients as shown in Table 38a. Process (iii) was followed for all compositions, using soybean lecithin (20% phospholipid, Avanti). The pH of all compositions was approximately 5.

TABLE 38a

| Concentrate composition | % w/w | | | |
|---|---|---|---|---|
| | Glyphosate a.e. | Lecithin | Fluorad FC-135 | MON 0818 |
| 38-01 | 30 | 3.0 | 3.0 | 0.75 |
| 38-02 | 25 | 2.5 | 2.5 | 0.63 |
| 38-03 | 20 | 2.0 | 2.0 | 0.50 |
| 38-04 | 15 | 1.5 | 1.5 | 0.38 |
| 38-05 | 10 | 1.0 | 1.0 | 0.25 |
| 38-06 | 5 | 0.5 | 0.5 | 0.13 |
| 38-07 | 30 | 3.0 | 3.0 | 1.50 |
| 38-08 | 25 | 2.5 | 2.5 | 0.63 |
| 38-09 | 20 | 2.0 | 2.0 | 0.50 |
| 38-10 | 15 | 1.5 | 1.5 | 0.38 |
| 38-11 | 10 | 1.0 | 1.0 | 0.25 |
| 38-12 | 5 | 0.5 | 0.5 | 0.13 |
| 38-13 | 25 | 2.5 | 2.5 | 0.94 |
| 38-14 | 20 | 2.0 | 2.0 | 0.75 |
| 38-15 | 15 | 1.5 | 1.5 | 0.56 |
| 38-16 | 10 | 1.0 | 1.0 | 0.38 |
| 38-17 | 5 | 0.5 | 0.5 | 0.19 |

Velvetleaf (*Abutilon theophrasti*, ABUTH) and Japanese millet (*Echinochloa crus-galli*, ECHCF) plants were grown and treated by the standard procedures given above. Applications of spray compositions were made 19 days after planting ABUTH and 21 days after planting ECHCF, and evaluation of herbicidal inhibition was done 14 days after application.

In addition to compositions 38-01 to 38-17, spray compositions were prepared by tank mixing Formulations B and C with Fluorad FC-135 at two concentrations. Formulations B and C alone were applied as comparative treatments. Results, averaged for all replicates of each treatment, are shown in Table 38b.

TABLE 38b

| Concentrate composition | Glyphosate rate g a.e./ha | % Inhibition | |
|---|---|---|---|
| | | ABUTH | ECHCF |
| Formulation C | 200 | 59 | 98 |
| | 400 | 96 | 96 |
| | 600 | 70 | 93 |
| | 800 | 100 | 97 |
| Formulation C + Fluorad FC-135 0.1% | 200 | 59 | 92 |
| | 400 | 93 | 93 |
| | 600 | 95 | 100 |
| | 800 | 100 | 97 |
| Formulation C + Fluorad FC-135 0.05% | 200 | 54 | 73 |
| | 400 | 95 | 76 |
| | 600 | 100 | 82 |
| | 800 | 100 | 95 |
| Formulation J | 200 | 55 | 87 |
| | 400 | 92 | 98 |
| | 600 | 97 | 94 |
| | 800 | 99 | 96 |
| Formulation J + Fluorad FC-135 0.1% | 200 | 67 | 88 |
| | 400 | 89 | 89 |
| | 600 | 94 | 87 |
| | 800 | 96 | 91 |
| Formulation J + Fluorad FC-135 0.05% | 200 | 71 | 81 |
| | 400 | 75 | 95 |
| | 600 | 96 | 99 |
| | 800 | 100 | 100 |
| 38-01 | 200 | 53 | 71 |
| | 400 | 74 | 87 |
| | 600 | 98 | 87 |
| 38-02 | 200 | 51 | 70 |
| | 400 | 88 | 96 |
| | 600 | 89 | 99 |
| 38-03 | 200 | 51 | 85 |

TABLE 38b-continued

| Concentrate composition | Glyphosate rate g a.e./ha | % Inhibition | |
|---|---|---|---|
| | | ABUTH | ECHCF |
| | 400 | 81 | 97 |
| | 600 | 96 | 94 |
| 38-04 | 200 | 51 | 63 |
| | 400 | 81 | 82 |
| | 600 | 96 | 97 |
| 38-05 | 200 | 47 | 60 |
| | 400 | 73 | 91 |
| | 600 | 94 | 94 |
| 38-06 | 200 | 54 | 43 |
| | 400 | 73 | 88 |
| | 600 | 92 | 87 |
| 38-07 | 200 | 60 | 70 |
| | 400 | 84 | 93 |
| | 600 | 90 | 98 |
| 38-08 | 200 | 49 | 55 |
| | 400 | 76 | 92 |
| | 600 | 88 | 83 |
| 38-09 | 200 | 57 | 53 |
| | 400 | 79 | 95 |
| | 600 | 91 | 87 |
| 38-10 | 200 | 55 | 85 |
| | 400 | 90 | 97 |
| | 600 | 94 | 96 |
| 38-11 | 200 | 64 | 43 |
| | 400 | 77 | 87 |
| | 600 | 93 | 96 |
| 38-12 | 200 | 54 | 72 |
| | 400 | 85 | 98 |
| | 600 | 96 | 100 |
| 38-13 | 200 | 61 | 61 |
| | 400 | 84 | 90 |
| | 600 | 95 | 99 |
| 38-14 | 200 | 57 | 86 |
| | 400 | 82 | 90 |
| | 600 | 99 | 98 |
| 38-15 | 200 | 59 | 89 |
| | 400 | 78 | 96 |
| | 600 | 93 | 97 |
| 38-16 | 200 | 53 | 87 |
| | 400 | 81 | 98 |
| | 600 | 96 | 98 |
| 38-17 | 200 | 48 | 87 |
| | 400 | 81 | 100 |
| | 600 | 91 | 100 |

As concentrate compositions in previous Examples have tended to exhibit weaker herbicidal effectiveness than has been seen with ready-made spray compositions, this test was conducted to determine if the degree of concentration at which a composition is prepared before dilution for spraying had an influence on effectiveness. No consistent trend was seen in this test.

EXAMPLE 39

Aqueous concentrate compositions were prepared containing glyphosate IPA salt and excipient ingredients as shown in Table 39a. Process (iii) was followed for all compositions, using soybean lecithin (45% phospholipid, Avanti). The pH of all compositions was approximately 5.

TABLE 39a

| | % w/w | | | | |
|---|---|---|---|---|---|
| Conc. comp. | Glyphosate a.e. | Lecithin | Fluorad FC-135 or FC-754 | Amine surfactant | Type of amine surfactant |
| 39-01 | 20 | 2.0 | | 0.25 | MON 0818 |
| 39-02 | 20 | 3.0 | | 0.25 | MON 0818 |

TABLE 39a-continued

| Conc. comp. | Gly-phosate a.e. (% w/w) | Leci-thin (% w/w) | Fluorad FC-135 or FC-754 (% w/w) | Amine surfactant (% w/w) | Type of amine surfactant |
|---|---|---|---|---|---|
| 39-03 | 20 | 3.0 | 3.0 (135) | 0.25 | MON 0818 |
| 39-04 | 20 | 3.0 | 3.0 (754) | 0.25 | MON 0818 |
| 39-05 | 20 | 2.0 | | 2.00 | Triton RW-20 |
| 39-06 | 20 | 2.0 | | 2.00 | Triton RW-50 |
| 39-07 | 20 | 2.0 | | 2.00 | Triton RW-75 |
| 39-08 | 20 | 2.0 | | 2.00 | Triton RW-100 |
| 39-09 | 20 | 2.0 | | 2.00 | Triton RW-150 |
| 39-10 | 20 | | | 2.00 | Triton RW-20 |
| 39-11 | 20 | | | 2.00 | Triton RW-50 |
| 39-12 | 20 | | | 2.00 | Triton RW-75 |
| 39-13 | 20 | | | 2.00 | Triton RW-100 |
| 39-14 | 20 | | | 2.00 | Triton RW-150 |

Velvetleaf (*Abutilon theophrasti,* ABUTH) and Japanese millet (*Echinochloa crus-galli,* ECHCF) plants were grown and treated by the standard procedures given above. Applications of spray compositions were made 14 days after planting ABUTH and 17 days after planting ECHCF, and evaluation of herbicidal inhibition was done 21 days after application.

Formulation C was applied as a comparative treatment. Results, averaged for all replicates of each treatment, are shown in Table 39b.

TABLE 39b

| Concentrate composition | Glyphosate rate g a.e./ha | % Inhibition ABUTH | % Inhibition ECHCF |
|---|---|---|---|
| Formulation C | 112 | 0 | 10 |
| | 224 | 10 | 20 |
| | 336 | 47 | 30 |
| | 448 | 63 | 40 |
| 39-01 | 112 | 8 | 15 |
| | 224 | 25 | 35 |
| | 336 | 55 | 56 |
| | 448 | 63 | 65 |
| 39-02 | 112 | 5 | 10 |
| | 224 | 23 | 33 |
| | 336 | 55 | 64 |
| | 448 | 66 | 60 |
| 39-03 | 112 | 28 | 15 |
| | 224 | 55 | 35 |
| | 336 | 74 | 58 |
| | 448 | 76 | 65 |
| 39-04 | 112 | 15 | 8 |
| | 224 | 53 | 45 |
| | 336 | 73 | 55 |
| | 448 | 75 | 64 |
| 39-05 | 112 | 0 | 8 |
| | 224 | 14 | 45 |
| | 336 | 45 | 70 |
| | 448 | 65 | 66 |
| 39-06 | 112 | 1 | 13 |
| | 224 | 5 | 43 |
| | 336 | 58 | 64 |
| | 448 | 66 | 75 |
| 39-07 | 112 | 0 | 15 |
| | 224 | 1 | 53 |
| | 336 | 45 | 78 |
| | 448 | 60 | 83 |
| 39-08 | 112 | 0 | 10 |
| | 224 | 25 | 45 |
| | 336 | 50 | 79 |
| | 448 | 68 | 88 |
| 39-09 | 112 | 0 | 13 |
| | 224 | 13 | 45 |

TABLE 39b-continued

| Concentrate composition | Glyphosate rate g a.e./ha | % Inhibition ABUTH | % Inhibition ECHCF |
|---|---|---|---|
| | 336 | 50 | 75 |
| | 448 | 70 | 81 |
| 39-10 | 112 | 0 | 18 |
| | 224 | 18 | 35 |
| | 336 | 48 | 65 |
| | 448 | 66 | 76 |
| 39-11 | 112 | 1 | 0 |
| | 224 | 35 | 25 |
| | 336 | 38 | 55 |
| | 448 | 50 | 78 |
| 39-12 | 112 | 8 | 25 |
| | 224 | 10 | 38 |
| | 336 | 48 | 70 |
| | 448 | 73 | 81 |
| 39-13 | 112 | 0 | 25 |
| | 224 | 5 | 33 |
| | 336 | 30 | 70 |
| | 448 | 74 | 75 |
| 39-14 | 112 | 0 | 12 |
| | 224 | 0 | 30 |
| | 336 | 12 | 70 |
| | 448 | 40 | 80 |

No difference in herbicidal effectiveness was seen between compositions 39-03 and 39-04. The only difference between these compositions is that 39-03 contained Fluorad FC-135 and 39-04 contained Fluorad FC-754.

EXAMPLE 40

Aqueous spray compositions were prepared containing glyphosate IPA salt and excipient ingredients as shown in Table 40a. Process (iii) was followed for all compositions, using soybean lecithin (20% or 45% phospholipid as indicated below, both sourced from Avanti). The pH of all compositions was adjusted to approximately 7.

TABLE 40a

| Spray composition | Leci-thin g/l | Lecithin % purity | Fluorad FC-135 (% w/w) | Fluorad FC-754 (% w/w) |
|---|---|---|---|---|
| 40-01 | 1.0 | 20 | | |
| 40-02 | 0.5 | 20 | | |
| 40-03 | 0.2 | 20 | | |
| 40-04 | 1.0 | 20 | 0.10 | |
| 40-05 | 0.5 | 20 | 0.05 | |
| 40-06 | 0.2 | 20 | 0.02 | |
| 40-07 | 1.0 | 20 | | 0.10 |
| 40-08 | 0.5 | 20 | | 0.05 |
| 40-09 | 0.2 | 20 | 0.02 | 0.02 |
| 40-10 | 0.5 | 45 | 0.05 | |
| 40-11 | 0.5 | 45 | | 0.05 |

Velvetleaf (*Abutilon theophrasti,* ABUTH) and Japanese millet (*Echinochloa crus-galli,* ECHCF) plants were grown and treated by the standard procedures given above. Applications of spray compositions were made 18 days after planting ABUTH and 21 days after planting ECHCF, and evaluation of herbicidal inhibition was done 18 days after application.

In addition to compositions 40-01 to 40-11, spray compositions were prepared by tank mixing Formulations B and C with Fluorad FC-135 or FC-754 at various concentrations. Formulations B and C alone were applied as comparative treatments. Results, averaged for all replicates of each treatment, are shown in Table 40b.

TABLE 40b

| Spray composition | Glyphosate rate g a.e./ha | % Inhibition ABUTH | % Inhibition ECHCF |
|---|---|---|---|
| Formulation B | 150 | 49 | 100 |
|  | 300 | 66 | 92 |
|  | 500 | 80 | 76 |
|  | 700 | 93 | 96 |
| Formulation C | 200 | 57 | 79 |
|  | 400 | 93 | 98 |
|  | 600 | 100 | 100 |
|  | 800 | 100 | 100 |
| Formulation B + Fluorad FC-135 0.1% | 200 | 58 | 80 |
|  | 400 | 63 | 100 |
|  | 600 | 82 | 100 |
| Formulation B + Fluorad FC-135 0.05% | 200 | 37 | 49 |
|  | 400 | 67 | 84 |
|  | 600 | 74 | 100 |
| Formulation B + Fluorad FC-135 0.02% | 200 | 33 | 82 |
|  | 400 | 58 | 94 |
|  | 600 | 81 | 87 |
| Formulation B + Fluorad FC-754 0.1% | 200 | 50 | 45 |
|  | 400 | 77 | 82 |
|  | 600 | 77 | 94 |
| Formulation B + Fluorad FC-754 0.05% | 200 | 44 | 45 |
|  | 400 | 71 | 65 |
|  | 600 | 74 | 90 |
| Formulation B + Fluorad FC-754 0.02% | 200 | 31 | 57 |
|  | 400 | 67 | 83 |
|  | 600 | 68 | 93 |
| Formulation C + Fluorad FC-135 0.1% | 200 | 69 | 65 |
|  | 400 | 91 | 99 |
|  | 600 | 97 | 100 |
| Formulation C + Fluorad FC-135 0.05% | 200 | 73 | 87 |
|  | 400 | 89 | 100 |
|  | 600 | 98 | 100 |
| Formulation C + Fluorad FC-135 0.02% | 200 | 51 | 60 |
|  | 400 | 91 | 100 |
|  | 600 | 98 | 100 |
| Formulation C + Fluorad FC-754 0.1% | 200 | 70 | 81 |
|  | 400 | 85 | 99 |
|  | 600 | 98 | 95 |
| Formulation C + Fluorad FC-754 0.05% | 200 | 68 | 54 |
|  | 400 | 78 | 88 |
|  | 600 | 91 | 88 |
| Formulation C + Fluorad FC-754 0.02% | 200 | 50 | 41 |
|  | 400 | 89 | 91 |
|  | 600 | 99 | 100 |
| 40-01 | 200 | 41 | 37 |
|  | 400 | 78 | 84 |
|  | 600 | 83 | 100 |
| 40-02 | 200 | 38 | 82 |
|  | 400 | 74 | 94 |
|  | 600 | 82 | 98 |
| 40-03 | 200 | 38 | 62 |
|  | 400 | 69 | 85 |
|  | 600 | 86 | 100 |
| 40-04 | 200 | 63 | 69 |
|  | 400 | 79 | 75 |
|  | 600 | 93 | 89 |
| 40-05 | 200 | 69 | 66 |
|  | 400 | 85 | 81 |
|  | 600 | 84 | 86 |
| 40-06 | 200 | 64 | 38 |
|  | 400 | 79 | 74 |
|  | 600 | 93 | 99 |
| 40-07 | 200 | 61 | 43 |
|  | 400 | 76 | 71 |
|  | 600 | 85 | 85 |
| 40-08 | 200 | 71 | 52 |
|  | 400 | 82 | 85 |
|  | 600 | 82 | 100 |
| 40-09 | 200 | 63 | 55 |
|  | 400 | 83 | 73 |
|  | 600 | 79 | 97 |
| 40-10 | 200 | 65 | 54 |
|  | 400 | 78 | 80 |
|  | 600 | 85 | 99 |
| 40-11 | 200 | 55 | 33 |
|  | 400 | 77 | 74 |
|  | 600 | 91 | 97 |

There was a tendency, although not consistently so, for compositions of this Example containing Fluorad FC-754 to show slightly weaker herbicidal effectiveness than corresponding compositions containing Fluorad FC-135.

EXAMPLE 41

Aqueous concentrate compositions were prepared containing glyphosate IPA salt and excipient ingredients as shown in Table 41a. Process (v) was followed for all compositions, using soybean lecithin (45% phospholipid, Avanti). The pH of all compositions was approximately 5.

TABLE 41a

| Concentrate composition | % w/w | | | | |
|---|---|---|---|---|---|
|  | Glyphosate a.e. | Lecithin | Fluorad FC-135 | Fluorad FC-754 | MON 0818 |
| 41-01 | 15.0 | 4.0 | 8.0 |  | 0.5 |
| 41-02 | 15.0 | 6.0 | 8.0 |  | 0.5 |
| 41-03 | 15.0 | 8.0 | 8.0 |  | 0.5 |
| 41-04 | 10.0 | 4.0 | 8.0 |  | 0.5 |
| 41-05 | 10.0 | 6.0 | 8.0 |  | 0.5 |
| 41-06 | 10.0 | 8.0 | 8.0 |  | 0.5 |
| 41-07 | 5.0 | 4.0 | 8.0 |  | 0.5 |
| 41-08 | 5.0 | 6.0 | 8.0 |  | 0.5 |
| 41-09 | 5.0 | 8.0 | 8.0 |  | 0.5 |
| 41-10 | 15.0 | 4.0 |  | 8.0 | 0.5 |
| 41-11 | 15.0 | 6.0 |  | 8.0 | 0.5 |
| 41-12 | 15.0 | 8.0 |  | 8.0 | 0.5 |
| 41-13 | 10.0 | 4.0 |  | 8.0 | 0.5 |
| 41-14 | 10.0 | 6.0 |  | 8.0 | 0.5 |
| 41-15 | 10.0 | 8.0 |  | 8.0 | 0.5 |
| 41-16 | 5.0 | 4.0 |  | 8.0 | 0.5 |
| 41-17 | 5.0 | 6.0 |  | 8.0 | 0.5 |
| 41-18 | 5.0 | 8.0 |  | 8.0 | 0.5 |

Velvetleaf (*Abutilon theophrasti*, ABUTH) and Japanese millet (*Echinochloa crus-galli*, ECHCF) plants were grown and treated by the standard procedures given above. Applications of spray compositions were made 18 days after planting ABUTH and 20 days after planting ECHCF, and evaluation of herbicidal inhibition was done 15 days after application.

In addition to compositions 41-01 to 41-18, spray compositions were prepared by tank mixing Formulations B and J with Fluorad FC-135 at two concentrations. Formulations B and J alone were applied as comparative treatments. Results, averaged for all replicates of each treatment, are shown in Table 41b.

TABLE 41b

| Concentrate composition | Glyphosate rate g a.e./ha | % Inhibition ABUTH | % Inhibition ECHCF |
|---|---|---|---|
| Formulation B | 150 | 49 | 41 |
|  | 300 | 41 | 55 |

TABLE 41b-continued

| Concentrate composition | Glyphosate rate g a.e./ha | % Inhibition ABUTH | % Inhibition ECHCF |
|---|---|---|---|
|  | 500 | 76 | 98 |
|  | 700 | 82 | 100 |
| Formulation J | 150 | 59 | 66 |
|  | 300 | 79 | 99 |
|  | 500 | 93 | 99 |
|  | 700 | 98 | 100 |
| Formulation B + Fluorad FC-135 0.1% | 150 | 52 | 85 |
|  | 300 | 69 | 93 |
|  | 500 | 89 | 97 |
| Formulation B + Fluorad FC-135 0.05% | 150 | 9 | 61 |
|  | 300 | 71 | 77 |
|  | 500 | 77 | 100 |
| Formulation J + Fluorad FC-135 0.1% | 150 | 52 | 99 |
|  | 300 | 74 | 100 |
|  | 500 | 82 | 99 |
| Formulation J + Fluorad FC-135 0.05% | 150 | 41 | 52 |
|  | 300 | 77 | 83 |
|  | 500 | 91 | 100 |
| 41-01 | 150 | 66 | 51 |
|  | 300 | 86 | 91 |
|  | 500 | 93 | 100 |
| 41-02 | 150 | 72 | 88 |
|  | 300 | 89 | 93 |
|  | 500 | 96 | 92 |
| 41-03 | 150 | 71 | 91 |
|  | 300 | 89 | 95 |
|  | 500 | 91 | 100 |
| 41-04 | 150 | 63 | 90 |
|  | 300 | 89 | 89 |
|  | 500 | 96 | 99 |
| 41-05 | 150 | 70 | 79 |
|  | 300 | 84 | 94 |
|  | 500 | 88 | 98 |
| 41-06 | 150 | 69 | 76 |
|  | 300 | 89 | 84 |
|  | 500 | 94 | 100 |
| 41-07 | 150 | 71 | 87 |
|  | 300 | 77 | 82 |
|  | 500 | 99 | 92 |
| 41-08 | 150 | 81 | 87 |
|  | 300 | 88 | 94 |
|  | 500 | 92 | 98 |
| 41-09 | 150 | 72 | 83 |
|  | 300 | 87 | 83 |
|  | 500 | 94 | 94 |
| 41-10 | 150 | 72 | 70 |
|  | 300 | 81 | 80 |
|  | 500 | 89 | 93 |
| 41-11 | 150 | 74 | 85 |
|  | 300 | 87 | 96 |
|  | 500 | 91 | 98 |
| 41-12 | 150 | 66 | 92 |
|  | 300 | 78 | 98 |
|  | 500 | 93 | 100 |
| 41-13 | 150 | 71 | 76 |
|  | 300 | 86 | 95 |
|  | 500 | 94 | 99 |
| 41-14 | 150 | 72 | 75 |
|  | 300 | 90 | 97 |
|  | 500 | 91 | 99 |
| 41-15 | 150 | 69 | 82 |
|  | 300 | 85 | 98 |
|  | 500 | 94 | 100 |
| 41-16 | 150 | 76 | 87 |
|  | 300 | 86 | 100 |
|  | 500 | 90 | 99 |
| 41-17 | 150 | 71 | 83 |
|  | 300 | 87 | 94 |
|  | 500 | 96 | 100 |
| 41-18 | 150 | 70 | 81 |
|  | 300 | 77 | 98 |
|  | 500 | 89 | 98 |

Good herbicidal effectiveness was obtained with the concentrate compositions of this Example containing lecithin and Fluorad FC-135 or Fluorad FC-754. No great or consistent difference was seen between compositions containing Fluorad FC-135 and their counterparts containing Fluorad FC-754.

EXAMPLE 42

Aqueous concentrate compositions were prepared containing glyphosate IPA salt and excipient ingredients as shown in Table 42a. Process (v) was followed for all compositions, using soybean lecithin (95% phospholipid, Avanti). The pH of all compositions was approximately 5.

TABLE 42a

| Conc. comp. | Glyphosate a.e. | Lecithin | MON 0818 | Agrimul PG-2069 | Fluorad FC-135 | Fluorad FC-754 | Westvaco H-240 |
|---|---|---|---|---|---|---|---|
| 42-01 | 30 | 3.0 |  | 0.25 | 3.0 |  | 9.0 |
| 42-02 | 30 | 3.0 |  | 0.25 | 1.0 |  | 9.0 |
| 42-03 | 30 | 3.0 | 0.25 |  | 3.0 |  | 9.0 |
| 42-04 | 30 | 1.0 | 0.50 |  | 3.0 |  | 9.0 |
| 42-05 | 30 | 1.0 |  | 0.50 | 3.0 |  | 9.0 |
| 42-06 | 30 | 1.0 |  |  | 1.0 |  | 9.0 |
| 42-07 | 30 | 1.0 |  | 0.25 | 1.0 |  | 9.0 |
| 42-08 | 30 | 3.0 |  | 0.50 | 2.0 |  | 9.0 |
| 42-09 | 30 | 2.0 |  |  | 3.0 |  | 9.0 |
| 42-10 | 30 | 3.0 |  |  |  |  | 5.0 |
| 42-11 | 30 | 3.0 |  | 0.50 |  | 3.0 | 9.0 |
| 42-12 | 30 | 2.0 |  | 0.38 |  | 2.0 | 9.0 |
| 42-13 | 30 | 1.0 |  | 0.25 |  | 1.0 | 9.0 |
| 42-14 | 30 | 3.0 | 0.50 |  |  | 3.0 | 9.0 |
| 42-15 | 15 | 6.0 | 2.00 |  | 8.3 |  |  |
| 42-16 | 15 | 6.0 | 4.00 |  | 8.3 |  |  |

Velvetleaf (*Abutilon theophrasti*, ABUTH) and Japanese millet (*Echinochloa crus-galli*, ECHCF) plants were grown and treated by the standard procedures given above. Applications of spray compositions were made 17 days after planting ABUTH and 20 days after planting ECHCF, and evaluation of herbicidal inhibition was done 15 days after application.

In addition to compositions 42-01 to 42-16, spray compositions were prepared by tank mixing Formulations B and J with Fluorad FC-135 at two concentrations. Formulations B and J alone were applied as comparative treatments. Results, averaged for all replicates of each treatment, are shown in Table 42b.

TABLE 42b

| Concentrate composition | Glyphosate rate g a.e./ha | % Inhibition ABUTH | % Inhibition ECHCF |
|---|---|---|---|
| Formulation B | 150 | 3 | 33 |
|  | 300 | 12 | 90 |
|  | 500 | 65 | 98 |
|  | 700 | 79 | 100 |
| Formulation J | 150 | 2 | 46 |
|  | 300 | 76 | 100 |
|  | 500 | 98 | 100 |
|  | 700 | 98 | 100 |
| Formulation B + Fluorad FC-135 0.1% | 150 | 10 | 38 |
|  | 300 | 50 | 85 |
|  | 500 | 65 | 68 |
| Formulation B + Fluorad FC-135 0.05% | 150 | 3 | 27 |
|  | 300 | 36 | 82 |
|  | 500 | 68 | 99 |
| Formulation J + Fluorad FC-135 0.1% | 150 | 18 | 79 |
|  | 300 | 57 | 98 |

TABLE 42b-continued

| Concentrate composition | Glyphosate rate g a.e./ha | % Inhibition ABUTH | % Inhibition ECHCF |
|---|---|---|---|
| | 500 | 79 | 100 |
| Formulation J + Fluorad FC-135 0.05% | 150 | 2 | 37 |
| | 300 | 56 | 97 |
| | 500 | 96 | 98 |
| 42-01 | 150 | 2 | 27 |
| | 300 | 2 | 74 |
| | 500 | 46 | 78 |
| 42-02 | 150 | 2 | 52 |
| | 300 | 41 | 64 |
| | 500 | 40 | 85 |
| 42-03 | 150 | 3 | 38 |
| | 300 | 39 | 47 |
| | 500 | 73 | 98 |
| 42-04 | 150 | 3 | 38 |
| | 300 | 42 | 63 |
| | 500 | 78 | 84 |
| 42-05 | 150 | 5 | 29 |
| | 300 | 37 | 89 |
| | 500 | 70 | 99 |
| 42-06 | 150 | 8 | 37 |
| | 300 | 30 | 89 |
| | 500 | 69 | 97 |
| 42-07 | 150 | 5 | 53 |
| | 300 | 32 | 80 |
| | 500 | 83 | 99 |
| 42-08 | 150 | 3 | 26 |
| | 300 | 10 | 40 |
| | 500 | 12 | 55 |
| 42-09 | 150 | 7 | 21 |
| | 300 | 57 | 86 |
| | 500 | 91 | 97 |
| 42-10 | 150 | 21 | 61 |
| | 300 | 73 | 89 |
| | 500 | 85 | 98 |
| 42-11 | 150 | 6 | 23 |
| | 300 | 53 | 70 |
| | 500 | 85 | 83 |
| 42-12 | 150 | 33 | 25 |
| | 300 | 34 | 43 |
| | 500 | 83 | 97 |
| 42-13 | 150 | 7 | 34 |
| | 300 | 62 | 39 |
| | 500 | 77 | 73 |
| 42-14 | 150 | 10 | 27 |
| | 300 | 59 | 40 |
| | 500 | 84 | 73 |
| 42-15 | 150 | 71 | 48 |
| | 300 | 97 | 65 |
| | 500 | 99 | 92 |
| 42-16 | 150 | 83 | 40 |
| | 300 | 98 | 89 |
| | 500 | 100 | 95 |

The only concentrate compositions in this test exhibiting excellent performance, at least on ABUTH, were 42-15 and 42-16.

EXAMPLE 43

Aqueous concentrate compositions were prepared containing glyphosate IPA salt and excipient ingredients as shown in Table 43a. Process (viii) was followed for composition 43-02 and process (ix) for compositions 43-03 to 43-13 which contain a colloidal particulate together with surfactant. Composition 43-01 contains colloidal particulate but no surfactant. The pH of all compositions was approximately 5.

TABLE 43a

| Concentrate composition | Glyphosate a.e. | Fluorad FC-135 | Aerosil 90 | Emphos PS-21A |
|---|---|---|---|---|
| 43-01 | 20 | | 3.3 | |
| 43-02 | 20 | 3.3 | | |
| 43-03 | 31 | 1.1 | 3.3 | 1.1 |
| 43-04 | 31 | 1.1 | 3.3 | 2.2 |
| 43-05 | 31 | 1.1 | 3.3 | 3.3 |
| 43-06 | 31 | 2.2 | 3.3 | 1.1 |
| 43-07 | 31 | 2.2 | 3.3 | 2.2 |
| 43-08 | 31 | 2.2 | 3.3 | 3.3 |
| 43-09 | 31 | 3.3 | 3.3 | 1.1 |
| 43-10 | 31 | 3.3 | 3.3 | 2.2 |
| 43-11 | 31 | 3.3 | 3.3 | 3.3 |
| 43-12 | 31 | 3.3 | 3.3 | |
| 43-13 | 31 | | 3.3 | 3.3 |

Velvetleaf (*Abutilon theophrasti*, ABUTH) and Japanese millet (*Echinochloa crus-galli*, ECHCF) plants were grown and treated by the standard procedures given above. Applications of spray compositions were made 14 days after planting ABUTH and 17 days after planting ECHCF, and evaluation of herbicidal inhibition was done 23 days after application.

Formulations B, C and J were applied as comparative treatments. Results, averaged for all replicates of each treatment, are shown in Table 43b.

TABLE 43b

| Concentrate composition | Glyphosate rate g a.e./ha | % Inhibition ABUTH | % Inhibition ECHCF |
|---|---|---|---|
| Formulation B | 150 | 0 | 8 |
| | 250 | 18 | 25 |
| | 350 | 35 | 40 |
| | 450 | 75 | 50 |
| Formulation C | 150 | 30 | 85 |
| | 250 | 92 | 95 |
| | 350 | 100 | 100 |
| | 450 | 100 | 100 |
| Formulation J | 150 | 40 | 70 |
| | 250 | 70 | 83 |
| | 350 | 93 | 92 |
| | 450 | 100 | 98 |
| 43-01 | 150 | 20 | 25 |
| | 250 | 35 | 30 |
| | 350 | 65 | 43 |
| | 450 | 73 | 35 |
| 43-02 | 150 | 5 | 5 |
| | 250 | 20 | 25 |
| | 350 | 45 | 35 |
| | 450 | 66 | 83 |
| 43-03 | 150 | 20 | 11 |
| | 250 | 40 | 30 |
| | 350 | 73 | 64 |
| | 450 | 88 | 83 |
| 43-04 | 150 | 15 | 3 |
| | 250 | 30 | 25 |
| | 350 | 40 | 35 |
| | 450 | 71 | 75 |
| 43-05 | 150 | 15 | 10 |
| | 250 | 33 | 30 |
| | 350 | 69 | 45 |
| | 450 | 78 | 65 |
| 43-06 | 150 | 11 | 8 |
| | 250 | 28 | 30 |
| | 350 | 30 | 35 |
| | 450 | 69 | 61 |
| 43-07 | 150 | 5 | 8 |
| | 250 | 13 | 20 |

TABLE 43b-continued

| Concentrate composition | Glyphosate rate g a.e./ha | % Inhibition ABUTH | ECHCF |
|---|---|---|---|
| | 350 | 51 | 30 |
| | 450 | 74 | 43 |
| 43-08 | 150 | 15 | 8 |
| | 250 | 30 | 15 |
| | 350 | 35 | 30 |
| | 450 | 56 | 45 |
| 43-09 | 150 | 15 | 15 |
| | 250 | 28 | 20 |
| | 350 | 43 | 33 |
| | 450 | 45 | 40 |
| 43-10 | 150 | 5 | 3 |
| | 250 | 25 | 20 |
| | 350 | 50 | 40 |
| | 450 | 48 | 58 |
| 43-11 | 150 | 14 | 6 |
| | 250 | 25 | 40 |
| | 350 | 64 | 76 |
| | 450 | 78 | 79 |
| 43-12 | 150 | 9 | 20 |
| | 250 | 20 | 33 |
| | 350 | 46 | 73 |
| | 450 | 59 | 80 |
| 43-13 | 150 | 15 | 11 |
| | 250 | 20 | 28 |
| | 350 | 30 | 59 |
| | 450 | 68 | 48 |

Most concentrate compositions containing Fluorad FC-135 showed enhanced herbicidal effectiveness by comparison with Formulation B but did not equal the performance of commercial standard Formulations C and J under the conditions of this test.

EXAMPLE 44

Aqueous concentrate compositions were prepared containing glyphosate IPA salt and excipient ingredients as shown in Table 44a. Process (viii) was followed for compositions 44-01, 44-03, 44-06, 44-07, 44-10, 44-14, 44-15, 44-18 and 44-19 and process (ix) for compositions 44-02, 44-08, 44-09, 44-16 and 44-17 which contain a colloidal particulate together with surfactant. Compositions 44-04, 44-05, 44-12 and 44-13 contain colloidal particulate but no surfactant. The pH of all compositions was approximately 5.

TABLE 44a

| Concentrate composite | % w/w | | | | | |
|---|---|---|---|---|---|---|
| | Glyphosate a.e. | Fluorad FC-135 | Ethomeen T/25 | Aluminum oxide C | Titanium dioxide P25 | Aerosol OT |
| 44-01 | 20 | | 3.30 | | | |
| 44-02 | 20 | | | | | 3.30 |
| 44-03 | 20 | 3.30 | | | | |
| 44-04 | 20 | | | 3.30 | | |
| 44-05 | 20 | | | 0.67 | | |
| 44-06 | 20 | | 3.30 | 3.30 | | |
| 44-07 | 20 | | 3.30 | 0.67 | | |
| 44-08 | 20 | | | 3.30 | | 3.30 |
| 44-09 | 20 | | | 0.67 | | 3.30 |
| 44-10 | 20 | 3.30 | | 3.30 | | |
| 44-11 | 20 | 3.30 | | 0.67 | | |
| 44-12 | 20 | | | | 3.30 | |
| 44-13 | 20 | | | | 0.67 | |
| 44-14 | 20 | | 3.30 | | 3.30 | |
| 44-15 | 20 | | 3.30 | | 0.67 | |
| 44-16 | 20 | | | | 3.30 | 3.30 |
| 44-17 | 20 | | | | 0.67 | 3.30 |
| 44-18 | 20 | 3.30 | | | 3.30 | |
| 44-19 | 20 | 3.30 | | | 0.67 | |

Velvetleaf (*Abutilon theophrasti*, ABUTH) and Japanese millet (*Echinochloa crus-galli*, ECHCF) plants were grown and treated by the standard procedures given above. Applications of spray compositions were made 18 days after planting ABUTH and 20 days after planting ECHCF, and evaluation of herbicidal inhibition was done 25 days after application.

Formulations B, C and J were applied as comparative treatments. Results, averaged for all replicates of each treatment, are shown in Table 44b.

TABLE 44b

| Concentrate composition | Glyphosate rate g a.e./ha | % Inhibition ABUTH | ECHCF |
|---|---|---|---|
| Formulation B | 150 | 8 | 45 |
| | 250 | 37 | 55 |
| | 350 | 40 | 60 |
| | 450 | 50 | 70 |
| Formulation C | 150 | 27 | 72 |
| | 250 | 73 | 92 |
| | 350 | 90 | 99 |
| | 450 | 92 | 99 |
| Formulation J | 150 | 25 | 66 |
| | 250 | 45 | 88 |
| | 350 | 78 | 99 |
| | 450 | 91 | 100 |
| 44-01 | 150 | 40 | 82 |
| | 250 | 55 | 93 |
| | 350 | 74 | 100 |
| | 450 | 83 | 100 |
| 44-02 | 150 | 9 | 20 |
| | 250 | 30 | 73 |
| | 350 | 38 | 73 |
| | 450 | 55 | 97 |
| 44-03 | 150 | 13 | 23 |
| | 250 | 35 | 79 |
| | 350 | 45 | 78 |
| | 450 | 75 | 100 |
| 44-04 | 150 | 18 | 45 |
| | 250 | 35 | 65 |
| | 350 | 35 | 70 |
| | 450 | 68 | 81 |
| 44-05 | 150 | 11 | 43 |
| | 250 | 35 | 50 |
| | 350 | 50 | 55 |
| | 450 | 59 | 78 |
| 44-06 | 150 | 25 | 75 |
| | 250 | 58 | 93 |
| | 350 | 88 | 100 |
| | 450 | 95 | 100 |
| 44-07 | 150 | 15 | 88 |
| | 250 | 68 | 100 |
| | 350 | 79 | 100 |
| | 450 | 90 | 100 |
| 44-08 | 150 | 28 | 38 |
| | 250 | 25 | 38 |
| | 350 | 35 | 55 |
| | 450 | 71 | 79 |
| 44-09 | 112 | 5 | 13 |
| | 224 | 23 | 48 |
| | 336 | 25 | 70 |

TABLE 44b-continued

| Concentrate composition | Glyphosate rate g a.e./ha | % Inhibition ABUTH | % Inhibition ECHCF |
|---|---|---|---|
| | 448 | 45 | 64 |
| 44-10 | 150 | 1 | 20 |
| | 250 | 40 | 74 |
| | 350 | 65 | 55 |
| | 450 | 84 | 96 |
| 44-11 | 150 | 25 | 25 |
| | 250 | 35 | 65 |
| | 350 | 45 | 61 |
| | 450 | 76 | 92 |
| 44-12 | 150 | 14 | 28 |
| | 250 | 40 | 43 |
| | 350 | 45 | 70 |
| | 450 | 65 | 79 |
| 44-13 | 150 | 20 | 45 |
| | 250 | 48 | 33 |
| | 350 | 60 | 55 |
| | 450 | 80 | 79 |
| 44-14 | 150 | 23 | 79 |
| | 250 | 73 | 100 |
| | 350 | 76 | 99 |
| | 450 | 85 | 99 |
| 44-15 | 150 | 25 | 83 |
| | 250 | 69 | 99 |
| | 350 | 75 | 99 |
| | 450 | 91 | 100 |
| 44-16 | 150 | 14 | 28 |
| | 250 | 23 | 40 |
| | 350 | 30 | 79 |
| | 450 | 69 | 86 |
| 44-17 | 150 | 1 | 20 |
| | 250 | 23 | 33 |
| | 350 | 16 | 45 |
| | 450 | 40 | 68 |
| 44-18 | 150 | 8 | 15 |
| | 250 | 49 | 56 |
| | 350 | 55 | 58 |
| | 450 | 83 | 83 |
| 44-19 | 150 | 6 | 15 |
| | 250 | 35 | 60 |
| | 350 | 61 | 63 |
| | 450 | 63 | 70 |

Concentrate compositions containing Fluorad FC-135 showed enhanced herbicidal effectiveness by comparison with Formulation B but did not provide herbicidal effectiveness equal to commercial standard Formulations C and J in this test.

EXAMPLE 45

Aqueous spray compositions were prepared containing glyphosate IPA salt and excipient ingredients as shown in Table 45a. Process (i) was followed for compositions 45-10 to 45-12 and process (iii) for compositions 45-01 to 45-09 using soybean lecithin (45% phospholipid, Avanti). The pH of all compositions was adjusted to approximately 7.

TABLE 45a

| Spray composition | % w/w Lecithin | % w/w Fluorad FC-135 | % w/w Surf H1 |
|---|---|---|---|
| 45-01 | 0.10 | | |
| 45-02 | 0.05 | | |
| 45-03 | 0.02 | | |
| 45-04 | 0.10 | 0.10 | |
| 45-05 | 0.05 | 0.05 | |
| 45-06 | 0.02 | 0.02 | |
| 45-07 | 0.10 | | 0.10 |
| 45-08 | 0.05 | | 0.05 |
| 45-09 | 0.02 | | 0.02 |
| 45-10 | | | 0.10 |
| 45-11 | | | 0.05 |
| 45-12 | | | 0.02 |

Velvetleaf (*Abutilon theophrasti*, ABUTH) and Japanese millet (*Echinochloa crus-galli*, ECHCF) plants were grown and treated by the standard procedures given above. Applications of spray compositions were made 23 days after planting ABUTH and 21 days after planting ECHCF, and evaluation of herbicidal inhibition was done 15 days after application.

In addition to compositions 45-01 to 45-12, spray compositions were prepared by tank mixing Formulations B and C with Fluorad FC-135 at various concentrations. Formulations B and C alone and Formulation J were applied as comparative treatments. Results, averaged for all replicates of each treatment, are shown in Table 45b.

TABLE 45b

| Spray composition | Glyphosate rate g a.e./ha | % Inhibition ABUTH | % Inhibition ECHCF |
|---|---|---|---|
| Formulation B | 150 | 16 | 21 |
| | 250 | 68 | 32 |
| | 350 | 68 | 63 |
| | 450 | 67 | 69 |
| Formulation C | 150 | 29 | 47 |
| | 250 | 76 | 74 |
| | 350 | 98 | 94 |
| | 450 | 100 | 85 |
| Formulation J | 150 | 37 | 31 |
| | 250 | 79 | 72 |
| | 350 | 93 | 82 |
| | 450 | 97 | 97 |
| Formulation B + Fluorad FC-135 0.1% w/v | 150 | 55 | 15 |
| | 250 | 73 | 28 |
| | 350 | 85 | 57 |
| | 450 | 83 | 83 |
| Formulation B + Fluorad FC-135 0.05% w/v | 150 | 59 | 15 |
| | 250 | 77 | 41 |
| | 350 | 81 | 72 |
| | 450 | 77 | 51 |
| Formulation B + Fluorad FC-135 0.02% w/v | 150 | 25 | 12 |
| | 250 | 54 | 27 |
| | 350 | 82 | 38 |
| | 450 | 75 | 47 |
| Formulation C + Fluorad FC-135 0.1% w/v | 150 | 51 | 26 |
| | 250 | 78 | 63 |
| | 350 | 86 | 71 |
| | 450 | 89 | 79 |
| Formulation C + Fluorad FC-135 0.05% w/v | 150 | 58 | 23 |
| | 250 | 74 | 89 |
| | 350 | 93 | 78 |
| | 450 | 89 | 91 |
| 45-01 | 150 | 29 | 26 |
| | 250 | 61 | 47 |
| | 350 | 73 | 48 |
| | 450 | 82 | 62 |
| 45-02 | 150 | 34 | 34 |
| | 250 | 67 | 34 |
| | 350 | 73 | 54 |
| | 450 | 85 | 43 |
| 45-03 | 150 | 20 | 29 |
| | 250 | 60 | 49 |
| | 350 | 68 | 84 |
| | 450 | 74 | 64 |

TABLE 45b-continued

| Spray composition | Glyphosate rate g a.e./ha | % Inhibition ABUTH | % Inhibition ECHCF |
|---|---|---|---|
| 45-04 | 150 | 78 | 24 |
|  | 250 | 83 | 33 |
|  | 350 | 96 | 64 |
|  | 450 | 97 | 59 |
| 45-05 | 150 | 81 | 21 |
|  | 250 | 89 | 27 |
|  | 350 | 82 | 34 |
|  | 450 | 99 | 31 |
| 45-06 | 150 | 92 | 14 |
|  | 250 | 85 | 64 |
|  | 350 | 86 | 31 |
|  | 450 | 90 | 60 |
| 45-07 | 150 | 71 | 27 |
|  | 250 | 81 | 46 |
|  | 350 | 84 | 66 |
|  | 450 | 88 | 62 |
| 45-08 | 150 | 46 | 29 |
|  | 250 | 70 | 43 |
|  | 350 | 78 | 61 |
|  | 450 | 86 | 58 |
| 45-09 | 150 | 55 | 25 |
|  | 250 | 76 | 33 |
|  | 350 | 80 | 50 |
|  | 450 | 78 | 62 |
| 45-10 | 150 | 65 | 26 |
|  | 250 | 85 | 28 |
|  | 350 | 91 | 37 |
|  | 450 | 89 | 53 |
| 45-11 | 150 | 73 | 27 |
|  | 250 | 77 | 28 |
|  | 350 | 92 | 41 |
|  | 450 | 92 | 49 |
| 45-12 | 150 | 71 | 20 |
|  | 250 | 74 | 31 |
|  | 350 | 79 | 39 |
|  | 450 | 93 | 53 |

Extremely high herbicidal effectiveness was noted on ABUTH with compositions 45-04 to 45-06, containing lecithin and Fluorad FC-135. Replacement of Fluorad FC-135 by "Surf H1", a hydrocarbon-based surfactant of formula $C_{12}H_{25}SO_2NH(CH_2)_3N^+(CH_3)_3I^-$, gave (in compositions 45-07 to 45-09) effectiveness on ABUTH still superior at low glyphosate rates to commercial standard Formulations C and J but not quite as great as that of compositions 45-04 to 45-06. Performance of compositions 45-04 to 45-12 on ECHCF was relatively low in this test but performance on ABUTH was remarkably high considering the very low surfactant concentrations present.

EXAMPLE 46

Aqueous spray compositions were prepared containing glyphosate IPA or tetrabutylammonium salt and excipient ingredients as shown in Table 46a. Process (i) was followed for compositions 46-10 to 46-13 and 46-15 and process (iii) for compositions 46-01 to 46-09 using soybean lecithin (45% phospholipid, Avanti). The pH of all compositions was adjusted to approximately 7.

TABLE 46a

| Spray composition | % w/w Lecithin | % w/w LI-700 | % w/w Fluorad FC-135 | % w/w Surf H1 | Glyphosate salt |
|---|---|---|---|---|---|
| 46-01 | 0.10 |  |  |  | IPA |
| 46-02 | 0.05 |  |  |  | IPA |
| 46-03 | 0.02 |  |  |  | IPA |
| 46-04 | 0.10 |  | 0.10 |  | IPA |
| 46-05 | 0.05 |  | 0.05 |  | IPA |
| 46-06 | 0.02 |  | 0.02 |  | IPA |
| 46-07 | 0.10 |  |  | 0.10 | IPA |
| 46-08 | 0.05 |  |  | 0.05 | IPA |
| 46-09 | 0.02 |  |  | 0.02 | IPA |
| 46-10 |  | 0.10 |  |  | IPA |
| 46-11 |  | 0.05 |  |  | IPA |
| 46-12 |  | 0.02 |  |  | IPA |
| 46-13 |  |  |  |  | $(Bu)_4N$ |
| 46-14 | 0.05 |  | 0.05 |  | $(Bu)_4N$ |
| 46-15 |  |  | 0.05 |  | $(Bu)_4N$ |

Velvetleaf (*Abutilon theophrasti*, ABUTH) and Japanese millet (*Echinochloa crus-galli*, ECHCF) plants were grown and treated by the standard procedures given above. Applications of spray compositions were made 19 days after planting ABUTH and 21 days after planting ECHCF, and evaluation of herbicidal inhibition was done 14 days after application.

In addition to compositions 46-01 to 46-15, spray compositions were prepared by tank mixing Formulations B and C with Fluorad FC-135 at various concentrations. Formulations B and C alone and Formulation J were applied as comparative treatments. Results, averaged for all replicates of each treatment, are shown in Table 46b.

TABLE 46b

| Spray composition | Glyphosate rate g a.e./ha | % Inhibition ABUTH | % Inhibition ECHCF |
|---|---|---|---|
| Formulation B | 150 | 33 | 24 |
|  | 300 | 51 | 27 |
|  | 500 | 68 | 36 |
|  | 700 | 83 | 43 |
| Formulation C | 150 | 32 | 30 |
|  | 300 | 78 | 68 |
|  | 500 | 90 | 81 |
|  | 700 | 96 | 89 |
| Formulation J | 150 | 16 | 27 |
|  | 300 | 74 | 56 |
|  | 500 | 88 | 79 |
|  | 700 | 93 | 92 |
| Formulation B + Fluorad FC-135 0.1% w/v | 150 | 22 | 18 |
|  | 300 | 71 | 26 |
|  | 500 | 73 | 51 |
| Formulation B + Fluorad FC-135 0.05% w/v | 150 | 19 | 16 |
|  | 300 | 60 | 28 |
|  | 500 | 72 | 33 |
| Formulation B + Fluorad FC-135 0.02% w/v | 150 | 14 | 14 |
|  | 300 | 23 | 26 |
|  | 500 | 69 | 38 |
| Formulation C + Fluorad FC-135 0.1% w/v | 150 | 31 | 11 |
|  | 300 | 73 | 27 |
|  | 500 | 82 | 48 |
| Formulation C + Fluorad FC 135 0.05% w/v | 150 | 43 | 23 |
|  | 300 | 71 | 49 |
|  | 500 | 93 | 50 |
| 46-01 | 150 | 20 | 18 |
|  | 300 | 65 | 29 |
|  | 500 | 85 | 34 |
| 46-02 | 150 | 22 | 19 |
|  | 300 | 63 | 35 |
|  | 500 | 83 | 51 |
| 46-03 | 150 | 24 | 29 |
|  | 300 | 64 | 35 |

TABLE 46b-continued

| Spray composition | Glyphosate rate g a.e./ha | % Inhibition ABUTH | ECHCF |
|---|---|---|---|
|  | 500 | 85 | 40 |
| 46-04 | 150 | 63 | 21 |
|  | 300 | 75 | 31 |
|  | 500 | 84 | 46 |
| 46-05 | 150 | 68 | 10 |
|  | 300 | 82 | 29 |
|  | 500 | 81 | 53 |
| 46-06 | 150 | 68 | 21 |
|  | 300 | 84 | 30 |
|  | 500 | 85 | 46 |
| 46-07 | 150 | 41 | 35 |
|  | 300 | 51 | 39 |
|  | 500 | 93 | 61 |
| 46-08 | 150 | 34 | 22 |
|  | 300 | 77 | 27 |
|  | 500 | 85 | 35 |
| 46-09 | 150 | 24 | 17 |
|  | 300 | 78 | 39 |
|  | 500 | 91 | 58 |
| 46-10 | 150 | 16 | 19 |
|  | 300 | 62 | 28 |
|  | 500 | 72 | 53 |
| 46-11 | 150 | 38 | 25 |
|  | 300 | 59 | 38 |
|  | 500 | 82 | 59 |
| 46-12 | 150 | 7 | 23 |
|  | 300 | 61 | 40 |
|  | 500 | 77 | 63 |
| 46-13 | 150 | 81 | 48 |
|  | 300 | 92 | 51 |
|  | 500 | 90 | 46 |
| 46-14 | 150 | 87 | 30 |
|  | 300 | 91 | 69 |
|  | 500 | 95 | 89 |
| 46-15 | 150 | 81 | 37 |
|  | 300 | 94 | 41 |
|  | 500 | 92 | 63 |

As in the previous Example, compositions containing "Surf H1" did not show as strong enhancement of glyphosate effectiveness as counterpart compositions containing Fluorad FC-135. The tetrabutylammonium salt of glyphosate (compositions 46-13 to 46-15) exhibited extremely high herbicidal effectiveness in this test.

EXAMPLE 47

Aqueous concentrate compositions were prepared containing glyphosate IPA salt and excipient ingredients as shown in Table 47a. Process (v) was followed for all compositions using soybean lecithin (45% phospholipid, Avanti), except that various orders of addition were tried as indicated below. The pH of all compositions was approximately 5.

TABLE 47a

| Concentrate composition | Glyphosate a.e. | Lecithin | Fluorad FC-135 | Fluorad FC-754 | MON 0818 | Agrimul PG-2069 | Order of addition (*) |
|---|---|---|---|---|---|---|---|
| 47-01 | 30 | 3.0 | 3.0 |  |  | 0.75 | A |
| 47-02 | 30 | 3.0 | 3.0 |  |  | 0.75 | B |
| 47-03 | 30 | 3.0 | 3.0 |  |  | 0.75 | C |
| 47-04 | 30 | 3.0 | 3.0 |  |  | 0.75 | D |
| 47-05 | 30 | 3.0 | 3.0 |  |  | 0.75 | E |
| 47-06 | 30 | 3.0 | 3.0 |  |  | 0.75 | F |
| 47-07 | 30 | 3.0 |  | 3.0 |  | 0.75 | A |
| 47-08 | 30 | 3.0 |  | 3.0 |  | 0.75 | B |
| 47-09 | 30 | 3.0 |  | 3.0 |  | 0.75 | C |
| 47-10 | 30 | 3.0 |  | 3.0 |  | 0.75 | D |
| 47-11 | 30 | 3.0 |  | 3.0 |  | 0.75 | E |
| 47-12 | 30 | 3.0 |  | 3.0 |  | 0.75 | F |
| 47-13 | 30 | 3.0 | 3.0 |  |  | 0.5 | A |
| 47-14 | 30 | 3.0 | 3.0 |  |  | 0.5 | B |
| 47-15 | 30 | 3.0 | 3.0 |  |  | 0.5 | C |
| 47-16 | 30 | 3.0 | 3.0 |  |  | 0.5 | D |
| 47-17 | 30 | 3.0 | 3.0 |  |  | 0.5 | E |
| 47-18 | 30 | 3.0 | 3.0 |  |  | 0.5 | F |

|  | 1st | 2nd | 3rd | 4th | 5th |
|---|---|---|---|---|---|
| A | lecithin | MON/PG | FC-135/754 | water | glyphosate |
| B | lecithin | FC-135 | MON/PG | water | glyphosate |
| C | glyphosate | water | FC-135/754 | MON/PG | lecithin |
| D | glyphosate | water | MON/PG | FC-135/754 | lecithin |
| E | glyphosate | lecithin | MON/PG | FC-135/754 | water |
| F | glyphosate | lecithin | FC-135/754 | MON/PG | water |

MON/PG means MON 0818 or Agrimul PG-2069
(*)Order of addition:

Velvetleaf (*Abutilon theophrasti*, ABUTH) and Japanese millet (*Echinochloa crus-galli*, ECHCF) plants were grown and treated by the standard procedures given above. Applications of spray compositions were made 15 days after planting ABUTH and 18 days after planting ECHCF, and evaluation of herbicidal inhibition was done 15 days after application.

Formulations C and J were applied as comparative treatments. Results, averaged for all replicates of each treatment, are shown in Table 47b.

TABLE 47b

| Concentrate composition | Glyphosate rate g a.e./ha | % Inhibition ABUTH | ECHCF |
|---|---|---|---|
| Formulation C | 150 | 26 | 69 |
|  | 300 | 75 | 100 |
|  | 500 | 85 | 99 |
|  | 700 | 94 | 100 |
| Formulation J | 150 | 38 | 78 |
|  | 300 | 76 | 87 |
|  | 500 | 87 | 100 |
|  | 700 | 90 | 100 |
| 47-01 | 150 | 10 | 35 |
|  | 300 | 51 | 56 |
|  | 500 | 71 | 91 |
|  | 700 | 77 | 100 |
| 47-02 | 150 | 24 | 35 |
|  | 300 | 57 | 71 |
|  | 500 | 77 | 93 |
|  | 700 | 94 | 100 |
| 47-03 | 150 | 11 | 33 |
|  | 300 | 48 | 55 |
|  | 500 | 73 | 87 |
|  | 700 | 83 | 93 |
| 47-04 | 150 | 37 | 36 |
|  | 300 | 50 | 38 |
|  | 500 | 68 | 94 |
| 47-05 | 150 | 24 | 32 |
|  | 300 | 48 | 47 |
|  | 500 | 77 | 85 |
|  | 700 | 76 | 100 |
| 47-06 | 150 | 12 | 32 |
|  | 300 | 61 | 40 |
|  | 500 | 83 | 86 |
|  | 700 | 88 | 95 |
| 47-07 | 150 | 17 | 25 |

TABLE 47b-continued

| Concentrate composition | Glyphosate rate g a.e./ha | % Inhibition ABUTH | % Inhibition ECHCF |
|---|---|---|---|
| | 300 | 58 | 77 |
| | 500 | 73 | 97 |
| | 700 | 86 | 81 |
| 47-08 | 150 | 12 | 34 |
| | 300 | 53 | 47 |
| | 500 | 69 | 72 |
| | 700 | 79 | 100 |
| 47-09 | 150 | 10 | 33 |
| | 300 | 47 | 70 |
| | 500 | 67 | 99 |
| | 700 | 83 | 81 |
| 47-10 | 150 | 13 | 25 |
| | 300 | 49 | 51 |
| | 500 | 70 | 73 |
| | 700 | 85 | 92 |
| 47-11 | 150 | 10 | 22 |
| | 300 | 56 | 37 |
| | 500 | 77 | 47 |
| | 700 | 85 | 85 |
| 47-12 | 150 | 13 | 27 |
| | 300 | 61 | 68 |
| | 500 | 78 | 52 |
| | 700 | 86 | 85 |
| 47-13 | 150 | 14 | 27 |
| | 300 | 62 | 35 |
| | 500 | 72 | 46 |
| | 700 | 87 | 67 |
| 47-14 | 150 | 15 | 27 |
| | 300 | 59 | 37 |
| | 500 | 76 | 63 |
| | 700 | 85 | 61 |
| 47-15 | 150 | 10 | 25 |
| | 300 | 40 | 46 |
| | 500 | 72 | 88 |
| | 700 | 79 | 51 |
| 47-16 | 150 | 12 | 27 |
| | 300 | 53 | 41 |
| | 500 | 63 | 49 |
| | 700 | 71 | 85 |
| 47-17 | 150 | 23 | 25 |
| | 300 | 59 | 35 |
| | 500 | 70 | 79 |
| | 700 | 75 | 86 |
| 47-18 | 150 | 10 | 27 |
| | 300 | 56 | 39 |
| | 500 | 69 | 57 |
| | 700 | 74 | 93 |

No great or consistent differences in herbicidal effectiveness were seen with different orders of addition of ingredients.

EXAMPLE 48

Aqueous concentrate compositions were prepared containing glyphosate IPA salt and excipient ingredients as shown in Table 48a. Process (v) was followed for all compositions using soybean lecithin (45% phospholipid, Avanti). Order of addition of ingredients was varied as indicated below. The pH of all compositions was approximately 5.

TABLE 48a

| Concentrate composition | Glyphosate a.e. | % w/w Lecithin | % w/w Fluorad FC-135 | % w/w MON 0818 | Order of addition (*) |
|---|---|---|---|---|---|
| 48-01 | 20 | 6.0 | 6.0 | 2.0 | A |
| 48-02 | 20 | 6.0 | 6.0 | 2.0 | B |
| 48-03 | 20 | 6.0 | 6.0 | 2.0 | C |
| 48-04 | 20 | 6.0 | 3.0 | 2.0 | A |
| 48-05 | 20 | 6.0 | 3.0 | 2.0 | B |
| 48-06 | 20 | 6.0 | 3.0 | 2.0 | C |
| 48-07 | 20 | 6.0 | 1.0 | 2.0 | A |
| 48-08 | 20 | 6.0 | 1.0 | 2.0 | B |
| 48-09 | 20 | 6.0 | 1.0 | 2.0 | C |
| 48-10 | 20 | 6.0 | 0.0 | 2.0 | A |
| 48-11 | 20 | 6.0 | 0.0 | 2.0 | B |
| 48-12 | 20 | 6.0 | 0.0 | 2.0 | C |
| 48-13 | 20 | 2.0 | 2.0 | 0.5 | A |
| 48-14 | 20 | 2.0 | 2.0 | 0.5 | B |
| 48-15 | 20 | 2.0 | 2.0 | 0.5 | C |

| | 1st | 2nd | 3rd | 4th | 5th |
|---|---|---|---|---|---|
| A | lecithin | MON 0818 | FC-135 | water | glyphosate |
| B | lecithin | MON 0818 | water | FC-135 | glyphosate |
| C | lecithin | water | MON 0818 | FC-135 | glyphosate |

(*)Order of addition:

Velvetleaf (*Abutilon theophrasti*, ABUTH) and Japanese millet (*Echinochloa crus-galli*, ECHCF) plants were grown and treated by the standard procedures given above. Applications of spray compositions were made 14 days after planting ABUTH and 16 days after planting ECHCF, and evaluation of herbicidal inhibition was done 15 days after application.

Formulations B, C and J were applied as comparative treatments. Results, averaged for all replicates of each treatment, are shown in Table 48b.

TABLE 48b

| Concentrate composition | Glyphosate rate g a.e./ha | % Inhibition ABUTH | % Inhibition ECHCF |
|---|---|---|---|
| Formulation B | 100 | 0 | 3 |
| | 200 | 17 | 28 |
| | 300 | 38 | 37 |
| | 500 | 78 | 68 |
| Formulation C | 100 | 8 | 63 |
| | 200 | 43 | 96 |
| | 300 | 88 | 96 |
| | 500 | 99 | 98 |
| Formulation J | 100 | 12 | 10 |
| | 200 | 35 | 60 |
| | 300 | 85 | 90 |
| | 500 | 98 | 92 |
| 48-01 | 100 | 10 | 0 |
| | 200 | 38 | 13 |
| | 300 | 73 | 28 |
| | 500 | 90 | 75 |
| 48-02 | 100 | 8 | 0 |
| | 200 | 40 | 23 |
| | 300 | 87 | 43 |
| | 500 | 98 | 62 |
| 48-03 | 100 | 12 | 0 |
| | 200 | 40 | 25 |
| | 300 | 83 | 47 |
| | 500 | 95 | 73 |
| 48-04 | 100 | 5 | 5 |
| | 200 | 45 | 38 |
| | 300 | 83 | 65 |
| | 500 | 98 | 83 |
| 48-05 | 100 | 10 | 3 |
| | 200 | 42 | 48 |
| | 300 | 82 | 53 |
| | 500 | 97 | 91 |
| 48-06 | 100 | 28 | 0 |
| | 200 | 67 | 43 |
| | 300 | 85 | 68 |
| | 500 | 97 | 93 |

TABLE 48b-continued

| Concentrate composition | Glyphosate rate g a.e./ha | % Inhibition ABUTH | ECHCF |
|---|---|---|---|
| 48-07 | 100 | 8 | 8 |
| | 200 | 37 | 35 |
| | 300 | 75 | 72 |
| | 500 | 97 | 90 |
| 48-08 | 100 | 0 | 1 |
| | 200 | 37 | 45 |
| | 300 | 57 | 68 |
| | 500 | 96 | 97 |
| 48-09 | 100 | 0 | 7 |
| | 200 | 35 | 40 |
| | 300 | 78 | 60 |
| | 500 | 96 | 93 |
| 48-10 | 100 | 0 | 3 |
| | 200 | 33 | 57 |
| | 300 | 82 | 72 |
| | 500 | 96 | 94 |
| 48-11 | 100 | 0 | 5 |
| | 200 | 35 | 50 |
| | 300 | 78 | 82 |
| | 500 | 97 | 87 |
| 48-12 | 100 | 3 | 5 |
| | 200 | 40 | 37 |
| | 300 | 77 | 78 |
| | 500 | 97 | 85 |
| 48-13 | 100 | 3 | 0 |
| | 200 | 45 | 33 |
| | 300 | 83 | 38 |
| | 500 | 95 | 75 |
| 48-14 | 100 | 0 | 0 |
| | 200 | 43 | 33 |
| | 300 | 77 | 50 |
| | 500 | 96 | 68 |
| 48-15 | 100 | 0 | 0 |
| | 200 | 42 | 30 |
| | 300 | 78 | 47 |
| | 500 | 88 | 73 |

No great or consistent differences were seen with different orders of addition of ingredients.

EXAMPLE 49

Aqueous concentrate compositions were prepared containing glyphosate IPA salt and excipient ingredients as shown in Table 49a. Process (v) was followed for all compositions using soybean lecithin (45% phospholipid, Avanti). The pH of all compositions was approximately 5.

TABLE 49a

| Concentrate composition | Glyphosate a.e. | Lecithin | Fluorad FC-135 | Fluorad FC-754 | MON 0818 |
|---|---|---|---|---|---|
| | | | % w/w | | |
| 49-01 | 15 | 4.0 | | 8.0 | 0.5 |
| 49-02 | 15 | 6.0 | | 8.0 | 0.5 |
| 49-03 | 15 | 8.0 | | 8.0 | 0.5 |
| 49-04 | 10 | 4.0 | | 8.0 | 0.5 |
| 49-05 | 10 | 6.0 | | 8.0 | 0.5 |
| 49-06 | 10 | 8.0 | | 8.0 | 0.5 |
| 49-07 | 15 | 4.0 | 8.00 | | 0.5 |
| 49-08 | 15 | 6.0 | 8.00 | | 0.5 |
| 49-09 | 15 | 8.0 | 8.00 | | 0.5 |
| 49-10 | 15 | 6.0 | 8.25 | | 0.5 |
| 49-11 | 15 | 6.0 | 8.25 | | 4.0 |
| 49-12 | 15 | 8.0 | 4.00 | 4.0 | 0.5 |
| 49-13 | 10 | 8.0 | 8.00 | | 0.5 |
| 49-14 | 10 | 8.0 | 4.00 | 4.0 | 0.5 |

Velvetleaf (*Abutilon theophrasti*, ABUTH) and Japanese millet (*Echinochloa crus-galli*, ECHCF) plants were grown and treated by the standard procedures given above. Applications of spray compositions were made 22 days after planting ABUTH and 23 days after planting ECHCF, and evaluation of herbicidal inhibition was done 17 days after application.

Formulations B and J were applied as comparative treatments. Results, averaged for all replicates of each treatment, are shown in Table 49b.

TABLE 49b

| Concentrate composition | Glyphosate rate g a.e./ha | % Inhibition ABUTH | ECHCF |
|---|---|---|---|
| Formulation B | 150 | 0 | 20 |
| | 250 | 17 | 37 |
| | 350 | 47 | 47 |
| | 450 | 53 | 60 |
| Formulation J | 150 | 27 | 38 |
| | 250 | 68 | 80 |
| | 350 | 78 | 95 |
| | 450 | 87 | 95 |
| 49-01 | 150 | 15 | 30 |
| | 250 | 78 | 68 |
| | 350 | 97 | 87 |
| | 450 | 97 | 78 |
| 49-02 | 150 | 47 | 30 |
| | 250 | 92 | 80 |
| | 350 | 97 | 97 |
| | 450 | 98 | 85 |
| 49-03 | 150 | 30 | 35 |
| | 250 | 83 | 45 |
| | 350 | 97 | 57 |
| | 450 | 97 | 67 |
| 49-04 | 150 | 47 | 32 |
| | 250 | 80 | 57 |
| | 350 | 95 | 87 |
| | 450 | 97 | 96 |
| 49-05 | 150 | 32 | 30 |
| | 250 | 81 | 89 |
| | 350 | 94 | 95 |
| | 450 | 98 | 94 |
| 49-06 | 150 | 60 | 28 |
| | 250 | 80 | 96 |
| | 350 | 92 | 95 |
| | 450 | 98 | 96 |
| 49-07 | 150 | 50 | 23 |
| | 250 | 70 | 72 |
| | 350 | 92 | 78 |
| | 450 | 97 | 60 |
| 49-08 | 150 | 45 | 40 |
| | 250 | 72 | 72 |
| | 350 | 90 | 89 |
| | 450 | 97 | 77 |
| 49-09 | 150 | 53 | 25 |
| | 250 | 80 | 78 |
| | 350 | 89 | 89 |
| | 450 | 96 | 93 |
| 49-10 | 150 | 72 | 48 |
| | 250 | 89 | 83 |
| | 350 | 98 | 95 |
| | 450 | 98 | 80 |
| 49-11 | 150 | 50 | 27 |
| | 250 | 77 | 63 |
| | 350 | 93 | 83 |
| | 450 | 97 | 72 |
| 49-12 | 150 | 52 | 15 |
| | 250 | 83 | 57 |
| | 350 | 94 | 68 |
| | 450 | 98 | 63 |
| 49-13 | 150 | 50 | 30 |
| | 250 | 75 | 32 |
| | 350 | 88 | 84 |
| | 450 | 97 | 77 |
| 49-14 | 150 | 67 | 23 |
| | 250 | 84 | 77 |
| | 350 | 97 | 73 |
| | 450 | 97 | 72 |

In this test compositions prepared with Fluorad FC-754 tended to provide greater herbicidal effectiveness on ECHCF than their counterparts prepared with Fluorad FC-135.

EXAMPLE 50

Aqueous concentrate compositions were prepared containing glyphosate IPA salt and excipient ingredients as shown in Table 50a. Process (v) was followed for all compositions using soybean lecithin (45% phospholipid, Avanti). The pH of all compositions was approximately 5.

TABLE 50a

| Concentrate composition | % w/w | | | | | |
|---|---|---|---|---|---|---|
| | Glyphosate a.e. | Lecithin | Fluorad FC-135 | Fluorad FC-754 | MON 0818 | Iso-propanol |
| 50-01 | 15 | 6.0 | 8.25 | | 4.0 | |
| 50-02 | 15 | 6.0 | | 8.25 | 4.0 | |
| 50-03 | 10 | 8.0 | 8.00 | | 0.5 | |
| 50-04 | 10 | 8.0 | | 8.00 | 0.5 | |
| 50-05 | 20 | 2.0 | 2.00 | | 0.5 | |
| 50-06 | 20 | 2.0 | | 2.00 | 0.5 | |
| 50-07 | 30 | 3.0 | 3.00 | | 0.5 | |
| 50-08 | 30 | 3.0 | | 3.00 | 0.5 | |
| 50-09 | 30 | 1.0 | 1.00 | | 0.5 | |
| 50-10 | 30 | 1.0 | | 1.00 | 0.5 | |
| 50-11 | 15 | 6.0 | 8.25 | | 4.0 | 5.0 |
| 50-12 | 15 | 6.0 | | 8.25 | 4.0 | 5.0 |
| 50-13 | 10 | 8.0 | 8.00 | | 2.0 | 5.0 |
| 50-14 | 10 | 8.0 | | 8.00 | 2.0 | 5.0 |
| 50-15 | 30 | 3.0 | | 3.00 | 0.8 | |
| 50-16 | 30 | 3.0 | 3.00 | | 0.8 | |
| 50-17 | 10 | 8.0 | 8.00 | | 2.0 | 7.5 |
| 50-18 | 10 | 8.0 | | 8.00 | 2.0 | 7.5 |
| 50-19 | 10 | 8.0 | 8.00 | | 2.0 | 10.0 |
| 50-20 | 10 | 8.0 | | 8.00 | 2.0 | 10.0 |
| 50-21 | 10 | 8.0 | 8.00 | | 4.0 | 5.0 |
| 50-22 | 10 | 8.0 | | 8.00 | 4.0 | 5.0 |

Velvetleaf (*Abutilon theophrasti*, ABUTH) and Japanese millet (*Echinochloa crus-galli*, ECHCF) plants were grown and treated by the standard procedures given above. Applications of spray compositions were made 17 days after planting ABUTH and 19 days after planting ECHCF, and evaluation of herbicidal inhibition was done 15 days after application.

Formulations B, C and J were applied as comparative treatments. Results, averaged for all replicates of each treatment, are shown in Table 50b.

TABLE 50b

| Concentrate composition | Glyphosate rate g a.e./ha | % Inhibition | |
|---|---|---|---|
| | | ABUTH | ECHCF |
| Formulation B | 150 | 2 | 22 |
| | 250 | 25 | 28 |
| | 350 | 63 | 38 |
| | 450 | 70 | 58 |
| Formulation C | 150 | 30 | 47 |
| | 250 | 75 | 82 |
| | 350 | 97 | 97 |
| | 450 | 100 | 99 |
| Formulation J | 150 | 10 | 43 |
| | 250 | 58 | 88 |
| | 350 | 87 | 96 |
| | 450 | 98 | 93 |
| 50-01 | 150 | 63 | 15 |
| | 250 | 78 | 32 |

TABLE 50b-continued

| Concentrate composition | Glyphosate rate g a.e./ha | % Inhibition | |
|---|---|---|---|
| | | ABUTH | ECHCF |
| | 350 | 83 | 70 |
| 50-02 | 150 | 60 | 28 |
| | 250 | 80 | 32 |
| | 350 | 88 | 65 |
| 50-03 | 150 | 53 | 37 |
| | 250 | 80 | 42 |
| | 350 | 91 | 27 |
| 50-04 | 150 | 72 | 18 |
| | 250 | 83 | 50 |
| | 350 | 96 | 80 |
| 50-05 | 150 | 50 | 2 |
| | 250 | 77 | 25 |
| | 350 | 78 | 43 |
| 50-06 | 150 | 22 | 25 |
| | 250 | 77 | 27 |
| | 350 | 87 | 40 |
| 50-07 | 150 | 27 | 20 |
| | 250 | 58 | 32 |
| | 350 | 87 | 37 |
| 50-08 | 150 | 32 | 3 |
| | 250 | 78 | 30 |
| | 350 | 82 | 52 |
| 50-09 | 150 | 5 | 0 |
| | 250 | 42 | 28 |
| | 350 | 68 | 43 |
| 50-10 | 150 | 2 | 23 |
| | 250 | 52 | 28 |
| | 350 | 75 | 42 |
| 50-11 | 150 | 72 | 27 |
| | 250 | 80 | 42 |
| | 350 | 85 | 73 |
| 50-12 | 150 | 58 | 23 |
| | 250 | 82 | 58 |
| | 350 | 87 | 97 |
| 50-13 | 150 | 70 | 8 |
| | 250 | 83 | 38 |
| | 350 | 85 | 45 |
| 50-14 | 150 | 68 | 37 |
| | 250 | 90 | 27 |
| | 350 | 89 | 67 |
| 50-15 | 150 | 28 | 28 |
| | 250 | 63 | 40 |
| | 350 | 87 | 35 |
| 50-16 | 150 | 23 | 13 |
| | 250 | 45 | 48 |
| | 350 | 82 | 68 |
| 50-17 | 150 | 67 | 2 |
| | 250 | 88 | 30 |
| | 350 | 87 | 58 |
| 50-18 | 150 | 60 | 38 |
| | 250 | 85 | 22 |
| | 350 | 95 | 53 |
| 50-19 | 150 | 74 | 38 |
| | 250 | 80 | 47 |
| | 350 | 95 | 28 |
| 50-20 | 150 | 70 | 25 |
| | 250 | 85 | 70 |
| | 350 | 97 | 81 |
| 50-21 | 150 | 78 | 5 |
| | 250 | 83 | 50 |
| | 350 | 90 | 83 |
| 50-22 | 150 | 73 | 33 |
| | 250 | 82 | 33 |
| | 350 | 95 | 83 |

Concentrate compositions having a high (20–30% a.e.) loading of glyphosate and consequently a relatively low loading of excipients showed enhancement of herbicidal effectiveness over that obtained with Formulation B, but in this test did not provide efficacy equal to commercial standard Formulations C and J.

EXAMPLE 51

Aqueous concentrate compositions were prepared containing glyphosate IPA salt and excipient ingredients as shown in Table 51a. Process (i) was followed for compositions 51-13 to 51-20 and process (v) for compositions 51-01 to 51-12 using soybean lecithin (45% phospholipid, Avanti). Compositions were stored in different conditions as indicated below before testing for herbicidal effectiveness. The pH of all compositions was approximately 5.

TABLE 51a

| Concentrate composition | Glyphosate a.e. | Lecithin | LI-700 | Fluorad FC-135 | Fluorad FC-754 | MON 0818 | Storage conditions |
|---|---|---|---|---|---|---|---|
| 51-01 | 20.0 | 2.0 | | | 2.0 | 0.5 | 60° C., 4 d |
| 51-02 | 15.0 | 6.0 | | 8.25 | | 4.0 | 60° C., 4 d |
| 51-03 | 20.0 | 2.0 | | | 2.0 | 0.5 | −10° C., 4 d |
| 51-04 | 15.0 | 6.0 | | 8.25 | | 4.0 | −10° C., 4 d |
| 51-05 | 20.0 | 2.0 | | | 2.0 | 0.5 | room temperature, 4 d |
| 51-06 | 15.0 | 6.0 | | 8.25 | | 4.0 | room temperature, 4 d |
| 51-07 | 20.0 | 2.0 | | | 2.0 | 0.5 | 60° C., 8 h then −10° C., 4d |
| 51-08 | 15.0 | 6.0 | | 8.25 | | 4.0 | 60° C., 8 h then −10° C., 4d |
| 51-09 | 20.0 | 2.0 | | | 2.0 | 0.5 | freshly made |
| 51-10 | 15.0 | 6.0 | | 8.25 | | 4.0 | freshly made |
| 51-11 | 20.0 | 2.0 | | | 2.0 | 0.5 | room temperature, 42 d |
| 51-12 | 15.0 | 6.0 | | 8.25 | | 4.0 | room temperature, 42 d |
| 51-13 | 15.0 | | 18.25 | | | | |
| 51-14 | 20.0 | | 4.50 | | | | |
| 51-15 | 15.0 | | 14.25 | | | 4.0 | |
| 51-16 | 20.0 | | 4.00 | | | 0.5 | |
| 51-17 | 15.0 | | 10.00 | 8.25 | | | |
| 51-18 | 20.0 | | 2.50 | | 2.0 | | |
| 51-19 | 15.0 | | 6.00 | 8.25 | | 4.0 | |
| 51-20 | 20.0 | | 2.00 | 2.00 | | 0.5 | |

Velvetleaf (*Abutilon theophrasti*, ABUTH) and Japanese millet (*Echinochloa crus-galli*, ECHCF) plants were grown and treated by the standard procedures given above. Applications of spray compositions were made 16 days after planting ABUTH and 18 days after planting ECHCF, and evaluation of herbicidal inhibition was done 18 days after application.

Formulations B and J were applied as comparative treatments. Results, averaged for all replicates of each treatment, are shown in Table 51b.

TABLE 51b

| Spray composition | Glyphosate rate g a.e./ha | % Inhibition ABUTH | % Inhibition ECHCF |
|---|---|---|---|
| Formulation B | 150 | 27 | 30 |
| | 250 | 37 | 38 |
| | 350 | 60 | 42 |
| | 450 | 69 | 45 |
| Formulation J | 150 | 45 | 61 |
| | 250 | 81 | 92 |
| | 350 | 93 | 97 |
| | 450 | 96 | 97 |
| 51-01 | 150 | 45 | 25 |
| | 250 | 49 | 41 |
| | 350 | 66 | 47 |
| | 450 | 75 | 63 |
| 51-02 | 150 | 49 | 65 |
| | 250 | 74 | 67 |
| | 350 | 83 | 88 |
| | 450 | 92 | 87 |
| 51-03 | 150 | 32 | 25 |
| | 250 | 71 | 70 |
| | 350 | 75 | 65 |
| | 450 | 77 | 67 |
| 51-04 | 150 | 54 | 68 |
| | 250 | 82 | 82 |
| | 350 | 91 | 95 |
| | 450 | 87 | 96 |
| 51-05 | 150 | 39 | 52 |
| | 250 | 63 | 65 |
| | 350 | 83 | 90 |
| | 450 | 85 | 93 |
| 51-06 | 150 | 67 | 81 |
| | 250 | 89 | 97 |
| | 350 | 94 | 100 |
| | 450 | 96 | 100 |
| 51-07 | 150 | 39 | 52 |
| | 250 | 60 | 88 |
| | 350 | 87 | 94 |
| | 450 | 85 | 96 |
| 51-08 | 150 | 54 | 82 |
| | 250 | 87 | 98 |
| | 350 | 93 | 100 |
| | 450 | 92 | 100 |
| 51-09 | 150 | 45 | 53 |
| | 250 | 67 | 88 |
| | 350 | 84 | 89 |
| | 450 | 93 | 93 |
| 51-10 | 150 | 56 | 63 |
| | 250 | 86 | 97 |
| | 350 | 94 | 99 |
| | 450 | 92 | 98 |
| 51-11 | 150 | 48 | 40 |
| | 250 | 69 | 55 |

TABLE 51b-continued

| Spray composition | Glyphosate rate g a.e./ha | % Inhibition ABUTH | % Inhibition ECHCF |
|---|---|---|---|
|  | 350 | 74 | 91 |
| 51-12 | 150 | 60 | 41 |
|  | 250 | 86 | 91 |
|  | 350 | 95 | 98 |
| 51-13 | 150 | 30 | 44 |
|  | 250 | 37 | 76 |
|  | 350 | 59 | 94 |
| 51-14 | 150 | 0 | 40 |
|  | 250 | 49 | 55 |
|  | 350 | 59 | 85 |
| 51-15 | 150 | 42 | 61 |
|  | 250 | 71 | 90 |
|  | 350 | 83 | 97 |
| 51-16 | 150 | 27 | 42 |
|  | 250 | 49 | 58 |
|  | 350 | 61 | 86 |
| 51-17 | 150 | 37 | 45 |
|  | 250 | 52 | 70 |
|  | 350 | 76 | 60 |
| 51-18 | 150 | 28 | 32 |
|  | 250 | 53 | 77 |
|  | 350 | 70 | 71 |
| 51-19 | 150 | 47 | 36 |
|  | 250 | 69 | 97 |
|  | 350 | 83 | 89 |
| 51-20 | 150 | 26 | 20 |
|  | 250 | 56 | 74 |
|  | 350 | 62 | 82 |

No great or consistent effect of storage conditions on herbicidal effectiveness of compositions was seen in this test.

EXAMPLE 52

Aqueous concentrate compositions were prepared containing glyphosate IPA salt and excipient ingredients as shown in Table 52a. Process (v) was followed for all compositions using soybean lecithin (45% phospholipid, Avanti). The pH of all compositions was approximately 5.

Velvetleaf (*Abutilon theophrasti,* ABUTH) and Japanese millet (*Echinochloa crus-galli,* ECHCF) plants were grown and treated by the standard procedures given above. Applications of spray compositions were made 16 days after planting ABUTH and ECHCF, and evaluation of herbicidal inhibition was done 15 days after application.

Formulation J was applied as a comparative treatment. Results, averaged for all replicates of each treatment, are shown in Table 52b.

TABLE 52b

| Concentrate composition | Glyphosate rate g a.e./ha | % Inhibition ABUTH | % Inhibition ECHCF |
|---|---|---|---|
| Formulation J | 150 | 38 | 45 |
|  | 250 | 80 | 63 |
|  | 350 | 78 | 82 |
|  | 450 | 75 | 55 |
| 52-01 | 150 | 23 | 27 |
|  | 250 | 57 | 53 |
|  | 350 | 70 | 85 |
|  | 450 | 70 | 83 |
| 52-02 | 150 | 7 | 25 |
|  | 250 | 52 | 45 |
|  | 350 | 82 | 88 |
|  | 450 | 82 | 90 |
| 52-03 | 150 | 38 | 35 |
|  | 250 | 50 | 40 |
|  | 350 | 82 | 92 |
|  | 450 | 83 | 93 |
| 52-04 | 150 | 40 | 48 |
|  | 250 | 73 | 75 |
|  | 350 | 78 | 92 |
|  | 450 | 88 | 92 |
| 52-05 | 150 | 50 | 53 |
|  | 250 | 68 | 80 |
|  | 350 | 85 | 98 |
|  | 450 | 89 | 96 |
| 52-06 | 150 | 50 | 43 |
|  | 250 | 55 | 80 |
|  | 350 | 78 | 97 |
|  | 450 | 85 | 91 |
| 52-07 | 150 | 3 | 28 |
|  | 250 | 22 | 43 |

TABLE 52a

| Concentrate composition | Glyphosate a.e. | Lecithin | Butyl stearate | Fluorad FC-754 | MON 0818 | Ethomeen T/25 | Ethanol |
|---|---|---|---|---|---|---|---|
| 52-01 | 20 | 2.0 | 0.5 |  |  | 1.25 | 1.0 |
| 52-02 | 20 | 2.0 | 0.5 |  | 1.00 | 1.00 | 1.0 |
| 52-03 | 20 | 2.0 | 0.5 |  | 1.25 |  | 1.0 |
| 52-04 | 20 | 6.0 | 1.5 |  |  | 3.00 | 3.0 |
| 52-05 | 20 | 6.0 | 1.5 |  | 2.00 | 2.00 | 2.0 |
| 52-06 | 20 | 6.0 | 1.5 |  | 3.00 |  | 3.0 |
| 52-07 | 20 | 2.0 | 0.5 |  |  | 0.50 |  |
| 52-08 | 20 | 2.0 | 0.5 |  |  | 2.50 |  |
| 52-09 | 20 | 2.0 | 0.5 |  | 1.25 | 1.25 |  |
| 52-10 | 20 | 6.0 | 1.5 |  |  | 0.50 |  |
| 52-11 | 20 | 6.0 | 1.5 |  |  | 3.00 |  |
| 52-12 | 20 | 6.0 | 1.5 |  |  | 6.00 |  |
| 52-13 | 20 | 6.0 | 1.5 |  | 3.00 | 3.00 |  |
| 52-14 | 20 | 2.0 |  | 2.0 | 0.50 |  |  |
| 52-15 | 20 | 6.0 |  | 3.0 | 6.00 |  |  |
| 52-16 | 20 | 6.0 |  | 6.0 | 6.00 |  |  |

TABLE 52b-continued

| Concentrate composition | Glyphosate rate g a.e./ha | % Inhibition ABUTH | % Inhibition ECHCF |
|---|---|---|---|
| | 350 | 67 | 72 |
| | 450 | 73 | 75 |
| 52-08 | 150 | 43 | 33 |
| | 250 | 77 | 63 |
| | 350 | 89 | 78 |
| | 450 | 97 | 85 |
| 52-09 | 150 | 57 | 27 |
| | 250 | 95 | 63 |
| | 350 | 89 | 86 |
| | 450 | 98 | 88 |
| 52-10 | 150 | 32 | 23 |
| | 250 | 33 | 55 |
| | 350 | 73 | 82 |
| | 450 | 67 | 60 |
| 52-11 | 150 | 45 | 32 |
| | 250 | 78 | 72 |
| | 350 | 95 | 92 |
| | 450 | 98 | 96 |
| 52-12 | 150 | 67 | 42 |
| | 250 | 80 | 75 |
| | 350 | 96 | 88 |
| | 450 | 97 | 90 |
| 52-13 | 150 | 73 | 42 |
| | 250 | 83 | 77 |
| | 350 | 96 | 91 |
| | 450 | 98 | 88 |
| 52-14 | 150 | 57 | 30 |
| | 250 | 77 | 72 |
| | 350 | 84 | 80 |
| | 450 | 96 | 75 |
| 52-15 | 150 | 72 | 38 |
| | 250 | 88 | 82 |
| | 350 | 98 | 92 |
| | 450 | 98 | 87 |
| 52-16 | 150 | 85 | 49 |
| | 250 | 97 | 47 |
| | 350 | 97 | 83 |
| | 450 | 98 | 85 |

Very high herbicidal effectiveness was obtained in this test with concentrate compositions containing lecithin and Fluorad FC-754. Composition 52-14, containing each of these excipients at the very low weight/weight ratio to glyphosate a.e. of 1:10, was at least as effective as commercial standard Formulation J, while compositions 52-15 and 52-16 were still more effective. Also performing very well in this test, particularly on ECHCF, were a number of concentrate compositions containing lecithin and butyl stearate.

EXAMPLE 53

Aqueous concentrate compositions were prepared containing glyphosate IPA salt and excipient ingredients as shown in Table 53a. Process (v) was followed for all compositions using soybean lecithin (45% phospholipid, Avanti). Order of addition of ingredients was varied for certain compositions as indicated below. The pH of all compositions was approximately 5.

TABLE 53a

| Concentrate composition | Glyphosate g/l a.e. | % w/w Lecithin | Fluorad FC-754/135 | Benzalkonium Cl | Butyl stearate | MON 0818 | Order of addition (*) |
|---|---|---|---|---|---|---|---|
| 53-01 | 345 | 4.0 | | 0.66 | | | |
| 53-02 | 345 | 4.0 | | 1.00 | | | |
| 53-03 | 347 | 3.0 | | 3.00 | | | |
| 53-04 | 347 | 4.0 | | 4.00 | | | |
| 53-05 | 347 | 4.0 | | 5.00 | | | |
| 53-06 | 345 | 4.6 | | 4.60 | | | |
| 53-07 | 348 | 4.0 | 2.0 (754) | 1.10 | | | |
| 53-08 | 351 | 4.0 | 4.0 (754) | 1.00 | | | A |
| 53-09 | 346 | 3.9 | 4.2 (754) | 1.00 | | | B |
| 53-10 | 350 | 4.0 | 2.0 (135) | 1.10 | | | |
| 53-11 | 352 | 4.0 | 4.0 (135) | 1.00 | | | A |
| 53-12 | 349 | 4.0 | 4.0 (135) | 1.00 | | | B |
| 53-13 | 348 | 4.0 | 4.0 (754) | 0.50 | 0.57 | | |
| 53-14 | 347 | 4.0 | | 0.50 | 0.52 | | |
| 53-15 | 348 | 3.7 | | 0.48 | | 3.7 | |
| 53-16 | 348 | 4.0 | | 0.58 | | 4.0 | |

(*) Order of addition:

| | 1st | 2nd | 3rd | 4th | 5th |
|---|---|---|---|---|---|
| A | lecithin | water | Benzalkonium Cl | FC-135/754 | glyphosate |
| B | glyphosate | FC-135/754 | Benzalkonium Cl | water | glyphosate |

Velvetleaf (*Abutilon theophrasti*, ABUTH) and Japanese millet (*Echinochloa crus-galli*, ECHCF) plants were grown and treated by the standard procedures given above. Applications of spray compositions were made 17 days after planting ABUTH and ECHCF, and evaluation of herbicidal inhibition was done 21 days after application.

Formulations B and J were applied as comparative treatments. Results, averaged for all replicates of each treatment, are shown in Table 53b.

TABLE 53b

| Concentrate composition | Glyphosate rate g a.e./ha | % Inhibition ABUTH | % Inhibition ECHCF |
|---|---|---|---|
| Formulation B | 100 | 5 | 5 |
|  | 200 | 15 | 20 |
|  | 300 | 47 | 30 |
|  | 400 | 65 | 37 |
| Formulation J | 100 | 0 | 8 |
|  | 200 | 70 | 37 |
|  | 300 | 78 | 70 |
|  | 400 | 83 | 73 |
| 53-01 | 100 | 3 | 10 |
|  | 200 | 17 | 27 |
|  | 300 | 45 | 37 |
|  | 400 | 75 | 40 |
| 53-02 | 100 | 2 | 5 |
|  | 200 | 13 | 30 |
|  | 300 | 43 | 40 |
|  | 400 | 75 | 47 |
| 53-03 | 100 | 0 | 8 |
|  | 200 | 17 | 43 |
|  | 300 | 65 | 78 |
|  | 400 | 78 | 83 |
| 53-04 | 100 | 2 | 10 |
|  | 200 | 30 | 37 |
|  | 300 | 68 | 72 |
|  | 400 | 75 | 88 |
| 53-05 | 100 | 2 | 20 |
|  | 200 | 25 | 65 |
|  | 300 | 63 | 88 |
|  | 400 | 82 | 83 |
| 53-06 | 100 | 10 | 17 |
|  | 200 | 25 | 33 |
|  | 300 | 47 | 77 |
|  | 400 | 83 | 75 |
| 53-07 | 100 | 0 | 10 |
|  | 200 | 48 | 30 |
|  | 300 | 73 | 37 |
|  | 400 | 83 | 43 |
| 53-08 | 100 | 3 | 10 |
|  | 200 | 33 | 30 |
|  | 300 | 68 | 37 |
|  | 400 | 78 | 40 |
| 53-09 | 100 | 5 | 10 |
|  | 200 | 40 | 27 |
|  | 300 | 65 | 50 |
|  | 400 | 70 | 57 |
| 53-10 | 100 | 0 | 10 |
|  | 200 | 30 | 27 |
|  | 300 | 67 | 40 |
|  | 400 | 73 | 40 |
| 53-11 | 100 | 0 | 10 |
|  | 200 | 33 | 27 |
|  | 300 | 52 | 37 |
|  | 400 | 82 | 40 |
| 53-12 | 100 | 0 | 10 |
|  | 200 | 40 | 20 |
|  | 300 | 65 | 40 |
|  | 400 | 72 | 40 |
| 53-13 | 100 | 0 | 10 |
|  | 200 | 40 | 20 |
|  | 300 | 60 | 33 |
|  | 400 | 78 | 33 |
| 53-14 | 100 | 0 | 10 |
|  | 200 | 7 | 47 |
|  | 300 | 28 | 33 |
|  | 400 | 43 | 43 |
| 53-15 | 100 | 0 | 13 |
|  | 200 | 27 | 33 |
|  | 300 | 73 | 53 |
|  | 400 | 77 | 67 |
| 53-16 | 100 | 0 | 13 |
|  | 200 | 30 | 37 |
|  | 300 | 75 | 47 |
|  | 400 | 77 | 68 |

Most concentrate compositions of this Example showed enhanced glyphosate effectiveness by comparison with Formulation B but did not equal the efficacy of commercial standard Formulation J in this test.

EXAMPLE 54

Aqueous spray and concentrate compositions were prepared containing glyphosate IPA salt and excipient ingredients as shown in Table 54a. Process (i) was followed for spray compositions 54-37 to 54-60 and process (iii) for spray compositions 54-01 to 54-36 using soybean lecithin (45% phospholipid, Avanti). Process (v) was followed for concentrate compositions 54-61 to 54-63 using soybean lecithin (45% phospholipid, Avanti). The pH of all compositions was approximately 5.

TABLE 54a

| Composition | Glyphosate g a.e./l | % w/w Lecithin | % w/w Fluoro-organic | Type of fluoro-organic |
|---|---|---|---|---|
| Spray composition | | | | |
| 54-01 | 1.60 | 0.027 | 0.027 | Fluorad FC-754 |
| 54-02 | 2.66 | 0.045 | 0.045 | Fluorad FC-754 |
| 54-03 | 3.72 | 0.062 | 0.062 | Fluorad FC-754 |
| 54-04 | 4.79 | 0.080 | 0.080 | Fluorad FC-754 |
| 54-05 | 1.60 | 0.027 | 0.027 | Fluorad FC-750 |
| 54-06 | 2.66 | 0.045 | 0.045 | Fluorad FC-750 |
| 54-07 | 3.72 | 0.062 | 0.062 | Fluorad FC-750 |
| 54-08 | 4.79 | 0.080 | 0.080 | Fluorad FC-750 |
| 54-09 | 1.60 | 0.027 | 0.027 | Fluorad FC-751 |
| 54-10 | 2.66 | 0.045 | 0.045 | Fluorad FC-751 |
| 54-11 | 3.72 | 0.062 | 0.062 | Fluorad FC-751 |
| 54-12 | 4.79 | 0.080 | 0.080 | Fluorad FC-751 |
| 54-13 | 1.60 | 0.027 | 0.027 | Fluorad FC-760 |
| 54-14 | 2.66 | 0.045 | 0.045 | Fluorad FC-760 |
| 54-15 | 3.72 | 0.062 | 0.062 | Fluorad FC-760 |
| 54-16 | 4.79 | 0.080 | 0.080 | Fluorad FC-760 |
| 54-17 | 1.60 | 0.027 | 0.027 | Fluorad FC-120 |
| 54-18 | 2.66 | 0.045 | 0.045 | Fluorad FC-120 |
| 54-19 | 3.72 | 0.062 | 0.062 | Fluorad FC-120 |
| 54-20 | 4.79 | 0.080 | 0.080 | Fluorad FC-120 |
| 54-21 | 1.60 | 0.027 | 0.027 | Fluorad FC-171 |
| 54-22 | 2.66 | 0.045 | 0.045 | Fluorad FC-171 |
| 54-23 | 3.72 | 0.062 | 0.062 | Fluorad FC-171 |
| 54-24 | 4.79 | 0.080 | 0.080 | Fluorad FC-171 |
| 54-25 | 1.60 | 0.027 | 0.027 | Fluorad FC-129 |
| 54-26 | 2.66 | 0.045 | 0.045 | Fluorad FC-129 |
| 54-27 | 3.72 | 0.062 | 0.062 | Fluorad FC-129 |
| 54-28 | 4.79 | 0.080 | 0.080 | Fluorad FC-129 |
| 54-29 | 1.60 | 0.027 | 0.027 | Fluorad FC-170C |
| 54-30 | 2.66 | 0.045 | 0.045 | Fluorad FC-170C |
| 54-31 | 3.72 | 0.062 | 0.062 | Fluorad FC-170C |
| 54-32 | 4.79 | 0.080 | 0.080 | Fluorad FC-170C |
| 54-33 | 1.60 |  | 0.027 | Fluorad FC-754 |
| 54-34 | 2.66 |  | 0.045 | Fluorad FC-754 |

TABLE 54a-continued

| Composition | Glyphosate g a.e./l | Lecithin | Fluoro-organic | Type of fluoro-organic |
|---|---|---|---|---|
| 54-35 | 3.72 | | 0.062 | Fluorad FC-754 |
| 54-36 | 4.79 | | 0.080 | Fluorad FC-754 |
| 54-37 | 1.60 | | 0.027 | Fluorad FC-750 |
| 54-38 | 2.66 | | 0.045 | Fluorad FC-750 |
| 54-39 | 3.72 | | 0.062 | Fluorad FC-750 |
| 54-40 | 4.79 | | 0.080 | Fluorad FC-750 |
| 54-41 | 1.60 | | 0.027 | Fluorad FC-760 |
| 54-42 | 2.66 | | 0.045 | Fluorad FC-760 |
| 54-43 | 3.72 | | 0.062 | Fluorad FC-760 |
| 54-44 | 4.79 | | 0.080 | Fluorad FC-760 |
| 54-45 | 1.60 | | 0.027 | Fluorad FC-120 |
| 54-46 | 2.66 | | 0.045 | Fluorad FC-120 |
| 54-47 | 3.72 | | 0.062 | Fluorad FC-120 |
| 54-48 | 4.79 | | 0.080 | Fluorad FC-120 |
| 54-49 | 1.60 | | 0.027 | Fluorad FC-171 |
| 54-50 | 2.66 | | 0.045 | Fluorad FC-171 |
| 54-51 | 3.72 | | 0.062 | Fluorad FC-171 |
| 54-52 | 4.79 | | 0.080 | Fluorad FC-171 |
| 54-53 | 1.60 | | 0.027 | Fluorad FC-129 |
| 54-54 | 2.66 | | 0.045 | Fluorad FC-129 |
| 54-55 | 3.72 | | 0.062 | Fluorad FC-129 |
| 54-56 | 4.79 | | 0.080 | Fluorad FC-129 |
| 54-57 | 1.60 | | 0.027 | Fluorad FC-170C |
| 54-58 | 2.66 | | 0.045 | Fluorad FC-170C |
| 54-59 | 3.72 | | 0.062 | Fluorad FC-170C |
| 54-60 | 4.79 | | 0.080 | Fluorad FC-170C |
| Concentrate compositions: | | | | |
| 54-61 | 180 | 1.5 | 1.5 | Fluorad FC-754 |
| 54-62 | 180 | 2.5 | 2.5 | Fluorad FC-754 |
| 54-63 | 180 | 3.0 | 6.0 | Fluorad FC-754 |

Velvetleaf (*Abutilon theophrasti*, ABUTH) and Japanese millet (*Echinochloa crus-galli*, ECHCF) plants were grown and treated by the standard procedures given above. Applications of spray compositions were made 19 days after planting ABUTH and 19 days after planting ECHCF, and evaluation of herbicidal inhibition was done 16 days after application.

Formulations B and J were applied as comparative treatments. Results, averaged for all replicates of each treatment, are shown in Table 54b.

TABLE 54b

| Spray or concentrate composition | Glyphosate rate g a.e./ha | % Inhibition ABUTH | % Inhibition ECHCF |
|---|---|---|---|
| Formulation B | 150 | 47 | 88 |
| | 250 | 68 | 96 |
| | 350 | 86 | 98 |
| | 450 | 93 | 100 |
| Formulation J | 150 | 68 | 89 |
| | 250 | 94 | 97 |
| | 350 | 98 | 100 |
| | 450 | 100 | 99 |
| 54-01 | 150 | 94 | 83 |
| 54-02 | 250 | 97 | 99 |
| 54-03 | 350 | 97 | 99 |
| 54-04 | 450 | 99 | 100 |
| 54-05 | 150 | 93 | 77 |
| 54-06 | 250 | 94 | 96 |
| 54-07 | 350 | 97 | 94 |
| 54-08 | 450 | 98 | 99 |
| 54-09 | 150 | 53 | 72 |
| 54-10 | 250 | 68 | 86 |
| 54-11 | 350 | 73 | 99 |
| 54-12 | 450 | 91 | 96 |
| 54-13 | 150 | 58 | 70 |
| 54-14 | 250 | 72 | 94 |
| 54-15 | 350 | 89 | 95 |
| 54-16 | 450 | 93 | 92 |
| 54-17 | 150 | 50 | 62 |
| 54-18 | 250 | 58 | 78 |
| 54-19 | 350 | 85 | 93 |
| 54-20 | 450 | 84 | 96 |
| 54-21 | 150 | 53 | 63 |
| 54-22 | 250 | 83 | 85 |
| 54-23 | 350 | 89 | 90 |
| 54-24 | 450 | 96 | 86 |
| 54-25 | 150 | 53 | 57 |
| 54-26 | 250 | 78 | 85 |
| 54-27 | 350 | 90 | 91 |
| 54-28 | 450 | 96 | 93 |
| 54-29 | 150 | 62 | 70 |
| 54-30 | 250 | 84 | 92 |
| 54-31 | 350 | 97 | 97 |
| 54-32 | 450 | 97 | 98 |
| 54-33 | 150 | 94 | 79 |
| 54-34 | 250 | 96 | 97 |
| 54-35 | 350 | 97 | 99 |
| 54-36 | 450 | 98 | 99 |
| 54-37 | 150 | 90 | 84 |
| 54-38 | 250 | 99 | 96 |
| 54-39 | 350 | 98 | 100 |
| 54-40 | 450 | 99 | 100 |
| 54-41 | 150 | 68 | 75 |
| 54-42 | 250 | 73 | 88 |
| 54-43 | 350 | 83 | 92 |
| 54-44 | 450 | 92 | 98 |
| 54-45 | 150 | 48 | 53 |
| 54-46 | 250 | 60 | 88 |
| 54-47 | 350 | 82 | 97 |
| 54-48 | 450 | 95 | 95 |
| 54-49 | 150 | 50 | 47 |
| 54-50 | 250 | 63 | 89 |
| 54-51 | 350 | 83 | 91 |
| 54-52 | 450 | 91 | 90 |
| 54-53 | 150 | 48 | 52 |
| 54-54 | 250 | 63 | 75 |
| 54-55 | 350 | 91 | 92 |
| 54-56 | 450 | 97 | 97 |
| 54-57 | 150 | 50 | 83 |
| 54-58 | 250 | 73 | 94 |
| 54-59 | 350 | 91 | 98 |
| 54-60 | 450 | 94 | 98 |
| 54-61 | 150 | 63 | 52 |
| | 250 | 96 | 96 |
| | 350 | 97 | 96 |
| 54-62 | 150 | 77 | 77 |
| | 250 | 93 | 87 |
| | 350 | 98 | 98 |
| 54-63 | 150 | 83 | 89 |
| | 250 | 96 | 96 |
| | 350 | 98 | 98 |

Outstanding herbicidal efficacy, even by comparison with Formulation J, was obtained in this test from spray compositions containing lecithin and Fluorad FC-754 (54-01 to 54-04). Substitution of other fluoro-organic surfactants for Fluorad FC-754 gave varying results. Fluorad FC-750 (compositions 54-05 to 54-08) was an acceptable substitute; however Fluorad FC-751, Fluorad FC-760, Fluorad FC-120, Fluorad FC-171, Fluorad FC-129 and Fluorad FC-170C (compositions 54-09 to 54-32) provided less enhancement. A similar pattern was seen with spray compositions (54-33 to 54-60) containing the same fluoro-organic surfactants as above with the exception of Fluorad FC-751, but no lecithin. It is noteworthy that of all the fluoro-organic surfactants included in this test, only Fluorad FC-754 and Fluorad FC-750 are cationic. Excellent herbicidal efficacy was also noted in this test from concentrate glyphosate compositions containing lecithin and Fluorad FC-754, especially composition 54-63.

EXAMPLE 55

Spray compositions were prepared containing glyphosate IPA salt and excipient ingredients as shown in Table 55a. Compositions were prepared by simple mixing of ingredients. Soybean lecithin (45% phospholipid, Avanti), where included, was first prepared with sonication in water to make a homogeneous composition. Four different concentrations of glyphosate (not shown in Table 55a) were prepared, calculated to provide, when applied in a spray volume of 93 l/ha, the glyphosate rates shown in Table 55b.

TABLE 55a

| Spray comp. | Lecithin | Fluorad FC-754 | Butyl stearate | Methyl oleate | Oleth-20 | Lecithin supplied as | Methyl oleate supplied as |
|---|---|---|---|---|---|---|---|
| 55-01 | 0.05 | 0.050 | | | | soybean lecithin | |
| 55-02 | 0.05 | | 0.050 | | | soybean lecithin | |
| 55-03 | 0.05 | | | 0.050 | | soybean lecithin | |
| 55-04 | | 0.050 | | | | | |
| 55-05 | | | 0.050 | | | | |
| 55-06 | 0.05 | | | | | LI-700 | |
| 55-07 | | | 0.005 | | 0.05 | | |
| 55-08 | | | | 0.01 | 0.05 | | |
| 55-09 | | | | | 0.05 | | |
| 55-10 | | | 0.005 | | | | |
| 55-11 | | | | 0.01 | | | pure |
| 55-12 | | | | 0.01 | | | methylated seed oil |

Velvetleaf (*Abutilon theophrasti*, ABUTH), Japanese millet (*Echinochloa crus-galli*, ECHCF) and Prickly sida (*Spida spinosa*, SIDSP) plants were grown and treated by the standard procedures given above. Applications of spray compositions were made 14 days after planting ABUTH and ECHCF and 21 days after planting SIDSP. Evaluation of herbicidal inhibition was done 14 days after application.

Formulations B and C were applied as comparative treatments, representing technical glyphosate IPA salt and a commercial formulation of glyphosate IPA salt respectively. Results, averaged for all replicates of each treatment, are shown in Table 55b.

TABLE 55b

| Spray composition | Glyphosate rate g a.e./ha | % Inhibition ABUTH | ECHCF | SIDSP |
|---|---|---|---|---|
| Formulation B | 50 | 0 | 0 | 0 |
| | 100 | 38 | 35 | 35 |
| | 200 | 87 | 50 | 90 |
| | 300 | 95 | 88 | 94 |
| Formulation C | 50 | 0 | 2 | 0 |
| | 100 | 32 | 55 | 25 |
| | 200 | 85 | 97 | 93 |
| | 300 | 96 | 99 | 96 |
| 55-01 | 50 | 78 | 53 | 88 |
| | 100 | 90 | 60 | 95 |
| | 200 | 99 | 96 | 99 |
| | 300 | 99 | 97 | 98 |
| 55-02 | 50 | 25 | 15 | 43 |
| | 100 | 72 | 30 | 82 |
| | 200 | 94 | 62 | 93 |
| | 300 | 95 | 77 | 94 |
| 55-03 | 50 | 20 | 8 | 32 |
| | 100 | 52 | 22 | 78 |
| | 200 | 87 | 55 | 91 |
| | 300 | 95 | 65 | 93 |
| 55-04 | 50 | 62 | 37 | 85 |
| | 100 | 82 | 68 | 92 |
| | 200 | 97 | 96 | 95 |
| | 300 | 98 | 95 | 97 |
| 55-05 | 50 | 15 | 10 | 25 |
| | 100 | 47 | 27 | 23 |
| | 200 | 85 | 62 | 87 |
| | 300 | 90 | 63 | 92 |
| 55-06 | 50 | 0 | 2 | 0 |
| | 100 | 20 | 15 | 20 |
| | 200 | 85 | 60 | 82 |
| | 300 | 90 | 65 | 90 |
| 55-07 | 50 | 67 | 27 | 82 |
| | 100 | 87 | 55 | 93 |
| | 200 | 94 | 92 | 96 |
| | 300 | 97 | 99 | 97 |
| 55-08 | 50 | 62 | 30 | 75 |
| | 100 | 78 | 63 | 91 |
| | 200 | 93 | 96 | 96 |
| | 300 | 94 | 98 | 98 |
| 55-09 | 50 | 65 | 45 | 77 |
| | 100 | 80 | 73 | 95 |
| | 200 | 93 | 98 | 97 |
| | 300 | 95 | 99 | 99 |
| 55-10 | 50 | 10 | 25 | 5 |
| | 100 | 23 | 35 | 37 |
| | 200 | 90 | 50 | 93 |
| | 300 | 92 | 73 | 94 |
| 55-11 | 50 | 10 | 25 | 0 |
| | 100 | 52 | 33 | 43 |
| | 200 | 88 | 72 | 93 |
| | 300 | 94 | 78 | 94 |
| 55-12 | 50 | 0 | 15 | 0 |
| | 100 | 43 | 35 | 33 |
| | 200 | 91 | 70 | 90 |
| | 300 | 94 | 82 | 93 |

Results of this test using glyphosate as the exogenous chemical are summarized as follows:

At the low concentration of 0.05% used here, soybean lecithin containing 45% phospholipid (55-03) was a much more effective excipient than the lecithin-based adjuvant LI-700 (55-06) widely used in the art.

Fluorad FC-754, either alone (55-04) or in combination with lecithin (55-01) gave extremely high effectiveness, superior to that obtained with the commercial standard.

EXAMPLE 56

Spray compositions were prepared containing paraquat dichloride and excipient ingredients. Compositions 56-01 to 56-12 were exactly like compositions 55-01 to 55-12 except that a different active ingredient was used and a range of active ingredient concentrations was selected appropriate to the active ingredient being applied.

Velvetleaf (*Abutilon theophrasti*, ABUTH), Japanese millet (*Echinochloa crus-galli*, ECHCF) and prickly sida (*Spida spinosa*, SIDSP) plants were grown and treated by the standard procedures given above. Applications of spray compositions were made 14 days after planting ABUTH, 8 days after planting ECHCF and 21 days after planting SIDSP. Evaluation of herbicidal inhibition was done 12 days after application.

Standards included technical paraquat dichloride and Gramoxone, a commercial formulation of paraquat from Zeneca. Results, averaged for all replicates of each treatment, are shown in Table 56.

TABLE 56

| Spray composition | Paraquat rate g a.i./ha | % Inhibition ABUTH | ECHCF | SIDSP |
| --- | --- | --- | --- | --- |
| Paraquat dichloride | 25 | 50 | 83 | 55 |
| (technical) | 50 | 57 | 78 | 60 |
|  | 100 | 73 | 84 | 69 |
|  | 200 | 85 | 95 | 99 |
| Gramoxone | 25 | 40 | 72 | 40 |
| (commercial) | 50 | 60 | 70 | 52 |
|  | 100 | 72 | 58 | 55 |
|  | 200 | 72 | 89 | 63 |
| 56-01 | 25 | 75 | 93 | 67 |
|  | 50 | 82 | 97 | 91 |
|  | 100 | 95 | 98 | 97 |
|  | 200 | 100 | 99 | 99 |
| 56-02 | 25 | 67 | 80 | 48 |
|  | 50 | 68 | 87 | 65 |
|  | 100 | 88 | 97 | 93 |
|  | 200 | 96 | 99 | 98 |
| 56-03 | 25 | 55 | 65 | 42 |
|  | 50 | 62 | 87 | 65 |
|  | 100 | 83 | 96 | 93 |
|  | 200 | 95 | 99 | 97 |
| 56-04 | 25 | 53 | 82 | 45 |
|  | 50 | 63 | 94 | 53 |
|  | 100 | 88 | 99 | 86 |
|  | 200 | 92 | 99 | 98 |
| 56-05 | 25 | 58 | 67 | 50 |
|  | 50 | 60 | 62 | 45 |
|  | 100 | 70 | 73 | 62 |
|  | 200 | 85 | 90 | 88 |
| 56-06 | 25 | 53 | 77 | 43 |
|  | 50 | 60 | 92 | 40 |
|  | 100 | 80 | 93 | 55 |
|  | 200 | 96 | 99 | 78 |
| 56-07 | 25 | 65 | 80 | 45 |
|  | 50 | 82 | 92 | 70 |
|  | 100 | 96 | 96 | 89 |
|  | 200 | 100 | 98 | 99 |
| 56-08 | 25 | 67 | 80 | 37 |

TABLE 56-continued

| Spray composition | Paraquat rate g a.i./ha | % Inhibition ABUTH | ECHCF | SIDSP |
| --- | --- | --- | --- | --- |
|  | 50 | 82 | 90 | 71 |
|  | 100 | 97 | 98 | 65 |
|  | 200 | 99 | 99 | 93 |
| 56-09 | 25 | 72 | 90 | 50 |
|  | 50 | 80 | 97 | 57 |
|  | 100 | 91 | 99 | 94 |
|  | 200 | 97 | 100 | 97 |
| 56-10 | 25 | 67 | 87 | 45 |
|  | 50 | 68 | 75 | 57 |
|  | 100 | 78 | 93 | 63 |
|  | 200 | 82 | 97 | 82 |
| 56-11 | 25 | 65 | 80 | 45 |
|  | 50 | 73 | 77 | 62 |
|  | 100 | 90 | 95 | 62 |
|  | 200 | 94 | 98 | 78 |
| 56-12 | 25 | 67 | 78 | 37 |
|  | 50 | 75 | 90 | 55 |
|  | 100 | 77 | 97 | 90 |
|  | 200 | 85 | 99 | 92 |

Results of this test using paraquat as the exogenous chemical are summarized as follows:

At the low concentration of 0.05% used here, soybean lecithin containing 45% phospholipid (56-03) was a much more effective excipient on SIDSP than the lecithin-based adjuvant LI-700 (56-06) widely used in the art.

Fluorad FC-754 (56-04) gave extremely high effectiveness, superior to that obtained with the commercial standard. In the presence of lecithin (56-01), effectiveness was further increased dramatically, suggesting a synergistic interaction between these two excipient substances.

EXAMPLE 57

Spray compositions were prepared containing acifluorfen sodium salt and excipient ingredients. Compositions 57-01 to 57-12 were exactly like compositions 55-01 to 55-12 respectively except that a different active ingredient was used and a range of active ingredient concentrations was selected appropriate to the active ingredient being applied.

Velvetleaf (*Abutilon theophrasti*, ABUTH), Japanese millet (*Echinochloa crus-galli*, ECHCF) and prickly sida (*Spida spinosa*, SIDSP) plants were grown and treated by the standard procedures given above. Applications of spray compositions were made 15 days after planting ABUTH, 9 days after planting ECHCF and 22 days after planting SIDSP. Evaluation of herbicidal inhibition was done 10 days after application.

Standards included technical acifluorfen sodium and Blazer, a commercial formulation of acifluorfen from Rohm & Haas. Results, averaged for all replicates of each treatment, are shown in Table 57.

TABLE 57

| Spray composition | Acifluorfen rate g a.i./ha | % Inhibition ABUTH | ECHCF | SIDSP |
| --- | --- | --- | --- | --- |
| Acifluorfen | 25 | 20 | 2 | 15 |
| (technical) | 50 | 32 | 7 | 17 |
|  | 100 | 52 | 18 | 35 |
|  | 200 | 62 | 35 | 40 |
| Blazer | 25 | 30 | 30 | 5 |
| (commercial) | 50 | 53 | 53 | 12 |

TABLE 57-continued

| Spray composition | Acifluorfen rate g a.i./ha | % Inhibition ABUTH | ECHCF | SIDSP |
|---|---|---|---|---|
| | 100 | 55 | 55 | 7 |
| | 200 | 65 | 65 | 32 |
| 57-01 | 25 | 60 | 7 | 20 |
| | 50 | 63 | 20 | 20 |
| | 100 | 65 | 43 | 33 |
| | 200 | 80 | 70 | 48 |
| 57-02 | 25 | 25 | 7 | 5 |
| | 50 | 42 | 12 | 25 |
| | 100 | 60 | 30 | 22 |
| | 200 | 68 | 68 | 50 |
| 57-03 | 25 | 22 | 5 | 10 |
| | 50 | 55 | 7 | 33 |
| | 100 | 62 | 25 | 27 |
| | 200 | 65 | 55 | 48 |
| 57-04 | 25 | 57 | 7 | 13 |
| | 50 | 67 | 10 | 32 |
| | 100 | 67 | 35 | 32 |
| | 200 | 70 | 70 | 45 |
| 57-05 | 25 | 30 | 3 | 15 |
| | 50 | 47 | 27 | 27 |
| | 100 | 55 | 42 | 37 |
| | 200 | 65 | 60 | 38 |
| 57-06 | 25 | 28 | 0 | 3 |
| | 50 | 50 | 0 | 10 |
| | 100 | 55 | 30 | 25 |
| | 200 | 67 | 58 | 47 |
| 57-07 | 25 | 35 | 20 | 17 |
| | 50 | 55 | 35 | 27 |
| | 100 | 58 | 63 | 32 |
| | 200 | 67 | 67 | 55 |
| 57-08 | 25 | 40 | 20 | 8 |
| | 50 | 57 | 30 | 28 |
| | 100 | 60 | 60 | 30 |
| | 200 | 70 | 77 | 48 |
| 57-09 | 25 | 47 | 20 | 22 |
| | 50 | 55 | 35 | 35 |
| | 100 | 62 | 65 | 38 |
| | 200 | 68 | 82 | 50 |
| 57-10 | 25 | 28 | 0 | 5 |
| | 50 | 48 | 0 | 10 |
| | 100 | 53 | 5 | 25 |
| | 200 | 62 | 35 | 40 |
| 57-11 | 25 | 35 | 0 | 5 |
| | 50 | 43 | 0 | 30 |
| | 100 | 50 | 0 | 35 |
| | 200 | 65 | 43 | 47 |
| 57-12 | 25 | 40 | 5 | 5 |
| | 50 | 55 | 18 | 35 |
| | 100 | 60 | 47 | 38 |
| | 200 | 70 | 62 | 48 |

Results of this test using acifluorfen as the exogenous chemical are summarized as follows:

At the low concentration of 0.05% used here, soybean lecithin containing 45% phospholipid (57-03) gave effectiveness similar to that obtained with the lecithin-based adjuvant LI-700 (57-06) widely used in the art.

Fluorad FC-754, either alone (57-04) or in combination with lecithin (57-01) gave effectiveness on ABUTH and SIDSP superior to that obtained with the commercial standard.

EXAMPLE 58

Spray compositions were prepared containing asulam and excipient ingredients. Compositions 58-01 to 58-12 were exactly like compositions 55-01 to 55-12 respectively except that a different active ingredient was used and a range of active ingredient concentrations was selected appropriate to the active ingredient being applied.

Velvetleaf (*Abutilon theophrasti*, ABUTH), Japanese millet (*Echinochloa crus-galli*, ECHCF) and prickly sida (*Spida spinosa*, SIDSP) plants were grown and treated by the standard procedures given above. Applications of spray compositions were made 14 days after planting ABUTH, 11 days after planting ECHCF and 21 days after planting SIDSP. Evaluation of herbicidal inhibition was done 14 days after application.

Standards included technical asulam and Asulox, a commercial formulation of asulam from Rhône-Poulenc. Results, averaged for all replicates of each treatment, are shown in Table 58.

TABLE 58

| Spray composition | Asulam rate g a.i./ha | % Inhibition ABUTH | ECHCF | SIDSP |
|---|---|---|---|---|
| Asulam (technical) | 200 | 0 | 12 | 0 |
| | 400 | 17 | 27 | 5 |
| | 800 | 48 | 32 | 20 |
| | 1400 | 42 | 50 | 37 |
| Asulox (commercial) | 200 | 3 | 5 | 0 |
| | 400 | 27 | 30 | 20 |
| | 800 | 52 | 45 | 25 |
| | 1400 | 50 | 60 | 40 |
| 58-01 | 200 | 5 | 8 | 13 |
| | 400 | 23 | 45 | 22 |
| | 800 | 50 | 50 | 30 |
| | 1400 | 60 | 65 | 48 |
| 58-02 | 200 | 0 | 20 | 17 |
| | 400 | 33 | 40 | 20 |
| | 800 | 47 | 48 | 33 |
| | 1400 | 53 | 68 | 55 |
| 58-03 | 200 | 3 | 20 | 3 |
| | 400 | 28 | 52 | 7 |
| | 800 | 50 | 50 | 23 |
| | 1400 | 50 | 58 | 43 |
| 58-04 | 200 | 3 | 40 | 7 |
| | 400 | 35 | 45 | 18 |
| | 800 | 52 | 50 | 25 |
| | 1400 | 58 | 60 | 42 |
| 58-05 | 200 | 0 | 10 | 3 |
| | 400 | 23 | 30 | 18 |
| | 800 | 33 | 50 | 32 |
| | 1400 | 45 | 57 | 38 |
| 58-06 | 200 | 2 | 30 | 10 |
| | 400 | 8 | 47 | 17 |
| | 800 | 50 | 55 | 28 |
| | 1400 | 52 | 63 | 40 |
| 58-07 | 200 | 0 | 43 | 3 |
| | 400 | 22 | 48 | 17 |
| | 800 | 40 | 55 | 28 |
| | 1400 | 52 | 60 | 33 |
| 58-08 | 200 | 7 | 47 | 22 |
| | 400 | 20 | 48 | 22 |
| | 800 | 53 | 55 | 30 |
| | 1400 | 57 | 60 | 33 |
| 58-09 | 200 | 0 | 45 | 7 |
| | 400 | 25 | 50 | 7 |
| | 800 | 53 | 60 | 32 |
| | 1400 | 55 | 63 | 37 |
| 58-10 | 200 | 22 | 37 | 10 |
| | 400 | 27 | 45 | 10 |
| | 800 | 50 | 43 | 23 |
| | 1400 | 52 | 52 | 27 |
| 58-11 | 200 | 25 | 33 | 5 |
| | 400 | 15 | 37 | 13 |
| | 800 | 48 | 42 | 25 |
| | 1400 | 42 | 52 | 28 |
| 58-12 | 200 | 3 | 25 | 17 |
| | 400 | 13 | 42 | 18 |
| | 800 | 50 | 45 | 30 |
| | 1400 | 52 | 50 | 33 |

Results of this test using asulam as the exogenous chemical are summarized as follows:

At the low concentration of 0.05% used here, soybean lecithin containing 45% phospholipid (58-03) gave similar enhancement to that obtained with the lecithin-based adjuvant LI-700 (58-06) widely used in the art.

Fluorad FC-754, either alone (58-04) or in combination with lecithin (58-01) gave effectiveness equal to that obtained with the commercial standard.

EXAMPLE 59

Spray compositions were prepared containing dicamba sodium salt and excipient ingredients. Compositions 59-01 to 59-12 were exactly like compositions 55-01 to 55-12 respectively except that a different active ingredient was used and a range of active ingredient concentrations was selected appropriate to the active ingredient being applied.

Velvetleaf (*Abutilon theophrasti*, ABUTH), Japanese millet (*Echinochloa crus-galli*, ECHCF) and prickly sida (*Spida spinosa*, SIDSP) plants were grown and treated by the standard procedures given above. Applications of spray compositions were made 14 days after planting ABUTH, 8 days after planting ECHCF and 21 days after planting SIDSP. Evaluation of herbicidal inhibition was done 17 days after application.

Standards included technical dicamba sodium and Banvel, a commercial formulation of dicamba from Sandoz. Results, averaged for all replicates of each treatment, are shown in Table 59.

TABLE 59

| Spray composition | Dicamba rate g a.i./ha | % Inhibition ABUTH | ECHCF | SIDSP |
|---|---|---|---|---|
| Dicamba | 25 | 47 | 0 | 30 |
| (technical) | 50 | 63 | 0 | 40 |
|  | 100 | 82 | 0 | 50 |
|  | 200 | 93 | 5 | 58 |
| Banvel | 25 | 47 | 0 | 35 |
| (commercial) | 50 | 68 | 0 | 40 |
|  | 100 | 91 | 0 | 53 |
|  | 200 | 93 | 3 | 63 |
| 59-01 | 25 | 42 | 0 | 38 |
|  | 50 | 67 | 0 | 48 |
|  | 100 | 92 | 0 | 67 |
|  | 200 | 93 | 3 | 73 |
| 59-02 | 25 | 43 | 0 | 43 |
|  | 50 | 58 | 0 | 50 |
|  | 100 | 85 | 0 | 62 |
|  | 200 | 89 | 8 | 72 |
| 59-03 | 25 | 50 | 0 | 32 |
|  | 50 | 65 | 0 | 45 |
|  | 100 | 90 | 0 | 60 |
|  | 200 | 94 | 13 | 68 |
| 59-04 | 25 | 43 | 0 | 35 |
|  | 50 | 65 | 0 | 42 |
|  | 100 | 94 | 0 | 53 |
|  | 200 | 94 | 13 | 67 |
| 59-05 | 25 | 50 | 0 | 35 |
|  | 50 | 68 | 0 | 40 |
|  | 100 | 88 | 0 | 53 |
|  | 200 | 92 | 15 | 60 |
| 59-06 | 25 | 40 | 0 | 40 |
|  | 50 | 65 | 0 | 45 |
|  | 100 | 88 | 0 | 52 |
|  | 200 | 92 | 8 | 70 |
| 59-07 | 25 | 45 | 0 | 42 |
|  | 50 | 57 | 0 | 45 |
|  | 100 | 88 | 0 | 62 |
|  | 200 | 88 | 20 | 68 |
| 59-08 | 25 | 40 | 0 | 38 |
|  | 50 | 62 | 0 | 45 |
|  | 100 | 97 | 18 | 62 |
|  | 200 | 93 | 17 | 73 |
| 59-09 | 25 | 33 | 0 | 35 |
|  | 50 | 60 | 0 | 45 |
|  | 100 | 93 | 0 | 63 |
|  | 200 | 96 | 15 | 73 |
| 59-10 | 25 | 35 | 0 | 30 |

TABLE 59-continued

| Spray composition | Dicamba rate g a.i./ha | % Inhibition ABUTH | ECHCF | SIDSP |
|---|---|---|---|---|
|  | 50 | 57 | 0 | 43 |
|  | 100 | 90 | 0 | 50 |
|  | 200 | 90 | 3 | 70 |
| 59-11 | 25 | 45 | 0 | 30 |
|  | 50 | 53 | 0 | 42 |
|  | 100 | 89 | 0 | 55 |
|  | 200 | 92 | 0 | 73 |
| 59-12 | 25 | 38 | 0 | 37 |
|  | 50 | 60 | 0 | 45 |
|  | 100 | 96 | 0 | 52 |
|  | 200 | 93 | 0 | 70 |

Results of this test using dicamba as the exogenous chemical are summarized as follows:

At the low concentration of 0.05% used here, soybean lecithin containing 45% phospholipid (59-03) gave similar enhancement of effectiveness to that obtained with the lecithin-based adjuvant LI-700 (59-06) widely used in the art.

Fluorad FC-754 (59-04) provided effectiveness similar to that obtained with the commercial standard. Further enhancement on SIDSP was obtained with the combination of Fluorad FC-754 and lecithin (59-01).

EXAMPLE 60

Spray compositions were prepared containing metsulfuron-methyl and excipient ingredients. Compositions 60-01 to 60-12 were exactly like compositions 55-01 to 55-12 respectively except that a different active ingredient was used and a range of active ingredient concentrations was selected appropriate to the active ingredient being applied.

Velvetleaf (*Abutilon theophrasti*, ABUTH), Japanese millet (*Echinochloa crus-galli*, ECHCF) and prickly sida (*Spida spinosa*, SIDSP) plants were grown and treated by the standard procedures given above. Applications of spray compositions were made 14 days after planting ABUTH, 8 days after planting ECHCF and 21 days after planting SIDSP. Evaluation of herbicidal inhibition was done 14 days after application.

Standards included technical metsulfuron-methyl and Ally, a commercial formulation of metsulfuron from Du Pont. Results, averaged for all replicates of each treatment, are shown in Table 60.

TABLE 60

| Spray composition | Metsulfuron rate g a.i./ha | % Inhibition ABUTH | ECHCF | SIDSP |
|---|---|---|---|---|
| Metsulfuron | 0.5 | 72 | 0 | 5 |
| (technical) | 1 | 90 | 0 | 23 |
|  | 5 | 96 | 0 | 50 |
|  | 10 | 97 | 30 | 55 |
| Ally | 0.5 | 75 | 0 | 5 |
| (commercial) | 1 | 85 | 0 | 22 |
|  | 5 | 95 | 0 | 42 |
|  | 10 | 97 | 25 | 53 |
| 60-01 | 0.5 | 95 | 0 | 47 |
|  | 1 | 96 | 20 | 53 |
|  | 5 | 97 | 25 | 62 |
|  | 10 | 98 | 45 | 62 |
| 60-02 | 0.5 | 87 | 0 | 40 |
|  | 1 | 90 | 10 | 55 |

TABLE 60-continued

| Spray composition | Metsulfuron rate g a.i./ha | % Inhibition ABUTH | ECHCF | SIDSP |
|---|---|---|---|---|
| | 5 | 95 | 10 | 58 |
| | 10 | 96 | 40 | 63 |
| 60-03 | 0.5 | 87 | 0 | 27 |
| | 1 | 90 | 0 | 40 |
| | 5 | 96 | 10 | 57 |
| | 10 | 97 | 33 | 63 |
| 60-04 | 0.5 | 90 | 0 | 33 |
| | 1 | 95 | 10 | 50 |
| | 5 | 98 | 17 | 62 |
| | 10 | 99 | 28 | 58 |
| 60-05 | 0.5 | 85 | 0 | 27 |
| | 1 | 90 | 0 | 33 |
| | 5 | 95 | 0 | 47 |
| | 10 | 95 | 13 | 60 |
| 60-06 | 0.5 | 77 | 0 | 30 |
| | 1 | 89 | 10 | 47 |
| | 5 | 96 | 17 | 62 |
| | 10 | 98 | 33 | 60 |
| 60-07 | 0.5 | 94 | 0 | 55 |
| | 1 | 97 | 10 | 60 |
| | 5 | 98 | 43 | 60 |
| | 10 | 97 | 55 | 65 |
| 60-08 | 0.5 | 93 | 0 | 55 |
| | 1 | 96 | 5 | 58 |
| | 5 | 97 | 42 | 60 |
| | 10 | 97 | 50 | 60 |
| 60-09 | 0.5 | 93 | 0 | 55 |
| | 1 | 97 | 10 | 62 |
| | 5 | 98 | 55 | 62 |
| | 10 | 98 | 65 | 63 |
| 60-10 | 0.5 | 85 | 0 | 28 |
| | 1 | 82 | 0 | 30 |
| | 5 | 95 | 10 | 52 |
| | 10 | 96 | 17 | 57 |
| 60-11 | 0.5 | 73 | 0 | 25 |
| | 1 | 88 | 20 | 28 |
| | 5 | 94 | 25 | 53 |
| | 10 | 96 | 32 | 57 |
| 60-12 | 0.5 | 75 | 0 | 32 |
| | 1 | 85 | 20 | 37 |
| | 5 | 94 | 23 | 55 |
| | 10 | 96 | 25 | 57 |

Results of this test using metsulfuron as the exogenous chemical are summarized as follows:

At the low concentration of 0.05% used here, soybean lecithin containing 45% phospholipid (60-03) was a slightly more effective excipient than the lecithin-based adjuvant LI-700 (60-06) widely used in the art in improving perfromance on ABUTH at the lowest exogenous chemical rate tested.

Fluorad FC-754, either alone (60-04) or in combination with lecithin (60-01) gave high effectiveness, superior to that obtained with the commercial standard.

EXAMPLE 61

Spray compositions were prepared containing imazethapyr and excipient ingredients. Compositions 61-01 to 61-12 were exactly like compositions 55-01 to 55-12 respectively except that a different active ingredient was used and a range of active ingredient concentrations was selected appropriate to the active ingredient being applied.

Velvetleaf (*Abutilon theophrasti,* ABUTH), Japanese millet (*Echinochloa crus-galli,* ECHCF) and prickly sida (*Spida spinosa,* SIDSP) plants were grown and treated by the standard procedures given above. Applications of spray compositions were made 14 days after planting ABUTH, 14 days after planting ECHCF and 21 days after planting SIDSP. Evaluation of herbicidal inhibition was done 14 days after application.

Standards included technical imazethapyr and Pursuit, a commercial formulation of imazethapyr from American Cyanamid. Results, averaged for all replicates of each treatment, are shown in Table 61.

TABLE 61

| Spray composition | Imazethapyr rate g a.i./ha | % Inhibition ABUTH | ECHCF | SIDSP |
|---|---|---|---|---|
| Imazethapyr (technical) | 5 | 78 | 5 | 20 |
| | 10 | 83 | 20 | 30 |
| | 25 | 93 | 35 | 40 |
| | 50 | 94 | 53 | 50 |
| Pursuit (commercial) | 5 | 70 | 5 | 25 |
| | 10 | 73 | 33 | 30 |
| | 25 | 90 | 50 | 42 |
| | 50 | 93 | 62 | 57 |
| 61-01 | 5 | 70 | 45 | 35 |
| | 10 | 75 | 62 | 52 |
| | 25 | 92 | 63 | 57 |
| | 50 | 93 | 72 | 62 |
| 61-02 | 5 | 73 | 57 | 32 |
| | 10 | 75 | 67 | 43 |
| | 25 | 90 | 70 | 52 |
| | 50 | 92 | 72 | 57 |
| 61-03 | 5 | 70 | 42 | 27 |
| | 10 | 78 | 42 | 35 |
| | 25 | 90 | 53 | 45 |
| | 50 | 92 | 62 | 52 |
| 61-04 | 5 | 73 | 55 | 33 |
| | 10 | 77 | 68 | 45 |
| | 25 | 93 | 68 | 47 |
| | 50 | 94 | 68 | 60 |
| 61-05 | 5 | 73 | 47 | 32 |
| | 10 | 73 | 45 | 40 |
| | 25 | 90 | 62 | 47 |
| | 50 | 91 | 68 | 52 |
| 61-06 | 5 | 78 | 72 | 30 |
| | 10 | 83 | 70 | 35 |
| | 25 | 93 | 77 | 62 |
| | 50 | 94 | 78 | 58 |
| 61-07 | 5 | 82 | 75 | 38 |
| | 10 | 90 | 90 | 52 |
| | 25 | 93 | 93 | 53 |
| | 50 | 97 | 97 | 62 |
| 61-08 | 5 | 75 | 77 | 38 |
| | 10 | 90 | 92 | 50 |
| | 25 | 95 | 93 | 57 |
| | 50 | 97 | 99 | 63 |
| 61-09 | 5 | 78 | 80 | 40 |
| | 10 | 83 | 89 | 63 |
| | 25 | 93 | 93 | 62 |
| | 50 | 96 | 93 | 60 |
| 61-10 | 5 | 85 | 50 | 37 |
| | 10 | 77 | 50 | 45 |
| | 25 | 91 | 63 | 48 |
| | 50 | 93 | 75 | 57 |
| 61-11 | 5 | 75 | 38 | 43 |
| | 10 | 80 | 38 | 37 |
| | 25 | 92 | 62 | 45 |
| | 50 | 93 | 73 | 53 |
| 61-12 | 5 | 75 | 55 | 38 |
| | 10 | 83 | 60 | 43 |
| | 25 | 92 | 67 | 53 |
| | 50 | 93 | 77 | 55 |

Results of this test using imazethapyr as the exogenous chemical are summarized as follows:

At the low concentration of 0.05% used here, soybean lecithin containing 45% phospholipid (61-03) was a less effective excipient than the lecithin-based adjuvant LI-700 (61-06).

Fluorad FC-754 (61-04) gave effectiveness on ECHCF superior to that obtained with the commercial standard. The combination of Fluorad FC-754 and lecithin (61-01) provided slight further enhancement of effectiveness on SIDSP.

EXAMPLE 62

Spray compositions were prepared containing fluazifop-p-butyl and excipient ingredients. Compositions 62-01 to 62-12 were exactly like compositions 55-01 to 55-12 respectively except that a different active ingredient was used and a range of active ingredient concentrations was selected appropriate to the active ingredient being applied.

Velvetleaf (*Abutilon theophrasti*, ABUTH), Japanese millet (*Echinochloa crus-galli*, ECHCF) and broadleaf signalgrass (*Brachiaria platyphylla*, BRAPP) plants were grown and treated by the standard procedures given above. Applications of spray compositions were made 15 days after planting ABUTH, 15 days after planting ECHCF and 16 days after planting BRAPP. Evaluation of herbicidal inhibition was done 10 days after application.

Standards included technical fluazifop-p-butyl and Fusilade 5, a commercial formulation of fluazifop-p-butyl from Zeneca. Results, averaged for all replicates of each treatment, are shown in Table 62.

TABLE 62

| Spray composition | Fluazifop-p rate g a.i./ha | % Inhibition ABUTH | ECHCF | BRAPP |
|---|---|---|---|---|
| Fluazifop-p butyl | 2 | 0 | 0 | 20 |
| (technical) | 5 | 0 | 3 | 35 |
|  | 15 | 5 | 45 | 65 |
|  | 30 | 5 | 57 | 78 |
| Fusilade 5 | 2 | 0 | 0 | 27 |
| (commercial) | 5 | 0 | 27 | 33 |
|  | 15 | 5 | 52 | 78 |
|  | 30 | 7 | 75 | 85 |
| 62-01 | 2 | 0 | 0 | 20 |
|  | 5 | 2 | 27 | 30 |
|  | 15 | 5 | 58 | 78 |
|  | 30 | 10 | 87 | 83 |
| 62-02 | 2 | 0 | 7 | 25 |
|  | 5 | 0 | 35 | 30 |
|  | 15 | 2 | 58 | 75 |
|  | 30 | 8 | 78 | 75 |
| 62-03 | 2 | 0 | 0 | 18 |
|  | 5 | 0 | 8 | 27 |
|  | 15 | 0 | 45 | 75 |
|  | 30 | 0 | 55 | 75 |
| 62-04 | 2 | 0 | 20 | 32 |
|  | 5 | 2 | 42 | 25 |
|  | 15 | 2 | 55 | 72 |
|  | 30 | 5 | 80 | 78 |
| 62-05 | 2 | 0 | 13 | 32 |
|  | 5 | 2 | 42 | 32 |
|  | 15 | 2 | 55 | 72 |
|  | 30 | 7 | 58 | 73 |
| 62-06 | 2 | 2 | 17 | 23 |
|  | 5 | 0 | 20 | 25 |
|  | 15 | 0 | 50 | 75 |
|  | 30 | 0 | 73 | 77 |
| 62-07 | 2 | 0 | 50 | 40 |
|  | 5 | 0 | 52 | 60 |
|  | 15 | 0 | 67 | 80 |
|  | 30 | 0 | 92 | 85 |
| 62-08 | 2 | 0 | 43 | 35 |
|  | 5 | 0 | 55 | 37 |
|  | 15 | 7 | 88 | 82 |
|  | 30 | 3 | 96 | 85 |
| 62-09 | 2 | 0 | 47 | 18 |
|  | 5 | 0 | 50 | 35 |
|  | 15 | 0 | 80 | 80 |
|  | 30 | 3 | 93 | 85 |
| 62-10 | 2 | 0 | 23 | 10 |
|  | 5 | 0 | 37 | 42 |
|  | 15 | 5 | 55 | 75 |
|  | 30 | 10 | 58 | 80 |
| 62-11 | 2 | 0 | 7 | 10 |
|  | 5 | 0 | 30 | 28 |
|  | 15 | 0 | 50 | 62 |

TABLE 62-continued

| Spray composition | Fluazifop-p rate g a.i./ha | % Inhibition ABUTH | ECHCF | BRAPP |
|---|---|---|---|---|
|  | 30 | 12 | 53 | 68 |
| 62-12 | 2 | 0 | 5 | 20 |
|  | 5 | 0 | 7 | 35 |
|  | 15 | 5 | 48 | 68 |
|  | 30 | 12 | 60 | 77 |

Results of this test using fluazifop-p-butyl as the exogenous chemical are summarized as follows:

At the low concentration of 0.05% used here, soybean lecithin containing 45% phospholipid (62-03) was a less effective excipient on ECHCF than the lecithin-based adjuvant LI-700 (62-06).

Fluorad FC-754, either alone (62-04) or in combination with lecithin (62-01) gave effectiveness equal or superior to that obtained with the commercial standard.

EXAMPLE 63

Spray compositions were prepared containing alachlor and excipient ingredients. Compositions 63-01 to 63-12 were exactly like compositions 55-01 to 55-12 respectively except that a different active ingredient was used and a range of active ingredient concentrations was selected appropriate to the active ingredient being applied.

Velvetleaf (*Abutilon theophrasti*, ABUTH), Japanese millet (*Echinochloa crus-galli*, ECHCF) and prickly sida (*Spida spinosa*, SIDSP) plants were grown and treated by the standard procedures given above. Applications of spray compositions were made 14 days after planting ABUTH, 8 days after planting ECHCF and 14 days after planting SIDSP. Evaluation of herbicidal inhibition was done 9 days after application.

Standards included technical alachlor and Lasso, a commercial formulation of alachlor from Monsanto Company. Results, averaged for all replicates of each treatment, are shown in Table 63.

TABLE 63

| Spray composition | Alachlor rate g a.i./ha | % Inhibition ABUTH | ECHCF | SIDSP |
|---|---|---|---|---|
| Alachlor | 500 | 0 | 0 | 0 |
| (technical) | 1000 | 0 | 0 | 0 |
|  | 2000 | 0 | 0 | 0 |
|  | 4000 | 0 | 0 | 0 |
| Lasso | 500 | 0 | 0 | 0 |
| (commercial) | 1000 | 0 | 5 | 13 |
|  | 2000 | 0 | 30 | 17 |
|  | 4000 | 15 | 43 | 65 |
| 63-01 | 500 | 0 | 0 | 0 |
|  | 1000 | 0 | 0 | 0 |
|  | 2000 | 0 | 0 | 0 |
|  | 4000 | 10 | 0 | 7 |
| 63-02 | 500 | 0 | 0 | 0 |
|  | 1000 | 0 | 0 | 0 |
|  | 2000 | 0 | 22 | 7 |
|  | 4000 | 12 | 47 | 12 |
| 63-03 | 500 | 0 | 0 | 0 |
|  | 1000 | 0 | 0 | 0 |
|  | 2000 | 0 | 0 | 0 |
|  | 4000 | 10 | 0 | 0 |
| 63-04 | 500 | 0 | 0 | 0 |
|  | 1000 | 0 | 0 | 0 |
|  | 2000 | 0 | 0 | 0 |
|  | 4000 | 5 | 0 | 15 |

TABLE 63-continued

| Spray composition | Alachlor rate g a.i./ha | % Inhibition ABUTH | ECHCF | SIDSP |
|---|---|---|---|---|
| 63-05 | 500 | 0 | 0 | 0 |
|  | 1000 | 0 | 0 | 0 |
|  | 2000 | 0 | 0 | 0 |
|  | 4000 | 3 | 0 | 5 |
| 63-06 | 500 | 0 | 0 | 0 |
|  | 1000 | 0 | 0 | 0 |
|  | 2000 | 0 | 13 | 7 |
|  | 4000 | 0 | 37 | 12 |
| 63-07 | 500 | 0 | 0 | 0 |
|  | 1000 | 0 | 8 | 0 |
|  | 2000 | 0 | 28 | 15 |
|  | 4000 | 12 | 50 | 20 |
| 63-08 | 500 | 0 | 0 | 0 |
|  | 1000 | 0 | 8 | 0 |
|  | 2000 | 0 | 8 | 0 |
|  | 4000 | 5 | 20 | 5 |
| 63-09 | 500 | 0 | 0 | 0 |
|  | 1000 | 0 | 0 | 0 |
|  | 2000 | 0 | 3 | 0 |
|  | 4000 | 12 | 42 | 32 |
| 63-10 | 500 | 0 | 0 | 0 |
|  | 1000 | 0 | 0 | 0 |
|  | 2000 | 0 | 0 | 0 |
|  | 4000 | 0 | 0 | 0 |
| 63-11 | 500 | 0 | 0 | 0 |
|  | 1000 | 0 | 0 | 0 |
|  | 2000 | 0 | 0 | 0 |
|  | 4000 | 0 | 0 | 0 |
| 63-12 | 500 | 0 | 0 | 0 |
|  | 1000 | 0 | 0 | 0 |
|  | 2000 | 0 | 0 | 0 |
|  | 4000 | 0 | 0 | 0 |

None of the compositions tested enhanced post-emergence foliar-applied herbicidal effectiveness of alachlor in this test. Alachlor is not known as a foliar-applied herbicide.

EXAMPLE 64

Spray compositions were prepared containing glufosinate ammonium salt and excipient ingredients. Compositions 64-01 to 64-12 were exactly like compositions 55-01 to 55-12 respectively except that a different active ingredient was used and a range of active ingredient concentrations was selected appropriate to the active ingredient being applied.

Velvetleaf (*Abutilon theophrasti*, ABUTH), Japanese millet (*Echinochloa crus-galli*, ECHCF) and prickly sida (*Spida spinosa*, SIDSP) plants were grown and treated by the standard procedures given above. Applications of spray compositions were made 14 days after planting ABUTH, 10 days after planting ECHCF and 17 days after planting SIDSP. Evaluation of herbicidal inhibition was done 11 days after application.

Standards included technical glufosinate ammonium and Liberty, a commercial formulation of glufosinate from AgrEvo. Results, averaged for all replicates of each treatment, are shown in Table 64.

TABLE 64

| Spray composition | Glufosinate rate g a.i./ha | % Inhibition ABUTH | ECHCF | SIDSP |
|---|---|---|---|---|
| Glufosinate (technical) | 50 | 0 | 0 | 5 |
|  | 100 | 47 | 0 | 10 |
|  | 300 | 90 | 23 | 96 |

TABLE 64-continued

| Spray composition | Glufosinate rate g a.i./ha | % Inhibition ABUTH | ECHCF | SIDSP |
|---|---|---|---|---|
|  | 600 | 98 | 43 | 94 |
| Liberty | 50 | 77 | 70 | 20 |
| (commercial) | 100 | 88 | 96 | 93 |
|  | 300 | 98 | 100 | 97 |
|  | 600 | 99 | 100 | 99 |
| 64-01 | 50 | 77 | 33 | 70 |
|  | 100 | 95 | 58 | 93 |
|  | 300 | 98 | 95 | 97 |
|  | 600 | 99 | 99 | 98 |
| 64-02 | 50 | 33 | 30 | 50 |
|  | 100 | 63 | 32 | 93 |
|  | 300 | 96 | 52 | 90 |
|  | 600 | 98 | 96 | 97 |
| 64-03 | 50 | 15 | 30 | 38 |
|  | 100 | 50 | 33 | 87 |
|  | 300 | 92 | 40 | 94 |
|  | 600 | 98 | 70 | 98 |
| 64-04 | 50 | 92 | 47 | 50 |
|  | 100 | 90 | 53 | 85 |
|  | 300 | 98 | 98 | 96 |
|  | 600 | 98 | 99 | 98 |
| 64-05 | 50 | 35 | 20 | 20 |
|  | 100 | 37 | 30 | 20 |
|  | 300 | 97 | 45 | 78 |
|  | 600 | 91 | 53 | 92 |
| 64-06 | 50 | 10 | 0 | 20 |
|  | 100 | 20 | 3 | 20 |
|  | 300 | 89 | 47 | 82 |
|  | 600 | 91 | 94 | 89 |
| 64-07 | 50 | 50 | 35 | 70 |
|  | 100 | 73 | 52 | 80 |
|  | 300 | 95 | 87 | 98 |
|  | 600 | 98 | 98 | 97 |
| 64-08 | 50 | 48 | 30 | 88 |
|  | 100 | 83 | 50 | 93 |
|  | 300 | 98 | 97 | 96 |
|  | 600 | 98 | 99 | 96 |
| 64-09 | 50 | 58 | 35 | 92 |
|  | 100 | 91 | 62 | 93 |
|  | 300 | 98 | 96 | 97 |
|  | 600 | 98 | 99 | 96 |
| 64-10 | 50 | 30 | 30 | 0 |
|  | 100 | 43 | 35 | 10 |
|  | 300 | 96 | 43 | 92 |
|  | 600 | 95 | 70 | 91 |
| 64-11 | 50 | 33 | 35 | 0 |
|  | 100 | 53 | 35 | 7 |
|  | 300 | 96 | 43 | 89 |
|  | 600 | 97 | 88 | 93 |
| 64-12 | 50 | 37 | 5 | 5 |
|  | 100 | 37 | 20 | 10 |
|  | 300 | 95 | 40 | 88 |
|  | 600 | 97 | 85 | 93 |

Results of this test using glufosinate as the exogenous chemical are summarized as follows:

At the low concentration of 0.05% used here, soybean lecithin containing 45% phospholipid (64-03) was a much more effective excipient than the lecithin-based adjuvant LI-700 (64-06) widely used in the art.

Fluorad FC-754, either alone (64-04) or in combination with lecithin (64-01) gave extremely high effectiveness, similar to that obtained with the commercial standard.

EXAMPLE 65

Aqueous concentrate compositions were prepared containing glyphosate IPA salt and excipient ingredients as shown in Table 65a. Process (v) was followed for compositions 65-01 to 65-07. Process (viii) was followed for composition 65-16. Process (x) was followed for compositions 65-08 to 65-15, 65-17 and 65-18. All lecithin-containing compositions were made using soybean lecithin (45% phospholipid, Avanti).

TABLE 65a

| Conc. comp. | Glyphosate g a.e./l | % w/w | | | | | | |
|---|---|---|---|---|---|---|---|---|
| | | Lecithin | Fluorad FC-754 | Butyl stearate | Ethomeen T/25 | Ceteareth-20 | Arcosolve DPM | Ceteareth-27 |
| 65-01 | 348 | 3.0 | 3.00 | | 0.75 | | | |
| 65-02 | 348 | 3.8 | 3.75 | | 5.00 | | | |
| 65-03 | 348 | 3.8 | 3.75 | | 7.50 | | | |
| 65-04 | 348 | 2.0 | 5.00 | | 0.75 | | | |
| 65-05 | 348 | 5.0 | 5.00 | | 0.75 | | | |
| 65-06 | 348 | 2.0 | 2.00 | | | | | |
| 65-07 | 348 | 1.0 | 1.00 | | | | | |
| 65-08 | 220 | 1.5 | | 1.5 | 3.00 | 3.0 | | |
| 65-09 | 220 | 1.5 | | 1.5 | 3.00 | | | 3.0 |
| 65-10 | 220 | 1.5 | | 1.5 | 6.00 | 3.0 | | |
| 65-11 | 220 | 1.5 | | 1.5 | 6.00 | | | 3.0 |
| 65-12 | 220 | 3.0 | | 1.5 | 3.00 | 3.0 | | |
| 65-13 | 220 | 3.0 | | 1.5 | 3.00 | | | 3.0 |
| 65-14 | 348 | 1.5 | | 1.5 | 6.00 | 3.0 | | |
| 65-15 | 348 | 3.0 | | 1.5 | 3.00 | 3.0 | | |
| 65-16 | 348 | | 3.00 | | | | | |
| 65-17 | 348 | 3.0 | | | | | 3.0 | |
| 65-18 | 348 | 5.0 | | | 13.00 | | 5.0 | |

Velvetleaf (*Abutilon theophrasti*, ABUTH) and Japanese millet (*Echinochloa crus-galli*, ECHCF) plants were grown and treated by the standard procedures given above. Applications of spray compositions were made 17 days after planting ABUTH and ECHCF, and evaluation of herbicidal inhibition was done 18 days after application.

Formulations B and J were applied as comparative treatments. Results, averaged for all replicates of each treatment, are shown in Table 65b.

TABLE 65b

| Concentrate composition | Glyphosate rate g a.e./ha | % Inhibition | |
|---|---|---|---|
| | | ABUTH | ECHCF |
| Formulation B | 100 | 28 | 32 |
| | 200 | 41 | 37 |
| | 300 | 73 | 64 |
| | 400 | 22 | 30 |
| Formulation J | 100 | 38 | 32 |
| | 200 | 82 | 73 |
| | 300 | 89 | 91 |
| | 400 | 97 | 89 |
| 65-01 | 100 | 73 | 28 |
| | 200 | 90 | 66 |
| | 300 | 97 | 92 |
| | 400 | 100 | 96 |
| 65-02 | 100 | 77 | 32 |
| | 200 | 87 | 67 |
| | 300 | 84 | 78 |
| | 400 | 98 | 84 |
| 65-03 | 100 | 79 | 33 |
| | 200 | 82 | 66 |
| | 300 | 99 | 81 |
| | 400 | 97 | 88 |
| 65-04 | 100 | 69 | 35 |
| | 200 | 95 | 59 |
| | 300 | 96 | 84 |
| | 400 | 92 | 91 |
| 65-05 | 100 | 82 | 32 |
| | 200 | 92 | 55 |
| | 300 | 96 | 71 |
| | 400 | 94 | 87 |
| 65-06 | 100 | 83 | 33 |
| | 200 | 100 | 52 |
| | 300 | 100 | 68 |
| | 400 | 99 | 75 |
| 65-07 | 100 | 77 | 35 |
| | 200 | 90 | 58 |
| | 300 | 95 | 71 |
| 65-08 | 400 | 94 | 90 |
| | 100 | 51 | 40 |
| | 200 | 89 | 75 |
| | 300 | 96 | 92 |
| | 400 | 95 | 98 |
| 65-09 | 100 | 76 | 57 |
| | 200 | 98 | 81 |
| | 300 | 97 | 86 |
| | 400 | 96 | 98 |
| 65-10 | 100 | 69 | 60 |
| | 200 | 98 | 63 |
| | 300 | 95 | 82 |
| | 400 | 99 | 90 |
| 65-11 | 100 | 61 | 60 |
| | 200 | 94 | 84 |
| | 300 | 97 | 89 |
| | 400 | 99 | 97 |
| 65-12 | 100 | 64 | 53 |
| | 200 | 95 | 82 |
| | 300 | 96 | 90 |
| | 400 | 95 | 98 |
| 65-13 | 100 | 61 | 58 |
| | 200 | 94 | 78 |
| | 300 | 88 | 87 |
| | 400 | 100 | 94 |
| 65-14 | 100 | 56 | 61 |
| | 200 | 88 | 77 |
| | 300 | 91 | 82 |
| | 400 | 97 | 89 |
| 65-15 | 100 | 42 | 52 |
| | 200 | 82 | 80 |
| | 300 | 86 | 90 |
| | 400 | 97 | 92 |
| 65-16 | 100 | 64 | 49 |
| | 200 | 86 | 75 |
| | 300 | 97 | 88 |
| | 400 | 100 | 82 |
| 65-17 | 100 | 57 | 32 |
| | 200 | 88 | 66 |
| | 300 | 95 | 73 |
| | 400 | 100 | 88 |
| 65-18 | 100 | 52 | 35 |
| | 200 | 70 | 77 |
| | 300 | 82 | 79 |
| | 400 | 97 | 73 |

Concentrate compositions 65-01 to 65-07, containing lecithin and Fluorad FC-754, exhibited outstanding herbicidal effectivness. On ABUTH, several of these were about as effective at 100 g a.e./ha as commercial standard Formulation J at 200 g a.e./ha. On ECHCF, all exhibited strong enhancement over Formulation B but most did not equal Formulation J on this species. The performance of composition 65-07, containing lecithin and Fluorad FC-754 each at the extremely low weight/weight ratio to glyphosate a.e. of about 1:30, was remarkably high. The inclusion of a relatively high concentration of Ethomeen T/25, as in compositions 65-02 and 65-03, was not helpful to herbicidal effectiveness in the presence of lecithin and Fluorad FC-754, and may even have been detrimental. The relatively poor performance of composition 65-18, having a high Ethomeen T/25 concentration but in this case no Fluorad FC-754, is consistent with this observation. Without being bound by theory, it is believed that the presence of such high concentrations of Ethomeen T/25 together with lecithin results in the formation of mixed micelles rather than liposomes in aqueous dispersion. Composition 65-16, containing Fluorad FC-754 at a weight/weight ratio to glyphosate a.e. of about 1:10, but no lecithin, exhibited herbicidal effectiveness similar to that of composition 65-01, suggesting that under the conditions of this test a large part of the enhancement due to the lecithin/Fluorad FC-754 combination was attributable to the Fluorad FC-754 component.

EXAMPLE 66

Aqueous spray compositions were prepared containing glyphosate IPA salt and excipient ingredients as shown in Table 66a. Process (i) was followed for compositions 66-61 to 66-64, 66-67, 66-69 and 66-71 and process (iii) for compositions 66-01 to 66-60, 66-66, 66-68, 66-70 and 66-72 using soybean lecithin (45% phospholipid, Avanti). The pH of all compositions was approximately 5.

TABLE 66a

| Spray composition | % w/w | | | | |
|---|---|---|---|---|---|
| | Lecithin | MON 0818 | Fluorad FC-754 | Ethomeen T/25 | Ethomeen C/12 |
| 66-01 | 0.020 | 0.025 | 0.02 | | |
| 66-02 | 0.030 | 0.025 | 0.02 | | |
| 66-03 | 0.050 | 0.025 | 0.02 | | |
| 66-04 | 0.020 | 0.025 | 0.03 | | |
| 66-05 | 0.030 | 0.025 | 0.03 | | |
| 66-06 | 0.050 | 0.025 | 0.03 | | |
| 66-07 | 0.020 | 0.025 | 0.04 | | |
| 66-08 | 0.030 | 0.025 | 0.04 | | |
| 66-09 | 0.050 | 0.025 | 0.04 | | |
| 66-10 | 0.020 | 0.025 | 0.05 | | |
| 66-11 | 0.030 | 0.025 | 0.05 | | |
| 66-12 | 0.050 | 0.025 | 0.05 | | |
| 66-13 | 0.020 | | 0.02 | | |
| 66-14 | 0.030 | | 0.02 | | |
| 66-15 | 0.050 | | 0.02 | | |
| 66-16 | 0.020 | | 0.03 | | |
| 66-17 | 0.030 | | 0.03 | | |
| 66-18 | 0.050 | | 0.03 | | |
| 66-19 | 0.020 | | 0.04 | | |
| 66-20 | 0.030 | | 0.04 | | |
| 66-21 | 0.050 | | 0.04 | | |
| 66-22 | 0.020 | | 0.05 | | |
| 66-23 | 0.030 | | 0.05 | | |
| 66-24 | 0.050 | | 0.05 | | |
| 66-25 | 0.020 | | 0.02 | 0.025 | |
| 66-26 | 0.030 | | 0.02 | 0.025 | |
| 66-27 | 0.050 | | 0.02 | 0.025 | |
| 66-28 | 0.020 | | 0.03 | 0.025 | |
| 66-29 | 0.030 | | 0.03 | 0.025 | |
| 66-30 | 0.050 | | 0.03 | 0.025 | |
| 66-31 | 0.020 | | 0.04 | 0.025 | |
| 66-32 | 0.030 | | 0.04 | 0.025 | |
| 66-33 | 0.050 | | 0.04 | 0.025 | |
| 66-34 | 0.020 | | 0.05 | 0.025 | |
| 66-35 | 0.030 | | 0.05 | 0.025 | |
| 66-36 | 0.050 | | 0.05 | 0.025 | |
| 66-37 | 0.020 | | 0.02 | | 0.025 |
| 66-38 | 0.030 | | 0.02 | | 0.025 |
| 66-39 | 0.050 | | 0.02 | | 0.025 |
| 66-40 | 0.020 | | 0.03 | | 0.025 |
| 66-41 | 0.030 | | 0.03 | | 0.025 |
| 66-42 | 0.050 | | 0.03 | | 0.025 |
| 66-43 | 0.020 | | 0.04 | | 0.025 |
| 66-44 | 0.030 | | 0.04 | | 0.025 |
| 66-45 | 0.050 | | 0.04 | | 0.025 |
| 66-46 | 0.020 | | 0.05 | | 0.025 |
| 66-47 | 0.030 | | 0.05 | | 0.025 |
| 66-48 | 0.050 | | 0.05 | | 0.025 |
| 66-49 | 0.020 | | 0.02 | 0.050 | |
| 66-50 | 0.025 | | 0.03 | 0.050 | |
| 66-51 | 0.050 | | 0.02 | 0.050 | |
| 66-52 | 0.020 | | 0.03 | 0.050 | |
| 66-53 | 0.030 | | 0.03 | 0.050 | |
| 66-54 | 0.050 | | 0.03 | 0.050 | |
| 66-55 | 0.020 | 0.050 | 0.02 | | |
| 66-56 | 0.025 | 0.050 | 0.03 | | |
| 66-57 | 0.050 | 0.050 | 0.02 | | |
| 66-58 | 0.020 | 0.050 | 0.03 | | |
| 66-59 | 0.030 | 0.050 | 0.03 | | |
| 66-60 | 0.050 | 0.050 | 0.03 | | |
| 66-61 | | 0.050 | | | |
| 66-62 | | | | 0.050 | |
| 66-63 | | | | | 0.025 |
| 66-64 | | 0.025 | | | |
| 66-65 | 0.050 | | 0.08 | 0.025 | |
| 66-66 | 0.025 | | 0.03 | | 0.025 |
| 66-67 | | | 0.05 | | |
| 66-68 | 0.050 | | | | |
| 66-69 | | | 0.05 | 0.050 | |
| 66-70 | 0.050 | | | 0.050 | |
| 66-71 | | 0.050 | 0.05 | | |
| 66-72 | 0.050 | 0.050 | | | |

Velvetleaf (*Abutilon theophrasti*, ABUTH) and Japanese millet (*Echinochloa crus-galli*, ECHCF) plants were grown and treated by the standard procedures given above. Applications of spray compositions were made 17 days after planting ABUTH and ECHCF, and evaluation of herbicidal inhibition was done 15 days after application.

Formulation J was applied as a comparative treatment. Results, averaged for all replicates of each treatment, are shown in Table 66b.

TABLE 66b

| Spray composition | Glyphosate rate g a.e./ha | % Inhibition | |
|---|---|---|---|
| | | ABUTH | ECHCF |
| Formulation J | 100 | 14 | 42 |
| | 187 | 44 | 87 |
| | 300 | 71 | 90 |
| | 400 | 92 | 97 |
| 66-01 | 187 | 80 | 80 |
| 66-02 | 187 | 80 | 97 |
| 66-03 | 187 | 79 | 94 |
| 66-04 | 187 | 79 | 91 |
| 66-05 | 187 | 81 | 80 |
| 66-06 | 187 | 73 | 88 |
| 66-07 | 187 | 86 | 90 |

TABLE 66b-continued

| Spray composition | Glyphosate rate g a.e./ha | % Inhibition ABUTH | % Inhibition ECHCF |
|---|---|---|---|
| 66-08 | 187 | 88 | 91 |
| 66-09 | 187 | 77 | 85 |
| 66-10 | 187 | 81 | 80 |
| 66-11 | 187 | 88 | 68 |
| 66-12 | 187 | 87 | 72 |
| 66-13 | 187 | 85 | 61 |
| 66-14 | 187 | 83 | 47 |
| 66-15 | 187 | 86 | 61 |
| 66-16 | 187 | 86 | 57 |
| 66-17 | 187 | 85 | 44 |
| 66-18 | 187 | 81 | 62 |
| 66-19 | 187 | 82 | 63 |
| 66-20 | 187 | 87 | 62 |
| 66-21 | 187 | 84 | 48 |
| 66-22 | 187 | 80 | 67 |
| 66-23 | 187 | 86 | 89 |
| 66-24 | 187 | 78 | 64 |
| 66-25 | 187 | 84 | 87 |
| 66-26 | 187 | 81 | 81 |
| 66-27 | 187 | 74 | 85 |
| 66-28 | 187 | 71 | 90 |
| 66-29 | 187 | 76 | 74 |
| 66-30 | 187 | 81 | 89 |
| 66-31 | 187 | 78 | 80 |
| 66-32 | 87 | 79 | 84 |
| 66-33 | 187 | 82 | 84 |
| 66-34 | 187 | 74 | 87 |
| 66-35 | 187 | 81 | 89 |
| 66-36 | 187 | 85 | 79 |
| 66-37 | 187 | 68 | 89 |
| 66-38 | 187 | 69 | 85 |
| 66-39 | 187 | 86 | 85 |
| 66-40 | 187 | 83 | 89 |
| 66-41 | 187 | 77 | 76 |
| 66-42 | 187 | 83 | 76 |
| 66-43 | 187 | 74 | 83 |
| 66-44 | 187 | 84 | 69 |
| 66-45 | 187 | 85 | 71 |
| 66-46 | 187 | 80 | 86 |
| 66-47 | 187 | 83 | 96 |
| 66-48 | 187 | 81 | 87 |
| 66-49 | 187 | 75 | 99 |
| 66-50 | 187 | 78 | 97 |
| 66-51 | 187 | 76 | 97 |
| 66-52 | 187 | 77 | 92 |
| 66-53 | 187 | 74 | 88 |
| 66-54 | 187 | 73 | 81 |
| 66-55 | 187 | 70 | 87 |
| 66-56 | 187 | 79 | 88 |
| 66-57 | 187 | 72 | 89 |
| 66-58 | 187 | 72 | 79 |
| 66-59 | 187 | 53 | 80 |
| 66-60 | 187 | 80 | 73 |
| 66-61 | 187 | 46 | 78 |
| 66-62 | 187 | 54 | 94 |
| 66-63 | 187 | 48 | 98 |
| 66-64 | 187 | 59 | 97 |
| 66-65 | 187 | 87 | 84 |
| 66-66 | 187 | 89 | 96 |
| 66-67 | 187 | 86 | 69 |
| 66-68 | 187 | 46 | 43 |
| 66-69 | 187 | 75 | 90 |
| 66-70 | 187 | 55 | 83 |
| 66-71 | 187 | 79 | 80 |
| 66-72 | 187 | 55 | 82 |

All compositions of this Example containing Fluorad FC-754 showed much greater herbicidal effectiveness on ABUTH at 187 g a.e./ha than did Formulation J at the same rate, in many cases giving inhibition of ABUTH equal to or greater than provided by Formulation J at 300 g a.e./ha. The only compositions of the Example not showing strong improvement over Formulation J on ABUTH were 66-61 to 66-64, 66-68, 66-70 and 66-72. These are the only formulations of the Example not containing Fluorad FC-754.

EXAMPLE 67

Aqueous spray compositions were prepared containing glyphosate IPA salt and excipient ingredients as shown in Table 67a. Process (i) was followed for compositions 67-02, 67-04, 67-06, 67-08, 67-10, 67-12, 67-14 and 67-16 to 67-18, and process (iii) for compositions 67-01, 67-03, 67-05, 67-07, 67-09, 67-11 and 67-13 using soybean lecithin (45% phospholipid, Avanti). The pH of all compositions was approximately 5.

TABLE 67a

| Spray composition | % w/w Lecithin | % w/w Surfactant | Type of surfactant |
|---|---|---|---|
| 67-01 | 0.05 | 0.05 | Surf H2 |
| 67-02 |  | 0.05 | Surf H2 |
| 67-03 | 0.05 | 0.05 | Surf H3 |
| 67-04 |  | 0.05 | Surf H3 |
| 67-05 | 0.05 | 0.05 | Surf H4 |
| 67-06 |  | 0.05 | Surf H4 |
| 67-07 | 0.05 | 0.05 | Surf H5 |
| 67-08 |  | 0.05 | Surf H5 |
| 67-09 | 0.05 | 0.05 | Fluorad FC-754 |
| 67-10 |  | 0.05 | Fluorad FC-754 |
| 67-11 | 0.05 | 0.05 | Surf H1 |
| 67-12 |  | 0.05 | Surf H1 |
| 67-13 | 0.05 | 0.05 | MON 0818 |
| 67-14 |  | 0.05 | MON 0818 |
| 67-15 | 0.05 | 0.05 | Ethomeen T/25 |
| 67-16 |  | 0.05 | Ethomeen T/25 |
| 67-17 |  | 0.10 | MON 0818 |
| 67-18 |  | 0.10 | Ethomeen T/25 |

Velvetleaf (*Abutilon theophrasti*, ABUTH) and Japanese millet (*Echinochloa crus-galli*, ECHCF) plants were grown and treated by the standard procedures given above. Applications of spray compositions were made 17 days after planting ABUTH and ECHCF, and evaluation of herbicidal inhibition was done 16 days after application.

Formulations B and J were applied as comparative treatments. Results, averaged for all replicates of each treatment, are shown in Table 67b.

TABLE 67b

| Spray composition | Glyphosate rate g a.e./ha | % Inhibition ABUTH | % Inhibition ECHCF |
|---|---|---|---|
| Formulation B | 100 | 12 | 22 |
|  | 200 | 43 | 43 |
|  | 300 | 63 | 78 |
|  | 400 | 75 | 82 |
| Formulation J | 100 | 47 | 27 |
|  | 200 | 89 | 83 |
|  | 300 | 98 | 98 |
|  | 400 | 99 | 97 |
| 67-01 | 100 | 65 | 60 |
|  | 200 | 94 | 84 |
|  | 300 | 99 | 97 |
|  | 400 | 100 | 98 |
| 67-02 | 100 | 40 | 45 |
|  | 200 | 77 | 75 |
|  | 300 | 91 | 90 |
|  | 400 | 94 | 98 |
| 67-03 | 100 | 63 | 37 |
|  | 200 | 82 | 82 |
|  | 300 | 97 | 99 |
|  | 400 | 99 | 97 |
| 67-04 | 100 | 52 | 38 |

TABLE 67b-continued

| Spray composition | Glyphosate rate g a.e./ha | % Inhibition ABUTH | % Inhibition ECHCF |
|---|---|---|---|
| | 200 | 79 | 73 |
| | 300 | 95 | 98 |
| | 400 | 99 | 97 |
| 67-05 | 100 | 73 | 68 |
| | 200 | 85 | 94 |
| | 300 | 98 | 99 |
| | 400 | 100 | 99 |
| 67-06 | 100 | 38 | 58 |
| | 200 | 73 | 92 |
| | 300 | 85 | 100 |
| | 400 | 100 | 98 |
| 67-07 | 100 | 50 | 43 |
| | 200 | 80 | 78 |
| | 300 | 94 | 86 |
| | 400 | 94 | 95 |
| 67-08 | 100 | 50 | 48 |
| | 200 | 75 | 62 |
| | 300 | 89 | 77 |
| | 400 | 90 | 79 |
| 67-09 | 100 | 91 | 47 |
| | 200 | 98 | 75 |
| | 300 | 99 | 97 |
| | 400 | 99 | 94 |
| 67-10 | 100 | 87 | 38 |
| | 200 | 89 | 73 |
| | 300 | 99 | 83 |
| | 400 | 100 | 94 |
| 67-11 | 100 | 77 | 73 |
| | 200 | 93 | 79 |
| | 300 | 98 | 96 |
| | 400 | 99 | 98 |
| 67-12 | 100 | 55 | 52 |
| | 200 | 82 | 89 |
| | 300 | 96 | 99 |
| | 400 | 99 | 100 |
| 67-13 | 100 | 75 | 63 |
| | 200 | 93 | 92 |
| | 300 | 98 | 99 |
| | 400 | 99 | 99 |
| 67-14 | 100 | 78 | 82 |
| | 200 | 88 | 86 |
| | 300 | 96 | 99 |
| | 400 | 99 | 100 |
| 67-15 | 100 | 77 | 68 |
| | 200 | 94 | 95 |
| | 300 | 98 | 97 |
| | 400 | 99 | 98 |
| 67-16 | 100 | 75 | 75 |
| | 200 | 88 | 99 |
| | 300 | 98 | 99 |
| | 400 | 99 | 100 |
| 67-17 | 100 | 72 | 77 |
| | 200 | 85 | 98 |
| | 300 | 98 | 100 |
| | 400 | 99 | 99 |
| 67-18 | 100 | 77 | 77 |
| | 200 | 90 | 96 |
| | 300 | 97 | 99 |
| | 400 | 99 | 100 |

Herbicidal activity with compositions 67-13 to 67-18, based on alkylamine based surfactants known in the art, was very high in this test. Compositions 67-01 to 67-12 of the present invention also exhibited excellent herbicidal effectiveness. Overall, surfactants "Surf H1" to "Surf H5" having hydrocarbon hydrophobes were not quite as effective as Fluorad FC-754 having a fluorocarbon hydrophobe, either when used as sole excipient substance or together with lecithin.

The preceding description of specific embodiments of the present invention is not intended to be a complete list of every possible embodiment of the invention. Persons skilled in this field will recognize that modifications can be made to the specific embodiments described here that would be within the scope of the present invention.

What is claimed is:

1. A plant treatment composition comprising:
   (a) an exogenous chemical,
   (b) a first excipient substance that is an amphiphilic quaternary ammonium compound or mixture of such compounds having the formula $$R^8-W_a-X-Y_b-(CH_2)_n-N^+(R^9)(R^{10})(R^{11})\ T^-$$

wherein $R^8$ is a hydrocarbyl or haloalkyl group having from about 6 to about 22 carbon atoms, W and Y are independently O or NH, a and b are independently 0 or 1 but at least one of a and b is 1, X is CO, SO or $SO_2$, n is 2 to 4, $R^9$, $R^{10}$ and $R^{11}$ are independently $C_{1-4}$ alkyl, and T is a suitable anion; and
   (c) a second excipient substance that is a liposome-forming substance in a liposome-forming amount.

2. The composition of claim 1 wherein the weight/weight ratio of the first excipient substance to the exogenous chemical is between about 1:3 and about 1:100.

3. The composition of claim 1, where $R^8$ is hydrocarbyl and has about 12 to about 18 carbon atoms.

4. The composition of claim 1, where $R^8$ is fluorinated.

5. The composition of claim 1, where $R^8$ is perfluorinated.

6. The composition of claim 5, where $R^8$ has about 6 to about 12 carbon atoms.

7. The composition of claim 1, where T is selected from the group consisting of hydroxide, chloride, bromide, iodide, sulfate, phosphate and acetate.

8. The composition of claim 1, where $R^8$ is saturated perfluoroalkyl having about 6 to about 12 carbon atoms, X is CO or $SO_2$, Y is NH, a is 0, b is 1, $R^9$, $R^{10}$ and $R^{11}$ are methyl, and T is selected from the group consisting of hydroxide, chloride, bromide, iodide, sulfate, phosphate and acetate.

9. The composition of claim 8, where X is $SO_2$, n is 3 and T is chloride, bromide or iodide.

10. The composition of claim 1 wherein the exogenous chemical is a foliar-applied exogenous chemical.

11. The composition of claim 10 wherein the exogenous chemical is a pesticide, gametocide or plant growth regulator.

12. The composition of claim 11 wherein the exogenous chemical is a herbicide, nematicide or plant growth regulator.

13. The composition of claim 12 wherein the exogenous chemical is a herbicide.

14. The composition of claim 13 wherein the herbicide is selected from the group consisting of acetanilides, bipyridyls, cyclohexenones, dinitroanilines, diphenylethers, fatty acids, hydroxybenzonitriles, imidazolinones, phenoxies, phenoxypropionates, substituted ureas, sulfonylureas, thiocarbamates and triazines.

15. The composition of claim 13 wherein the herbicide is selected from the group consisting of acetochlor, alachlor, metolachlor, aminotriazole, asulam, bentazon, bialaphos, diquat, paraquat, bromacil, clethodim, sethoxydim, dicamba, diflufenican, pendimethalin, acifluorfen, $C_{9-10}$ fatty acids, fomesafen, oxyfluorfen, fosamine, flupoxam, glufosinate, glyphosate, bromoxynil, imazaquin, imazethapyr, isoxaben, norflurazon, 2,4-D, diclofop, fluazifop, quizalofop, picloram, propanil, fluometuron, isoproturon, chlorimuron, chlorsulfuron, halosulfuron, metsulfuron, primisulfuron, sulfometuron, sulfosulfuron, triallate, atrazine, metribuzin, triclopyr and herbicidal derivatives thereof.

16. The composition of claim 15 wherein the herbicide is glyphosate or a herbicidal derivative thereof.

17. The composition of claim 16 wherein the herbicide is glyphosate in its acid form.

18. The composition of claim 12 wherein the exogenous chemical is water-soluble.

19. The composition of claim 18 wherein the exogenous chemical is a salt having an anion portion and a cation portion.

20. The composition of claim 19 wherein at least one of said anion and cation portions is biologically active and has a molecular weight of less than about 300.

21. The composition of claim 20 wherein the exogenous chemical is paraquat or diquat.

22. The composition of claim 20 wherein the exogenous chemical exhibits systemic biological activity in the plant.

23. The composition of claim 22 wherein the exogenous chemical has one or more functional groups selected from the group consisting of amine, amide, carboxylate, phosphonate and phosphinate groups.

24. The composition of claim 23 wherein the exogenous chemical is a salt of 3,4,4-trifluoro-3-butenoic acid or of N-(3,4,4-trifluoro-1-oxo-3-butenyl)glycine that exhibits nematicidal activity.

25. The composition of claim 23 wherein the exogenous chemical is a herbicidal or plant growth regulating compound having at least one of each of amine, carboxylate and either phosphonate or phosphinate functional groups.

26. The composition of claim 25 wherein the herbicidal or plant growth regulating compound is a salt of glufosinate.

27. The composition of claim 26 wherein the salt of glufosinate is the ammonium salt.

28. The composition of claim 25 wherein the herbicidal or plant growth regulating compound is a salt of N-phosphonomethylglycine.

29. The composition of claim 28 wherein the salt of N-phosphonomethylglycine is selected from the group consisting of sodium, potassium, ammonium, mono-, di-, tri- and tetra-$C_{1-4}$-alkylammonium, mono-, di- and tri-$C_{1-4}$-alkanolammonium, mono-, di- and tri-$C_{1-4}$-alkylsulfonium and sulfoxonium salts.

30. The composition of claim 29 wherein the salt of N-phosphonomethylglycine is the ammonium, monoisopropylammonium or trimethylsulfonium salt.

31. The composition of claim 1, wherein the second excipient substance comprises an amphiphilic compound or mixture of such compounds having two hydrophobic moieties, each of which is a saturated alkyl or acyl chain having from about 8 to about 22 carbon atoms; wherein said amphiphilic compound or mixture of such compounds having said two hydrophobic moieties constitutes from about 40 to 100 percent by weight of all amphiphilic compounds having two hydrophobic moieties present in said liposome-forming material.

32. The composition of claim 31, wherein the second excipient substance has a hydrophilic head group comprising a cationic group.

33. The composition of claim 32, wherein the cationic group is an amine or ammonium group.

34. The composition of claim 1, wherein the second excipient substance comprises a liposome-forming compound having a hydrophobic moiety comprising two independently saturated or unsaturated hydrocarbyl groups $R^1$ and $R^2$ each independently having about 7 to about 21 carbon atoms, said liposome-forming compound having a formula selected from the group consisting of:

(a) $N^+(CH_2R^1)(CH_2R^2)(R^3)(R^4)$ $Z^-$
wherein $R^3$ and $R^4$ are independently hydrogen, $C_{1-4}$ alkyl or $C_{1-4}$ hydroxyalkyl and Z is a suitable anion;

(b) $N^+(R^5)(R^6)(R^7)CH_2CH(OCH_2R^1)CH_2(OCH_2R^2)$ $Z^-$
wherein $R^5$, $R^6$ and $R^7$ are independently hydrogen, $C_{1-4}$ alkyl or $C_{1-4}$ hydroxyalkyl and Z is a suitable anion;

(c) $N^+(R^5)(R^6)(R^7)CH_2CH(OCOR^1)CH_2(OCOR^2)$ $Z^-$
wherein $R^5$, $R^6$, $R^7$ and Z are as defined above; and (d) $N^+(R^5)(R^6)(R^7)CH_2CH_2OPO(O^-)OCH_2CH(OCOR^1)CH_2(OCOR^2)$
wherein $R^5$, $R^6$, and $R^7$ are as defined above.

35. The composition of claim 34, wherein Z is selected from the group consisting of hydroxide, chloride, bromide, iodide, sulfate, phosphate and acetate.

36. The composition of claim 34, wherein $R^1$ and $R^2$ are independently saturated straight-chain alkyl groups each having about 7 to about 21 carbon atoms.

37. The composition of claim 34, wherein the second excipient substance is a phospholipid selected from the group consisting of di-$C_{8-22}$-alkanoylphosphatidylcholines and di-$C_{8-22}$-alkanoylphosphatidylethanolamines.

38. The composition of claim 37, wherein the second excipient substance is a dipalmitoyl or distearoyl ester of phosphatidylcholine or a mixture thereof.

39. The composition of claim 1, further comprising water in an amount effective to make the composition a dilute aqueous composition ready for application to foliage of a plant.

40. A plant treatment method, comprising contacting foliage of a plant with a biologically effective amount of a composition according to any of claims 1 to 39.

41. The composition of claim 1, wherein the composition is a shelf-stable concentrate composition comprising the exogenous chemical in an amount of about 15 to about 90 percent by weight.

42. The composition of claim 41, wherein the composition is a solid composition comprising the exogenous chemical substance in an amount of about 30 to about 90 percent by weight.

43. The composition of claim 42, wherein the composition is a water-soluble or water-dispersible granular formulation.

44. The composition of claim 41, further comprising a liquid diluent, and wherein the composition comprises the exogenous chemical substance in an amount of about 15 to about 60 percent by weight.

45. The composition of claim 44 wherein the exogenous chemical substance is water-soluble and is present in an aqueous phase of the composition in an amount of about 15 to about 45 percent by weight of the composition.

46. The composition of claim 45, wherein the composition is an aqueous solution concentrate.

47. The composition of claim 45, wherein the composition is an emulsion having an oil phase.

48. The composition of claim 47, wherein the composition is an oil-in-water emulsion.

49. The composition of claim 47, wherein the composition is a water-in-oil emulsion.

50. The composition of claim 47, wherein the composition is a water-in-oil-in-water multiple emulsion.

* * * * *